(12) United States Patent
Guia et al.

(10) Patent No.: US 9,146,221 B2
(45) Date of Patent: Sep. 29, 2015

(54) HIGH-DENSITY ION TRANSPORT MEASUREMENT BIOCHIP DEVICES AND METHODS

(71) Applicant: AVIVA BIOSCIENCES CORPORATION, San Diego, CA (US)

(72) Inventors: Antonio Guia, San Diego, CA (US); George Walker, San Diego, CA (US); Jia Xu, Washington, DC (US); Julian Yuan, San Diego, CA (US); Lei Wu, San Diego, CA (US); Mingxian Huang, San Diego, CA (US)

(73) Assignee: Aviva Biosciences Corporation, San Diego, CA (US)

( * ) Notice: Subject to any disclaimer, the term of this patent is extended or adjusted under 35 U.S.C. 154(b) by 35 days.

(21) Appl. No.: 13/802,207

(22) Filed: Mar. 13, 2013

(65) Prior Publication Data
US 2013/0266490 A1 Oct. 10, 2013

Related U.S. Application Data

(63) Continuation-in-part of application No. 12/233,565, filed on Sep. 18, 2008, which is a continuation of application No. 11/175,789, filed on Jul. 5, 2005, now abandoned, which is a continuation-in-part of
(Continued)

(51) Int. Cl.
*G01N 31/22* (2006.01)
*B65B 31/00* (2006.01)
(Continued)

(52) U.S. Cl.
CPC .............. *G01N 31/22* (2013.01); *B65B 31/00* (2013.01); *G01N 33/48728* (2013.01); *B01L 3/5088* (2013.01); *B01L 3/502761* (2013.01); *B01L 3/502792* (2013.01); *B01L 2200/027* (2013.01); *B01L 2200/0647* (2013.01); *B01L 2200/0668* (2013.01); *B01L 2300/0819* (2013.01); *B01L 2400/049* (2013.01); *B03C 5/026* (2013.01); *C12Q 2565/629* (2013.01); *C23C 16/452* (2013.01); *G01N 15/1031* (2013.01); *H01J 2237/3142* (2013.01)

(58) Field of Classification Search
None
See application file for complete search history.

(56) References Cited

U.S. PATENT DOCUMENTS 3,364,087 A 1/1968 Solomon et al.
3,410,979 A 11/1968 Larson
(Continued)

FOREIGN PATENT DOCUMENTS

CA 2 316 966 6/1999
CA 2 334 770 12/1999
(Continued)

OTHER PUBLICATIONS

About Axon Instruments (Axoclamp and Axopatch Series Microelectrode Amplifiers).
(Continued)

*Primary Examiner* — Jennifer Wecker
(74) *Attorney, Agent, or Firm* — Morrison & Foerser LLP

(57) ABSTRACT

The present invention includes biochips for the measurement of cellular ion channels and methods of use and manufacture. The biochips of the present invention have enhanced sealing capabilities provided in part by chemically modifying the surface of the biochip surface or substrate or by exposure to an ionized gas. The present invention also includes novel cartridges for biochips.

25 Claims, 48 Drawing Sheets

Related U.S. Application Data application No. 11/033,015, filed on Jan. 10, 2005, now abandoned, which is a continuation-in-part of application No. 10/858,339, filed on Jun. 1, 2004, now abandoned, said application No. 11/033,015 is a continuation-in-part of application No. 10/760,886, filed on Jan. 20, 2004, now abandoned, which is a continuation-in-part of application No. 10/428,565, filed on May 2, 2003, now abandoned, said application No. 11/033,015 is a continuation-in-part of application No. 10/642,014, filed on Aug. 16, 2003, now abandoned, which is a continuation-in-part of application No. 10/351,019, filed on Jan. 23, 2003, now abandoned, said application No. 11/033,015 is a continuation-in-part of application No. 10/104,300, filed on Mar. 22, 2002, now Pat. No. 7,968,305, said application No. 11/175,789 is a continuation-in-part of application No. 11/153,825, filed on Jun. 15, 2005, now Pat. No. 7,723,029.

(60) Provisional application No. 60/474,508, filed on May 31, 2003, provisional application No. 60/380,007, filed on May 4, 2002, provisional application No. 60/351,849, filed on Jan. 24, 2002, provisional application No. 60/311,327, filed on Aug. 10, 2001, provisional application No. 60/278,308, filed on Mar. 24, 2001, provisional application No. 60/535,461, filed on Jan. 10, 2004, provisional application No. 60/585,822, filed on Jul. 6, 2004.

(51) Int. Cl.
| | | |
|---|---|---|
| *G01N 33/567* | (2006.01) | |
| *C12M 1/34* | (2006.01) | |
| *G01N 33/487* | (2006.01) | |
| *G01N 15/06* | (2006.01) | |
| *B01L 3/00* | (2006.01) | |
| *B03C 5/02* | (2006.01) | |
| *G01N 15/10* | (2006.01) | |
| *C23C 16/452* | (2006.01) | |

(56) References Cited

U.S. PATENT DOCUMENTS

| | | |
|---|---|---|
| 3,722,504 A | 3/1973 | Sawyer |
| 3,732,620 A | 5/1973 | Misch et al. |
| 4,055,799 A | 10/1977 | Coster et al. |
| 4,160,645 A | 7/1979 | Ullman |
| 4,275,149 A | 6/1981 | Litman et al. |
| 4,318,980 A | 3/1982 | Boguslaski et al. |
| 4,324,255 A | 4/1982 | Barach et al. |
| 4,454,032 A | 6/1984 | Dupont |
| 4,478,094 A | 10/1984 | Salomaa et al. |
| 4,562,157 A | 12/1985 | Lowe et al. |
| 4,894,343 A | 1/1990 | Tanaka et al. |
| 4,894,443 A | 1/1990 | Greenfield et al. |
| 4,906,803 A | 3/1990 | Albrechta et al. |
| 4,952,518 A | 8/1990 | Johnson et al. |
| 5,021,294 A | 6/1991 | Karasawa et al. |
| 5,079,169 A | 1/1992 | Chu et al. |
| 5,200,051 A | 4/1993 | Cozzette et al. |
| 5,292,418 A | 3/1994 | Morita et al. |
| 5,364,744 A | 11/1994 | Buican et al. |
| 5,389,215 A | 2/1995 | Horiuchi et al. |
| 5,422,272 A | 6/1995 | Papp et al. |
| 5,506,141 A | 4/1996 | Weinreb et al. |
| 5,514,850 A | 5/1996 | Miyazaki et al. |
| 5,585,277 A | 12/1996 | Bowie et al. |
| 5,612,474 A | 3/1997 | Patel |
| 5,653,939 A | 8/1997 | Hollis et al. |
| 5,661,035 A | 8/1997 | Tsien et al. |
| 5,679,582 A | 10/1997 | Bowie et al. |
| 5,840,041 A | 11/1998 | Petter et al. |
| 5,846,396 A | 12/1998 | Zanzucchi et al. |
| 5,858,666 A | 1/1999 | Weiss |
| 5,880,071 A | 3/1999 | Parce et al. |
| 5,883,760 A | 3/1999 | Yamada et al. |
| 5,932,485 A | 8/1999 | Schofield |
| 5,948,684 A | 9/1999 | Weigl et al. |
| 5,972,710 A | 10/1999 | Weigl et al. |
| 5,981,268 A | 11/1999 | Kovacs |
| 5,998,129 A | 12/1999 | Schutze et al. |
| 6,020,026 A | 2/2000 | Birch et al. |
| 6,063,260 A | 5/2000 | Oleson |
| 6,071,702 A | 6/2000 | Yamamoto et al. |
| 6,107,066 A | 8/2000 | Tsien et al. |
| 6,117,291 A | 9/2000 | Olesen et al. |
| 6,120,666 A | 9/2000 | Jacobsen et al. |
| 6,130,056 A | 10/2000 | Correges |
| 6,159,749 A | 12/2000 | Liu |
| 6,171,865 B1 | 1/2001 | Weigl et al. |
| 6,172,330 B1 | 1/2001 | Yamamoto et al. |
| 6,177,000 B1 | 1/2001 | Peterson |
| 6,225,059 B1 | 5/2001 | Ackley et al. |
| 6,228,326 B1 | 5/2001 | Boxer et al. |
| 6,251,691 B1 | 6/2001 | Seul |
| 6,267,872 B1 | 7/2001 | Akeson et al. |
| 6,284,113 B1 | 9/2001 | Bjornson et al. |
| 6,284,459 B1 | 9/2001 | Nova et al. |
| 6,306,613 B1 | 10/2001 | Florkiewicz et al. |
| 6,315,940 B1 | 11/2001 | Nisch |
| 6,352,853 B1 | 3/2002 | King |
| 6,355,491 B1 | 3/2002 | Zhou et al. |
| 6,376,028 B1 | 4/2002 | Laurent et al. |
| 6,387,707 B1 | 5/2002 | Weigl et al. |
| 6,396,462 B1 | 5/2002 | Mead et al. |
| 6,416,642 B1 | 7/2002 | Alajoki et al. |
| 6,426,183 B1 | 7/2002 | Beattie |
| 6,426,483 B1 | 7/2002 | Blankenship et al. |
| 6,440,600 B1 | 8/2002 | Starzak |
| 6,448,794 B1 | 9/2002 | Cheng et al. |
| 6,488,829 B1 | 12/2002 | Schroeder et al. |
| 6,531,678 B2 | 3/2003 | Yamamoto |
| 6,548,263 B1 | 4/2003 | Kapur et al. |
| 6,594,025 B2 | 7/2003 | Forouhi et al. |
| 6,689,986 B2 | 2/2004 | Patel et al. |
| 6,699,697 B2 | 3/2004 | Klemic |
| 6,758,961 B1 | 7/2004 | Vogel |
| 6,766,817 B2 | 7/2004 | Da Silva |
| 6,780,582 B1 | 8/2004 | Wagner et al. |
| 6,936,462 B1 | 8/2005 | Owen |
| 7,001,608 B2 | 2/2006 | Fishman et al. |
| 2002/0006357 A1* | 1/2002 | McGeoch et al. .......... 422/82.01 |
| 2002/0009729 A1* | 1/2002 | McGall et al. ................. 435/6 |
| 2002/0014408 A1 | 2/2002 | Schroeder |
| 2002/0022219 A1 | 2/2002 | Clements et al. |
| 2002/0025573 A1 | 2/2002 | Maher et al. |
| 2002/0028160 A1 | 3/2002 | Xiao et al. |
| 2002/0045159 A1 | 4/2002 | Maher et al. |
| 2002/0053915 A1 | 5/2002 | Weaver et al. |
| 2002/0063067 A1 | 5/2002 | Bech |
| 2002/0064841 A1 | 5/2002 | Klemic et al. |
| 2002/0086280 A1 | 7/2002 | Lynes |
| 2002/0104757 A1 | 8/2002 | Schmidt |
| 2002/0108869 A1 | 8/2002 | Savchenko |
| 2002/0123134 A1 | 9/2002 | Huang et al. |
| 2002/0144905 A1* | 10/2002 | Schmidt ................... 204/403.01 |
| 2002/0146845 A1 | 10/2002 | Parce et al. |
| 2002/0164777 A1* | 11/2002 | Kelly et al. ................ 435/287.1 |
| 2002/0182627 A1 | 12/2002 | Wang et al. |
| 2002/0195337 A1 | 12/2002 | Osipchuk et al. |
| 2003/0010638 A1 | 1/2003 | Hansford et al. |
| 2003/0031829 A1 | 2/2003 | Tanner et al. |
| 2003/0052002 A1 | 3/2003 | Vogel et al. |
| 2003/0080314 A1* | 5/2003 | Nisch et al. ................. 252/62.2 |
| 2003/0098248 A1 | 5/2003 | Vogel et al. |
| 2003/0146091 A1 | 8/2003 | Vogel et al. |
| 2004/0146849 A1* | 7/2004 | Huang et al. ..................... 435/4 |
| 2004/0224002 A1 | 11/2004 | Fishman et al. |
| 2005/0009004 A1* | 1/2005 | Xu et al. ........................... 435/4 |

(56) References Cited

U.S. PATENT DOCUMENTS

| | | | | |
|---|---|---|---|---|
| 2005/0058990 | A1* | 3/2005 | Guia et al. | 435/5 |
| 2005/0196746 | A1 | 9/2005 | Xu et al. | |
| 2006/0029955 | A1 | 2/2006 | Guia et al. | |
| 2006/0160235 | A1* | 7/2006 | Craighead et al. | 436/86 |
| 2006/0191882 | A1 | 8/2006 | Watkins et al. | |

FOREIGN PATENT DOCUMENTS

| | | |
|---|---|---|
| CA | 2 413 663 | 1/2002 |
| CA | 2 424 498 | 4/2002 |
| EP | 0500110 | 8/1992 |
| EP | 1195432 | 10/2002 |
| JP | 2001127397 | 5/2001 |
| WO | WO-94/25862 | 11/1994 |
| WO | WO-96/13721 | 5/1996 |
| WO | WO-98/50791 | 11/1998 |
| WO | WO-99/19729 | 4/1999 |
| WO | WO-99/31503 | 6/1999 |
| WO | WO-99/66329 | 12/1999 |
| WO | WO-00/25121 | 5/2000 |
| WO | WO-00/54882 | 9/2000 |
| WO | WO-00/71742 | 11/2000 |
| WO | WO-01/25769 | 4/2001 |
| WO | WO-01/27614 | 4/2001 |
| WO | WO-01/34764 | 5/2001 |
| WO | WO-01/48474 | 7/2001 |
| WO | WO-01/59447 | 8/2001 |
| WO | WO-01/69241 | 9/2001 |
| WO | WO-02/04943 | 1/2002 |
| WO | WO-02/52045 | 1/2002 |
| WO | WO-02/12986 | 2/2002 |
| WO | WO 02/16647 | 2/2002 |
| WO | WO-02/24862 | 3/2002 |
| WO | WO-02/27909 | 4/2002 |
| WO | WO-02/28523 | 4/2002 |
| WO | WO-02/29400 | 4/2002 |
| WO | WO-02/29402 | 4/2002 |
| WO | WO-02/30562 | 4/2002 |
| WO | WO-02/31505 | 4/2002 |
| WO | WO-02/31506 | 4/2002 |
| WO | WO-02/42766 | 5/2002 |
| WO | WO-02/059603 | 8/2002 |
| WO | WO-02/065092 | 8/2002 |
| WO | WO-02/066596 | 8/2002 |
| WO | WO-02/075309 | 9/2002 |
| WO | WO-02/077259 | 10/2002 |
| WO | WO-03/093494 | 11/2003 |

OTHER PUBLICATIONS

Ahn et al., J. Microelectromechanical Systems (1996) 5:151-158.
Almers et al., J. Physiol. (1981) 312:159-176.
Armstrong and Gilly, Methods in Enzymology (1992) 207:100-122.
Asada, Proc. SPIE (2000) 4088:132-135 (Abstract).
Aston-Jones and Siggins, www.acnp.org/GA/GN401000005/CH005.html.
Automated Patch-Clamp, CeNes Ltd. Homepage.
Axon Instruments, Inc. Press Release May 25, 2000.
Axon Instruments, Inc. Press Release Aug. 9, 2000.
Axon Instruments, Inc. Press Release Oct. 30, 2000.
Axon Instruments, Inc. Press Release Apr. 17, 2001.
Batra et al., Molecular Immunol. (1993) 30:379-386.
Bean, Methods in Enzymology (1992) 207:181-193.
Becker et al., J. Phys. D: Appl. Phys. (1994) 27:2659-2662.
Becker et al., Proc. Natl Acad. Sci. USA (1995) 92:860-864.
Blick et al., Physics 6 E (2000) pp. 821-827.
Bustamante and Verranda, Brazilian Journal (1998) 31:333-354.
Cahalan and Neher, Methods in Enzymology (1992) 207:3-14.
Cheng et al., Nature Biotechnology (1998) 16:541-546.
Chiu et al., Science (1999) 283(5409):1892-1895 (Abstract).
Chun et al., IEEE (1999) pp. 406-411.
Cole-Parmer Catalog, Cole-Parmer Instrument Company, 1997-1998, p. 757.

Costa et al., Biophysical Journal (1994) 64:395-401.
Course Description for MEM System, taught by James Klemic.
Cumber et al., Bioconj. Chem. (1992) 3:397-401.
De Gasperis et al., Biomedical Microdevices (1999) 2:41-49.
Dunsky, Proc. SPIE (2001) 4443:135-149 (Abstract).
Erbe et al., App. Phys. Lett. (2000) 77(19):3102-3104.
Fertig et al., Appl. Phys. Lett. (2000) 77(8):1218-1220.
Fiedler et al., Anal. Chem. (1998) 70:1909-1915.
Fuhr et al., Biochim. Biophys. Acta. (1992) 1108:215-233.
Fuhr et al., Biochim. Biophys. Acta. (1995) 1269:221-232.
Gascoyne et al., IEEE Transactions (1997) 33(3):670-678.
Gutmann et al., Pharma. Research (1999) 16:402-407.
Hamill and McBride, Ann. Rev. Physiol. (1997) 59:621-637.
Heinmann and Conti, Methods in Enzymology (1992) 207:131-148.
Herness, Physiology and Behavior (2000) 69:17-27.
Huang et al., Biophys J. (1997) 73:1118-1129.
Huang et al., J. Phys. D: Appl. Phys. (1993) 26:1528-1535.
Huang and Pethig, Meas. Sci. Technol. (1991) 2:1142-1146.
Hughes et al., Biochim. Biophys. Acta. (1998) 1425:119-126.
Huston et al., Proc. Natl. Acad. Sci. USA (1998) 85:5879-5883.
Islas and Sigworth, J. Gen. Physiol. (2001) 117(1):68-69 (Abstract).
Jardemark et al., Anal. Chem. (1998) 70(13):2468-2474 (Abstract).
Karnakis et al., Proc. SPIE (2001) 4443:150-158 (Abstract).
Knowles, Proc. SPIE (2000) 3888:210-216 (Abstract).
Kreutz, Proc. SPIE (1996) 2879:37-44 (Abstract).
Krommer et al., Europhys. Lett. (2000) 50(1):101-106.
Kung et al., Journal of Virological Methods (2000) 90:205-212.
Ladurner et al., J. Mol. Biol. (1997) 273:330-337.
Laser Drilling, Fabrication Image Transferring KPJ.
Lester, Ann. Rev. Physiol. (1991) 53:477-496.
Levis and Rae, Methods in Enzymology (1992) 207:14-66.
Liakopoulos et al., Transducers 97, pp. 484-488, presented in 1997 International Conference on Solid State Sensors and Actuators, Chicago, Jun. 16, 1997.
Liem et al., Neurosurgery (1995) 36:382-392.
Lindner et al., Microelectronic Engineering (1998) 41/42:75-78.
Liu et al., J. Chromotogr. (2000) 891(1):149-156 (Abstract).
Luong et al., Anal. Chem. (2001) 73:1844-1848.
Madou, Proc. SPIE (1999) 3877:44-53 (Abstract).
Markx et al., Microbiology (1994) 140:585-591.
Martinez-Pardon and Ferrus, Current Topics in Development. Biol. (1998) 36:303-312.
Mathes, DDT (2003) 8:1022-1024.
Micro Vacuum Ltd. A Surface Engineering Approach Towards the Development of Cell Based Biochips, www.microvacuum.com/research/memocs/meeting1/.
Morgan et al., Biophys. J. (1999) 77:516-525.
Morgan et al., J. Micromech. Microeng. (1997) 7:65-70.
Muller et al., Biosensors and Bioelectronics (1999) 14:247-256.
Neher et al., Pflueger Arch. (1978) 375:219-278.
Neher and Sakman, Scientific American (1992) 266:44-51.
Newton et al., Biochemistry (1996) 35:545-553.
Nishimae, Proc. SPIE (2000) 4088:209-211 (Abstract).
Niwa et al., Anal. Chem. (1996) 68(11):18650 (Abstract).
Niwa et al., Anal. Chem. (2000) 72(5):949-955 (Abstract).
Okada, Proc. SPIE (2000) 4088:148-153 (Abstract).
Patch Clamp—Method of Choice for Receptor Anaysis, www.cytion.com/principle.htm.
Presentation—Cambridge Healthtech Institutes HTT Expo (High-Throughput Technologies), Philadelphia, Jun. 13, 2001.
Protein Chip Data Archive Archive—Yale Gershein Lab, http://entry.eng.yale.edu/genome/yeast/chip, Mar. 13, 2001.
Richter et al., Biophysical Journal (2003) 85:3035-3047.
Ryttsen et al., Biophys. J. (2000) 79(4):1993-2001 (Abstract).
Safarik and Safarikova, J. Chromatography (1999) 722(B):33-53.
Sakman and Neher, Ann. Rev. Physiol. (1984) 46:455-472.
Schnelle et al., Biosensors and Bioelectronics (1999) 1157:127-140.
Stephens et al., Bone Marrow Transplantation (1996) 18:777-782.
Straub et al., Nature Biotechnology (2001) 19:121-124.
Summary of Projects in the Laboratory of Dr. Albert Folch.
Tilke et al., Superlattices and Microstructures (2000) 27(5/6):597-601.
Vogler et al., Microelectronic Engineering (2000) 53:149-152.

(56) References Cited

OTHER PUBLICATIONS

Wang et al., Biochim. Biophys. Acta. (1995) 1243:185-194.
Wang et al., Biophys. J. (1997) 72:1887-1899.
Wang et al., Biophys. J. (1998) 74:2689-2701.
Wang et al., IEEE Transaction on Industry Applications (1997) 33(3):660-669.
Wang et al., J. Phys. D: Appl. Phys. (1993) 26:1278-1285.
Wang and Li, Assay and Drug Devel. Technol. (2003) 1:1-13.
Washizu et al., IEEE Trans. Ind. Appl. (1990) 26:352-358.
Washizu et al., IEEE Trans. Ind. Appl. (1994) 30:835-843.
Wegener et al., Exp. Cell Research (2000) 259:158-166.
Whitlow et al., Protein Engineering (1993) 6:989-995.
Vegel, Development of Bioassays for Odorant Molecule Analysis, www.ehrat.ch/topnano21/english/11e.html (Abstract).
Vegel, http://bioweb.psi.ch/abstracts.html (Abstract).
Xiao et al., Anal. Chem. (2002) 74:1333-1339.
Xiao et al., Anal. Chem. (2002) 74:5748-5753.
Xiao et al., Biotechnol. Prog. (2003) 19:1000-1005.
Yang et al., Anal. Chem. (1999) 71(5):911-918.
Zhu et al., Nature Genetics (2000) 26:283-289.
Invitation to Pay Additional Fees and, Where Applicable, Protest Fee for PCT/US04/17134, mailed Jul. 11, 2006.
International Search Report and Written Opinion for PCT/04/17134, mailed Apr. 26, 2007.
Written Opinion of the International Searching Authority for PCTUS2005/023993, mailed on Oct. 12, 2006.
International Search Report for PCT/US2005/023993, mailed on Oct. 12, 2006.
International Preliminary Report on Patentability for PCT/US2005/023993, mailed on Feb. 2007, 8 pages.
International Search Report and Written Opinion for PCT/US05/00732, mailed Aug. 5, 2008.
U.S. Appl. No. 60/164,128, filed Nov. 8, 1999 (Schmidt).
U.S. Appl. No. 60/233,800, filed Sep. 19, 2000 (Schmidt).
U.S. Appl. No. 60/322,178, filed Sep. 13, 2001 (Schmidt).
U.S. Appl. No. 60/322,365, filed Sep. 14, 2000 (Schmidt).
U.S. Appl. No. 10/428,565, filed May 2, 2003.
U.S. Appl. No. 10/858,339, filed Jun. 1, 2004.
Preliminary Amendment for U.S. Appl. No. 10/858,339, filed on Nov. 26, 2004.
U.S. Appl. No. 11/033,015, filed Jan. 10, 2005.
U.S. Appl. No. 11/175,789, filed Jul. 5, 2005.
Restriction Requirement for U.S. Appl. No. 11/175,789, date mailed on Jul. 11, 2007.
Response to Restriction Requirement for U.S. Appl. No. 11/175,789, filed on Dec. 11, 2007.
Non-Final Office Action for U.S. Appl. No. 11/175,789, mailed on Mar. 18, 2008.
U.S. Appl. No. 10/760,886, filed Jan. 20, 2004.
Restriction Requirement for U.S. Appl. No. 10/760,886, date mailed on Dec. 28, 2005.
Response to Restriction Requirement for U.S. Appl. No. 10/760,886, filed on May 25, 2006.
Non-Final Office Action for U.S. Appl. No. 10/760,886, date mailed on Aug. 29, 2006.
Amendment in Response to Non-Final Office Action for U.S. Appl. No. 10/760,886, filed on Nov. 29, 2006.
Final Office Action for U.S. Appl. No. 10/760,886, date mailed on Feb. 22, 2007.
Notice of Appeal for U.S. Appl. No. 10/760,886, filed on Aug. 22, 2007.
Request for Continued Examination for U.S. Appl. No. 10/760,886, filed on Oct. 31, 2007.
Non-Final Office Action for U.S. Appl. No. 10/760,886, date mailed on Jan. 10, 2008.
Response to Office Action for U.S. Appl. No. 10/760,866, dated Jul. 10, 2008.
Non-Final Office Action for U.S. Appl. No. 10/760,836, dated Dec. 5, 2008.
Response to Office Action for U.S. Appl. No. 10/760,886, dated Jun. 5, 2009.
Final Office Action for U.S. Appl. No. 10/760,886, dated Sep. 15, 2009.
RCE and Preliminary Amendment for U.S. Appl. No. 10/760,886. Dated Feb. 16, 2010.
Office Action for U.S. Appl. No. 10/760,836, dated Apr. 27, 2010.
Response to Office Action for U.S. Appl. No. 10/760,886, dated Jul. 27, 2010.
Final Office Action for U.S. Appl. No. 10/760,886, dated Oct. 25, 2010.
U.S. Patent Application for U.S. Appl. No. 11/841,985, filed Aug. 20, 2007.
Restriction Requirement for U.S. Appl. No. 11/841,985, mailed Feb. 11, 2011.
Response to Restriction Requirement for U.S. Appl. No. 11/841,985, mailed Mar. 11, 2011.
Office Action for U.S. Appl. No. 11/841,985, mailed Apr. 22, 2011.
Office Action for U.S. Appl. No. 10/858,339 dated Apr. 25, 2008.
Response to Office Action U.S. Appl. No. 10/858,339, dated Jul. 23, 2008.
Final Office Action for U.S. Appl. No. 10/858,339, mailed on Nov. 19, 2008.
RCE and Preliminary Amendment for U.S. Appl. No. 10/858,339, mailed on Mar. 2, 2009.
Non-Final Office Action for U.S. Appl. No. 10/858,339, mailed on Jun. 1, 2009.
Response to Office Action for U.S. Appl. No. 10/858,339, mailed on Nov. 2, 2009.
Final Office Action for U.S. Appl. No. 10/858,339, mailed on Mar. 16, 2010.
RCE and Preliminary Amendment for U.S. Appl. No. 10/858,339, mailed on Aug. 16, 2010.
Non-Final Office Action for U.S. Appl. No. 10/858,339, mailed on Nov. 9, 2010.
Restriction Requirement for U.S. Appl. No. 11/033,015, mailed on May 30, 2008.
Response to Restriction Requirement for U.S. Appl. No. 11/033,015, mailed on Dec. 1, 2008.
Non-Final Office Action for U.S. Appl. No. 11/033,015, mailed on Dec. 22, 2008.
Response to Non-Final Office Action for U.S. Appl. No. 11/033,015, mailed on Jun. 22, 2009.
Final Office Action for U.S. Appl. No. 11/033,015, mailed on Oct. 26, 2009.
RCE and Preliminary Amendment for U.S. Appl. No. 11/033,015, mailed on Feb. 25, 2010.
Non-Final Office Action for U.S. Appl. No. 11/033,015, mailed on Mar. 18, 2010.
Response to Non-Final Office Action for U.S. Appl. No. 11/033,015, mailed on Aug. 17, 2010.
Final Office Action for U.S. Appl. No. 11/033,015, mailed on Oct. 27, 2010.
Supplementary Partial Search Report for European Application No. 03724439.9, dated Sep. 14, 2005.
Supplementary Search Report or European Application No. 03724439.9, dated Mar. 28, 2006.
Office Action for European Application No. 03724439.9, dated Oct. 23, 2006.
Response to Office Action for European Application No. 03724439.9, filed on Apr. 23, 2007.
Office Action for European Application No. 03724439.9, dated Dec. 9, 2008.
Response to Office Action for European Application No. 03724439.9, dated Jun. 19, 2009.
Office Action for European Application No. 03724439.9, dated Apr. 28, 2011.
Supplementary Search Report for European Patent Application No. 04776200.0, mailed Jun. 8, 2009.
Office Action for European Patent Application No. 04776200.0, mailed Sep. 9, 2011.
Voluntary Amendment for Canadian Application No. 2,554,376, filed on Dec. 19, 2006.

(56) References Cited

OTHER PUBLICATIONS

Office Action for Canadian Patent Application No. 2,485,099, mailed on Jun. 6, 2012.
Response to Office Action for Canadian Patent Application No. 2,485,099, mailed Dec. 6, 2012.
Office Action for Canadian Patent Application No. 2,485,099, mailed Oct. 4, 2013.
Office Action for Canadian Patent Application No. 2,527,660, mailed Apr. 11, 2013.
Response to Office Action for Canadian Patent Application No. 2,527,660, mailed Oct. 10, 2013.
International Search Report for International Patent Application No. PCT/US03/14000, mailed Dec. 3, 2003.
Written Opinion for International Patent Application No. PCT/US03/14000, mailed Jun. 25, 2004.
International Preliminary Report on Patentability for PCT/US03/14000, mailed May 3, 2005, 3 pages.
Office Action for U.S. Appl. No. 12/233,565, mailed Jan. 3, 2014, 12 pages.
Response to Office Action for U.S. Appl. No. 12/233,565, filed Apr. 3, 2014, 12 pages.
Response to Office Action for CA 2,485,099, filed Apr. 4, 2014, 10 pages.
Final Office Action for U.S. Appl. No. 12/233,565, mailed May 13, 2014, 14 pages.
Office Action for CA 2,527,660, mailed Jul. 8, 2014, 3 pages.
Response to Final Office Action for U.S. Appl. No. 12/233,565, filed Oct. 14, 2014, 14 pages.
Advisory Action for U.S. Appl. No. 12/233,565, mailed Oct. 23, 2014, 3 pages.
Request for Continued Examination for U.S. Appl. No. 12/233,565, filed Nov. 13, 2014, 19 pages.
Office Action for U.S. Appl. No. 12/233,565, mailed Dec. 23, 2014, 14 pages.
Response to Office Action for CA 2,527,660, filed Jan. 8, 2015, 18 pages.
Office Action for CA 2,485,099, mailed Feb. 19, 2015, 10 pages.
Final Office Action for U.S. Appl. No. 12/233,565, mailed Jul. 15, 2015, 17 pages.

\* cited by examiner 48 x 32 = 1536 array on 8 -inch Si. SOI. or glass wafer

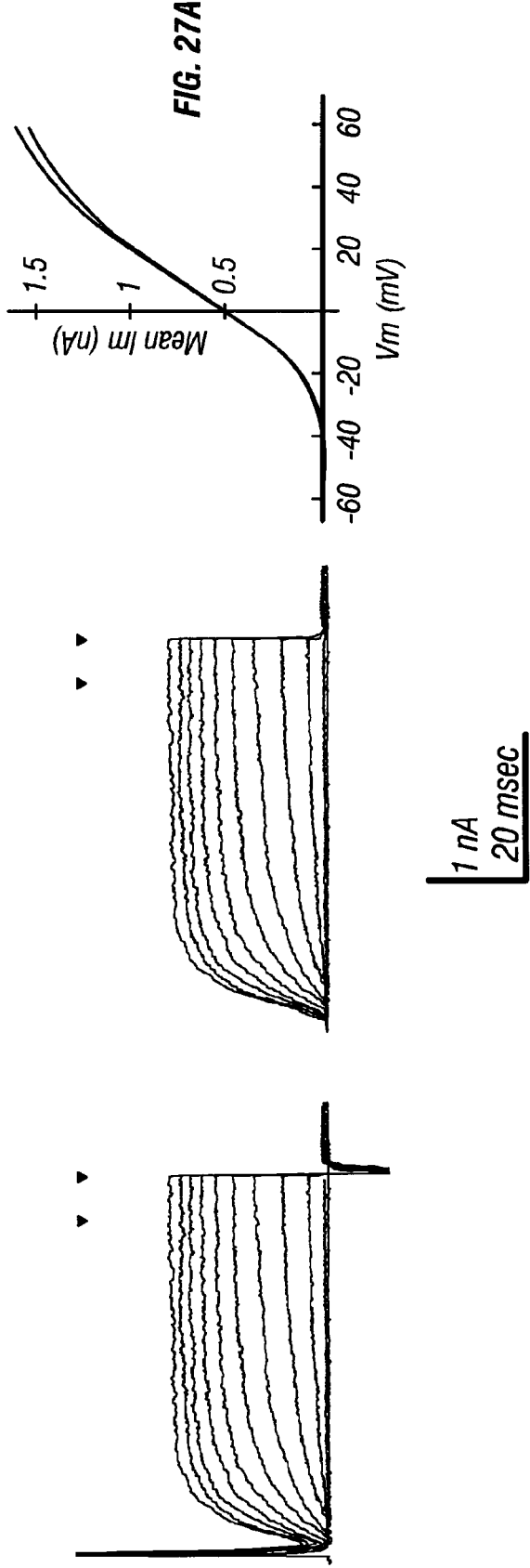
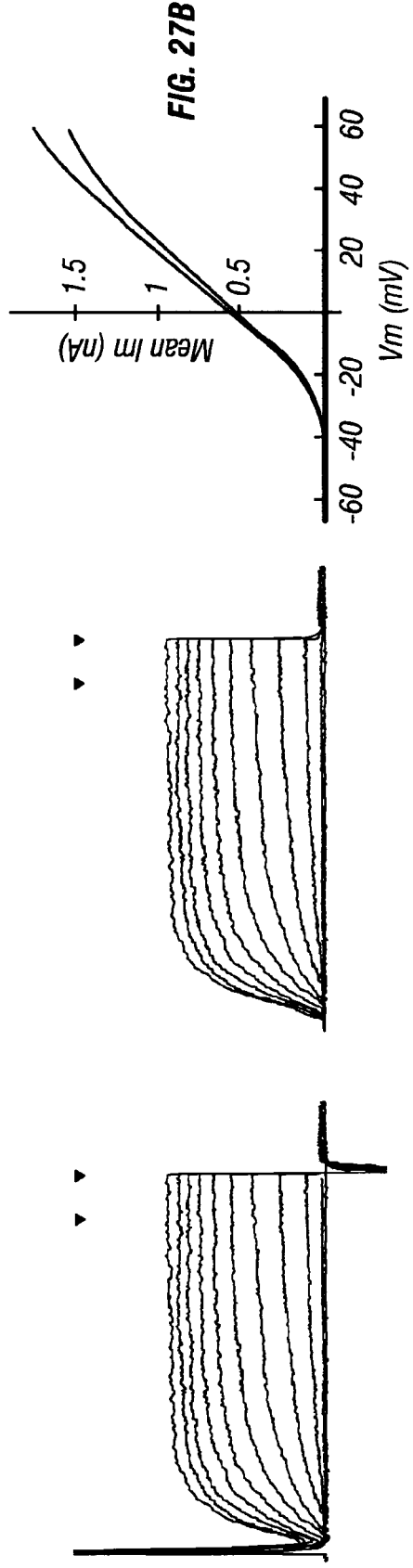

Shoulders

| Parameter | Avg | SE |
|---|---|---|
| Re | 1.12 MOhm | 0.02 |
| Rs | 1.2 GOhm | 0.1 |
| Sealing Time | 9 sec | 2 |
| WC Pressure | 58 torr | 4 |
| Cm | 8.0 pF | 0.6 |
| Rm | 0.94 GOhm | 0.09 |
| Ra | 4.7 MOhm | 0.5 |
FIG. 31A
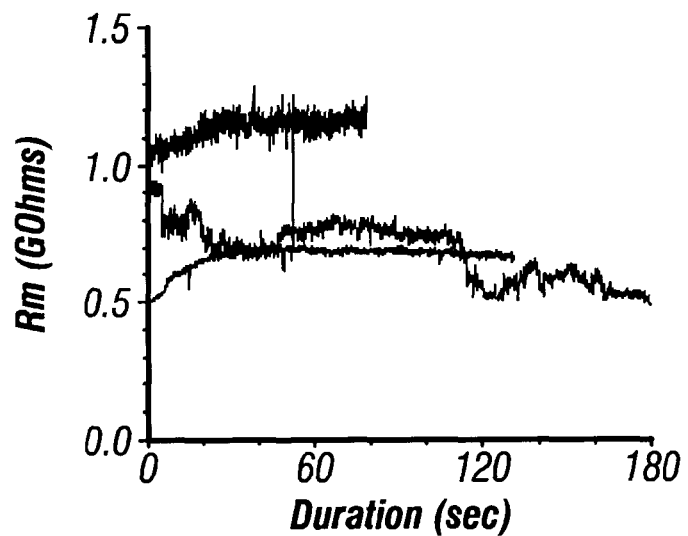
FIG. 31B
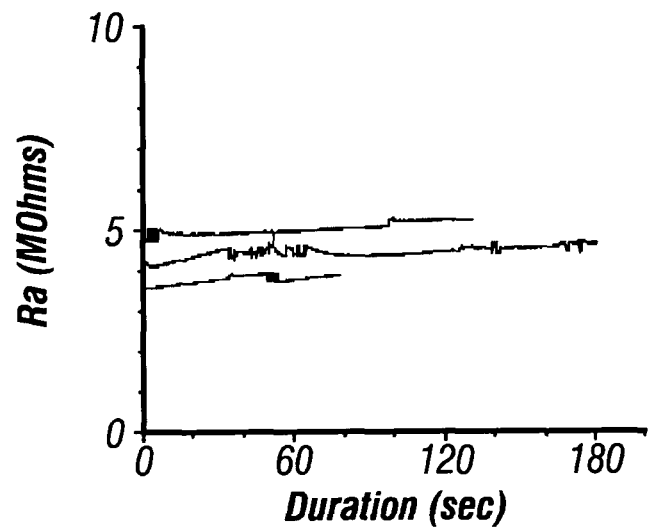
FIG. 31C

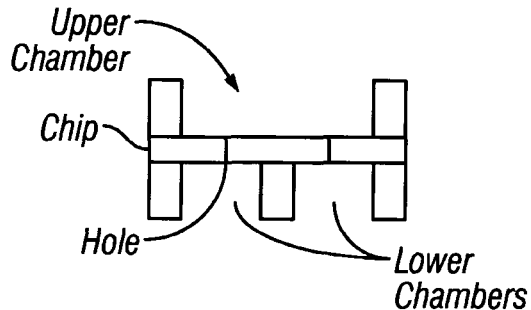
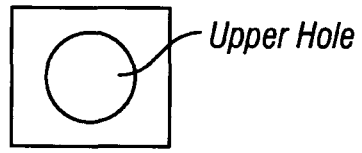
FIG. 46A  FIG. 46B
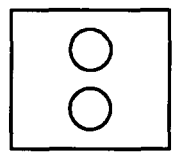
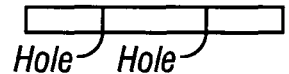
FIG. 47A  FIG. 47B
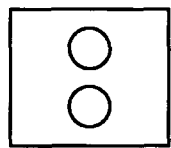
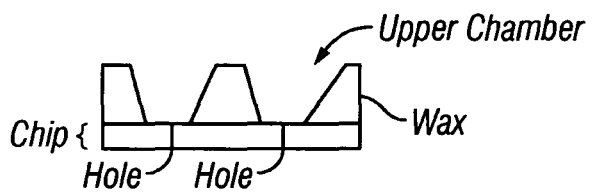
FIG. 48A  FIG. 48B

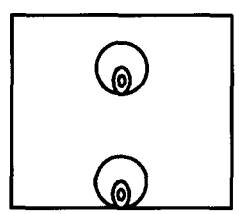
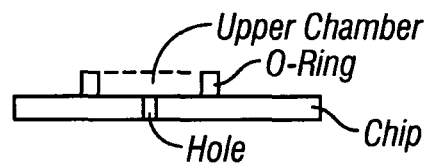
FIG. 49A  FIG. 49B
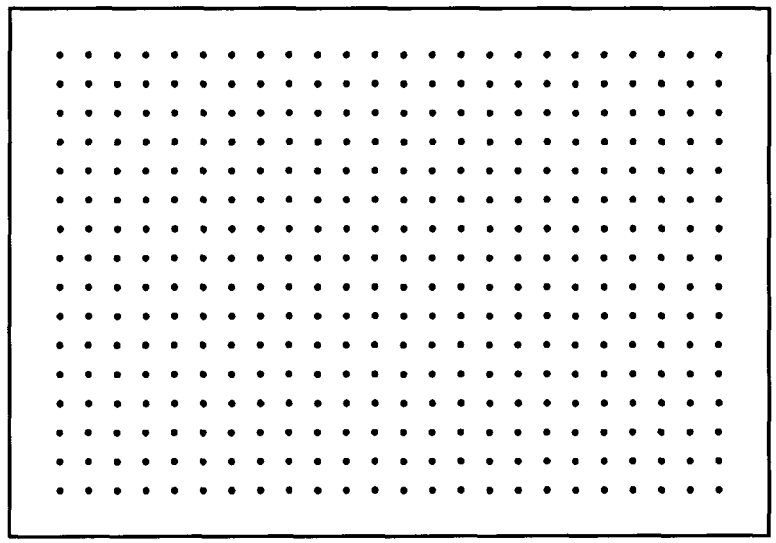
FIG. 50A
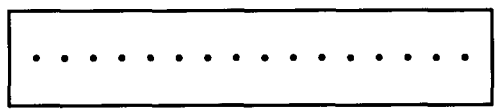
FIG. 50B

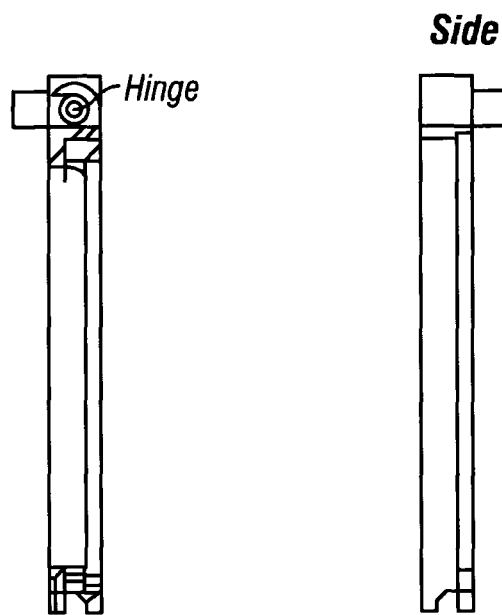
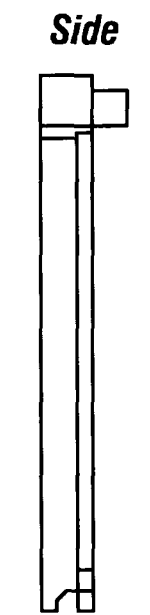
Section A-A
FIG. 56C
FIG. 56D
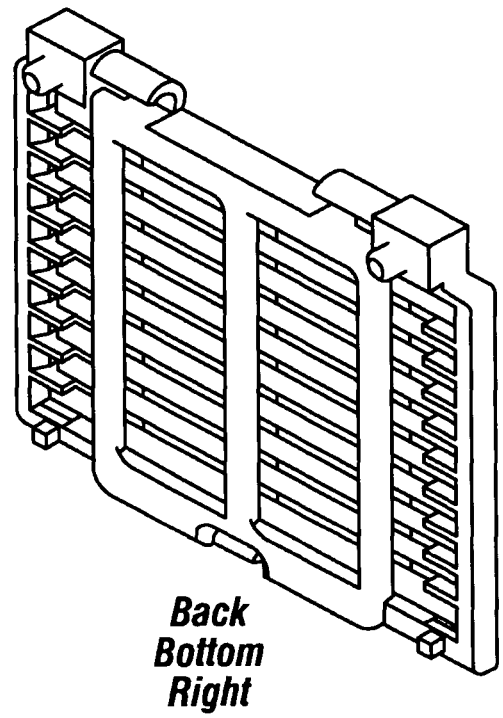
Back Bottom Right
FIG. 56E

HIGH-DENSITY ION TRANSPORT MEASUREMENT BIOCHIP DEVICES AND METHODS

CROSS-REFERENCE TO RELATED APPLICATIONS

This Application is a Continuation of application Ser. No. 12/233,565 filed on Sep. 18, 2008, which is a Continuation of application Ser. No. 11/175,789 filed on Jul. 5, 2005, now abandoned, which is a continuation-in-part of U.S. patent application Ser. No. 11/033,015 filed on Jan. 10, 2005, now abandoned, which is a continuation-in-part of U.S. patent application Ser. No. 10/858,339 filed on Jun. 1, 2004, now abandoned, which claims benefit of priority to U.S. Patent Application Ser. No. 60/474,508 filed on May 31, 2003; U.S. patent application Ser. No. 11/033,015 is also a continuation-in-part of U.S. patent application Ser. No. 10/760,886 filed on Jan. 20, 2004, now abandoned, which is a continuation-in-part of U.S. patent application Ser. No. 10/428,565 filed on May 2, 2003, now abandoned, which claims benefit of priority to U.S. Patent Application Ser. No. 60/380,007 filed on May 4, 2002; U.S. patent application Ser. No. 11/033,015 is also a continuation-in-part of U.S. patent application Ser. No. 10/642,014 filed on Aug. 16, 2003, now abandoned, which is a continuation-in-part of U.S. patent application Ser. No. 10/351,019 filed on Jan. 23, 2003, which claims benefit of priority of U.S. Patent Application Ser. No. 60/351,849 filed on Jan. 24, 2002; U.S. patent application Ser. No. 11/033,015 is also a continuation-in-part of U.S. patent application Ser. No. 10/104,300 filed on Mar. 22, 2002, which is now U.S. Pat. No. 7,968,305, which claims benefit of priority to U.S. Patent Application Ser. No. 60/311,327 filed on Aug. 10, 2001 and claims benefit of 20 priority to U.S. Patent Application Ser. No. 60/278,308 filed on Mar. 24, 2001; U.S. patent application Ser. No. 11/033,015 also claims benefit of priority of U.S. Patent Application Ser. No. 60/535,461 filed on Jan. 10, 2004 and claims benefit of priority of U.S. Patent Application Ser. No. 60/585,822 filed on Jul. 6, 2004; U.S. patent application Ser. No. 11/175,789 is also a continuation-in-part of U.S. patent application Ser. No. 11/153,825 25 filed on Jun. 15, 2005, which is now U.S. Pat. No. 7,723,029. The contents of the above-listed applications are incorporated herein by this reference in their entireties.

TECHNICAL FIELD

The present invention relates, generally to the field of ion transport detection ("patch clamp") systems and methods, more particularly the present invention includes a novel ion channel chip including a high resistance seal for use with automated or high throughput systems and methods.

BACKGROUND

Ion transports are channels, transporters, pore forming proteins, or other entities that are located within cellular membranes and regulate the flow of ions across the membrane. Ion transports participate in diverse processes, such as generating and timing of action potentials, synaptic transmission, secretion of hormones, contraction of muscles etc. Ion transports are popular candidates for drug discovery, and many known drugs exert their effects via modulation of ion transport functions or properties. For example, antiepileptic compounds such as phenytoin and lamotrigine which block voltage dependent sodium ion transports in the brain, anti-hypertension drugs such as nifedipine and diltiazem which block voltage dependent calcium ion transports in smooth muscle cells, and stimulators of insulin release such as glibenclamide and tolbutamine which block an ATP regulated potassium ion transport in the pancreas.

One popular method of measuring an ion transport function or property is the patch-clamp method, which was first reported by Neher, Sakmann and Steinback (Pflueger Arch. 375:219-278 (1978)). This first report of the patch clamp method relied on pressing a glass pipette containing acetylcholine (Ach) against the surface of a muscle cell membrane, where discrete jumps in electrical current were attributable to the opening and closing of Ach-activated ion transports.

The method was refined by fire polishing the glass pipettes and applying gentle suction to the interior of the pipette when contact was made with the surface of the cell. Seals of very high resistance (between about 1 and about 100 giga ohms) could be obtained. This advancement allowed the patch clamp method to be suitable over voltage ranges which ion transport studies can routinely be made.

A variety of patch clamp methods have been developed, such as whole cell, vesicle, outside-out and inside-out patches (Liem et al., Neurosurgery 36:382-392 (1995)). Additional methods include whole cell patch clamp recordings, pressure patch clamp methods, cell free ion transport recording, perfusion patch pipettes, concentration patch clamp methods, perforated patch clamp methods, loose patch voltage clamp methods, patch clamp recording and patch clamp methods in tissue samples such as muscle or brain (Boulton et al, Patch-Clamp Applications and Protocols, Neuromethods V. 26 (1995), Humana Press, New Jersey).

These and later methods relied upon interrogating one sample at a time using large laboratory apparatus that require a high degree of operator skill and time. Attempts have been made to automate patch clamp methods, but these have met with little success. Alternatives to patch clamp methods have been developed using fluorescent probes, such as cumarin-lipids (cu-lipids) and oxonol fluorescent dyes (Tsien et al., U.S. Pat. No. 6,107,066, issued August 2000). These methods rely upon change in polarity of membranes and the resulting motion of oxonol molecules across the membrane. This motion allows for the detection of changes in fluorescence resonance energy transfer (FRET) between cu-lipids and oxonol molecules. Unfortunately, these methods do not measure ion transport directly but measure the change of indirect parameters as a result of ionic flux. For example, the characteristics of the lipid used in the cu-lipid can alter the biological and physical characteristics of the membrane, such as fluidity and polarizability.

Thus, what is needed is a simple device and method to measure ion transport directly. Preferably, these devices would utilize patch clamp detection methods because these types of methods represent a gold standard in this field of study. The present invention provides these devices and methods particularly miniaturized devices and automated methods for the screening of chemicals or other moieties for their ability to modulate ion transport functions or properties.

BRIEF SUMMARY OF THE INVENTION

The present invention recognizes that the determination of one or more ion transport functions or properties using direct detection methods, such as patch-clamp, whole cell recording, or single channel recording, are preferable to methods that utilize indirect detection methods, such as fluorescence-based detection systems.

The present invention provides biochips for ion transport measurement, ion transport measuring devices that comprise biochips, and methods of using the devices and biochips that allow for the direct analysis of ion transport functions or properties. The present invention provides biochips, devices, apparatuses, and methods that allow for automated detection of ion transport functions or properties. The present invention also provides methods of making biochips and devices for ion transport measurement that reduce the cost and increase the efficiency of manufacture, as well as improve the performance of the biochips and devices. These biochips and devices are particularly appropriate for automating the detection of ion transport functions or properties, particularly for screening purposes.

A first aspect of the present invention is a biochip device for ion transport measurement. A biochip device comprises an upper chamber piece that comprises one or more upper chambers, and a biochip that comprises at least one ion transport measuring means. In one preferred embodiment of this aspect of the present invention, a biochip device also comprises at least one conduit that that can be positioned to engage the one or more upper chambers, where the conduit comprises an electrode or can provide an electrolyte bridge to an electrode.

A second aspect of the present invention is a biochip device having one or more flow-through lower chambers. The device comprises an upper chamber piece that comprises one or more upper chambers, a biochip that comprises at least one ion transport measuring means, and at least one lower chamber base piece that comprises at least two conduits that connect with at least one lower chamber.

A third aspect of the invention is biochip devices that are adapted for microscope stages. The devices comprise an upper chamber piece that comprises one or more upper chambers, a biochip that comprises at least one ion transport measuring means, and at least one lower chamber base piece, in which the bottom surface of the lower chamber base piece is transparent. Preferably, the device also includes a base-plate adapted to a microscope stage into which a lower chamber base piece can fit.

A fourth aspect of the invention is methods of making an upper chamber piece for a biochip device for ion transport measurement. In one preferred embodiment of this aspect of the present invention, an upper chamber piece can be molded as two pieces, an upper well portion piece and a well hole portion piece. Preferably, a well hole portion piece comprises at least one groove into which at least one electrode can be inserted. After insertion of the electrode, the upper well portion piece and the well hole portion piece are attached to form an upper chamber piece. In another embodiment of this aspect, an upper chamber piece can be molded as a single piece, where an electrode, such as a wire electrode, can be positioned in a mold and then the upper chamber piece can be molded around it. In yet another preferred embodiment of this aspect, an upper chamber piece can be molded as a single piece without an electrode.

A fifth aspect of the invention is methods for making chips comprising ion transport measuring holes. An ion transport measuring hole can be fabricated by laser drilling one or more counterbores, and then laser drilling a through hole through the one or more counterbores.

A sixth aspect of the invention is ion transport measuring devices that comprise an inverted chip comprising ion transport measuring holes. A chip used in inverted orientation can comprise one or more ion transport measuring holes that are fabricated by laser drilling of one or more counterbores and a through hole through the one or more counterbores.

A seventh aspect of the invention is methods of treating ion transport measuring chips to enhance their sealing properties. In one aspect of the present invention, the chip or substrate comprising an ion transport measuring means is modified to become more electronegative and/or smoother. In another aspect of the present invention, the chip or substrate comprising the ion transport measuring means is modified chemically, such as with acids, bases, or a combination thereof. Treatment of chips of the present invention with chemical solution can be performed using treatment racks that fit into vessels that hold the chemical solutions and can hold multiple glass chips while allowing access of the chemical solutions to the chip surfaces.

An eighth aspect of the invention is a method to measure surface energy on a surface, such as the surface of a chemically-treated ion transport measurement biochip. The surface energy measurement can be used to evaluate the hydrophilicity of a biochip biochip of the present invention that has been chemically treated to improve its electrical sealing properties, such as, for example, at chip that has been treated with base. It can also be used for any surface characterization purpose where a measurement of surface energy or hydrophilicity is desired.

A ninth aspect of the invention is the substrates, biochips, devices, apparatuses, and/or cartridges comprising ion transport measuring means with enhanced electric seal properties. In preferred embodiments, at least a portion of at least one chip that comprises at least one ion transport measuring means has been treated with at least one base, at least one acid, or both.

A tenth aspect of the present invention is a method for storing the substrates, biochips, cartridges, apparatuses, and/or devices comprising ion transport measuring means with enhanced electrical seal properties.

An eleventh aspect of the present invention is a method for shipping the substrates, biochips, cartridges, apparatuses, and/or devices comprising ion transport measuring means with enhanced electrical seal properties.

A twelfth aspect of the invention is methods for assembling devices and cartridges of the present invention. The methods include attaching an upper chamber piece to a biochip that comprises at least one ion transport measuring means using a UV adhesive. Preferably, the chip has been chemically treated to enhance its electrical sealing properties. During UV activation of the adhesive, at least a portion of the biochip is masked to prevent UV irradiation of ion transport measuring means on the chip.

A thirteenth aspect of the present invention is a method of producing biochips comprising ion transport measuring means by fabricating the biochips as detachable units of a large sheet. Ion transport measuring holes can be made by wet etching and laser drilling appropriate substrates, and the sheet can be scored with a laser such that portions of the sheet having a desired number of ion transport measuring holes can be separated along the score lines. In some embodiments, upper chamber pieces are attached to the substrate sheet after the fabrication of holes and before separation of sections of the sheet. In this case, the detachable units that are separated to produce devices comprise cartridges having upper chambers attached to an ion transport measuring chip.

A fourteenth aspect of the invention is a method of producing high density ion transport measuring chips. The ion transport measuring chips preferably have more than 16 ion transport measuring holes, and wells can be fabricated in a chip using wet etching, followed by laser drilling of ion transport measuring holes through the bottoms of the wells.

A fifteenth aspect of the invention is a biochip device for ion transport measurement comprising fluidic channel upper and lower chambers. The fluidic channels have apertures that are aligned with ion transport measuring holes on the chip.

The fluidic channels can be connected to sources for generating or promoting fluid flow, such as pumps, pressure sources, and valves. The fluidic channels preferably provide electrolyte bridge to one or more electrodes that can be used in ion transport measurement.

A sixteenth aspect of the present invention is methods of preparing cells for ion transport measurement. The methods include the use of filters that can allow the passage of single cells through their pores and monitoring of cell health parameters important for electrophysiological measurements.

A seventeenth aspect of the present invention is a logic and program that uses a pressure profile to direct an ion transport measurement apparatus to achieve and maintain a high-resistance electrical seal. The logic can follow decision pathways based on information from electrical measurements made by ion transport measuring electrodes in a feedback system.

An eighteenth aspect of the present invention is an ion channel chip having a plastic substrate or surface that is chemically modified and methods of use. Chemical modification may provide enhanced sealing properties. Modification of the plastic substrate or surface may occur by treatment with an ionized gas, by interaction with laser or other high energy radiation, by chemical reaction, or by any combination of these.

A nineteenth aspect of the present invention is an ion channel chip or biochip utilizing a lipid layer or lipid bilayer for enhancing the sealing properties. The lipid bilayer is capable of interacting with the membrane of a cell having to facilitate measurement of a cell's ion channel.

A twentieth aspect of the present invention is a method of making a pre-assembled ion transport measurement cartridge and method of use. A chip without a hole or aperture may be provided in the cartridge. The cartridge may be oriented such that a drill may form an aperture through the chip. The cartridge may then be treated for surface modification to promote the formation of tight seals for ion transport measurement.

A twenty-first aspect of the present invention is a method of layering a plastic chip with a thin sheet of glass and method of use. Holes or apertures may be drilled through the layered chip using a laser drill or wet etching.

A twenty-second aspect of the present invention is a method of protecting fragile devices and parts by packing and shipping the devices or parts in a fluid such as water.

A twenty-third aspect of the present invention is a method of laser beam splitting and method of use to laser drill holes in ion channel chips and methods of use. The method may utilize a homogenizer to obtain a "top hat" power profile from a laser beam source. The laser beam may optionally be masked to provide additional profiles. The laser beam may then be split to form two or more laser beamlets.

A twenty-fourth aspect of the present invention is a method of making glass more readily wet etched, ion channel chips made using this method and methods of use thereof. The method may include exposing the glass to a laser beam in the ultra-violet (UV) range.

A twenty-fifth aspect of the present invention are methods for bonding glass to glass and products produced by these methods. The methods may include treating one or more surfaces of the glass with an acid or base, contacting the glass surfaces together and heating the glass. Alternatively, NaSiO4 may be applied between the glass surfaces and heated.

A twenty-sixth aspect of the present invention is an in situ method of making a cartridge for use in ion transport measurement and methods of use. The cartridge may include a chip with gaskets defining top and bottom chamber perimeters.

A twenty-seventh aspect of the present invention is a gasket for use ion transport measurement and methods of use thereof. The gasket may engage the chip and define a boundary of a chamber.

A twenty-eighth aspect of the present invention is a system for automated processing of chips for use in ion transport measurement. The method may include exposing the chip to a treatment solution and exposing the chip to a negative or positive pressure.

A twenty-ninth aspect of the present invention is a method for making a silicon-based chip with laser—drilled holes and surface modifications. The method may include providing a silicon based chip, drilling holes in the chip and treating the chip to form surface modifications.

A thirtieth aspect of the present invention is a device that can hold chips for methods of treating chips and/or for storage of chips. The device may include a bottom structure having chip holding structures, and a hinged top structure.

BRIEF DESCRIPTION OF THE DRAWINGS

FIG. 24 depicts success duration (min.) and accumulative success rate in relation to chip number.

FIG. 25 depicts a histogram of parameters achievable with pressure control protocol.

FIGS. 27 (A)-(B) and FIG. 28 depict the recordings from a typical experiment.

FIGS. 31 (A)-(C) depict an exemplary patch clamp on inverted chip. FIG. 31(A) is averaged from multiple experiments.

FIG. 33 depicts an embodiment of a plastic injection molded carrier or cartridge for the purpose of holding the chip, offering two additional views of the same embodiment shown in cross section in FIG. 29, but illustrating an example where the measurement device is replicated 16 times across a single device offering 16 recording and testing locations.

FIG. 46 depicts one embodiment of an ion transport measuring device having a single flow-through upper chamber and a multiple lower chambers. A) cross sectional view. B) top view.

FIG. 47 depicts one embodiment of a single use chip of the present invention. A) top view. B) cross sectional view.

FIG. 48 depicts one embodiment of a chip of the present invention in which wax forms the upper chambers. A) top view. B) cross sectional view.

FIG. 49 depicts one embodiment of a chip of the present invention in which O-rings form the upper chambers. A) top view. B) cross sectional view.

FIG. 50 depicts a schematic of a (A)16×24 hole array at a pitch of 4.5 mm for an ion channel chip design and (B) a 16×1 hole array at a pitch of 4.5 mm for an ion channel chip design.

DETAILED DESCRIPTION OF THE INVENTION

Definitions

Figure 1A:
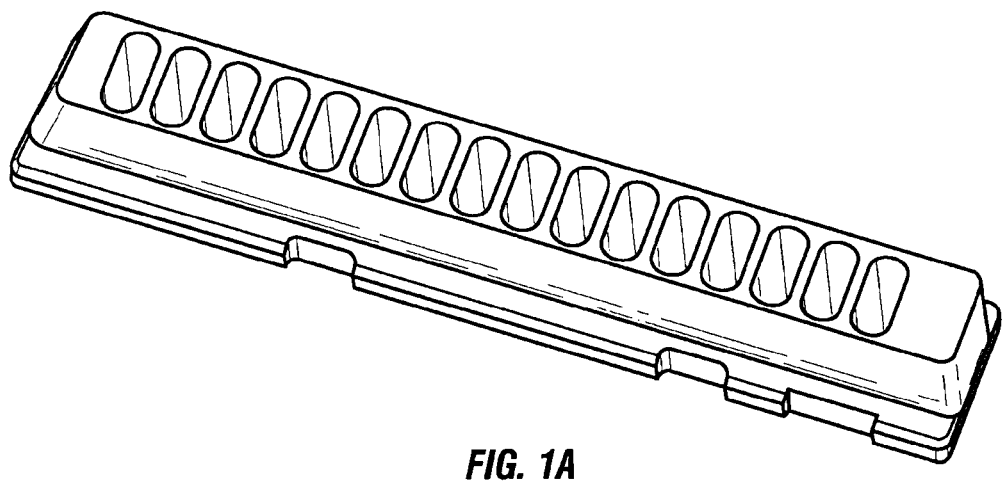
FIG. 1 depicts views an upper chamber piece of the present invention comprising glue spillage grooves and alignment bump.
Figure 1B:
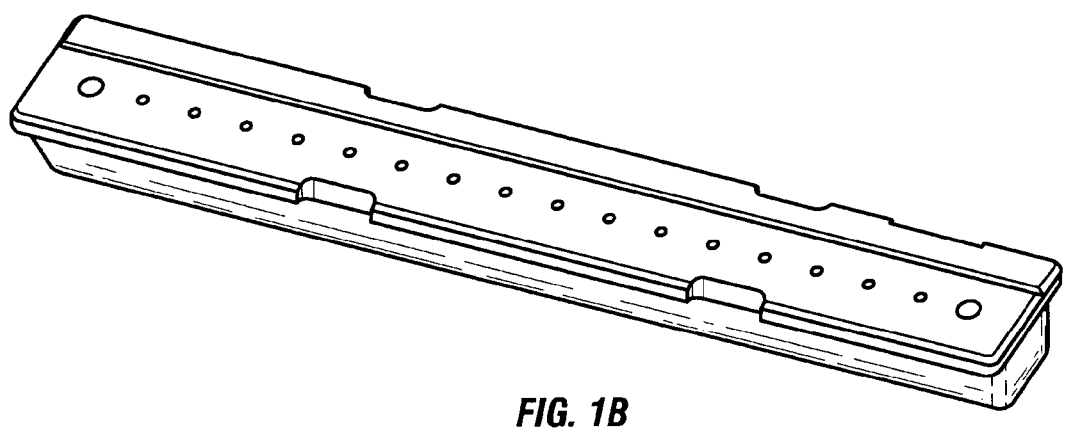

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Terms of orientation such as "up" and "down", "top" and "bottom", "upper" or "lower" and the like refer to orientation of parts during use of a device. Where a term is provided in the singular, the inventors also contemplate the plural of that term. Where there are discrepancies in terms and definitions used in references that are incorporated by reference, the terms used in this application shall have the definitions given herein. As employed throughout the disclosure, the following terms, unless otherwise indicated, shall be understood to have the following meanings:

"Ion transport measurement" is the process of detecting and measuring the movement of charge and/or conducting ions across a membrane (such as a biological membrane), or from the inside to the outside of a particle or vice versa. In most applications, particles will be cells, organelles, vesicles, biological membrane fragments, artificial membranes, bilayers or micelles. In general, ion transport measurement involves achieving a high resistance electrical seal of a membrane or particle with a surface that has an aperture, and positioning electrodes on either side of the membrane or particle to measure the current and/or voltage across the portion of the membrane sealed over the aperture, or "clamping" voltage across the membrane and measuring current applied to an electrode to maintain that voltage. However, ion transport measurement does not require that a particle or membrane be sealed to an aperture if other means can provide electrode contact on both sides of a membrane. For example, a particle can be impaled with a needle electrode and a second electrode can be provided in contact with the solution outside the particle to complete a circuit for ion transport measurement. Several techniques collectively known as "patch clamping" can be included as "ion transport measurement".

An "ion transport measuring means" refers to a structure that can be used to measure at least one ion transport function, property, or a change in ion channel function, property in response to various chemical, biochemical or electrical stimuli. Typically, an ion transport measuring means is a structure with an opening that a particle can seal against, but this need not be the case. For example, needles as well as holes, apertures, capillaries, and other detection structures of the present invention can be used as ion transport measuring means. An ion transport measuring means is preferably positioned on or within a biochip or a chamber. Where an ion transport measuring means refers to a hole or aperture, the use of the terms "ion transport measuring means" "hole" or "aperture" are also meant to encompass the perimeter of the hole or aperture that is in fact a part of the chip or substrate (or coating) surface (or surface of another structure, for example, a channel) and can also include the surfaces that surround the interior space of the hole that is also the chip or substrate (or coating) material or material of another structure that comprises the hole or aperture.

A "hole" is an aperture that extends through a chip. Descriptions of holes found herein are also meant to encompass the perimeter of the hole that is in fact a part of the chip or substrate (or coating) surface, and can also include the surfaces that surround the interior space of the hole that is also the chip or substrate (or coating) material. Thus, in the present invention, where particles are described as being positioned on, at, near, against, or in a hole, or adhering or fixed to a hole, it is intended to mean that a particle contacts the entire perimeter of a hole, such that at least a portion of the surface of the particle lies across the opening of the hole, or in some cases, descends to some degree into the opening of the whole, contacting the surfaces that surround the interior space of the hole.

A "patch clamp detection structure" refers to a structure that is on or within a biochip or a chamber that is capable of measuring at least one ion transport function or property via patch clamp methods.

A "chip" is a solid substrate on which one or more processes such as physical, chemical, biochemical, biological or biophysical processes can be carried out. Such processes can be assays, including biochemical, cellular, and chemical assays; ion transport or ion channel function or activity determinations, separations, including separations mediated by electrical, magnetic, physical, and chemical (including biochemical) forces or interactions; chemical reactions, enzymatic reactions, and binding interactions, including captures. The micro structures or micro-scale structures such as, channels and wells, electrode elements, electromagnetic elements, may be incorporated into or fabricated on the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, for example, from about 1 $mm^2$ to about 0.25 $m^2$. Preferably, the size of the chips is from about 4 $mm^2$ to about 25 $cm^2$ with a characteristic dimension from about 1 mm to about 5 cm. The chip surfaces may be flat, or not flat. The chips with non-flat surfaces may include wells fabricated on the surfaces.

A "biochip" is a chip that is useful for a biochemical, biological or biophysical process. In this regard, a biochip is preferably biocompatible.

A "chamber" is a structure that comprises or engages a chip and that is capable of containing a fluid sample. The chamber may have various dimensions and its volume may vary between 0.001 microliters and 50 milliliters. In devices of the present invention, an "upper chamber" is a chamber that is above a biochip, such as a biochip that comprises one or more ion transport measuring means. In the devices of the present invention, a chip that comprises one or more ion transport measuring means can separate one or more upper chambers from one or more lower chambers. During use of a device, an upper chamber can contain measuring solutions and particles or membranes. An upper chamber can optionally comprise one or more electrodes. In devices of the present invention, a "lower chamber" is a chamber that is below a biochip. During use of a device, a lower chamber can contain measuring solutions and particles or membranes. A lower chamber can optionally comprise one or more electrodes.

A "lower chamber piece" is a part of a device for ion transport measurement that forms at least a portion of one or more lower chambers of the device. A lower chamber portion piece preferably comprises at least a portion of one or more walls of one or more lower chambers, and can optionally comprise at least a portion of a bottom surface of one or more lower chambers, and can optionally comprise one or more conduits that lead to one or more lower chambers, or one or more electrodes.

A "lower chamber base piece" is a part of a device for ion transport measurement that forms the bottom surface of one or more lower chambers of the device. A lower chamber base piece can also optionally comprise one or more walls of one or more lower chambers, one or more conduits that lead to one or more lower chambers, or one or more electrodes.

As used herein, a "platform" is a surface on which a device of the present invention can be positioned. A platform can comprises the bottom surface of one or more lower chambers of a device.

An "upper chamber piece" is a part of a device for ion transport measurement that forms at least a portion of one or more upper chambers of the device. An upper chamber piece can comprise one or more walls of one or more upper chambers, and can optionally comprise one or more conduits that lead to an upper chamber, and one or more electrodes.

An "upper chamber portion piece" is a part of a device for ion transport measurement that forms a portion of one or more upper chambers of the device. An upper chamber portion piece can comprise at least a portion of one or more walls of one or more upper chambers, and can optionally comprise one or more conduits that lead to an upper chamber, or one or more electrodes.

A "well" is a depression in a substrate or other structure. For example, in devices of the present invention, upper chambers can be wells formed in an upper chamber piece. The upper opening of a well can be of any shape and can be of an irregular conformation. The walls of a well can extend upward from the lower surface of a well at any angle or in any way. The walls can be of any shape and can be of an irregular conformation, that is, they may extend upward in a sigmoidal or otherwise curved or multi-angled fashion.

A "well hole" is a hole in the bottom of a well. A well hole can be a well-within-a well, having its own well shape with an opening at the bottom.

A "well hole piece" is a part of a device for ion transport measurement that comprises one or more well holes of the wells of the device.

When wells or chambers (including fluidic channel chambers) are "in register with" ion transport measuring means of a chip, there is a one-to-one correspondence of each of the referenced wells or chambers to each of the referenced ion transport measuring means, and an ion transport measuring means is positioned so that it is exposed to the interior of the well or chamber it is in register with, such that ion transport measurement can be performed using the chamber as a compartment for measuring current or voltage through or across the ion transport measuring means.

A "port" is an opening in a wall or housing of a chamber through which a fluid sample or solution can enter or exit the chamber. A port can be of any dimensions, but preferably is of a shape and size that allows a sample or solution to be dispensed into a chamber by means of a pipette, syringe, or conduit, or other means of dispensing a sample.

A "conduit" is a means for fluid to be transported from one area to another area of a device, apparatus, or system of the present invention or to another structure, such as a dispensation or detection device. In some aspects, a conduit can engage a port in the housing or wall of a chamber. In some aspects, a part of a device, such as, for example, an upper chamber piece or a lower chamber piece can comprise conduits in the form of tunnels that pass through the upper chamber piece and connect, for example, one area or compartment with another area or compartment. A conduit can be drilled or molded into a chip, chamber, housing, or chamber piece, or a conduit can comprise any material that permits the passage of a fluid through it, and can be attached to any part of a device. In one preferred aspect of the present invention, a conduit extends through at least a portion of a device, such as a wall of a chamber, or an upper chamber piece or lower chamber piece, and connects the interior space of a chamber with the outside of a chamber, where it can optionally connect to another conduit, such as tubing. Some preferred conduits can be tubing, such as, for example, rubber, Teflon, or Tygon tubing. A conduit can be of any dimensions, but preferably ranges from 10 microns to 5 millimeters in internal diameter.

A "device for ion transport measurement" or an "ion transport measuring device" is a device that comprises at least one chip that comprises one or more ion transport measuring means, at least a portion of at least one upper chamber, and, preferably, at least a portion of at least one lower chamber. A device for ion transport measurement preferably comprises one or more electrodes, and can optionally comprise conduits, particle positioning means, or application-specific integrated circuits (ASICs).

A "cartridge for ion transport measurement" comprises an upper chamber piece and at least one biochip comprising one or more ion transport measuring means attached to the upper chamber piece, such that the one or more ion transport measuring means are in register with the upper chambers of the upper chamber piece.

An "ion transport measuring unit" is a portion of a device that comprises at least a portion of a chip having an ion transport measuring means and an upper chamber, where the ion transport measuring means connects the upper chamber with a portion of a lower chamber.

A "measuring solution" is an aqueous solution containing electrolytes, with pH, osmolarity, and other physical-chemical traits that are compatible with conducting function of the ion transports to be measured.

An "intracellular solution" is a measuring solution used in the upper or lower chamber that is compatible with the electrolyte composition and physical-chemical traits of the intracellular content of a living cell.

An "extracellular solution" is a measuring solution used in the upper or lower chamber that is compatible with the electrolyte composition and physical-chemical traits of the extracellular content of a living cell.

To be "in electrical contact with" means one component is able to receive and conduct electrical signals (voltage, current, or change of voltage or current) from another component.

An "ion transport" can be any protein or non-protein moiety that modulates, regulates or allows transfer of ions across a membrane, such as a biological membrane or an artificial membrane. Ion transport include but are not limited to ion channels, proteins allowing transport of ions by active transport, proteins allowing transport of ions by passive transport, toxins such as from insects, viral proteins or the like. Viral proteins, such as the M2 protein of influenza virus can form an ion channel on cell surfaces.

A "particle" refers to an organic or inorganic particulate that is suspendable in a solution and can be manipulated by a particle positioning means. A particle can include a cell, such as a prokaryotic or eukaryotic cell, or can be a cell fragment, such as a vesicle or a microsome that can be made using methods known in the art. A particle can also include artificial membrane preparations that can be made using methods known in the art. Preferred artificial membrane preparations are lipid bilayers, but that need not be the case. A particle in the present invention can also be a lipid film, such as a black-lipid film (see, Houslay and Stanley, Dynamics of Biological Membranes, Influence on Synthesis, Structure and Function, John Wiley & Sons, New York (1982)). In the case of a lipid film, a lipid film can be provided over a hole, such as a hole or capillary of the present invention using methods known in the art (see, Houslay and Stanley, Dynamics of Biological Membranes, Influence on Synthesis, Structure and Function, John Wiley & Sons, New York (1982)). A particle preferably includes or is suspected of including at least one ion transport or an ion transport of interest. Particles that do not include an ion transport or an ion transport of interest can be made to include such ion transport using methods known in the art, such as by fusion of particles or insertion of ion transports into such particles such as by detergents, detergent removal, detergent dilution, sonication or detergent catalyzed incorporation (see, Houslay and Stanley, Dynamics of Biological Membranes, Influence on Synthesis, Structure and Function, John Wiley & Sons, New York (1982)). A microparticle, such as a bead, such as a latex bead or magnetic bead, can be attached to a particle, such that the particle can be manipulated by a particle positioning means.

A "cell" refers to a viable or non-viable prokaryotic or eukaryotic cell. A eukaryotic cell can be any eukaryotic cell from any source, such as obtained from a subject, human or non-human, fetal or non-fetal, child or adult, such as from a tissue or fluid, including blood, which are obtainable through appropriate sample collection methods, such as biopsy, blood collection or otherwise. Eukaryotic cells can be provided as is in a sample or can be cell lines that are cultivated in vitro. Differences in cell types also include cellular origin, distinct surface markers, sizes, morphologies and other physical and biological properties.

A "cell fragment" refers to a portion of a cell, such as cell organelles, including but not limited to nuclei, endoplasmic reticulum, mitochondria or Golgi apparatus. Cell fragments can include vesicles, such as inside out or outside out vesicles or mixtures thereof. Preparations that include cell fragments can be made using methods known in the art.

A "population of cells" refers to a sample that includes more than one cell or more than one type of cell. For example, a sample of blood from a subject is a population of white cells and red cells. A population of cells can also include a sample including a plurality of substantially homogeneous cells, such as obtained through cell culture methods for a continuous cell lines.

A "population of cell fragments" refers to a sample that includes more than one cell fragment or more than one type of cell fragments. For example, a population of cell fragments can include mitochondria, nuclei, microsomes and portions of Golgi apparatus that can be formed upon cell lysis.

A "microparticle" is a structure of any shape and of any composition that is manipulatable by desired physical force(s). The microparticles used in the methods could have a dimension from about 0.01 micron to about ten centimeters. Preferably, the microparticles used in the methods have a dimension from about 0.1 micron to about several hundred microns. Such particles or microparticles can be comprised of any suitable material, such as glass or ceramics, and/or one or more polymers, such as, for example, nylon, polytetrafluoroethylene (Teflon™), polystyrene, polyacrylamide, sepaharose, agarose, cellulose, cellulose derivatives, or dextran, and/or can comprise metals. Examples of microparticles include, but are not limited to, plastic particles, ceramic particles, carbon particles, polystyrene microbeads, glass beads, magnetic beads, hollow glass spheres, metal particles, particles of complex compositions, microfabricated free-standing microstructures, etc. The examples of microfabricated free-standing microstructures may include those described in "Design of asynchronous dielectric micromotors" by Hagedorn et al., in Journal of Electrostatics, Volume: 33, Pages 159-185 (1994). Particles of complex compositions refer to the particles that comprise or consists of multiple compositional elements, for example, a metallic sphere covered with a thin layer of non-conducting polymer film.

"A preparation of microparticles" is a composition that comprises microparticles of one or more types and can optionally include at least one other compound, molecule, structure, solution, reagent, particle, or chemical entity. For example, a preparation of microparticles can be a suspension of microparticles in a buffer, and can optionally include specific binding members, ligands, enzymes, inert particles, surfactants, ligands, detergents, etc.

"Coupled" means bound. For example, a moiety can be coupled to a microparticle by specific or nonspecific binding. As disclosed herein, the binding can be covalent or noncovalent, reversible or irreversible.

"Micro-scale structures" are structures integral to or attached on a chip, wafer, or chamber that have characteristic dimensions of scale for use in microfluidic applications ranging from about 0.1 micron to about 20 mm. Example of micro-scale structures that can be on chips of the present invention are wells, channels, scaffolds, electrodes, electromagnetic units, or microfabricated pumps or valves.

A "particle positioning means" refers to a means that is capable of manipulating the position of a particle relative to the X-Y coordinates or X-Y-Z coordinates of a biochip. Positions in the X-Y coordinates are in a plane. The Z coordinate is perpendicular to the plane. In one aspect of the present invention, the X-Y coordinates are substantially perpendicular to gravity and the Z coordinate is substantially parallel to gravity. This need not be the case, however, particularly if the biochip need not be level for operation or if a gravity free or gravity reduced environment is present. Several particle positioning means are disclosed herein, such as but not limited to dielectric structures, dielectric focusing structures, quadrupole electrode structures, electrorotation structures, traveling wave dielectrophoresis structures, concentric electrode structures, spiral electrode structures, circular electrode structures, square electrode structures, particle switch structures, electromagnetic structures, DC electric field induced fluid motion structure, acoustic structures, negative pressure structures and the like.

A "dielectric focusing structure" refers to a structure that is on or within a biochip or a chamber that is capable of modulating the position of a particle in the X-Y or X-Y-Z coordinates of a biochip using dielectric forces or dielectrophoretic forces.

A "horizontal positioning means" refers to a particle positioning means that can position a particle in the X-Y coordinates of a biochip or chamber wherein the Z coordinate is substantially defined by gravity.

A "vertical positioning means" refers to a particle positioning means that can position a particle in the Z coordinate of a biochip or chamber wherein the Z coordinate is substantially defined by gravity.

A "quadrupole electrode structure" refers to a structure that includes four electrodes arranged around a locus such as a hole, capillary or needle on a biochip and is on or within a biochip or a chamber that is capable of modulating the position of a particle in the X-Y or X-Y-Z coordinates of a biochip using dielectrophoretic forces or dielectric forces generated by such quadrupole electrode structures.

An "electrorotation structure" refers to a structure that is on or within a biochip or a chamber that is capable of producing a rotating electric field in the X-Y or X-Y-Z coordinates that can rotate a particle. Preferred electrorotation structures include a plurality of electrodes that are energized using phase offsets, such as 360/N degrees, where N represents the number of electrodes in the electroroation structure (see generally U.S. patent application Ser. No. 09/643,362 entitled "Apparatus and Method for High Throughput Electrorotation Analysis" filed Aug. 22, 2000, naming Jing Cheng et al. as inventors). A rotating electrode structure can also produce dielectrophoretic forces for positioning particles to certain locations under appropriate electric signal or excitation. For example, when N=4 and electrorotation structure corresponds to a quadrupole electrode structure.

A "traveling wave dielectrophoresis structure" refers to a structure that is on or within a biochip or a chamber that is capable of modulating the position of a particle in the X-Y or X-Y-Z coordinates of a biochip using traveling wave dielectrophoretic forces (see generally U.S. patent application Ser. No. 09/686,737 filed Oct. 10, 2000, to Xu, Wang, Cheng, Yang and Wu; and U.S. application Ser. No. 09/678,263, entitled "Apparatus for Switching and Manipulating Particles and Methods of Use Thereof" filed on Oct. 3, 2000 and naming as inventors Xiaobo Wang, Weiping Yang, Junquan Xu, Jing Cheng, and Lei Wu).

A "concentric circular electrode structure" refers to a structure having multiple concentric circular electrodes that are on or within a biochip or a chamber that is capable of modulating the position of a particle in the X-Y or X-Y-Z coordinates of a biochip using dielectrophoretic forces.

A "spiral electrode structure" refers to a structure having multiple parallel spiral electrode elements that is on or within a biochip or a chamber that is capable of modulating the position of a particle in the X-Y or X-Y-Z coordinates of a biochip using dielectric forces.

A "square spiral electrode structure" refers to a structure having multiple parallel square spiral electrode elements that are on or within a biochip or a chamber that is capable of modulating the position of a particle in the X-Y or X-Y-Z coordinates of a biochip using dielectrophoretic or traveling wave dielectrophoretic forces.

A "particle switch structure" refers to a structure that is on or within a biochip or a chamber that is capable of transporting particles and switching the motion direction of a particle or particles in the X-Y or X-Y-Z coordinates of a biochip. The particle switch structure can modulate the direction that a particle takes based on the physical properties of the particle or at the will of a programmer or operator (see, generally U.S. application Ser. No. 09/678,263, entitled "Apparatus for Switching and Manipulating Particles and Methods of Use Thereof" filed on Oct. 3, 2000 and naming as inventors Xiaobo Wang, Weiping Yang, Junquan Xu, Jing Cheng, and Lei Wu.

An "electromagnetic structure" refers to a structure that is on or within a biochip or a chamber that is capable of modulating the position of a particle in the X-Y or X-Y-Z coordinates of a biochip using electromagnetic forces. See generally U.S. patent application Ser. No. 09/685,410 filed Oct. 10, 2000, to Wu, Wang, Cheng, Yang, Zhou, Liu and Xu and WO 00/54882 published Sep. 21, 2000 to Zhou, Liu, Chen, Chen, Wang, Liu, Tan and Xu.

A "DC electric field induced fluid motion structure" refers to a structure that is on or within a biochip or a chamber that is capable of modulating the position of a particle in the X-Y or X-Y-Z coordinates of a biochip using DC electric field that produces a fluidic motion.

An "electroosomosis structure" refers to a structure that is on or within a biochip or a chamber that is capable of modulating the position of a particle in the X-Y or X-Y-Z coordinates of a biochip using electroosmotic forces. Preferably, an electroosmosis structure can modulate the positioning of a particle such as a cell or fragment thereof with an ion transport measuring means such that the particle's seal (or the particle's sealing resistance) with such ion transport measuring means is increased.

An "acoustic structure" refers to a structure that is on or within a biochip or a chamber that is capable of modulating the position of a particle in the X-Y or X-Y-Z coordinates of a biochip using acoustic forces. In one aspect of the present invention, the acoustic forces are transmitted directly or indirectly through an aqueous solution to modulate the positioning of a particle. Preferably, an acoustic structure can modulate the positioning of a particle such as a cell or fragment thereof with an ion transport measuring means such that the particle's seal with such ion transport measuring means is increased.

A "negative pressure structure" refers to a structure that is on or within a biochip or a chamber that is capable of modulating the position of a particle in the X-Y or X-Y-Z coordinates of a biochip using negative pressure forces, such as those generated through the use of pumps or the like. Preferably, a negative pressure structure can modulate the positioning of a particle such as a cell or fragment thereof with an ion transport measuring means such that the particle's seal with such ion transport measuring means is increased.

"Dielectrophoresis" is the movement of polarized particles in electrical fields of nonuniform strength. There are generally two types of dielectrophoresis, positive dielectrophoresis and negative dielectrophoresis. In positive dielectrophoresis, particles are moved by dielectrophoretic forces toward the strong field regions. In negative dielectrophoresis, particles are moved by dielectrophoretic forces toward weak field regions. Whether moieties exhibit positive or negative dielectrophoresis depends on whether particles are more or less polarizable than the surrounding medium.

A "dielectrophoretic force" is the force that acts on a polarizable particle in an AC electrical field of non-uniform strength. The dielectrophoretic force $\vec{F}_{DEP}$ acting on a particle of radius r subjected to a non-uniform electrical field can be given, under the dipole approximation, by:

$$\vec{F}_{DEP} = 2\pi \epsilon_m r^3 \chi_{DEP} \nabla E_{rms}^2$$

where $E_{rms}$ is the RMS value of the field strength, the symbol $\nabla$ is the symbol for gradient-operation, $\epsilon_m$ is the dielectric permittivity of the medium, and $\chi_{DEP}$ is the particle polarization factor, given by:

$$\chi_{DEP} = \text{Re}\left(\frac{\epsilon_p^* - \epsilon_m^*}{\epsilon_p^* + 2\epsilon_m^*}\right),$$

"Re" refers to the real part of the "complex number". The symbol $\epsilon_x^* = \epsilon_x - j\sigma_x/2\pi f$ is the complex permittivity (of the particle x=p, and the medium x=m) and $j=\sqrt{-1}$. The parameters $\epsilon_p$ and $\sigma_p$ are the effective permittivity and conductivity of the particle, respectively. These parameters may be frequency dependent. For example, a typical biological cell will have frequency dependent, effective conductivity and permittivity, at least, because of cytoplasm membrane polarization. Particles such as biological cells having different dielectric properties (as defined by permittivity and conductivity) will experience different dielectrophoretic forces. The dielectrophoretic force in the above equation refers to the simple dipole approximation results. However, the dielectrophoretic force utilized in this application generally refers to the force generated by non-uniform electric fields and is not limited by the dipole simplification. The above equation for the dielectrophoretic force can also be written as $$\vec{F}_{DEP} = 2\pi \epsilon_m r^3 \chi_{DEP} V^2 \nabla p(x,y,z)$$

where p(x,y,z) is the square-field distribution for a unit-voltage excitation (Voltage V=1 V) on the electrodes, V is the applied voltage.

"Traveling-wave dielectrophoretic (TW-DEP) force" refers to the force that is generated on particles or molecules due to a traveling-wave electric field. An ideal traveling-wave field is characterized by the distribution of the phase values of AC electric field components, being a linear function of the position of the particle. In this case the traveling wave dielectrophoretic force $\vec{F}_{TW-DEP}$ on a particle of radius r subjected to a traveling wave electrical field $E=E \cos(2\pi(ft-z/\lambda_0))\vec{a}_x$ (i.e., a x-direction field is traveling along the z-direction) is given, again; under the dipole approximation, by $$\vec{F}_{TW-DEP} = -\frac{4\pi^2 \epsilon_m}{\lambda_0} r^3 \zeta_{TW-DEP} E^2 \cdot \vec{a}_z$$

where E is the magnitude of the field strength, $\epsilon_m$ is the dielectric permittivity of the medium. $\zeta$TW-DEP is the particle polarization factor, given by $$\zeta_{TW-DEP} = \text{Im}\left(\frac{\epsilon_p^* - \epsilon_m^*}{\epsilon_p^* + 2\epsilon_m^*}\right),$$

"Im" refers to the imaginary part of the "complex number". The symbol $\epsilon x^* = \epsilon x - j\sigma x/2\pi f$ is the complex permittivity (of the particle x=p, and the medium x=m). The parameters $\epsilon_p$ and $\sigma_p$ are the effective permittivity and conductivity of the particle, respectively. These parameters may be frequency dependent.

A traveling wave electric field can be established by applying appropriate AC signals to the microelectrodes appropriately arranged on a chip. For generating a traveling-wave-electric field, it is necessary to apply at least three types of electrical signals each having a different phase value. An example to produce a traveling wave electric field is to use four phase-quadrature signals (0, 90, 180 and 270 degrees) to energize four linear, parallel electrodes patterned on the chip surfaces. Such four electrodes may be used to form a basic, repeating unit. Depending on the applications, there may be more than two such units that are located next to each other. This will produce a traveling-electric field in the spaces above or near the electrodes. As long as electrode elements are arranged following certain spatially sequential orders, applying phase-sequenced signals will result in establishing traveling electrical fields in the region close to the electrodes.

"Electric field pattern" refers to the field distribution in space or in a region of interest. An electric field pattern is determined by many parameters, including the frequency of the field, the magnitude of the field, the magnitude distribution of the field, and the distribution of the phase values of the field components, the geometry of the electrode structures that produce the electric field, and the frequency and/or magnitude modulation of the field.

"Dielectric properties" of a particle are properties that determine, at least in part, the response of a particle to an electric field. The dielectric properties of a particle include the effective electric conductivity of a particle and the effective electric permittivity of a particle. For a particle of homogeneous composition, for example, a polystyrene bead, the effective conductivity and effective permittivity are independent of the frequency of the electric field at least for a wide frequency range (e.g. between 1 Hz to 100 MHz). Particles that have a homogeneous bulk composition may have net surface charges. When such charged particles are suspended in a medium, electrical double layers may form at the particle/ medium interfaces. Externally applied electric field may interact with the electrical double layers, causing changes in the effective conductivity and effective permittivity of the particles. The interactions between the applied field and the electrical double layers are generally frequency dependent. Thus, the effective conductivity and effective permittivity of such particles may be frequency dependent. For moieties of nonhomogeneous composition, for example, a cell, the effective conductivity and effective permittivity are values that take into account the effective conductivities and effective permittivities of both the membrane and internal portion of the cell, and can vary with the frequency of the electric field. In addition, the dielectrophoretic force experience by a particle in an electric field is dependent on its size; therefore, the overall size of particle is herein considered to be a dielectric property of a particle. Properties of a particle that contribute to its dielectric properties include but are not limited to the net charge on a particle; the composition of a particle (including the distribution of chemical groups or moieties on, within, or throughout a particle); size of a particle; surface configuration of a particle; surface charge of a particle; and the conformation of a particle. Particles can be of any appropriate shape, such as geometric or non-geometric shapes. For example, particles can be spheres, non-spherical, rough, smooth, have sharp edges, be square, oblong or the like.

"Magnetic forces" refer to the forces acting on a particle due to the application of a magnetic field. In general, particles have to be magnetic or paramagnetic when sufficient magnetic forces are needed to manipulate particles. For a typical magnetic particle made of super-paramagnetic material, when the particle is subjected to a magnetic field $\vec{B}$, a magnetic dipole $\vec{\mu}$ is induced in the particle $$\vec{\mu} = V_p(\chi_p - \chi_m)\frac{\vec{B}}{\mu_m},$$
$$= V_p(\chi_p - \chi_m)\vec{H}_m$$

where $V_p$ is the particle volume, $\chi_p$ and $\chi_m$ are the volume susceptibility of the particle and its surrounding medium, $\mu_m$ is the magnetic permeability of medium, $\vec{H}_m$ is the magnetic field strength. The magnetic force $\vec{F}_{magnetic}$ acting on the particle is determined, under the dipole approximation, by the magnetic dipole moment and the magnetic field gradient:

$$\vec{F}_{magnetic} = -0.5 V_p(\chi_p - \chi_m)\vec{H}_m \bullet \nabla \vec{B}_m,$$

where the symbols "$\bullet$" and "$\nabla$" refer to dot-product and gradient operations, respectively. Whether there is magnetic force acting on a particle depends on the difference in the volume susceptibility between the particle and its surrounding medium. Typically, particles are suspended in a liquid, non-magnetic medium (the volume susceptibility is close to zero) thus it is necessary to utilize magnetic particles (its volume susceptibility is much larger than zero). The particle velocity $v_{particle}$ under the balance between magnetic force and viscous drag is given by:

$$v_{particle} = \frac{\vec{F}_{magnetic}}{6\pi r \eta_m}$$

where r is the particle radius and $\eta_m$ is the viscosity of the surrounding medium.

As used herein, "manipulation" refers to moving or processing of the particles, which results in one-, two- or three-dimensional movement of the particle, in a chip format, whether within a single chip or between or among multiple chips. Non-limiting examples of the manipulations include transportation, focusing, enrichment, concentration, aggregation, trapping, repulsion, levitation, separation, isolation or linear or other directed motion of the particles. For effective manipulation, the binding partner and the physical force used in the method should be compatible. For example, binding partner such as microparticles that can be bound with particles, having magnetic properties are preferably used with magnetic force. Similarly, binding partners having certain dielectric properties, for example, plastic particles, polystyrene microbeads, are preferably used with dielectrophoretic force.

A "sample" is any sample from which particles are to be separated or analyzed. A sample can be from any source, such as an organism, group of organisms from the same or different species, from the environment, such as from a body of water or from the soil, or from a food source or an industrial source. A sample can be an unprocessed or a processed sample. A sample can be a gas, a liquid, or a semi-solid, and can be a solution or a suspension. A sample can be an extract, for example a liquid extract of a soil or food sample, an extract of a throat or genital swab, or an extract of a fecal sample. Samples are can include cells or a population of cells. The population of cells can be a mixture of different cells or a population of the same cell or cell type, such as a clonal population of cells. Cells can be derived from a biological sample from a subject, such as a fluid, tissue or organ sample. In the case of tissues or organs, cells in tissues or organs can be isolated or separated from the structure of the tissue or organ using known methods, such as teasing, rinsing, washing, passing through a grating and treatment with proteases. Samples of any tissue or organ can be used, including mesodermally derived, endodermally derived or ectodermally derived cells. Particularly preferred types of cells are from the heart and blood. Cells include but are not limited to suspensions of cells, cultured cell lines, recombinant cells, infected cells, eukaryotic cells, prokaryotic cells, infected with a virus, having a phenotype inherited or acquired, cells having a pathological status including a specific pathological status or complexed with biological or non-biological entities.

"Separation" is a process in which one or more components of a sample is spatially separated from one or more other components of a sample or a process to spatially redistribute particles within a sample such as a mixture of particles, such as a mixture of cells. A separation can be performed such that one or more particles is translocated to one or more areas of a separation apparatus and at least some of the remaining components are translocated away from the area or areas where the one or more particles are translocated to and/or retained in, or in which one or more particles is retained in one or more areas and at least some or the remaining components are removed from the area or areas. Alternatively, one or more components of a sample can be translocated to and/or retained in one or more areas and one or more particles can be removed from the area or areas. It is also possible to cause one or more particles to be translocated to one or more areas and one or more moieties of interest or one or more components of a sample to be translocated to one or more other areas. Separations can be achieved through the use of physical, chemical, electrical, or magnetic forces. Examples of forces that can be used in separations include but are not limited to gravity, mass flow, dielectrophoretic forces, traveling-wave dielectrophoretic forces, and electromagnetic forces.

"Capture" is a type of separation in which one or more particles is retained in one or more areas of a chip. In the methods of the present application, a capture can be performed when physical forces such as dielectrophoretic forces or electromagnetic forces are acted on the particle and direct the particle to one or more areas of a chip.

An "assay" is a test performed on a sample or a component of a sample. An assay can test for the presence of a component, the amount or concentration of a component, the composition of a component, the activity of a component, the electrical properties of an ion transport protein, etc. Assays that can be performed in conjunction with the compositions and methods of the present invention include, but not limited to, biochemical assays, binding assays, cellular assays, genetic assays, ion transport assay, gene expression assays and protein expression assays.

A "binding assay" is an assay that tests for the presence or the concentration of an entity by detecting binding of the entity to a specific binding member, or an assay that tests the ability of an entity to bind another entity, or tests the binding affinity of one entity for another entity. An entity can be an organic or inorganic molecule, a molecular complex that comprises, organic, inorganic, or a combination of organic and inorganic compounds, an organelle, a virus, or a cell. Binding assays can use detectable labels or signal generating systems that give rise to detectable signals in the presence of the bound entity. Standard binding assays include those that rely on nucleic acid hybridization to detect specific nucleic acid sequences, those that rely on antibody binding to entities, and those that rely on ligands binding to receptors.

A "biochemical assay" is an assay that tests for the composition of or the presence, concentration, or activity of one or more components of a sample.

A "cellular assay" is an assay that tests for or with a cellular process, such as, but not limited to, a metabolic activity, a catabolic activity, an ion transport function or property, an intracellular signaling activity, a receptor-linked signaling activity, a transcriptional activity, a translational activity, or a secretory activity.

An "ion transport assay" is an assay useful for determining ion transport functions or properties and testing for the abilities and properties of chemical entities to alter ion transport functions. Preferred ion transport assays include electrophysiology-based methods which include, but are not limited to patch clamp recording, whole cell recording, perforated patch or whole cell recording, vesicle recording, outside out and inside out recording, single channel recording, artificial membrane channel recording, voltage gated ion transport recording, ligand gated ion transport recording, stretch activated (fluid flow or osmotic) ion transport recording, and recordings on energy requiring ion transporters (such as ATP), non energy requiring transporters, and channels formed by toxins such a scorpion toxins, viruses, and the like. See, generally Neher and Sakman, Scientific American 266: 44-51 (1992); Sakmann and Heher, Ann. Rev. Physiol. 46:455-472 (1984); Cahalan and Neher, Methods in Enzymology 207:3-14 (1992); Levis and Rae, Methods in Enzymology 207:14-66 (1992); Armstrong and Gilly, Methods in Enzymology 207:100-122 (1992); Heinmann and Conti, Methods in Enzymology 207:131-148 (1992); Bean, Methods in Enzymology 207:181-193 (1992); Leim et al., Neurosurgery 36:382-392 (1995); Lester, Ann. Rev. Physiol 53:477-496 (1991); Hamill and McBride, Ann. Rev. Physiol 59:621-631 (1997); Bustamante and Varranda, Brazilian Journal 31:333-354 (1998); Martinez-Pardon and Ferrus, Current Topics in Developmental Biol. 36:303-312 (1998); Herness, Physiology and Behavior 69:17-27 (2000); Aston-Jones and Siggins, www.acnp.org/GA/GN40100005/CH005.html (Feb. 8, 2001); U.S. Pat. No. 6,117,291; U.S. Pat. No. 6,107,066; U.S. Pat. No. 5,840,041 and U.S. Pat. No. 5,661,035; Boulton et al., Patch-Clamp Applications and Protocols, Neuromethods V. 26 (1995), Humana Press, New Jersey; Ashcroft, Ion Channels and Disease, Cannelopathies, Academic Press, San Diego (2000); Sakmann and Neher, Single Channel Recording, second edition, Plenuim Press, New York (1995) and Soria and Cena, Ion Channel Pharmacology, Oxford University Press, New York (1998), each of which is incorporated by reference herein in their entirety.

An "electrical seal" refers to a high-resistance engagement between a particle such as a cell or cell membrane and an ion transport measuring means, such as a hole, capillary or needle of a chip or device of the present invention. Preferred resistance of such an electrical seal is between about 1 mega ohm and about 100 giga ohms, but that need not be the case. Generally, a large resistance results in decreased noise in the recording signals. For specific types of ion channels (with different magnitude of recording current) appropriate electric sealing in terms of mega ohms or giga ohms can be used.

An "acid" includes acid and acidic compounds and solutions that have a pH of less than 7 under conditions of use.

A "base" includes base and basic compounds and solutions that have a pH of greater than 7 under conditions of use.

"More electronegative" means having a higher density of negative charge. In the methods of the present invention, a chip or ion transport measuring means that is more electronegative has a higher density of negative surface charge.

An "electrolyte bridge" is a liquid (such as a solution) or a solid (such as an agar salt bridge) conductive connection with at least one component of the electrolyte bridge being an electrolyte so that the bridge can pass current with no or low resistance.

A "ligand gated ion transport" refers to ion transporters such as ligand gated ion channels, including extracellular ligand gated ion channels and intracellular ligand gated ion channels, whose activity or function is activated or modulated by the binding of a ligand. The activity or function of ligand gated ion transports can be detected by measuring voltage or current in response to ligands or test chemicals. Examples include but are not limited to $GABA_A$, strychnine-sensitive glycine, nicotinic acetylcholine (Ach), ionotropic glutamate (iGlu), and 5-hydroxytryptamine$_3$ (5-HT$_3$) receptors.

A "voltage gated ion transport" refers to ion transporters such as voltage gated ion channels whose activity or function is activated or modulated by voltage. The activity or function of voltage gated ion transports can be detected by measuring voltage or current in response to different commanding currents or voltages respectively. Examples include but are not limited to voltage dependent $Na^+$ channels.

"Perforated" patch clamp refers to the use of perforation agents such as but not limited to nystatin or amphotericin B to form pores or perforations that are preferably ion-conducting, which allows for the measurement of current, including whole cell current.

An "electrode" is a structure of highly electrically conductive material. A highly conductive material is a material with conductivity greater than that of surrounding structures or materials. Suitable highly electrically conductive materials include metals, such as gold, chromium, platinum, aluminum, and the like, and can also include nonmetals, such as carbon, conductive liquids and conductive polymers. An electrode can be any shape, such as rectangular, circular, castellated, etc. Electrodes can also comprise doped semi-conductors, where a semi-conducting material is mixed with small amounts of other "impurity" materials. For example, phosphorous-doped silicon may be used as conductive materials for forming electrodes.

A "channel" is a structure with a lower surface and at least two walls that extend upward from the lower surface of the channel, and in which the length of two opposite walls is greater than the distance between the two opposite walls. A channel therefore allows for flow of a fluid along its internal length. A channel can be covered (a "tunnel") or open.

"Continuous flow" means that fluid is pumped or injected into a chamber of the present invention continuously during the separation process. This allows for components of a sample that are not selectively retained on a chip to be flushed out of the chamber during the separation process.

"Binding partner" refers to any substances that both bind to the moieties with desired affinity or specificity and are manipulatable with the desired physical force(s). Non-limiting examples of the binding partners include cells, cellular organelles, viruses, particles, microparticles or an aggregate or complex thereof, or an aggregate or complex of molecules.

A "specific binding member" is one of two different molecules having an area on the surface or in a cavity that specifically binds to and is thereby defined as complementary with a particular spatial and polar organization of the other molecule. A specific binding member can be a member of an immunological pair such as antigen-antibody, can be biotin-avidin or biotin streptavidin, ligand-receptor, nucleic acid duplexes, IgG-protein A, DNA-DNA, DNA-RNA, RNA-RNA, and the like.

A "nucleic acid molecule" is a polynucleotide. A nucleic acid molecule can be DNA, RNA, or a combination of both. A nucleic acid molecule can also include sugars other than ribose and deoxyribose incorporated into the backbone, and thus can be other than DNA or RNA. A nucleic acid can comprise nucleobases that are naturally occurring or that do not occur in nature, such as xanthine, derivatives of nucleobases, such as 2-aminoadenine, and the like. A nucleic acid molecule of the present invention can have linkages other than phosphodiester linkages. A nucleic acid molecule of the present invention can be a peptide nucleic acid molecule, in which nucleobases are linked to a peptide backbone. A nucleic acid molecule can be of any length, and can be single-stranded, double-stranded, or triple-stranded, or any combination thereof. The above described nucleic acid molecules can be made by a biological process or chemical synthesis or a combination thereof.

A "detectable label" is a compound or molecule that can be detected, or that can generate readout, such as fluorescence, radioactivity, color, chemiluminescence or other readouts known in the art or later developed. Such labels can be, but are not limited to, photometric, colorimetric, radioactive or morphological such as changes of cell morphology that are detectable, such as by optical methods. The readouts can be based on fluorescence, such as by fluorescent labels, such as but not limited to, Cy-3, Cy-5, phycoerythrin, phycocyanin, allophycocyanin, FITC, rhodamine, or lanthanides; and by fluorescent proteins such as, but not limited to, green fluorescent protein (GFP). The readout can be based on enzymatic activity, such as, but not limited to, the activity of beta-galactosidase, beta-lactamase, horseradish peroxidase, alkaline phosphatase, or luciferase. The readout can be based on radioisotopes (such as $^{33}P$, $^{3}H$, $^{14}C$, $^{35}S$, $^{125}I$, $^{32}P$ or $^{131}I$). A label optionally can be a base with modified mass, such as, for example, pyrimidines modified at the C5 position or purines modified at the N7 position. Mass modifying groups can be, for examples, halogen, ether or polyether, alkyl, ester or polyester, or of the general type XR, wherein X is a linking group and R is a mass-modifying group. One of skill in the art will recognize that there are numerous possibilities for mass-modifications useful in modifying nucleic acid molecules and oligonucleotides, including those described in Oligonucleotides and Analogues: A Practical Approach, Eckstein, ed. (1991) and in PCT/US94/00193.

A "signal producing system" may have one or more components, at least one component usually being a labeled binding member. The signal producing system includes all of the reagents required to produce or enhance a measurable signal including signal producing means capable of interacting with a label to produce a signal. The signal producing system provides a signal detectable by external means, often by measurement of a change in the wavelength of light absorption or emission. A signal producing system can include a chromophoric substrate and enzyme, where chromophoric substrates are enzymatically converted to dyes which absorb light in the ultraviolet or visible region, phosphors or fluorophores. However, a signal producing system can also provide a detectable signal that can be based on radioactivity or other detectable signals.

The signal producing system can include at least one catalyst, usually at least one enzyme, and can include at least one substrate, and may include two or more catalysts and a plurality of substrates, and may include a combination of enzymes, where the substrate of one enzyme is the product of the other enzyme. The operation of the signal producing system is to produce a product that provides a detectable signal at the predetermined site, related to the presence of label at the predetermined site.

In order to have a detectable signal, it may be desirable to provide means for amplifying the signal produced by the presence of the label at the predetermined site. Therefore, it will usually be preferable for the label to be a catalyst or luminescent compound or radioisotope, most preferably a catalyst. Preferably, catalysts are enzymes and coenzymes that can produce a multiplicity of signal generating molecules from a single label. An enzyme or coenzyme can be employed which provides the desired amplification by producing a product, which absorbs light, for example, a dye, or emits light upon irradiation, for example, a fluorophore. Alternatively, the catalytic reaction can lead to direct light emission, for example, chemiluminescence. A large number of enzymes and coenzymes for providing such products are indicated in U.S. Pat. No. 4,275,149 and U.S. Pat. No. 4,318,980, which disclosures are incorporated herein by reference. A wide variety of non-enzymatic catalysts that may be employed are found in U.S. Pat. No. 4,160,645, issued Jul. 10, 1979, the appropriate portions of which are incorporated herein by reference.

The product of the enzyme reaction will usually be a dye or fluorophore. A large number of illustrative fluorophores are indicated in U.S. Pat. No. 4,275,149, which is incorporated herein by reference.

Other technical terms used herein have their ordinary meaning in the art that they are used, as exemplified by a variety of technical dictionaries.

INTRODUCTION

The present invention recognizes that using direct detection methods to determine an ion transport function or property, such as patch-clamps, is preferable to using indirect detection methods, such as fluorescence-based detection systems. The present invention provides biochips and methods of use that allow for the direct detection of one or more ion transport functions or properties using chips and devices that can allow for automated detection of one or more ion transport functions or properties. These biochips and methods of use thereof are particularly appropriate for automating the detection of ion transport functions or properties, particularly for screening purposes.

As a non-limiting introduction to the breath of the present invention, the present invention includes several general and useful aspects, including:

1) a biochip device for ion transport measurement that comprises at least one upper chamber piece and at least one biochip that comprises at least one ion transport measuring means. The device can comprise one or more conduits that provide an electrolyte bridge to at least one electrode.
2) a biochip ion transport measuring device having one or more flow-through lower chambers.
3) a biochip devices adapted for a microscope stage.
4) methods of making an upper piece for a biochip device for ion transport measurement.
5) methods for making chips comprising ion transport measurement holes using laser drilling techniques.
6) devices that include an inverted chip for ion transport measurement.
7) methods of treating ion transport measuring chips to enhance their sealing properties.
8) a method to measure surface energy, such as on the surface of a chemically-treated ion transport measurement biochip.
9) substrates, biochips, cartridges, apparatuses, and/or devices comprising ion transport measuring means with enhanced electric seal properties.
10) methods for storing the substrates, biochips, cartridges, apparatuses, and/or devices comprising ion transport measuring means with enhanced electrical seal properties.
11) methods for shipping the substrates, biochips, cartridges, apparatuses, and/or devices comprising ion transport measuring means with enhanced electrical seal properties.
12) methods for assembling devices and cartridges of the present invention using UV adhesives.
13) a method of producing ion transport measuring chips by fabricating them as detachable units of a large sheet.
14) a method of producing high density ion transport measuring chips.
15) a biochip device for ion transport measurement comprising fluidic channel upper and lower chambers.
16) methods of preparing cells for ion transport measurement.
17) a software program logic that controls a pressure profile to direct an ion transport measurement apparatus to achieve and maintain a high-resistance electrical seal.
18) an ion channel chip having chemical surface modification on plastics and methods of use. Preferably, the plastic surface is modified to improve the chip's ability for form tight seals for ion transport measurement. Preferably, plastic surfaces can be plasma etched, which makes the surface clean and creates chemical functional groups that can be used for further chemical reactions and/or polymerizations to provide functionalities on the surface. These modifications are preferably made after holes are provided on the chip, such as through laser drilling. A variety of formats of holes can be provided, preferably in a standard format or footprint, such as between 1 and 1536 holes or more on a chip. These chips can be used in methods of determining ion channel activities, including high throughput methods.
19) a bilayer-bilayer junction for forming tight seals and method of use. A lipid bilayer is provided to cover a hole in a chip used for ion transport measurement. The lipid is probably attached to a surface of a chip, such as through covalent or non-covalent attachment. Preferably, head groups of a lipid bilayer are attached to the surface. The surface thus has a negative charge that would promote the formation of a tight seal for use in ion transport measurement.
20) a method of making a pre-assembled ion transport measurement cartridge and method of use. In this aspect of the present invention, a chip without a hole is provided in a cartridge, such as described herein or in the applications incorporated by reference. The assembled cartridge is then oriented for drilling of the chip to form holes for use in ion transport measurement. The resulting cartridge with a chip with holes can then be treated for surface modification to promote the formation of tight seals for ion transport measurement. The treatment can be any appropriate treatment, preferably those described herein, the applications incorporated by reference herein, or as known or described in the art. These cartridges can be used to perform ion transport measurements as described herein, the applications incorporated by reference herein, or as known or described in the art.
21) a method of coating a plastic chip with glass and method of use. Generally, a plastic chip is coated with glass. The glass coated chip is then laser drilled or wet-etched to form holes useful for determination of ion channel activity.
22) a method of protecting fragile devices and parts by packing and shipping in a fluid such as water. Many of the chips, either alone or in combination with cartridge structures, can be fragile and difficult to transport without breakage. By packaging, storing and shipping fragile structures in a fluid such as water, breakage can be reduced.
23) a method laser beam splitting and method of use to laser drill holes in ion channel chips and methods of use. The method utilizes a homogenizer to obtain a "top hat" power profile from a laser beam source. The laser beam is then optionally masked at this point in order to provide one or more profiles for laser drilling a substrate for use as an ion channel detection structure. The laser beam is then passed through a beam splitter to make two or more laser beamlets. The laser beamlets are then optionally masked to provide one or more profiles for laser drilling a substrate for use as an ion channel detection structure. Either the first, second or both of the masking steps can be used. The laser beamlets are then focused through a single or multiple lenses onto a work-piece. The work-piece is in one or more parts and is laser drilled to form structures for use in ion channel detection methods.
24) a method of making glass more readily wet etched, ion channel chips made using this method, and methods of use thereof Generally, the invention converts glass to a form that is more readily wet etched by interaction with a laser in the UV range. The glass that is exposed to such laser light changes structure to become more readily wet etched. The methods are preferably used for making counter-bores, thinnings and through-holes. Glass appropriate for such procedures is an amorphous glass or glass ceramic that it thermal sensitive. One example of such glass is commercially available from Invenions or Schott, and has a product name of Foturan.

25) methods for bonding glass to glass and products produced by such methods. The method makes use of flat surfaces of glass that an operator is desires to bond together. The two pieces of glass can be untreated or treated independently with acid and/or base. The resulting laminate is heated to bond the two pieces of glass together. Alternatively, the two pieces of glass can be untreated or treated independently with acid and/or base. NaSiO4 powder is placed between the two pieces of glass. The laminate is heated to melt the NaSiO4 and thus bond the two pieces of glass together.

Figure 53:
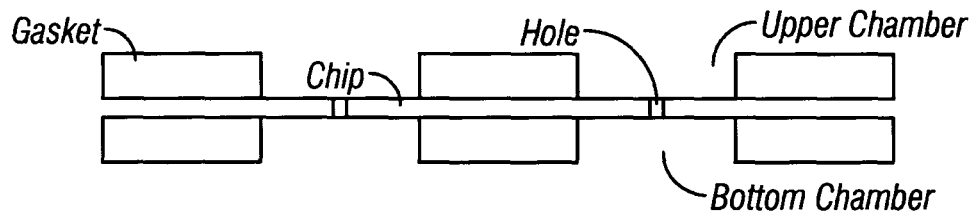
FIG. 53 depicts one aspect of the present invention wherein a chip engaged with gaskets to form upper chambers and lower chambers.

26) an in situ method of making a cartridge for use in ion transport measurement and methods of use. A chip with at least one hole for use in ion transport measurement is provided to an instrument used to make ion transport measurement. The chip is placed such that gaskets are provided on the top surface of the chip and the bottom surface of the chip to form top and bottom chambers. The chambers leave the hole or holes exposed for use in ion transport measurement. A cross section of such a configuration wherein the gaskets engage a chip with holes is provided in FIG. 53.

Figure 54A:
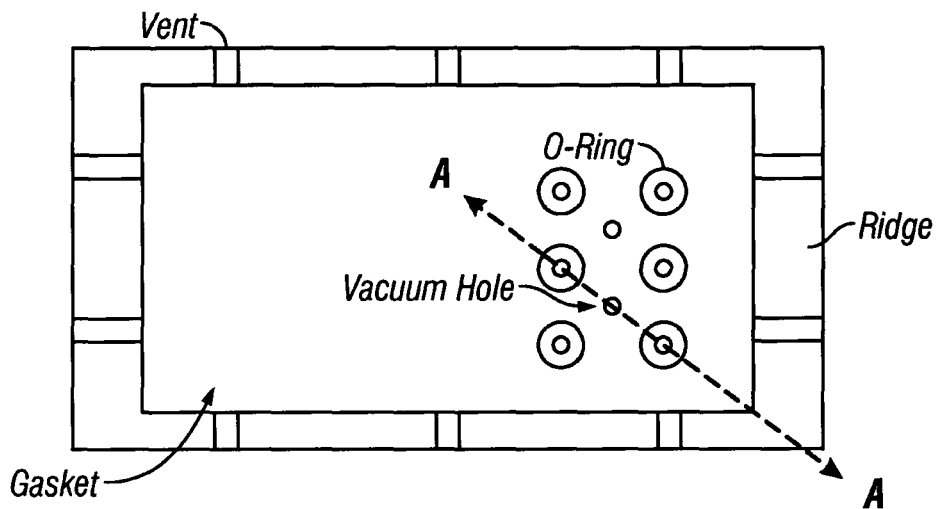
FIG. 54 depicts one aspect of the present invention wherein a gasket is for use in ion transport measurement. (A) represents a top view of one aspect of the present invention wherein the gasket includes o-ring structures and holes for use in engaging a chip for use in ion transport measurement and for providing negative pressure to secure the chip to the gasket to assist in preventing or reducing cross-talk between recording sites during ion transport measurement. Vents can be provided to assist in modulating the negative pressure used to secure the chip to the gasket and remove fluids from the gasket. (B) depicts a partial cross section along A-A.
Figure 54B:
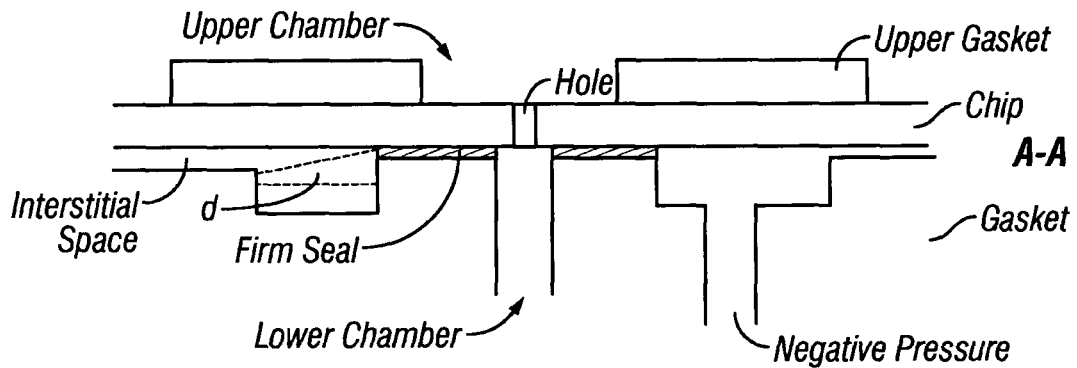

27) a gasket for use in ion transport measurement and methods of use thereof. One aspect of the present invention is depicted in FIG. 54. A gasket is provided to engage a chip for use in ion transport measurement. The gasket can be made of any appropriate material that can form a water tight or water resistant seal with a chip. Preferred materials include, but are not limited to, plastics, rubbers, silicones, gels and the like. The gasket includes a variety of structures to engage a chip and form chambers for use in ion transport measurement. These structures include 0-rings, vacuum holes and vents.

28) a system for automated processing of chips for use in ion transport measurement. One aspect of the invention is provided in FIG. 55. Briefly, a chip is provided in a treatment storage solution. A treated chip is picked up by a structure having negative pressure to engage a chip. The chip is passed over structures providing negative and positive pressure to dry the chip. The chip is then further dried in a structure having negative pressure and optionally moving the chip from side to side. The chip is then removed using the structure having negative pressure and assembled into a cartridge, a storage structure or an instrument for use in ion transport measurement.

29) a device that can hold chips for methods of treating chips and/or for storage of chips. One aspect of the present invention is provided in FIG. 56. The structure has a hinged top structure that engages a bottom structure, wherein the top structure and bottom structure are reversibly engaged using a clip. The bottom structure includes separate structures to hold or otherwise engage chips of the present invention at a location for chips. In the structure set forth in FIG. 56, the location for chip is configured for long thin chips. Other configurations for other chip sizes can be readily designed and made within the scope and spirit of the present invention. In operation, the top structure is lifted away from the bottom structure via the hinge. One or more chips are placed individually in the location for chips. Preferably, only one chip is placed in one location for chip. The top structure engages the bottom structure and is reversibly held in place by the clip. The structure with the chips can be used to store chips or be used to hold chips during treatment. Alternatively, the structure with chips can be provided to instrumentation and/or robotics for movement of chips. The structure can be made of any appropriate material, such as but not limited to plastic, glass, rubber and the like. The structure is preferably made of plastic and is preferably made using injection molding.

These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

Device for Ion Transport Measurement

The present invention comprises devices for ion transport measurement and components of ion transport measuring devices that reduce the costs of manufacture and use and are efficient and convenient to use. The devices of the present invention are also designed for maximum versatility, providing for different assay formats within the same basic design.

In some aspects, the present invention contemplates devices and apparatuses that have parts that are manufactured separately and can be assembled to form ion transport measuring devices that have at least one, and preferably multiple, ion transport measuring units, each of which comprises an upper chamber, at least a portion of a biochip that comprises an ion transport measuring means that connects the upper chamber with a lower chamber. These devices comprising ion channel measuring units can be assembled before the assay procedure, and pieces that make up the device can be reversibly or irreversibly attached to one another. In many preferred aspects of the present invention, one or more portions of an ion transport measuring device will be permanent and reusable (for example, at least a portion of a lower chamber; one or more electrodes) and one or more parts of a device can be removed from an apparatus and can be disposable (for example, a chip comprising ion transport measuring means; one or more upper chambers designed to contain cells). In some aspects of the present invention, a device comprising one or more upper chamber pieces and at least one biochip (called a cartridge) are single-use and disposable, and lower chamber pieces, one or more electrodes, and platforms or lower base pieces are reusable. In these aspects, upper chamber pieces and biochips can be reversibly or irreversibly attached to one another and during use of the device or apparatus, these attached upper chamber/biochip devices can be reversibly attached to or contacted with lower chamber pieces, conduits, or electrodes.

In one embodiment, the present invention contemplates an ion transport measuring device in the form of a cartridge that comprises an upper chamber piece that comprises at least one well that is open at its upper and lower ends, and a biochip that comprises at least one ion transport measuring means. The upper well or wells are in register with the ion transport measuring means, providing independent upper chambers each in contact with a single ion transport measuring means. Preferably a biochip that is part of an ion transport measuring device of the present invention comprises one or more holes used as ion transport measuring means, and an upper chamber piece comprises multiple upper chambers such that upper chambers are in register with ion transport measuring means of the chip.

Figure 1C:
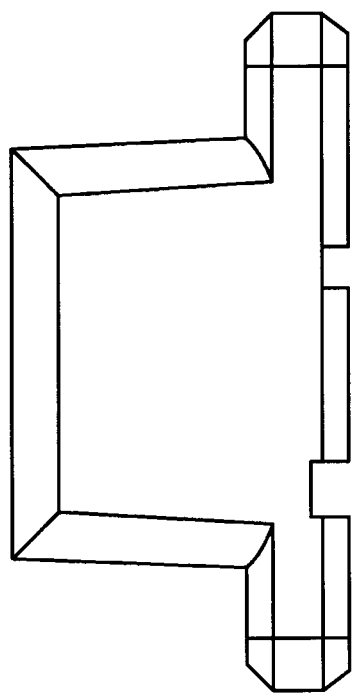
Figure 1D:

An upper chamber piece can be made of any suitable material, but for ease of manufacturing is preferably made of a moldable plastic, such as, for example, polyallomer, polyethylene, polyimide, polypropylene, polystyrene, polycarbonate, cylco-olefin polymer, polyphenylene ether/PPO, NORYL®, ZEONOR® or composite polymers. A cross section of one design of an upper base piece is shown in FIG. 1(D). A chip can be sealed to the lower surface of the upper base piece to form a cartridge The chip used in a device of the present invention is preferably a chip that comprises ion transport measuring means in the form of holes. Methods of fabricating such chips, including methods of fabricating ion transport measuring holes in chips, are disclosed herein. The chips are preferably chemically treated to have enhanced sealing properties. Methods of treating ion transport measuring chips with basic solutions to enhance their ability to form electrical seals with particles such as cells are also disclosed herein. A preferred cartridge, known as the SEALCHIP™, comprises a chip with enhanced electrical sealing properties that is reversibly or irreversibly attached to an upper chamber piece.

An upper chamber piece can optionally comprise one or more electrodes. An upper chamber piece that comprises multiple upper chambers can comprise multiple electrodes, where each well contacts an independent electrode (such as, for example, independent recording electrodes), or can have a single electrode that contacts all of the upper chambers of the device (which can be, for example, a reference electrode). Where the upper chamber piece does not comprise one or more electrodes, the upper chamber piece can optionally be used as part of an apparatus for ion transport measurement in which one or more electrodes can be introduced into one or more upper chambers (such as, for example, introduced via a conduit that can be connected to or can be inserted into one or more chambers). In an alternative configuration, conduits connected with or introduced into one or more upper chambers can, during the use of the apparatus, be filled with a measuring solution and provide electrolyte bridges to one or more electrodes.

A cartridge comprising an upper chamber piece and at least one biochip comprising one or more ion transport measuring means can be assembled with a lower chamber piece that comprises at least a portion of at least one lower chamber. The cartridge can be assembled with a lower chamber piece that comprises at least a portion of a single lower chamber, such as a dish, tray, or channel that provides a common lower chamber for ion transport measuring means that connect to separate upper chambers. In one embodiment, a lower chamber piece can be in the form of a gasket that seals around the bottom of the biochip that when sealed against a lower chamber base piece provides an inner space as a lower chamber.

Alternatively, the device can be assembled with a lower chamber piece that comprises at least a portion of more than one lower chamber. In this case, each individual lower chamber would connect with a single upper chamber via the ion transport measuring hole in the biochip.

Preferred embodiments encompass devices that comprise multiple ion transport measuring units, comprising an upper chamber piece that comprises at least two upper chambers that are open at both their upper and lower ends, a chip that comprises at least two ion transport measuring means in the form of holes through the chip that are in register with the upper chambers, and a lower chamber piece that comprises at least a portion of at least two lower chambers that are in register with the ion transport measuring means and upper chambers.

Lower chamber pieces that comprise at least a portion of more than one lower chamber can be provided in a variety of designs. Lower chamber pieces can comprise complete chamber units, or can comprise all or a portion of the walls of the multiple chamber units, such that when the lower chamber piece is fixed to or pressed against the lower side of a biochip and pressed down on a platform or lower chamber base piece, the lower chamber piece forms the walls and the platform or lower chamber base piece forms the bottoms of the lower chambers.

For example, a device for measuring ion transport function or activity can be a multiple unit device that comprises an upper chamber piece having multiple upper chambers in the form of wells that are open at both the top and bottom, a chip attached to the upper chamber piece, where the chip comprises multiple holes for ion transport measurement that are spaced such that when the device is assembled each upper chamber is over a hole, and a lower chamber piece that can be held or fastened against the lower side of the chip, in which the lower chamber piece comprises multiple openings that fit over the biochip holes to form lower chambers.

In this preferred embodiment, the lower chamber piece can comprise at least one compressible plastic or polymer on its upper surface that can form a seal with the bottom of the biochip. The lower chamber piece can also comprise at least one compressible polymer as a gasket on its upper surface that can form a seal with a platform or a lower base piece. When the device is positioned on a lower base piece or platform so that the lower chamber piece is pressed against the lower base piece or platform, the lower base piece or platform forms the bottom of the lower chambers. Mechanical pressure can provide a seal between the biochip and the lower chamber piece, and between the lower chamber piece and the platform. Clamps can optionally be employed to hold the seal. The compressible plastic or polymer can comprise rubber, a plastic, or an elastomer, such as for example, polydimethylsiloxane (PDMS), silicon polyether urethane, polyester elastomer, polyether ester elastomer, olefinic elastomer, polyurethane elastomer, polyether block amide, or styrenic elastomer. Preferably, in cases where the compressible plastic or polymer contacts cells, the compressible plastic or polymer is made of a biocompatible material, such as PDMS. Portions of the lower chamber piece that do not form a gasket can be of any suitable material, including polymers, metals, and ceramics. Portions of the lower chamber piece that contact measuring solutions preferably comprise materials that are not affected by electrical current (such as nonmetals).

For example, one preferred design of a device for ion transport measurement comprises an upper chamber piece, a chip comprising ion transport measuring holes, a lower chamber piece, and a lower base piece in the form of a platform. The chip has been chemically treated, preferably with at least one base, to enhance its sealing properties. The lower chambers that are formed by a lower chamber piece that comprises an aluminum frame having a PDMS gasket on its upper surface that fits over the lower surface of a chip. PDMS is also used to coat the inner surfaces of the holes that form the lower chambers, and is also used as a gasket on the bottom of the lower chamber piece. The lower chambers can be filled with a solution while the device is held in inverted orientation prior to positioning the device on the platform. During use of the device, mechanical pressure holds the lower chamber piece against the chip and against the platform.

The lower base piece can optionally comprise one or more electrodes. For example, separate individual electrodes can be fabricated on or attached to the platform so that separate lower chambers of the device have independent electrodes that can be attached to independent circuits and used as patch clamp recording electrodes. In an alternative design, the platform can comprise a common lower chamber with a reference electrode, or a common electrode that can contact all of the lower chambers of the device (optionally through separate electrode extensions that meet a common connector outside of the chambers) and can be used as a reference electrode.

The lower base piece can optionally comprise or engage one or more conduits connected to tubing that can allow for the flow of fluids into and out of individual lower chambers. In this type of design the lower chambers can be filled with a measuring solution (such as an intracellular solution) after the gasket is positioned on a lower base piece. The conduits can also be used for the exchange of solutions during the use of the device. For example, solutions containing test compounds, ionophores, inhibitors, drugs, different concentrations or combinations of ions or compounds, etc., can be delivered into and out of a chamber during ion transport measuring assays. At least some of the conduits or tubing can optionally comprise or lead to electrodes (such as, but not limited to, recording electrodes).

In one preferred design, a lower chamber piece having a platform that forms the bottom of lower chambers comprises conduits that engage each lower chamber from one side (one per chamber), and conduits that engage each lower chamber from the opposite side. Conduits on one side of the lower chamber piece can be used for introducing solutions, such as "intracellular solutions" that can optionally comprise test compounds, into the chambers, and conduits on the opposite side of the lower chamber piece can be used for flushing solutions and/or air bubbles out of the lower chambers. At least one set of the conduits (such as, for example, the inflow conduits) comprises wire electrodes that are independently connected (with respect to other ion transport measuring units) to a signal amplifier and used for ion transport activity recording.

Devices such as those described herein can be part of apparatuses that also comprise patch clamp signal amplifiers and conduits, fluid dispensing means, pumps, electrodes, or other components. The apparatuses are preferably mechanized, for automated fluid dispensing or pumping, pressure generation for sealing of particles, and ion transport recording. The apparatuses can be part of a biochip system for ion transport measurement, in which software controls the automated functions.

An Ion Channel Measurement Device Adapted for Microscopes

The present invention also includes a lower chamber base piece for use in a device for ion transport measurement that can optionally be used independently of a larger automated apparatus and can be used to observe cells and particles within the device using an inverted microscope. At least a portion of the lower chamber base piece is transparent, and preferably the lower chamber base piece comprises at least two conduits that are capable of transferring fluid from one surface of the lower chamber platform to another surface of the base piece in a flow-through manner. As part of a device for ion transport measurement, the base piece forms a bottom surface of lower chambers. The conduits that extend through the base piece allow for fluids, and liquid solutions in particular, to be delivered in and out of lower chambers of ion transport measuring devices.

The two or more conduits go through the base piece, with one opening on one surface of the base piece, and the other opening on a different surface of the base piece. In preferred embodiments of the present invention, the conduits extend from a side of the base piece essentially horizontally toward the center, and then turn or curve upward to end in an opening on the top surface of the base piece. The side opening can be the site where the conduit connects with tubing connected to solution reservoirs, pressure sources, and/or electrodes, and the top opening of the conduits is the site where the conduit opens into a lower chamber. Each lower chamber of an ion transport measuring device preferably is connected to two such conduits, and the conduits can provide for solutions to be delivered into and washed out of a lower chamber.

The part or parts of a lower chamber base piece that will form the bottom of one or more lower chambers of an ion transport measuring device is preferably made of a transparent material that is impermeable to aqueous liquids so that cells or particles inside an ion transport measuring unit are visible using an inverted microscope. Although not a requirement of the present invention, to simplify manufacture of the base piece, the entire base piece (with the exception of separate attachments such as connectors, pins, screws, etc.) is preferably made of a single material by molding or machining. Glass and transparent polymers are preferred materials, with transparent polymers such as polycarbonate and polystyrene having the advantage of easier manufacture.

The conduits are molded or drilled through the base piece, and can be fitted with connectors. (Connectors can comprise glass, polymers, plastics, ceramics, or metals.) The connectors can be connected to tubing that can be used to provide in-flow and outflow of solutions to a lower chamber of an ion transport measuring unit.

The conduits can also be used to deliver pressure to the lower chamber and to an ion transport measuring hole of a chip exposed to the chamber. Pressure can be generated, for example, by a pump or a pressure source connected to the tubing that will be filled with an appropriate solution in at least the segment connecting the lower chamber. Preferably the pressure is regulatable and can be used for purging air bubbles and or other blocking micro-particles in the ion transport measuring hole, cell and particle positioning, sealing, and optionally, membrane rupture of an attached cell when carrying out ion transport measurement procedures.

In preferred embodiments, the conduits, or tubes leading to the conduits, can also comprise electrodes. For example, a wire electrode can be threaded through tubing that is connected to a conduit of a base piece. The wire electrode can optionally extend through the conduit to the upper surface of the base piece (which will be the lower surface of a lower chamber of an ion transport measuring unit).

In the alternative, the base piece can comprise one or more electrodes on its upper surface. Electrodes fabricated or attached to the upper surface of the base piece can be connected through leads to connectors on the outer edge of the base piece, and the connectors can be connected to a patch clamp amplifier.

In preferred aspects of the present invention, a lower chamber base piece is designed to fit a base plate that is adapted to fit the stage of a microscope, such as an inverted light microscope. The dimensions can be altered to fit a microscope of choice, such as, for example, an inverted light microscope sold by Leica, Nikon, Olympus, Zeiss, or other companies.

A base plate can be made of any suitable material, such as glass, plastics, polymers, ceramics, or metals. Metals, such as but not limited to stainless steel, are preferred, because metal materials have high mechanical strength needed during pressure sealing of the lower chamber. A metal base plate can also, together with a grounded microscope stage, form an electrical noise shield around a lower chamber piece fitted to the base plate.

The base plate can be carved on the top side to catch any fluids that may leak or spill and prevent the contamination of the microscope with the fluids. Preferably, the base plate is sealed around the lower chamber base piece, for example, with silicone glue, silicone grease, Vaseline, etc.

Figure 2A:
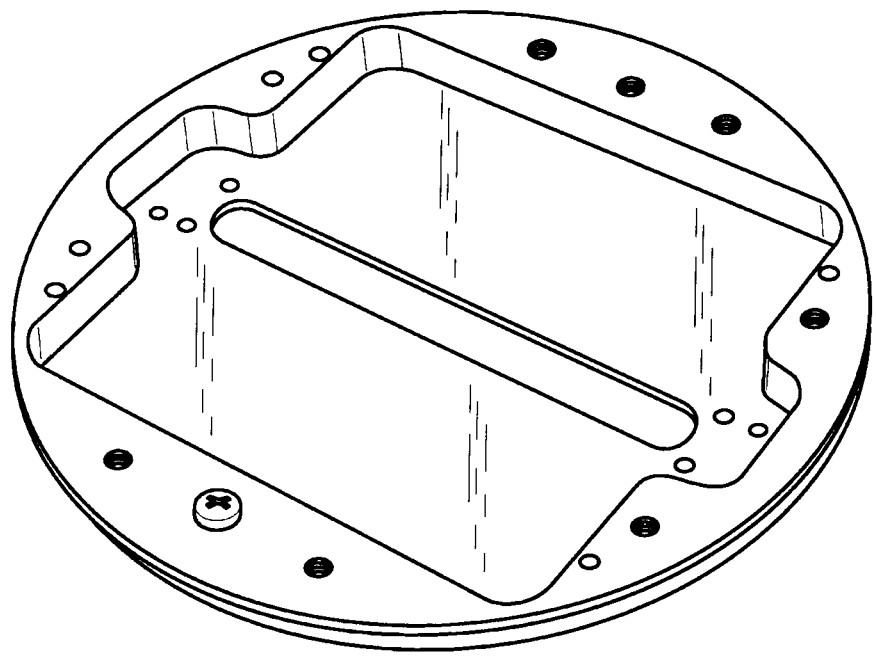
FIG. 2 depicts a biochip device of the present invention that is adapted to a microscope stage. (A) Top view and (B) bottom view of a base plate cut from aluminum stock. The holes are threaded except for the four holes closest to the corners of the square-cut carve-out. The four unthreaded holes are sized to accept a press-in 1 mm socket connector.
Figure 2B:
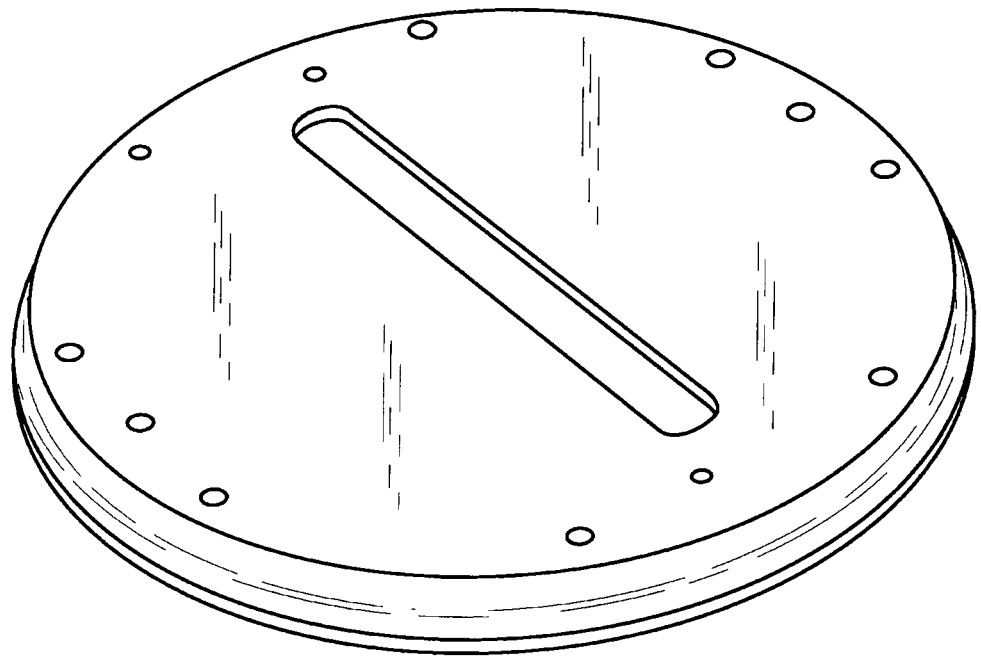

The base plate is preferably drilled and tapped so as to provide a mounting point for the lower chamber base piece and for a clamp that can hold additional components of the ion transport measuring device together (for example, gasket, chip, upper chamber piece) to form the upper and lower chambers of ion transport measuring units. The base plate is designed to hold an ion transport measuring device within a few millimeters of the level of the top of the microscope stage so as to ensure that the chip function may be monitored within the focal range of the microscope. FIG. 2 illustrates the design of a base plate as adapted for a Nikon Microscope.

In preferred aspects of the present invention, a lower chamber base piece is designed to form the bottom of more than one lower chamber of an ion transport measuring device. Preferably, a lower chamber base piece is designed to form the bottoms of all the lower chambers of an ion transport measuring device that comprises at least two ion transport measuring units, more preferably at least three ion transport measuring units, and more preferably yet, at least six ion transport measuring units. In a preferred embodiment described in detail in Example 5, a lower chamber base piece forms the bottom of 16 lower chambers of a 16 unit device. In many cases (as illustrated in the example) multiple lower chambers will be arranged linearly in a row, but this is not a requirement of the present invention.

Figure 3:
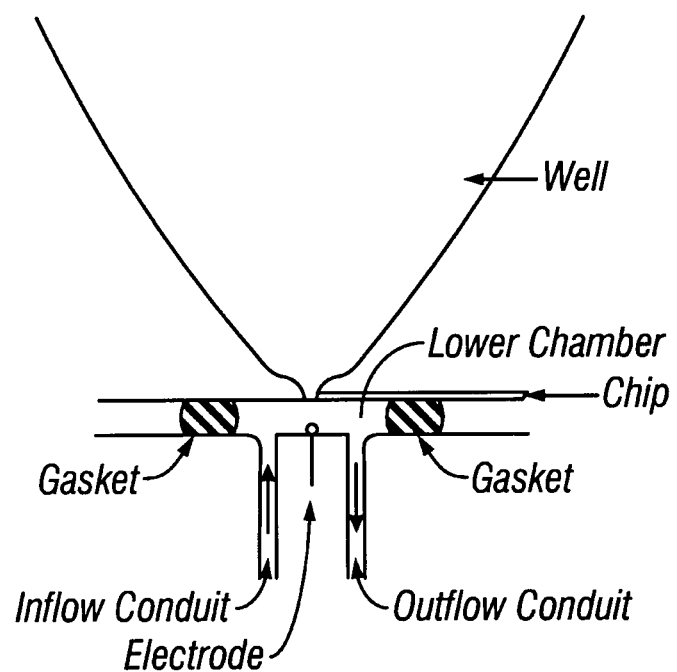
FIG. 3 is a cross-sectional view of a device of the present invention having a flow through lower chamber.

Thus, in preferred embodiments of the present invention, a lower chamber base piece will comprise multiple conduits, two for each lower chamber that will occur in the ion transport measuring device (a first conduit for inflow of solutions, and a second conduit for outflow of solutions). A cross-sectional view of a chamber of one design of a lower base piece is shown in FIG. 3. One of each pair of conduits that leads to a single chamber of an ion transport measuring device can optionally contain or contact an electrode.

Figure 4:
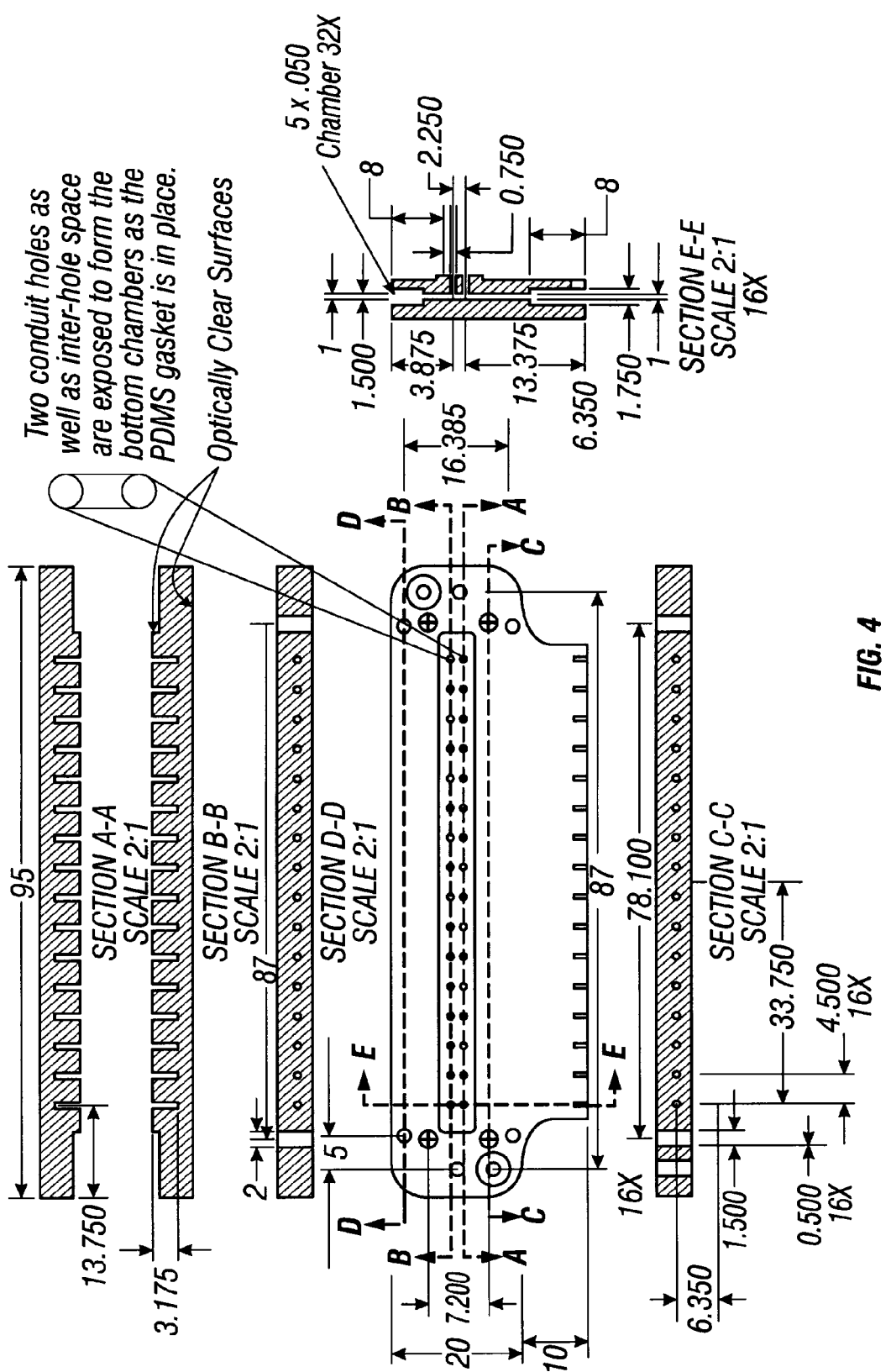
FIG. 4 provides drawings of a design of a flow through chamber lower base piece of a device of the present invention.

The present invention also includes devices for ion transport measurement that include a lower chamber base piece of the present invention. Such apparatuses include: a lower chamber base piece that comprises at least two conduits; where at least a portion of the lower chamber base piece is transparent; a chip comprising at least one ion transport measuring hole; at least one gasket that fits between the lower chamber base piece and the biochip and comprises at least one hole, such that the gasket forms the walls of the one or more lower chambers and seals the lower chamber base piece to the chip such that a lower chamber formed by the gasket comprises a lower surface having the openings of two conduits, and an upper surface comprising a portion of a chip having a single ion transport measuring hole; and an upper chamber piece that comprises at least one chamber that attaches to said chip. Drawings of one preferred design of the present invention with flow-through lower chambers are provided as FIG. 4.

Preferably, tubing is attached to "out" openings of the conduits, and preferably at least one electrode is within one of the two tubes that engages a conduit that leads to a single lower chamber, or an electrode is in electrical contact with the solution in one or the two tubes that engages a conduit that leads to a single lower chamber. FIGS. 5-10.

Upper chambers of such devices can comprise electrodes. Such electrodes can be fabricated, positioned, or attached on a surface of an upper chamber, such as those described in a later section of this application on two-piece molding of upper chambers, or can be provided as within a tube or part of a tube that can be placed inside the upper chamber (such as a tube that delivers solutions or cell suspensions). Preferably, electrodes of upper chambers are connected as a common reference electrode, but this is not a requirement of the present invention. It is also possible for each upper well to have an individual (recording) electrode, and to have the electrodes of the lower chambers connected as a common reference electrode.

The upper piece can optionally comprise one or more electrodes. In some preferred embodiments, the upper piece comprises a common reference electrode that contacts all of the wells. In other preferred embodiments, an electrode is not within or attached to the upper piece, but an electrode can be brought into electrical contact with an upper chamber by way of a conduit that comprises an electrode or can provide an electrolyte solution bridge to an electrode. Electrodes that are connected through electrolyte bridges can be recording electrodes, but in most preferred embodiments are reference electrodes.

The present invention also encompasses compositions and devices that incorporate novel elements of the compositions and devices described herein, including: transparent platform beneath lower chambers, base-plate for microscope stage, bottom chamber flow through tubing, reference or recording electrodes outside of upper or lower chambers and connected to chamber(s) through electrolyte bridge, reference or recording electrodes introduced into tubing attached to upper or lower chambers, manufacture procedures and features for enhancing efficiency or accuracy of manufacture, tapering of upper chamber wells, geometry of holes drilled into chips, counterbore drilling of holes in chips, treatment of chips to enhance electrical sealing of particles such as cells, etc.

Method of Making an Upper Chamber Piece of a Device for Ion Transport Measurement In ion transport measuring devices contemplated by the present invention, an upper chamber is designed to contain the cells or particles on which ion transport measurements are to be performed. In these embodiments, an upper chamber of an ion transport measuring device can comprise or engage at least a portion of an electrode used to monitor ion transport activity. In the alternative, an upper chamber, when filled with an ion transport measuring solution, can be brought into electrical contact with at least a portion of an electrode. For example, an electrode (such as, but not limited to, a metal wire) can be inserted into the well so that electrical current from the electrode would be transmitted through the conductive measuring solution. Alternatively, a tube that comprises a measuring solution (or otherwise conductive solution) that contains or contacts an electrode or a portion thereof can be put in contact with the upper chamber solution. In the latter case, the electrode (or a portion thereof) need not be within the upper chamber at all, as long as it is electrically connected to the inner part of the upper chamber conductive solution (electrolyte bridge).

Typically, an upper chamber electrode will be a reference electrode, although this need not be the case. In cases in which upper chamber electrodes are reference electrodes, electrode extensions or electrolyte bridges that contact individual upper chambers can be connected with one another either outside or inside the upper chamber piece.

In many of the devices of the present invention, an upper chamber piece comprises at least one upper chambers in the form of a well. Preferably, an upper chamber piece comprises multiple upper chambers or wells that allow several ion transport assays to be performed simultaneously. The upper chamber piece can optionally comprise one or more electrodes. The present invention provides methods of making upper chamber pieces that increase the efficiency and reduce the cost of making devices that measure ion transport activity of cells and particles.

Two-Piece Molding followed by Electrode Insertion

Figure 11A:
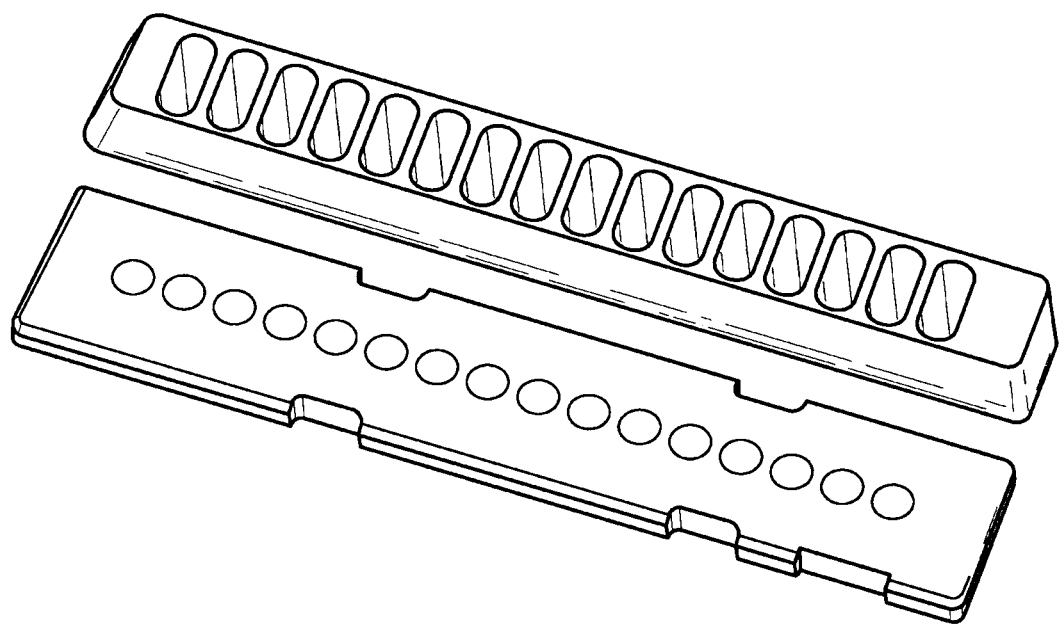
FIG. 11 depicts an upper chamber piece of the present invention that is made from an upper well portion piece and a well hole portion piece. (A) is the upper well portion piece is shown above the well hole portion piece. (B) is the upper well portion piece is shown fitted on the well hole portion piece, with the groove visible along the back of the wells.
Figure 11B:
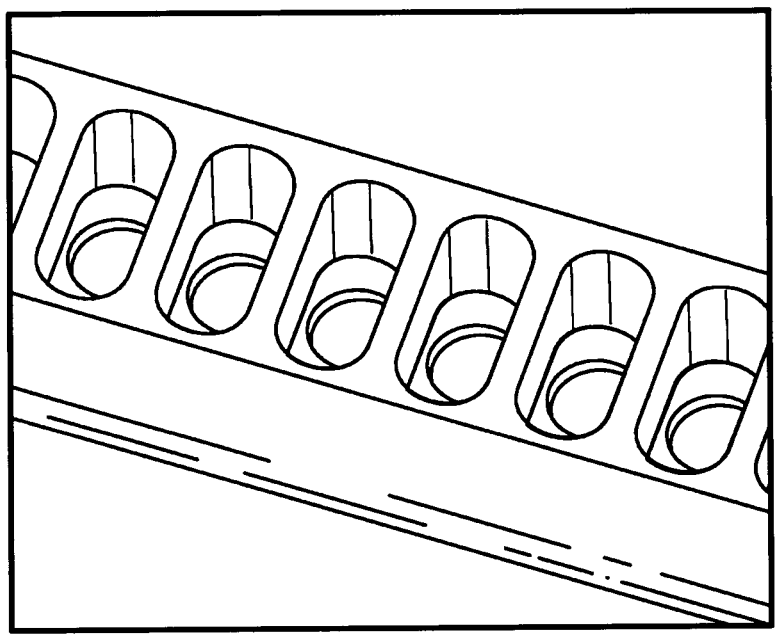

In one aspect of the present invention, an upper chamber piece that comprises one or more wells is made in two pieces, an upper well portion piece and a well hole portion piece, and the well hole portion piece has a groove into which a wire electrode can fit. An upper well portion piece comprises the upper portion of one or more wells. The upper well portions are open at both ends. The well hole piece comprises one or more well holes that will form the bottom portion of the one or more wells. A well hole is, in effect, the lower portion of a well and can have different dimensions (height, diameter, and taper angle) than the upper well portion. The well holes are also open at their upper and lower ends. The well holes have an upper diameter that is equal or smaller than the diameter of the lower opening of the upper well portion. When the upper well portion piece is attached on top of the well hole piece, the upper well portions are aligned over the well holes to form upper chambers (wells) that have well holes at their lower end. An example of this arrangement (upper well portion piece having upper portions of wells and lower well piece having well holes) is depicted in FIG. 11. After manufacturing the upper well portion piece and the well hole piece, a wire electrode is inserted into the groove of the well hole piece, and then the upper well portion piece is attached, via, for example ultrasonic welding, to the well hole piece to form an upper chamber piece comprising one or more wells, each of which is in contact with a portion of a wire electrode.

The method includes: molding a well hole portion piece of an upper chamber piece of an ion transport measuring device, wherein said well hole portion piece comprises: at least one well hole, and a groove that extends longitudinally from one end of the well hole portion piece toward the opposite end of the well hole portion piece, such that the groove contacts the one or more well holes; molding an upper well portion piece of an upper chamber piece that comprises at least one upper well; inserting a wire electrode into the groove of the well hole portion piece; and attaching the upper well portion piece to the well hole portion piece to form an upper chamber piece that comprises one or more wells, such that the wire electrode is exposed to the interior of said one or more wells.

In this embodiment, the upper piece is made from one or more plastics and comprises wells that are open at either end, and each well contacts or contains a portion of a common electrode that can be used as a reference electrode in ion transport measuring assays. This method of manufacture is particularly suited embodiments where the upper piece comprises multiple wells (at least two) that will contact a common electrode, and wells are arranged linearly in a row. However, this is not a requirement of the present invention, and the principle of two-piece molding and wire insertion can be adapted to the manufacture of device components in which multiple wells or chambers that will share a common electrode are arranged in different geometries. In such embodiments, the path of the groove can be designed such that it contacts all of the wells or chambers that are intended to be in contact with the electrode. This includes embodiments where there are multiple rows of wells or chambers, arrangement of wells or chambers in concentric circles or spirals as well as other arrangements of wells or chambers.

It is also possible to adapt the methods of the present invention to designs in which one or more wells are to be contacted by one electrode and one or more other wells are to be contacted by a different electrode. It is also possible that one well be contacted with more that one electrode. In such cases, the well hole portion piece will comprise more than one continuous groove such that more than one wire electrode can be inserted into the lower well portion piece.

Injection molding or compression molding techniques as they are known in the art can be used to make the well hole portion piece and the upper well portion piece. In the methods of the present invention, the upper well portion piece comprises an upper portion of at least one well or chamber and the well hole portion piece comprises a lower portion of at least one well or chamber, such that when the upper well portion piece is attached to the well hole portion piece, the two pieces together form at least one upper well or upper chamber. The well hole portion piece comprises at least one groove whose diameter corresponds to that of a wire electrode, and the groove contacts the well holes. Preferably, the well hole portion piece comprises a well hole whose upper diameter is equal to or smaller than the lower diameter of the upper portion of the well that is part of the upper well portion piece. Thus, in preferred embodiments, the well hole portion piece will have a top surface around the upper diameter of the well hole (see FIG. 11), that, when looking down into a well after the entire top chamber piece is assembled, appears as a ledge around the top of the well hole. The groove can be in this top surface or ledge. In this way the wire electrode can be easily inserted into the groove, and its placement on this "ledge" ensures that it will be exposed to the interior of the well after attachment of the upper well portion piece.

The wire is easily inserted into the groove of the lower well portion piece, as the groove is totally accessible prior to attachment the upper and lower portion pieces.

After insertion of the wire electrode, the upper well portion piece and well hole portion piece are fused together to form a complete upper chamber piece. Any glues appropriate to the materials and applications of the devices can be used for this purpose. UV glues and other fast-curing glues are preferred for mass production of the upper chamber pieces, although slow-cure glues can also be used for mass production if a high capacity production process is used. Ultrasonic welding, pressuring, heating, or other bonding methods can also be used.

Upper Chamber Pieces and Devices

The present invention includes upper chamber pieces that are made using the methods of the present invention, and devices that comprise such pieces. Such pieces and devices can comprise wells or chambers that are open or closed at one or both ends, can comprise other components, such as, but not limited to, membranes, microstructures, ports (optionally with attached conduits), fluidic channels, particles positioning means, specific binding members, polymers, etc., and are not limited to use as ion transport measuring devices. In fact, the same design and manufacturing principles can be used to fabricate pieces that comprise wells or chambers that need not function as "upper" pieces of devices or apparatuses. Two-piece molding, wire insertion, and attachment of two pieces can be used to make devices or components of devices that comprise wells or chambers regardless of whether the components, chambers, or wells, can be considered "upper".

Plastics that can be used in the manufacture of upper and lower pieces include, but are not limited to polyallomer, polypropylene, polystyrene, polycarbonate, cyclo-olefin polymer, polyimide, paralene, PDMS, polyphenylene ether/PPO, Noryl®, Zeonor®, etc. A very large number and variety of moldable plastics and their properties are known. For example, a database of materials, including plastics and polymers useful in the present invention, can be found at http://www.matweb.com.

Electrodes can comprise conductive materials such as metals that can be shaped into wires. Various metals, including aluminum, chromium, copper, gold, nickel, palladium, platinum, silver, steel, and tin can be used as electrode materials.

For electrodes used in ion channel measurement, wires made of silver or other metal halides are preferred, such as Ag/AgCl wires.

The design and dimensions of the upper and lower well pieces, as well as the dimension of the upper wells and lower wells, can vary according to the preferences of the user and are not limiting to the present invention.

Preferred Embodiments

Upper Chamber Pieces and Devices

Figure 5A:
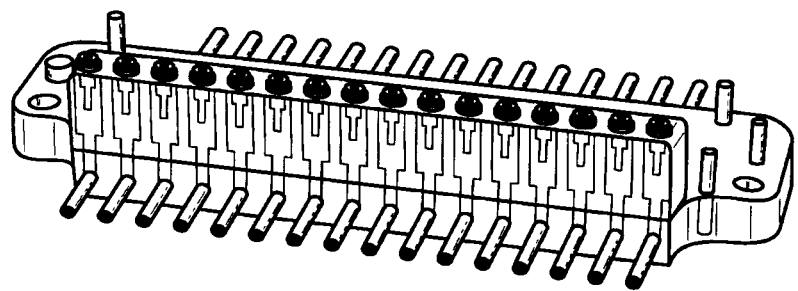
FIG. 5 depicts a biochip device of the present invention having flow through lower chambers that is adapted to fit a microscope stage. A) view of a plastic lower chamber piece from behind the electrodes, B) a zoomed-in side view of the lower chamber piece to demonstrate cuts in the top side, inflow and outflow tubes, and an edge for gasket alignment, C) the lower chamber piece installed in a base late.
Figure 5B:
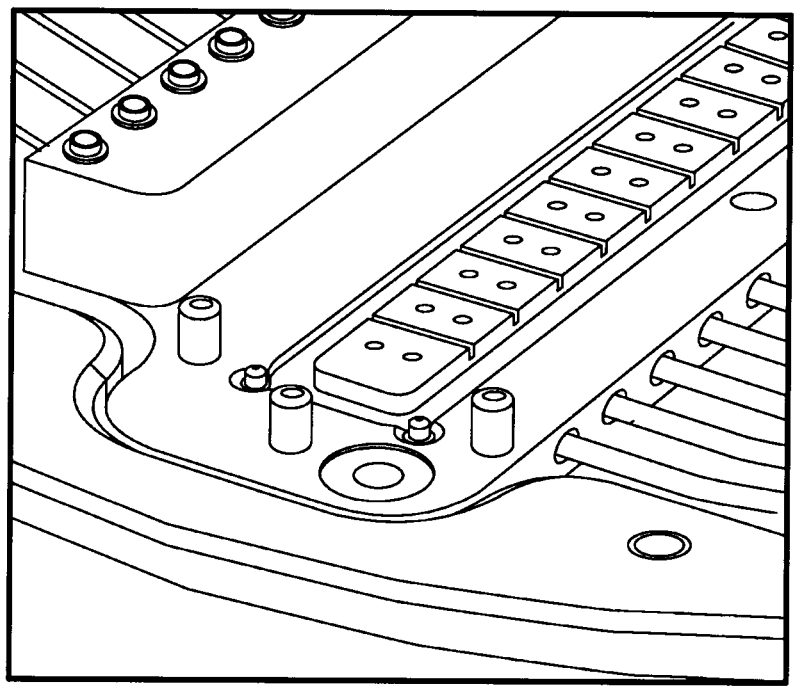
Figure 5C:
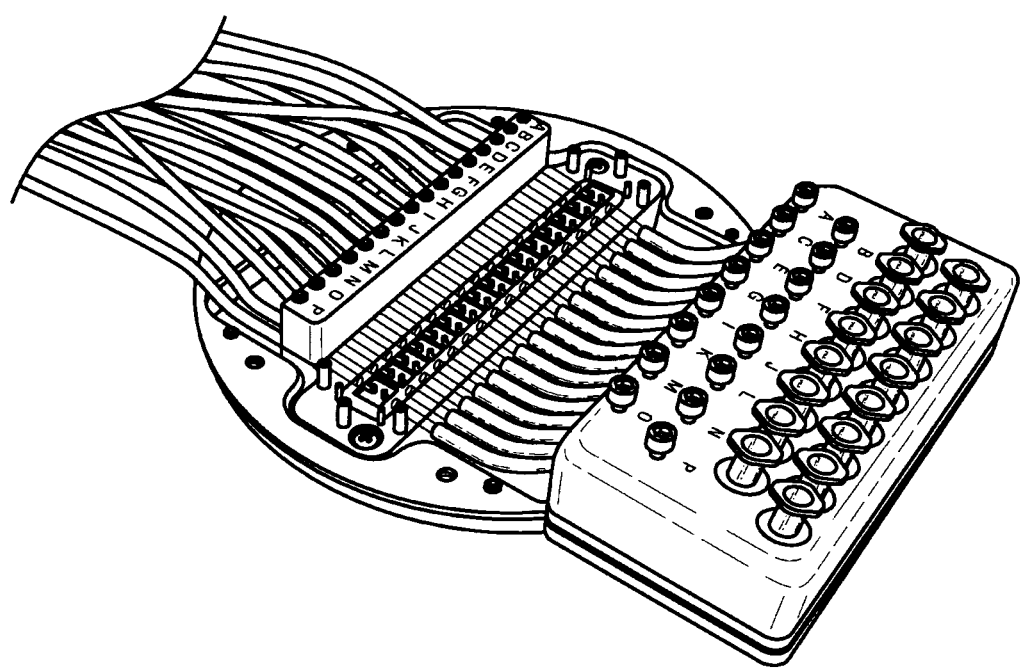
Figure 6A:
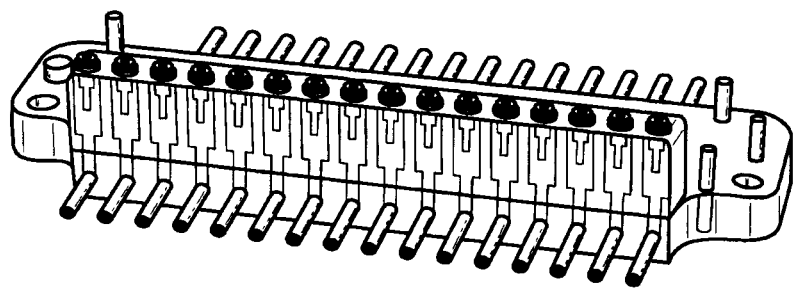
FIG. 6 A) depicts the lower chamber piece of FIG. 5 viewed from behind the electrode array with connectors on top (brass inserts) and wires extending into the fluidics of each chamber below. B) A schematic demonstrates shows the 16× device fully assembled with a cartridge within.
Figure 6B:
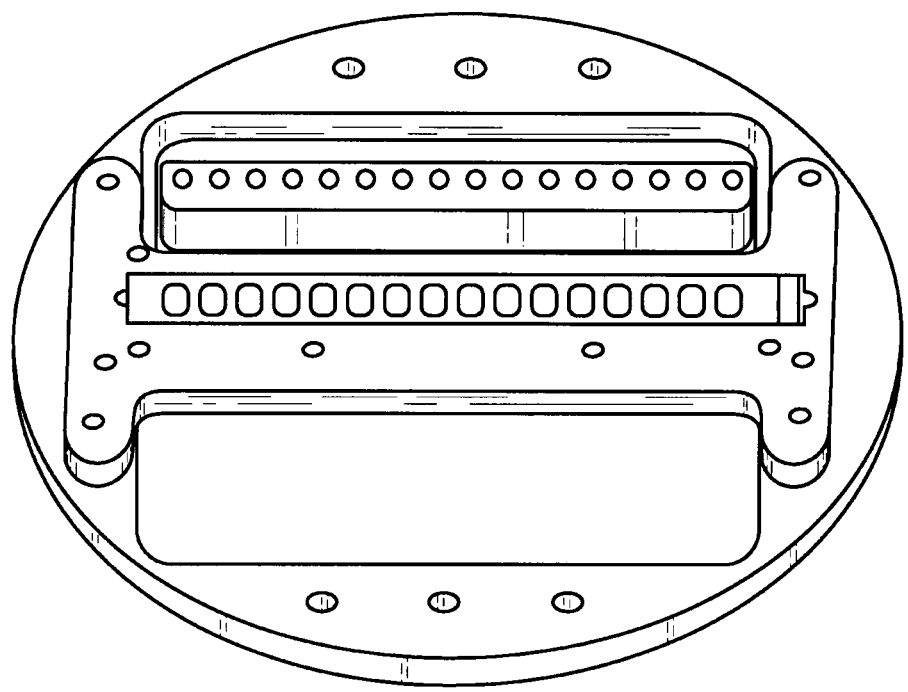

In preferred embodiments of the present invention, the upper chamber piece comprises one or more upper wells that can function as the upper chambers of ion transport measuring units of ion transport measuring devices. Preferably, an upper chamber piece of the present invention comprises more than one upper well, and more preferably more than two upper wells. Even more preferably, an upper chamber piece comprises six or more upper wells, each of which can be a part of an ion transport measuring unit of an ion transport measuring device, where all of the six or more upper wells of the manufactured upper chamber piece contact a portion of a common wire electrode that extends along the upper chamber piece. FIGS. 5 and 6 depict a preferred upper chamber piece of the present invention that comprises sixteen wells.

The wells of an upper chamber piece that can be part of an ion transport measuring device preferably can hold a volume of between about 5 microliters and about 5 milliliters, more preferably between about 10 microliters and about 2 milliliters, and more preferably yet between about 25 microliters and about 1 milliliter. The depth, or height of a well can vary from about 1 to 25 millimeters, and more preferably will be from about 2 milliliters to about 10 milliliters in depth. In preferred embodiments of the present invention in which an upper well portion and a lower well portion together make up the well, the upper well portion is preferably from about 1 to about 25 milliliters in depth, and the lower well is preferably from about 100 microns to about 10 milliliters in depth.

A low cell or particle density is often preferred for attaining a high success rate when using the ion channel measuring device described herein. In order to reduce the cell or particle density required for optimal cell or particle landing to the recording apertures, it is desirable to have an accurate means for delivering the cells or particles to the recording aperture. For a more accurate delivery of cells or particles to the recording aperture, the upper chamber well can have one or more tapered walls, The walls can be contoured such that the cells or particles, when delivered to the upper chamber well wall (such as by robotic dispenser), are directed to the recording aperture.

In these preferred embodiments, the shape of the well can vary, and can be irregular or regular, and in many cases will be generally circular or oval at its circumference. In a preferred embodiment of the present invention depicted in FIG. 11 and FIG. 1, the wells of the upper chamber piece are horseshoe-shaped, and at least a portion of the sides of the wells are tapered. FIG. 1c, for example, shows that the wall of the well corresponding to the rounded end of the horseshoe shape tapers toward the bottom of the upper portion of the well. In other preferred embodiments, the walls along entire well taper toward the bottom of the upper portion of the well. In these preferred embodiments, the diameter of a well at its upper end will generally be from about 2 millimeter to about 10 millimeters.

In some preferred embodiments of the present invention the angle of the taper of a portion of the walls of the well or the entire well walls (the difference from vertical) is from about one degree to about 80 degrees. More preferably, the angle of the taper of the well walls is between about 5 degrees and 60 degrees from vertical. The taper can extend down the full height of the well, or the well can be tapered for only a portion of its height.

The upper well portion can optionally be tapered, or the well hole can optionally be tapered, or both the upper well portion and the lower well portion can be tapered. Where both are tapered, the tapering need not be to the same degree or extend around the well to the same extent.

Molding of Single Upper Chamber Piece around Electrode

In another aspect of the present invention, an upper chamber piece with at least one wire electrode can be manufactured as a single piece by molding an upper piece around a wire electrode. In this case, the mold has a means for positioning the wire electrode such that the upper chamber piece that includes the wells can be molded around it. The method includes: positioning an electrode in a mold; and injection molding an upper chamber piece using the mold such that the electrode contacts one or more wells of the upper chamber piece. The electrode can be positioned in any of a number of ways, for example it can extend through the mold and be held by apertures that it is threaded through on either end of the mold.

The injection molded upper chamber piece can comprise one or more wells or upper chambers, preferably two or more, more preferably six or more wells. The wells can be of any dimension of size, and can comprise a well hole within the well as described in the previous section.

Molding of Single Upper Piece without Electrode

In yet another aspect of the present invention, an upper chamber piece can be manufactured without an electrode. In this case, an upper chamber piece with a desirable number of wells is injection molded using a suitable plastic, such as, but not limited to, polyallomer, polypropylene, polystyrene, polycarbonate, polyimide, paralene, PDMS, cyclo-olefin polymer, polyphenylene ether/PPO, Noryl®, or Zeonor®.

When the upper chamber piece is integrated into a device for ion transport measurement, electrodes (for example, metal wires) can be inserted into the wells. Such electrodes are preferably reference electrodes and are preferably connected outside the chambers, but inserted electrodes can also be recording electrodes connected separately to a power source/signal amplifier.

In a preferred embodiment of the present invention, an electrode connection can be provided by a conduit that can be introduced into the upper chambers during use of the device. The conduit can comprise an electrode, or, when the conduit is filled with a conductive solution, can be in electrical contact with an electrode. When both the upper chamber and the conduit contain a conductive solution (such as a measuring solution), the upper chamber is in electrical contact with the electrode through the "electrolyte bridge" of solution provided by the conduit.

Insert Molding of Glass Chip

In yet another embodiment, a pre-diced glass chip is insert-molded together with an upper chamber piece to make a one-piece cartridge. In this process, a glass chip is inserted into a mold, and the upper chamber piece is molded around the glass chip such that it forms the bottoms of upper chambers of the upper chamber piece. Laser drilling of the recording apertures is done after the molding process, and then the cartridge is chemically treated to enhance its electrical sealing properties. In this embodiment, materials that can be treated with acid and base (such as, for example, NORYL® and ZEONOR®) are used for the construction of the cartridge other than the biochip.

Additional Features

In some preferred embodiments of the present invention, the upper chamber pieces of the present invention or components of the upper chamber pieces of the present invention can have additional features that can aid in the manufacture of upper chamber pieces or of ion transport measuring devices. One such feature is an alignment bump seen on the left of the chamber piece depicted in FIG. 1D. One or more alignment bumps on the lower surface of an upper chamber piece can be used during attachment of a chip that comprises ion transport measuring means to the upper chamber piece. Attachment of the chip and the upper chamber piece must occur such that every ion transport measuring hole in the chip is aligned with a well hole. The alignment bump allows a person or machine assembling the device to detect the location where the edge of the chip must be positioned.

Another useful feature for the manufacture of ion transport measuring devices that can occur on upper chamber piece of the present invention is a glue spillage groove. This allows for overflow of glue that is used for the attachment of a chip, such as a chip that comprises ion transport measuring means. The glue spillage groove is also shown as notches in the bottom surface of the part shown in FIG. 1C.

Yet another optional feature useful in the manufacturing process of an upper chamber piece is the presence of sinkholes. Depicted in FIG. 1D, these sinkholes allow for the escape of gas during the molding process.

Methods of Making a Chip Comprising Holes for Ion Transport Measurement

Fabrication of Ion Transport Measuring Holes in a Chip

The present invention also comprises methods of making chips comprising holes for ion transport measurement. The method includes: providing a substrate; laser drilling at least one counterbore in said substrate, and laser drilling at least one hole in said substrate. Preferably, laser drilling is done with sequential or simultaneous measurement of the glass thickness at the site of the pore.

For optimal quality ion transport recording, ion transport measurement chips comprising holes for ion transport measurement ideally should have a low hole resistance (Re) across the chip at the site of the hole. For chips having multiple holes, it is also desirable to have a high degree of uniformity of hole resistance from recording site to recording site. The hole resistance decreases with decreasing depth of the hole in the chip and widening of the exit hole (see FIGS. 12 and 13). A wider tapering (greater angle from vertical) of the hole also decreases Re.

Figure 12:
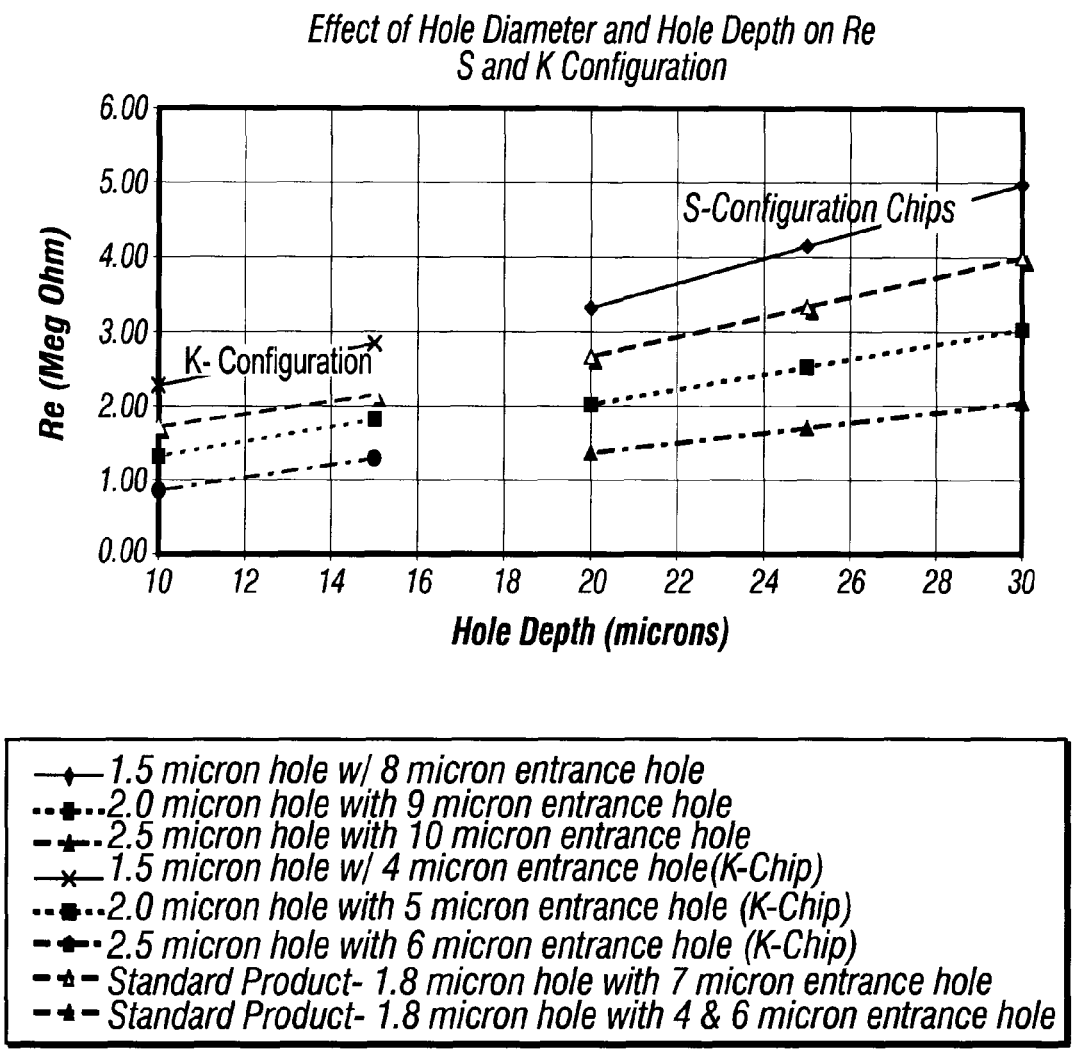
FIG. 12 is a graph that illustrates that a decreasing hole depth and widening the exit hole decreases Ra.
Figure 13:
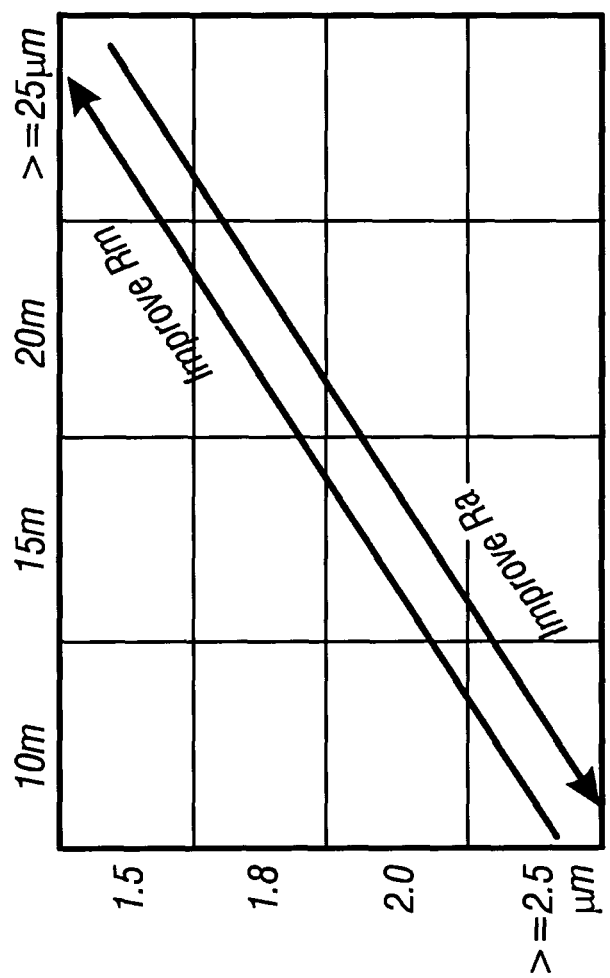
FIG. 13 is a graph illustrating that thinner chips ("K-configuration chips") have a lower Ra than those with greater hole depth.

The methods of the present invention seek to reduce hole resistance by reducing hole depth. This is achieved by laser drilling holes in thin substrates, such as glass, quartz, silicon, silicon dioxide, or polymer substrates. The graph provided in FIG. 13 illustrates that thinner chips ("K-configuration chips") have a lower Re than those with greater hole depth. The graph provided in FIG. 12 illustrates that a decreasing hole depth and widening the exit hole decreases Ra.

A chip with shortened holes for ion transport measurement can be made by laser drilling one or more counterbores into a glass chip, and then laser drilling a through hole through the one or more counterbores. While a wide counterbore is preferred for lower Re, increased width of the counterbore can weaken the chip. It is also difficult to control the drilling of the counterbore as the bottom of the counterbore gets thinner and thinner. In addition, with increased (deeper) drilling, the peripheral areas of the counterbores tend to be deeper than the more central portions of the counterbore due to optical waveguide effects (this is sometimes called the "Batman Effect"). To avoid these problems, a second counterbore is laser drilled into the bottom of a first counterbore. This makes drilling to a greater depth easier control, and has the effect of reducing the thickness of the chip in the vicinity of the through hole. Thus, synthesis of biochips for ion transport measurement can include laser drilling at least one counterbore through a substrate, and then drilling a through hole through the one or more counterbores. Preferably two counterbores are laser drilled into a substrate, such that a second counterbore is drilled through a first counterbore, that is, the counterbores are nested to form (along with a through hole) a single hole structure. In some embodiments of the present invention, three, four, or more nested counterbores can be drilled into a substrate prior to drilling a through hole through the counterbores.

Control of the depth of laser drilling can be done by using a separate laser device that can measure the thickness of the glass. In preferred aspects of this embodiment of the present invention, a measuring laser is used to measure the thickness of the substrate before or as it is being drilled, and the laser used for drilling can be regulated by the thickness of the remaining substrate at the bottom surface of the counterbore. Laser-based measuring devices have been used for the determination of glass thickness to an accuracy of 0.1 micron. Such a laser measurement device is available from the Keyence Company. A laser based measurement is made to determine the exact thickness of the substrate. This measurement determines the number of pulses to be used by the drilling laser to drill a counterbore and thereby achieve uniformity of hole depth. To improve the consistency of through hole depth and hole resistance, the invention contemplates the integration of a laser unit with an excimer laser drilling device, together with automated control software.

In practice, a substrate made of glass, quartz, silicon, silicon dioxide, polymers, or other substrates that preferably ranges in thickness from 5 to 1000 microns, and more preferably from 10 to 200 microns, is provided. A first counterbore is laser drilled, where the entrance of the counterbore has a diameter from about 20 to about 200 microns, preferably from about 40 to about 120 microns. The first counterbore can be drilled to a depth of from about 100 microns to the thickness of the substrate minus the through hole depth. Depending on the thickness of the substrate and the number of counterbores that each ion transport measuring hole will have. Subsequent counterbores will have a smaller diameter than the first counterbore, and can be of lesser depth than the first counterbore. In general, after drilling of all of the counterbores that will be part of an ion transport measuring hole, the remaining thickness of the substrate that is to be drilled out to form the through hole (that is, the depth of the through hole) will range from about 0.5 to about 200 microns, and preferably will range from about 2 to about 50 microns, more preferably from about 5 to about 30 microns. The diameter of the through hole can be from about 0.2 to about 8 microns, and preferably will be from about 0.5 to about 5 microns, and even more preferably, from about 0.5 to about 3 microns.

Counterbores can be tapered. Preferably, a counterbore is tapered at an angle ranging from about 1 degree to about 80 degrees from vertical, and more preferably from about 3 degrees to about 45 degrees from vertical. Ion transport measuring holes comprising multiple counterbores can have different taper angles for different counterbores.

Through holes can also be tapered. The angle of taper for a through hole can range from about 0 degree to about 75 degrees from vertical, and more preferably, where a through hole is tapered, is from about 0 degree to about 45 degrees from vertical. In general an exit hole of a through hole will have a narrower diameter than an entrance hole, although this is not a requirement of the present invention.

Inverted Chip

The present invention also includes methods of using chips comprising ion transport measuring holes that are in inverted orientation for ion transport measurement, that is, using chips in which the holes (or at least a portion of the holes, such as a portion of the holes made by at least one counterbore) have a negative taper.

The method comprises: assembling a device for ion transport measurement that comprises: at least one upper chamber, wherein the one or more upper chambers comprise or are in electrical contact with at least one electrode; at least one chip that comprises a measuring hole, wherein the one or more chips are assembled in the device in inverted orientation; and at least one lower chamber, wherein the one or more lower chambers comprise or are in electrical contact with at least one electrode; connecting the electrodes with a power supply/signal amplifier; introducing at least one particle or at least one cell into at least one upper chamber, and measuring ion transport activity of at least one cell or at least one particle.

By "inverted orientation" is meant that, for a chip which ion transport measuring holes are made by drilling, the chip is positioned such that the side of the chip having the laser entrance hole opening is exposed to a chamber that will contain cells or particles, instead of the side having the laser exit hole. This is contrary to what has previously been done in the art. Thus, sealing of a cell or particles against the ion transport measuring hole occurs on the side of the chip opposite to the side that has smaller hole size (the "back side" of the chip).

The inverted chip orientation has several advantages. One advantage is that the chip does not require a laser polishing step, since the laser drilling performs this function as a "side-effect". A second advantage is that sealing occurs with high efficiency due to the geometry of the particle-chip interaction. Yet another advantage is that a stable low Ra can be produced using larger holes (for example, from about 2 to about 5 microns in diameter), due to the position at which break-in occurs during whole cell recording.

When one or counterbores are used to reduced the through hole depth, the through hole can be drilled from either the same direction as the counterbores, or from the opposite direction to the counterbores. In the former case, the chips is produced just like the "normal" chips are produced, they are simply assembled up side down.

The present invention includes devices and apparatuses having chips comprising ion transport measuring holes that are in inverted orientation, as well as methods of using chips comprising ion transport measuring holes that are in inverted orientation for ion transport measurement.

Methods of Treating Chips Comprising Ion Transport Measuring Means to Enhance the Electrical Seal of a Particle The present invention also includes methods of modifying an ion transport measuring means to enhance the electrical seal of a particle or membrane with the ion transport measuring means. Ion transport measuring means includes, as non-limiting examples, holes, apertures, capillaries, and needles. "Modifying an ion transport measuring means" means modifying at least a portion of the surface of a chip, substrate, coating, channel, or other structure that comprises or surrounds the ion transport measuring means. The modification may refer to the surface surrounding all or a portion of the ion transport measuring means. For example, a biochip of the present invention that comprises an ion transport measuring means can be modified on one or both surfaces (e.g. upper and lower surfaces) that surround an ion transport measuring hole, and the modification may or may not extend through all or a part of the surface surrounding the portion of the hole that extends through the chip. Similarly, for capillaries, pipettes, or for channels or tube structures that comprises ion transport measuring means (such as apertures), the inner surface, outer surface, or both, of the channel, tube, capillary, or pipette can be modified, and all or a portion of the surface that surrounds the inner aperture and extends through the substrate (and optionally, coating) material can also be modified.

As used herein, "enhance the electrical seal", "enhance the electric seal", "enhance the electric sealing" or "enhance the electrical sealing properties (of a chip or an ion transport measuring means)" means increase the resistance of an electrical seal that can be achieved using an ion transport measuring means, increase the efficiency of obtaining a high resistance electrical seal (for example, reducing the time necessary to obtain one or more high resistance electrical seals), or increasing the probability of obtaining a high resistance electrical seal (for example, the number of high resistance seals obtained within a given time period).

The method comprises: providing an ion transport measuring means and treating the ion transport measuring means to enhance the electrical sealing properties of the ion transport measuring means. Preferably, treating an ion transport measuring means to enhance the electrical sealing properties results in a change in surface properties of the ion transport measuring means. The change in surface properties can be a change in surface texture, a change in surface cleanness, a change in surface composition such as ion composition, a change in surface adhesion properties, or a change in surface electric charge on the surface of the ion transport measuring means. In some preferred aspects of the present invention, a substrate or structure that comprises an ion transport measuring means is subjected to chemical treatment (for example, treated in acid, and/or base for specified lengths of time under specified conditions). For example, treatment of a glass chip comprising a hole through the chip as an ion transport measuring means with acid and/or base solutions may result in a cleaner and smoother surface in terms of surface texture for the hole. In addition, treating a surface of a biochip or fluidic channel that comprises an ion transport measuring means (such as a hole or aperture) or treating the surface of a pipette or capillary with acid and/or base may alter the surface composition, and/or modify surface hydrophobicity and/or change surface charge density and/or surface charge polarity.

Preferably, the altered surface properties improve or facilitate a high resistance electric seal or high resistance electric sealing between the surface-modified ion transport measuring means and a membranes or particle. In preferred embodiments of the present invention in which the ion transport measuring means are holes through one or more biochips, one or more biochips having ion transport measuring means with enhanced sealing properties (or, simply, a "biochip having enhanced sealing properties") preferably has a rate of at least 50% high resistance sealing, in which a seal of 1 Giga Ohm or greater occurs at 50% of the ion transport measuring means takes place in under 2 minutes after a cell lands on an ion transport measuring hole, and preferably within 10 seconds, and more preferably, in 2 seconds or less. Preferably, for biochips with enhanced sealing properties, a 1 Giga Ohm resistance seal is maintained for at least 3 seconds.

In practice, in preferred aspects of the present invention the method comprises providing an ion transport measuring means and treating the ion transport measuring means with one or more of the following: heat, a laser, microwave radiation, high energy radiation, salts, reactive compounds, oxidizing agents (for example, peroxide, oxygen plasma), acids, or bases. Preferably, an ion transport measuring means or a structure (as nonlimiting examples, a structure can be a substrate, chip, tube, or channel, any of which can optionally comprise a coating) that comprises at least one ion transport measuring means is treated with one or more agents to alter the surface properties of the ion transport measuring means to make at least a portion of the surface of the ion transport measuring means smoother, cleaner, or more electronegative.

An ion transport measuring means can be any ion transport measuring means, including a pipette, hole, aperture, or capillary. An aperture can be any aperture, including an aperture in a channel, such as within the diameter of a channel (for example, a narrowing of a channel), in the wall of a channel, or where a channel forms a junction with another channel. (As used herein, "channel" also includes subchannels.) In some preferred aspects of the present invention, the ion transport measuring means is on a biochip, on a planar structure, but the ion transport measuring means can also be on a non-planar structure.

The ion transport measuring means or surface surrounding the ion transport measuring means modified to enhance electrical sealing can comprise any suitable material. Preferred materials include silica, glass, quartz, silicon, plastic materials, polydimethylsiloxane (PDMS), or oxygen plasma treated PDMS. In some preferred aspects of the present invention, the ion transport measuring means comprises SiOM surface groups, where M can be hydrogen or a metal, such as, for example, Na, K, Mg, Ca, etc. In such cases, the surface density of said SiOM surface groups (or oxidized SiOM groups ($SiO^-$)) is preferably more than about 1%, more preferably more than about 10%, and yet more preferably more than about 30%. The SiOM group can be on a surface, for example, that comprises glass, for example quartz glass or borosilicate glass, thermally oxidized $SiO_2$ on silicon, deposited $SiO_2$, deposited glass, polydimethylsiloxane (PDMS), or oxygen plasma treated PDMS.

In preferred embodiments, the method comprises treating said ion transport measuring means with acid, base, salt solutions, oxygen plasma, or peroxide, by treating with radiation, by heating (for example, baking or fire polishing) by laser polishing said ion transport measuring means, or by performing any combinations thereof.

An acid used for treating an ion transport measuring means can be any acid, as nonlimiting examples, HCl, $H_2SO_4$, $NaHSO_4$, $HSO_4$, $HNO_3$, HF, $H_3PO_4$, HBr, HCOOH, or $CH_3COOH$ can be. The acid can be of a concentration about 0.1 M or greater, and preferably is about 0.5 M or higher in concentration, and more preferably greater than about 1 M in concentration. Optimal concentrations for treating an ion transport measuring means to enhance its electrical sealing properties can be determined empirically. The ion transport measuring means can be placed in a solution of acid for any length of time, preferably for more than one minute, and more preferably for more than about five minutes. Acid treatment can be done under any non-frozen and non-boiling temperature, preferably at greater or equal than room temperature.

An ion transport measuring means can be treated with a base, such as a basic solution, that can comprise, as nonlimiting examples, NaOH, KOH, $Ba(OH)_2$, LiOH, CsOH, or $Ca(OH)_2$. The basic solution can be of a concentration of about 0.01 M or greater, and preferably is greater than about 0.05 M, and more preferably greater than about 0.1 M in concentration. Optimal concentrations for treating an ion transport measuring means to enhance its electrical sealing properties can be determined empirically (see examples). The ion transport measuring means can be placed in a solution of base for any length of time, preferably for more than one minute, and more preferably for more than about five minutes. Base treatment can be done under any non-frozen and non-boiling temperature, preferably at greater or equal than room temperature.

An ion transport measuring means can be treated with a salt, such as a metal salt solution, that can comprise, as nonlimiting examples, NaCl, KCl, $BaCl_2$, LiCl, CsCl, $Na_2SO_4$, $NaNO_3$, or CaCl, etc. The salt solution can be of a concentration of about 0.1 M or greater, and preferably is greater than about 0.5 M, and more preferably greater than about 1 M in concentration. Optimal concentrations for treating an ion transport measuring means to enhance its electrical sealing properties can be determined empirically (see examples). The ion transport measuring means can be placed in a solution of metal salt for any length of time, preferably for more than one minute, and more preferably for more than about five minutes. Salt solution treatment can be done under any non-frozen and non-boiling temperature, preferably at greater or equal than room temperature.

Where treatments such as baking, fire polishing, or laser polishing are employed, they can be used to enhance the smoothness of a glass or silica surface. Where laser polishing of a chip or substrate is used to make the surface surrounding an ion transport measuring means more smooth, it can be performed on the front side of the chip, that is, the side of the chip or substrate that will be contacted by a sample comprising particles during the use of the ion transport measuring chip or device.

Appropriate temperatures and times for baking, and conditions for fire and laser polishing to achieve the desired smoothness for improved sealing properties of ion transport measuring means can be determined empirically.

In some aspects of the present invention, it can be preferred to rinse the ion transport measuring means, such as in water (for example, deionized water) or a buffered solution after acid or base treatment, or treatment with an oxidizing agent, and, preferably but optionally, before using the ion transport measuring means to perform electrophysiological measurements on membranes, cells, or portions of cells. Where more than one type of treatment is performed on an ion transport measuring means, rinses can also be performed between treatments, for example, between treatment with an oxidizing agent and an acid, or between treatment with an acid and a base. An ion transport measuring means can be rinsed in water or an aqueous solution that has a pH of between about 3.5 and about 10.5, and more preferably between about 5 and about 9. Nonlimiting examples of suitable aqueous solutions for rinsing ion transport measuring means can include salt solutions (where salt solutions can range in concentration from the micromolar range to 5M or more), biological buffer solutions, cell media, or dilutions or combinations thereof. Rinsing can be performed for any length of time, for example from minutes to hours.

Some preferred methods of treating an ion transport measuring means to enhance its electrical sealing properties include one or more treatments that make the surface more electronegative, such as treatment with a base, treatment with electron radiation, or treatment with plasma. Not intending to be limiting to any mechanism, base treatment can make a glass surface more electronegative. This phenomenon can be tested by measuring the degree of electro-osmosis of dyes in glass capillaries that have or have not been treated with base. In such tests, increasing the electronegativity of glass ion transport measuring means correlates with enhanced electrical sealing by the base-treated ion transport measuring means. Base treatment can optionally be combined with one or more other treatments, such as, for example, treatment with heat (such as by baking or fire polishing) or laser treatment, or treatment with acid, or both. Optionally, one or more rinses in water, a buffer, or a salt solution can be performed before or after any of the treatments.

For example, after manufacture of a glass chip that comprises one or more holes as ion transport measuring means, the chip can be baked, and subsequently incubated in a base solution and then rinse in water or a dilution of PBS. In another example, after manufacture of a glass chip that comprises one or more holes as ion transport measuring means, the chip can optionally be baked, subsequently incubated in an acid solution, rinsed in water, incubated in a base solution, and finally rinsed in water or a dilution of PBS. In some preferred embodiments, the surfaces of a chip surrounding ion transport measuring means can be laser polished prior to treating the chip with acid and base.

Figure 14A:
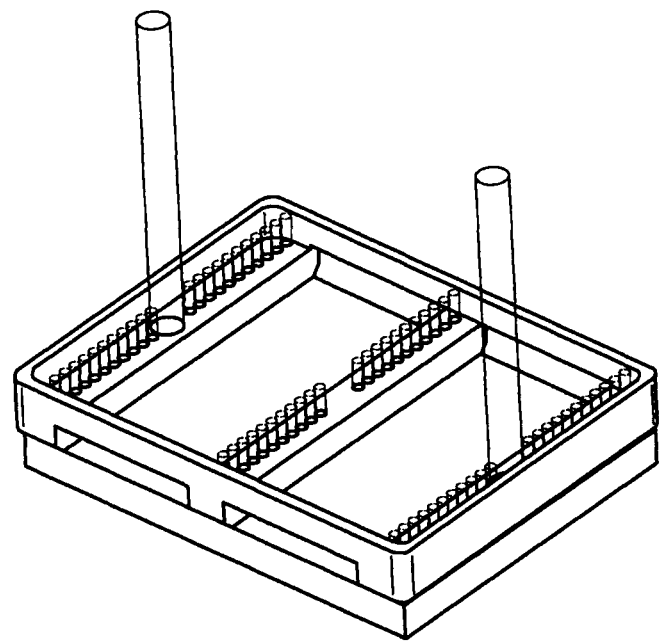
FIG. 14 depicts treatment fixtures for chemically treating chips and devices. (A) shows a single layer treatment fixture that can fit into a glass jar containing acid, base, or other chemical solutions. (B) shows the stacked fixture.
Figure 14B:
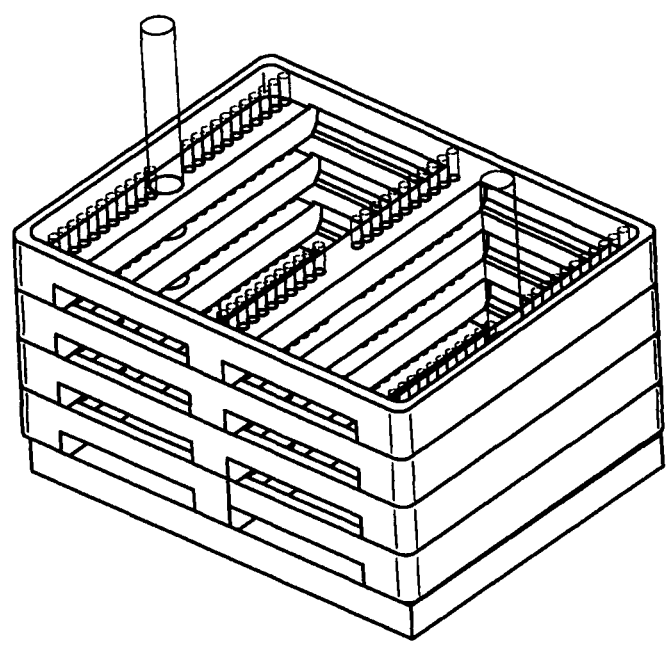

To facilitate batch treatment of glass biochips, we have used the treatment fixtures illustrated in FIG. 14. FIG. 14A shows a single layer treatment fixture that can fit into a glass jar containing acid, base, or other chemical solutions. FIG. 14B shows the stacked treatment fixture. The fixture is made of acid and base resistant materials such as cyclo-olefin polymer, polyphenylene ether/PPO, NORYL®, ZEONOR®, polytetrafluoroethylene, TEFLON™, etc. Glass pins are inserted and held in the holes, so that one piece of glass biochip to be treated is fit into one slot between two glass pins. Multiple layers of these racks can be stacked up to fit into one glass container. This design also allows mechanisms of moving fluid to occur such as that brought about by a rotary or reciprocal shaker or a magnetic stir bar.

In some aspects of the present invention, it can be preferable to store an ion transport measuring means that has been treated to have enhanced sealing capacity in an environment having decreased carbon dioxide relative to the ambient environment. This can preserve the enhanced electrical sealing properties of the ion transport measuring means. Such an environment can be, for example, water, a salt solution (including a buffered salt solution), acetone, a vacuum, or in the presence of one or more drying agents or desicants (for example, silica gel, $CaCl_2$ or NaOH) or under nitrogen or an inert gas. Where an ion transport measuring means or structure comprising an ion transport measuring means is stored in water or an aqueous solution, preferably the pH of the water or solution is greater than 4, more preferably greater than about 6, and more preferably yet greater than about 7. For example, an ion transport measuring means or a structure comprising an ion transport measuring means can be stored in a solution having a pH of approximately 8.

Glass chips that have been base treated and stored in water with neutral pH levels can maintain their enhanced sealability for as long as 10 months or longer. In addition, patch clamp chips bonded to plastic cartridges via adhesives such as UV-acrylic or UV-epoxy glues can be stored in neutral pH water for months without affecting the sealing properties.

We have also tested patch clamp biochips and cartridges that were stored in a dry environment with desiccant for 30 days. The chips were re-hydrated and tested for sealing. In one experiment, we got 6/7 seals for the dry-stored chips. Similarly, we stored mounted chips in dry environment and were able to obtain seals after a few weeks of storage.

Dehydration can, however, reduce the sealability of chemically treated chips. To improve the seal rate for dry-stored chips, NaOH, NaCl, $CaCl_2$ and other salt or basic solutions can be used to rejuvenate the chips out of dry storage to restore the sealability.

The present invention also includes methods of shipping or transporting ion transport measuring means modified by the methods of the present invention to have enhanced electric sealing properties and structures comprising ion transport means that have been modified using the methods of the present invention to have enhanced electric sealing properties. Such ion transport measuring means and structures comprising ion transport measuring means can be shipped or transported in closed containers that maintain the ion transport measuring means in conditions of low $CO_2$ or air. For example, the ion transport measuring means can be submerged in water, acetone, alcohol, buffered solutions, salt solutions, or under nitrogen ($N_2$) or inert gases (e.g., argon). Where the ion transport measuring means or structure comprising an ion transport measuring means is stored in water or an aqueous solution, preferably the pH of the water or solution is greater than 4, more preferably greater than about 6, and more preferably yet greater than about 7. For example, an ion transport measuring means or a structure comprising an ion transport measuring means can be shipped in a solution having a pH of approximately 8.

Figure 15A:
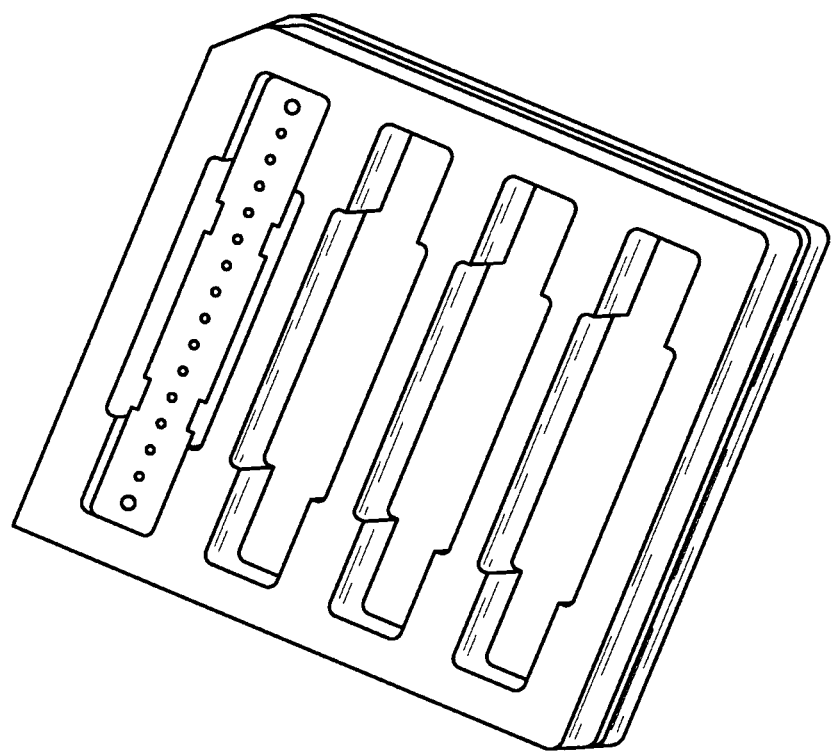
FIG. 15 shows a shipping fixture for cartridges of the present invention.
Figure 15B:
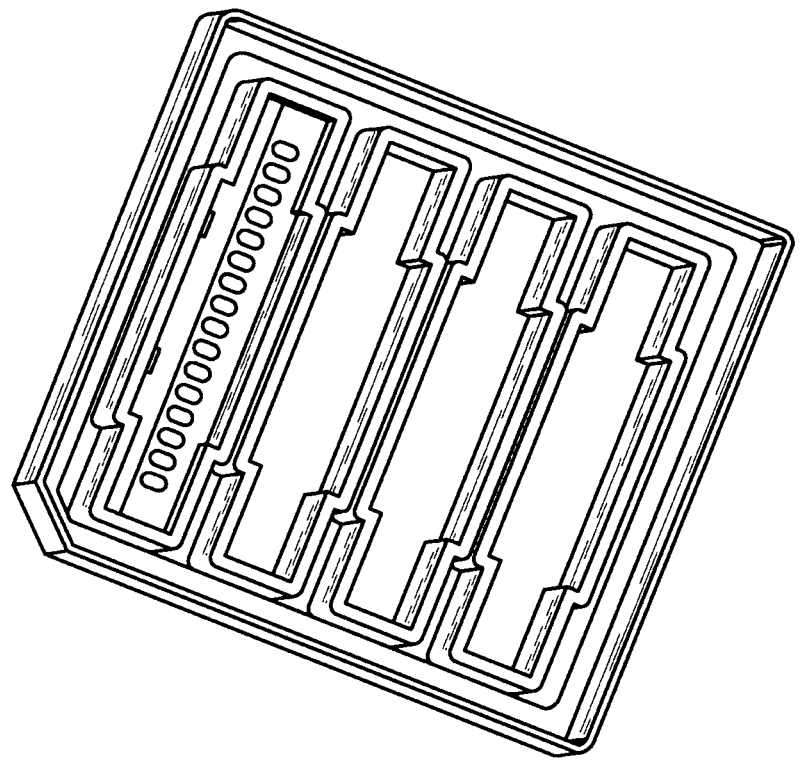

In one method of shipping a chip that has been treated to have enhanced sealing properties, the ion transport measuring devices comprising base-treated chips are shipped such that the chips are loaded up side down. The package for commercial shipments is designed to hold cartridges up side down, although the up side up configuration can also be used for shipping. To allow easy opening and facilitate automation in sequential loading of the devices onto apparatuses for use, a blister pack with film sealing is designed. As illustrated in the FIG. 15, a blister pack is provided in the form of a molded plastic frame with an opening on both top and bottom sides for film sealing. The sealing film or "lidstock" is a thin foil with temperature activated adhesive and an inert coating such as EVA (ethyl vinyl acetate) polymer. For wet (water) storage, the blister pack is first sealed from top (the opening side, flipped over, and the cartridges are loaded up side up. A preservative solution such as water is then injected into each well and the rest of the open space in each chamber of the package. Mother lidstock film is then used to seal the blister package from the bottom. The blister package can be optionally sterilized with radiation for long shelf life.

Figure 16A:
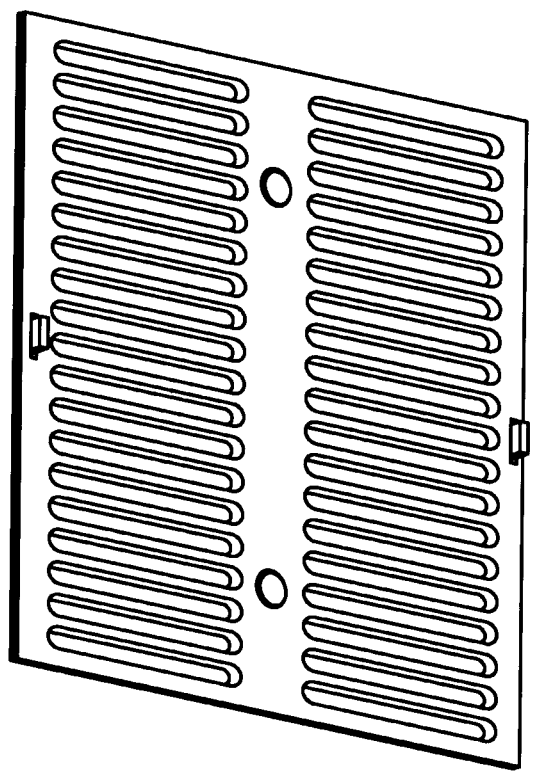
FIG. 16 shows a shipping fixture for chips of the present invention.
Figure 16B:
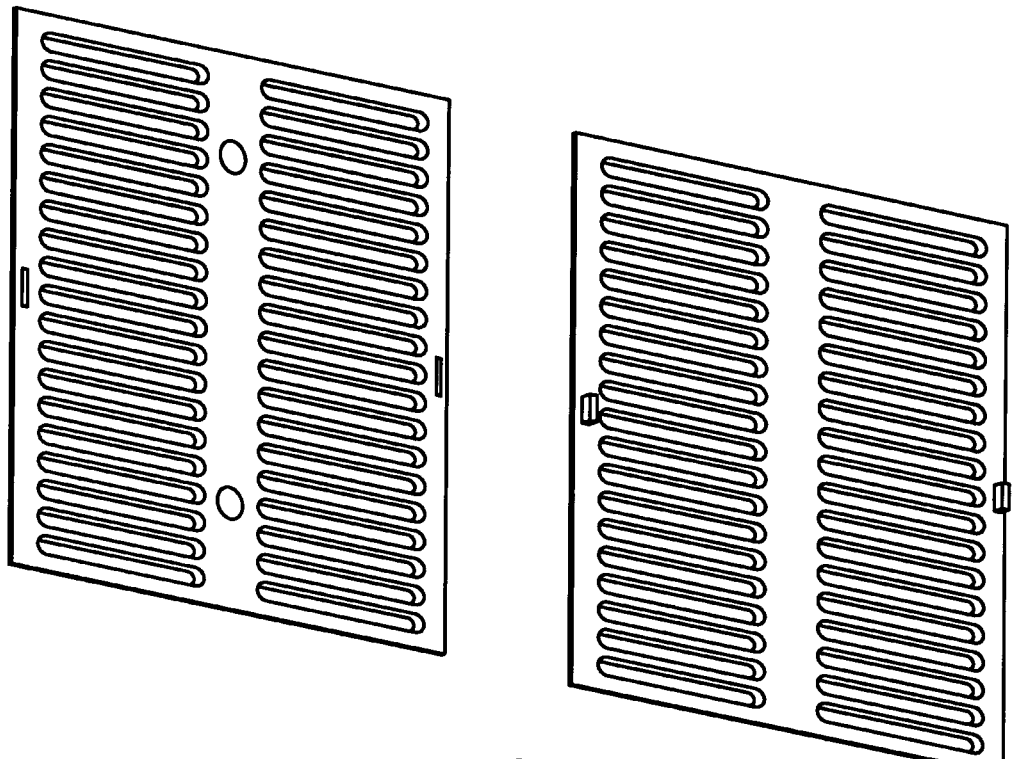

Yet another aspect is related to the shipping of laser processed glass chips as finished goods between to production processes, particularly if the two processes are in different production locations. The current invention describes a shipping fixture allowing individual placement and securing of laser-processed glass chips for shipment. The same fixture-chips assembly is then directly used for subsequent chemical processing. FIG. 16 is an illustration of the closed (left) and opened (right) shipping fixture. To withstand strong acid and base treatment, the shipping fixtures are molded with inert materials such as Noryl, Teflon, and Zeonor. A stack of these fixtures can be secured in one container for chemical treatments, or for shipping in aqueous solutions such as water. The liquid shipping provides buffering for vibrations during transportation, giving maximum protection of glass chips from being damaged.

The present invention also includes ion transport measuring means treated to have enhanced electrical sealing properties, such as by methods disclosed herein. The ion transport measuring means can be any ion transport measuring means, including those disclosed herein. The present invention also includes chips, pipettes, substrates, and cartridges, including those disclosed herein, comprising ion transport measuring means treated using the methods of the present invention to have enhanced electrical sealing properties.

The present invention also includes methods of using ion transport measuring means and structures comprising ion transport measuring means, such as biochips, to measure ion transport activity or functions of one or more particles, such as cells. The methods include: contacting a sample comprising at least one particle with an ion transport measuring means that has been modified to enhance the electrical seal of a particle or membrane with the ion transport measuring means, engaging at least one particle or at least one membrane on or at the modified ion transport measuring means, and measuring at least one ion transport function or property of the particle or membrane. The methods can be practices using the methods and devises disclosed herein. Generally, the methods of the present invention provide the following characteristics, but not all such characteristics are required such that some characteristics can be removed and others optionally added: 1) the introduction of particles into a chamber that includes a biochip of the present invention, 2) optionally positioning particles at or near an ion transport detection structure, 3) electronic sealing of the particle with the ion transport detection structure, and 4) performing ion transport recording. Methods known in the art and disclosed herein can be performed to measure ion transport functions and properties using modified ion transport measuring means of the present invention, such as surface-modified capillaries, pipette, and holes and apertures on biochips and channel structures.

Methods for Measuring the Surface Energy of the Surface of a Chemically Treated Ion Transport Measuring Biochip Another aspect of the current invention originated from the need for an inexpensive, fast, and sensitive method to measure surface energy on solid/liquid surface such as that of a chemically treated ion transport measurement biochip.

The method includes: dispensing a drop of defined volume of water or an aqueous solution on a surface, measuring the time it takes for the drop to evaporate; and estimating the relative or absolute surface energy of the surface based on the evaporation time, and the difference in evaporation time with respect to control samples.

The method can be used to determine the hydrophilicity of at least a portion of the surface of an ion transport measuring chip. In this case, a drop of water or aqueous solution is dispensed on the surface of a biochip comprising at least one ion transport measuring means, preferably a biochip that has been chemically treated to improve its electrical sealing properties. Evaporation is monitored, and the time elapsed between the time the drop contacts the chip and the time it has totally evaporated is measured. The elapsed time is used as an index for hydrophilicity. This index can be used to determine whether a chemically treated chip is within the optimal range for achieving high resistance electrical seals.

Evaporation can be monitored by diffraction, reflectance, or interference at the surface where the drop is deposited, or simply by visual observation. Evaporation can also be monitored by measuring the change in intensity or other physical or chemical properties of a dye or tracer agent that has been used to color or label the solution.

The invention uses the evaporation time of a liquid drop on a solid surface as a measure of the solid/liquid surface energy. The method has very low cost (an accurate liquid dispenser is the only equipment needed). It is also very fast and accurate for low surface energy systems.

The contact angle of a liquid drop on a solid surface is a measure of the surface energy, assuming constant liquid/air surface energy. Very low liquid/solid energy results in extremely small contact angles (close to 0 degrees). For that reason, contact angle measurements might not be a very sensitive method for low surface energy systems.

When a liquid drop with fixed volume is in contact with a solid surface, the air/liquid surface of the drop will be inversely proportional to the liquid/solid surface energy. Lower liquid/solid surface energy will result in bigger spreading of the drop. The evaporation of the drop will be proportional to the air/liquid surface area at any given moment. Thus the evaporation time will be proportional to the liquid/solid surface energy.

Using the drop evaporation technique, we have demonstrated that the evaporation time of a 0.25 microliters water drop is 2.5 times shorter for a highly hydrophilic glass surface (treated with base) compared to chemically untreated glass.

Methods of Manufacturing Chips for Ion Transport Measurement Devices

Yet another aspect of the present invention is a method of making a chip for ion transport measurement devices by fabricating a chip that comprises multiple rows of ion transport measuring holes and subsequently breaking the chip into discrete segments that comprise a subset of the total number of ion transport measuring holes.

In this method, a glass sheet is pre-processed with a laser to create patch clamp recording apertures, and preferably treated chemically to improve sealability as described in this application. The glass sheet has also been pre-scored with a laser to produce mark lines by which sets of holes can be separated from one another. Preferably, the mark lines are continuous slashes that go through the glass to a depth of about 50% or more of the thickness of the sheet.

Figure 17:
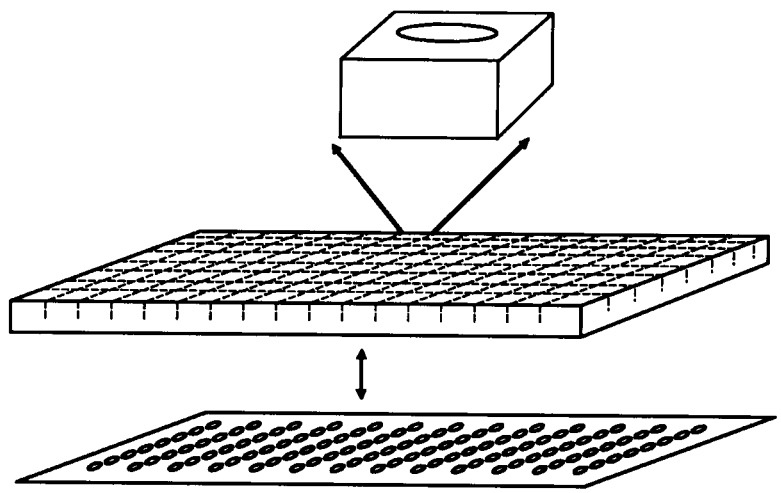
FIG. 17 depicts a glass chip with multiple ion transport units (below) that can be attached to a multichamber upper chamber piece. Cartridges with a smaller number of units (above) can be separated from the larger multicartridge unit.

In some preferred embodiments, an injection molded multi-unit well plate is bonded to the glass with adhesives so that each well of the plate is in register with one of the ion transport recording holes. Units comprising a portion of the multi-unit well plate and a portion of the glass chip are separated later by two metal plates closing in from two sides of the scored mark lines against the glass sheet, followed by bending of the bonded multi-well devices along with the metal plates and pulling of the segments away from each other (see FIG. 17).

This approach allows for low cost, automated assembly of single well or low-density arrays, such as 16-well planar patch clamp consumables. This method of manufacture improves automation, and reduces individual unit assembly time.

High Density Ion Transport Measurement Chips

Another aspect of the present invention is a high density, high throughput chip for ion transport measurement. A high density chip for ion transport measurement comprises multiple ion transport measuring holes. The invention also encompasses methods of making high-density consumable patch clamp arrays for ultra high throughput screening of ion transport function.

A high density chip for ion transport measurement comprises at least 24 ion transport measuring holes, preferably at least 48 ion transport measuring holes, and more preferably, at least 96 ion transport measuring holes. A high density, high throughput chip for ion transport measurement of the present invention can comprise at least 384 ion transport measuring holes, or at least 1536 ion transport measuring holes.

A high density ion transport measuring chip can be made using a silicon, glass, or silicon-on-insulator (SOI) wafer. The wafer is first wet-etched to create wells on the top surface, and then laser drilling is used to form the through holes. The dimensions of the wafer and the wells can vary, however, in preferred embodiments in which a 1536 well array is fabricated, the thickness of the wafer can range from about 0.1 micron to 10 millimeters, preferably from about 0.5 micron to 2 millimeters, depending on the substrate.

For wafers in the range of 1 millimeter thick, the etching tolerance should be within 2% if the through holes are approximately 30 microns in depth. This applies to Si wafers etched with alkaline solutions such as KOH or glass wafers etched with buffered HF. With SOI wafers, a defined thickness of $SiO_2$ covers the Si wafers, and etching of the wells through the Si side with KOH will stop at the $SiO_2$ interface. This way the thickness of the remaining material is consistent across the whole wafer, and even consistent among different batches of etched wafers. This permits laser drilling on these etched substrates to be more standardized, and reduces the time needed for laser measurement. In a preferred embodiment, the etched Si wells have a volume of approximately 2 microliters, assuming a footprint of approximately 2 millimeters x 2 millimeters for each well that extends as a prism or inverted pyramid shape through the Si substrate during anisotropic etching, leaving a distance of approximately 1 millimeter between adjacent wells.

In one design, the bottom of the chip can be sealed against a single common reservoir for measuring solution that is connected to a common reference electrode, while individual recording electrodes can be connected at the upper surface directly or via electrolyte bridges.

Alternatively, a structure with 1536 or any preferred number of individual isolated chambers can be sealed against the bottom of the 1536 or any preferred number of well plate so that each chamber is in register with a well. In some designs of this embodiment, the top surface of the SOI wafer can be a common electrode, with the conductivity of Si material being adequate to provide electrical connection; however, additional metal coating on the top surface (applied before etching as mask layer) can increase conductivity of the upper surface. Wet etching that creates the wells removes this metal coating from the wells themselves. Chemical treatment with acid and/or base can optionally be performed on the chip for improved sealing.

Another way to make a high density chip is to use very thin wafers made of glass, $SiO_2$, quartz, Si, PDMS, plastics, polymers, or other materials, or a thin sheet, with thickness between about 1 micron and about 1 millimeter. Laser drilling can be performed on such sheets to create through holes. A separate, "well plate" with 1536 or any preferred number of wells, manufactured by molding, etching, micro-machining or other processes, is then sealed against the holes via gluing or by using other bonding methods.

Figure 18:
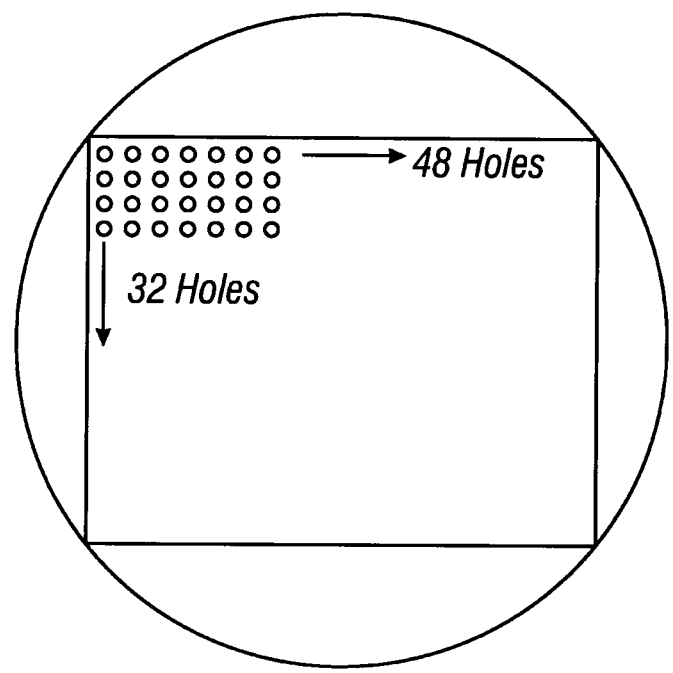
FIG. 18 depicts a high density array chip of the present invention.
Figure 19:
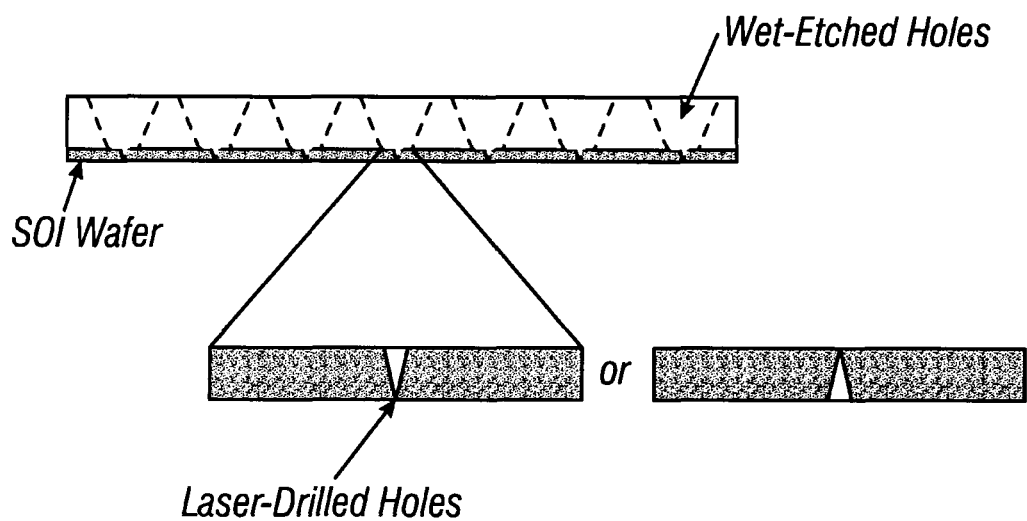
FIG. 19 depicts a cross sectional view of a high density array chip of the present invention.

FIG. 18 shows a high density array made on a Si, glass, or SOI wafer. It is made with a wet etch process, which creates the wells on the top surface, followed by laser drilling through the remaining of the material on the bottom of each of the wells (FIG. 19). The laser drilling of the holes can be from the front or back side of the chip.

For high density ion transport measuring chips, either a "standard" or inverted drilling configuration can be used as described herein.

Methods for Assembling Ion Transport Measurement Cartridges

Use of Adhesives

An ion transport measurement cartridge comprises one or more upper chamber pieces bonded via adhesive or other means to one or more ion transport measurement chips that have been treated to have enhanced electrical sealing properties which contain at least one microfabricated ion transport measurement aperture (hole), optionally but preferably drilled by a laser. The one or more ion transport measurement chips are optionally laser polished on the side of the small exit hole, and treated with a combination of acid and base treatment as described herein.

The present invention also includes a method of assembling ion transport measurement cartridges by bonding the ion transport measurement chip(s) with an upper chamber piece. In one embodiment, an ion transport measurement chip containing one or more ion transport measuring apertures is bonded to an upper chamber piece via a UV-activated adhesive, such that each well of the upper chamber piece is in register with a recording aperture on the ion transport measurement chip, and the smaller, exit holes from laser drilling of the ion transport measuring holes are exposed to the wells of the upper chamber piece.

To facilitate efficient assembly, a registration bump can preferably be molded on the bottom of the upper chamber piece so that when the biochip is pressed against the bump and shoulder at the bottom of the upper chamber piece, the recording apertures on the ion channel measurement chip are in register with the wells of the upper chamber piece.

Preferred UV adhesive include, but are not limited to, UV-epoxy, UV-acrylic, UV-silicone, and UV-PDMS.

Figure 20:
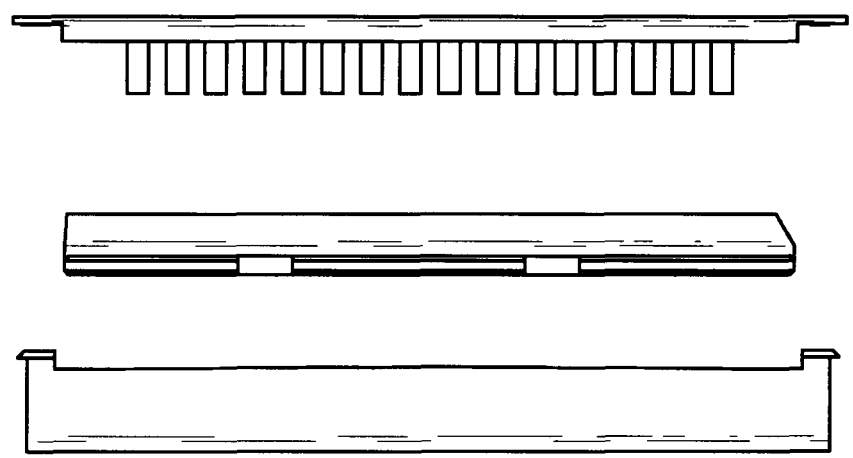
FIG. 20 depicts a side view of an exemplary mask that can be mounted to a cartridge being assembled.
Figure 21:
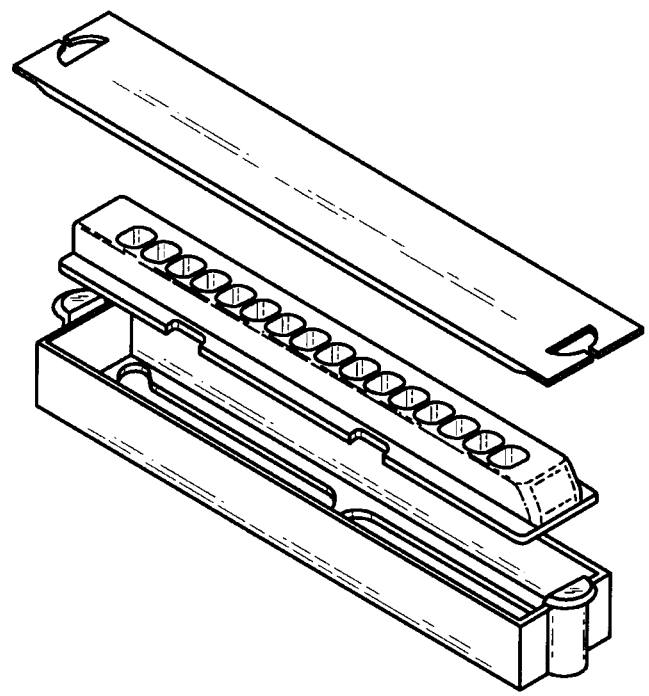
FIG. 21 depicts a view of an exemplary mask that can be mounted to a cartridge being assembled.
Figure 22:
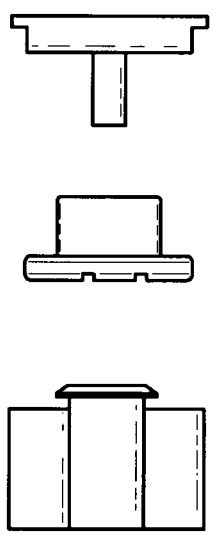
FIG. 22 depicts an isometric view of an exemplary mask that can be mounted to a cartridge being assembled. It contains a peg that masks UV and is not of transparent material, instead it is UV opaque. A transparent UV mask would look more like that in FIG. 50(B) but sits on top of the cartridge after removing the boxy part of the deposition mask shown in FIGS. 20-22. The deposition mask (the box) is used to deposit silver on the cartridge, then it's removed for assembly of the chip, and finally the UV mask is placed on the assembly during curing of the glue under the chip. The pegs of the deposition mask caps can be used during UV curing to also block UV coming from below a view of an exemplary UV-permeate glass mask that can be mounted to a cartridge being assembled.

The UV dose required to completely cure the UV adhesive can at times inactivate the treated surface of the chip. To avoid UV radiation to chip surface areas near the recording apertures where seals are to occur, a mask made of UV-permeate glass on which spots of size between 0.5 to 5 mm are provided by depositing a thin metal layer or paint (preferably a dark or black) layer. One such mask that can be mounted to the cartridge being assembled is illustrated in FIGS. 20, 21, and 22.

Pressure Mounting

Figure 23:
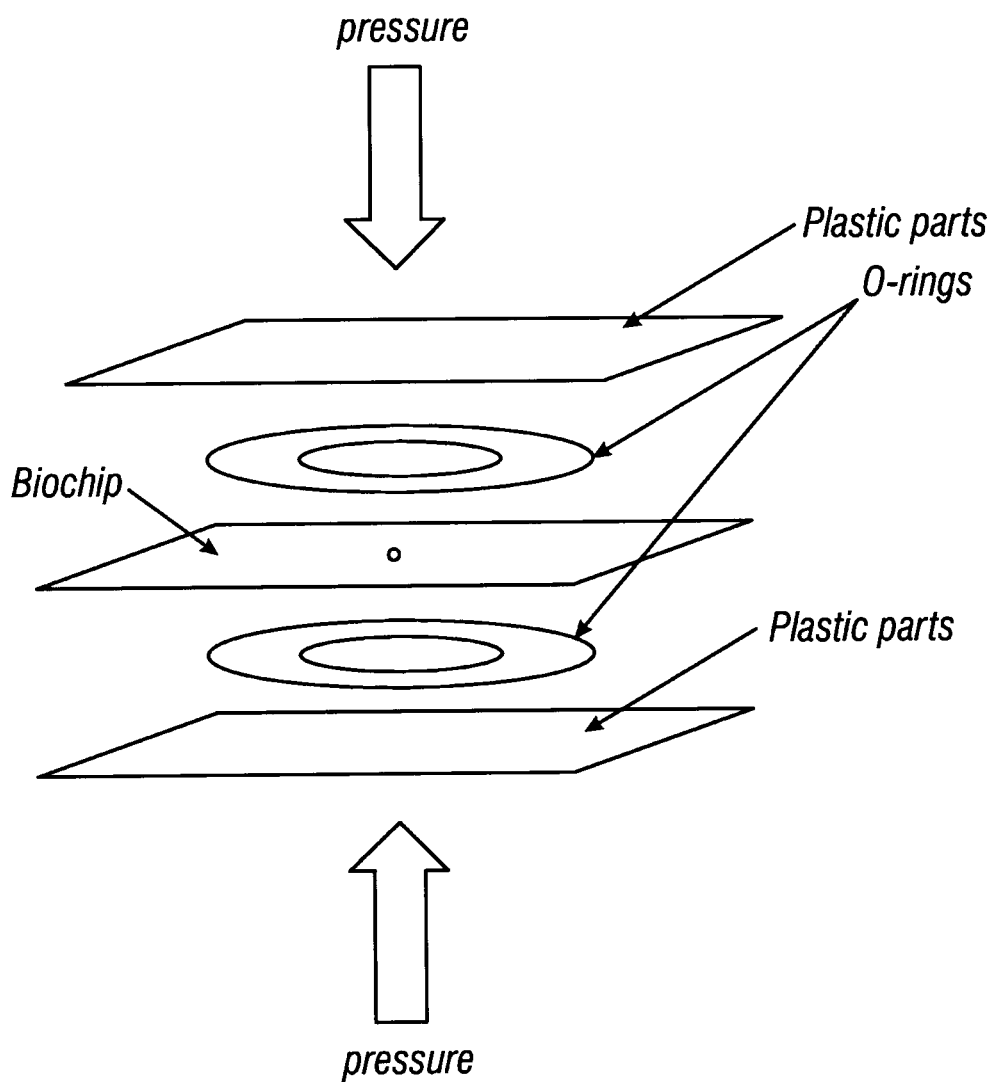
FIG. 23 depicts an exemplary sandwich-type pressure mounting procedure.

As an alternative to glue-based bonding, the upper chamber piece can be designed to allow an O-ring type of gasket made with PDMS to be used as seal cushion between the upper chamber piece and a biochip during a sandwich-type pressure mounting procedure (see FIG. 23).

Biochip Device for Ion Transport Measurement Comprising Fluidic Channel Chambers A further aspect of the present invention is a flow-through fluidic channel ion transport measuring device that can be part of a fully automated ion transport measuring device and apparatus. This device comprises a planar chip that comprises ion transport measuring holes, and upper and lower chambers on either side of the chip that are fluidic channels. One or more fluidic channels is positioned above the chip and one or more fluid channels is positioned below the chip. Apertures are positioned in the fluidic channels such that an ion transport measuring hole in the chip has access to an upper fluidic channel (serving as an upper chamber) and a lower fluidic channel (serving as a lower chamber).

A chip of a fluidic channel ion transport measuring device can have multiple ion transport measuring holes, and each of the holes can be in fluid communication with an upper fluidic channel and a lower fluidic channel. The upper fluidic channels can be connected with one another, when the lower fluidic channels are independent; or the upper fluidic channels can be independent while the lower fluidic channels can be connected with one another. In a yet another alternative, upper fluidic channels that service different ion transport measuring holes can be separate from one another and the lower fluidic channels that service different ion transport measuring holes can also be separate from one another.

In FIG. 24, a dashed line outlines the planar patch clamping chip, and upper and lower fluidic channels for an extracellular solution (ES) and intracellular solution (IS), are shown. The upper and lower channels are interfaced at a point where the recording aperture of the planar electrode resides. Separate fluidic pumps drive the flow of fluids through the two (upper and lower) fluidic channels. Recording and reference electrodes external to the fluidic patch clamp chip are connected via a electrolyte solution bridge to the top and bottom fluidic channels. A pressure source such as a pump with pressure controller that can generate both positive and negative pressures is linked to the lower fluidic channels. A multi-way valve is used to connect the lower fluidic channel to different solution reservoirs (IS1, IS2, etc), while a multi-way valve is used to connect the upper fluidic channel to cell reservoirs, compound plate, wash buffers and other solutions.

This design has several advantages. The external electrodes can be of multiple use, but replaceable. This reduces the cost of the biochip. The flow-through fluidics of both the upper and lower chambers minimizes the generation of air bubbles. Importantly, the closed fluidic channels allow for controlled delivery of low volume fluids without evaporation.

Methods of Preparing Cells for Ion Transport Measurement

In a further aspect of the present invention, methods for isolating attached cells for planar patch clamp electrophysiology are provided. Conventional cell isolation methods by non-enzymatic, trypsin, or reagent-based methods will not produce cells that are in optimal condition for high throughput electrophysiology. Typically cells produced by available protocols are either over-digested and tend to function less than optimally in planar patch clamp studies, or under-digested and resulting in cell clumps with the cell suspension. In addition, the cells isolated by conventional methods tend to have large amounts of debris which are a major source of contamination at the recording aperture. The current protocols are optimized for better cell health, single cell suspension, less debris and good patch clamp performance. The current protocols can be used to isolate cells for any purpose, particularly when cells in an optimal state of health and integrity are desirable, including purposes that are not related to electrophysiology studies.

This invention was developed to produce suspension CHO and HEK cells that give high quality patch clamp recording when used with chips and devices of the present invention. Parameters such as cell health, seal rate, Rm (membrane resistance), Ra (access resistance), stable whole cell access, and current density, were among the parameters optimized. The method includes: providing a population of attached cells, releasing the attached cells using a divalent cation solution, an enzyme-containing solution, or a combination thereof; washing the cells with a buffered cell-compatible salt solution; and filtering the cells to produce suspension cells that give high quality patch clamp recordings using ion transport measuring chips.

Enzyme-free Cell Preparation

Enzyme-free dissociation is desirable when an ion transport expressed on a cell surface can be digested by enzymatic methods, thereby causing a change in ion transport properties. Enzyme-free methods involve a dissociation buffer that is either Ca-chelator-based or non-$Ca^{++}$-chelator-based. The former is typically a solution of EDTA, while the latter can be calcium-free PBS. In such methods, attached cells grown on plates are first washed with calcium-free PBS, and then incubated with the dissociation buffer. In case of the calcium chelator-based dissociation, the dissociated cells must be washed at least once with a chelator-free solution before they can be used for ion transport measurement assays. The suspended cells are then passed through a filter, such as a filter having a pore size of from about 15 to 30 microns (this can vary depending on the type of cells and their average size).

Preparation of Cells Using Enzyme

In some methods (see Example 6), trypsin is used to dissociate attached cells. In such methods, the cells are typically rinsed with a solution devoid of divalent cations, and then briefly treated with trypsin. The trypsin digestion is stopped with a quench medium carefully designed to achieve the optimal divalent cation mix and concentration. In the methods provided herein, the suspended cells are then passed through a filter, such as a filter having a pore size of from about 15 to 30 microns (this can vary depending on the type of cells and their average size).

Another enzyme-based method uses a preparation commercially available from Innovative Cell Technology (San Diego). Accumax is an enzyme mix containing protease, collagenase, and DNAse. Example 6 provides a protocol for CHO cells using Accumax and filtration.

Some preferred methods of the present invention use a combination of enzyme-free dissociation buffer, Accumax reagent, and filtration to isolate high quality cells for patch clamping (see Example 6).

Pressure Profile Protocol for Ion Transport Measurement

The present invention also provides a pressure protocol control program logic that can be used by an apparatus for ion transport measurement to achieve a high-resistance electrical seal between a cell or particle and an ion transport measuring means on a chip of the present invention in a fully automated fashion. In this aspect, the program interfaces with a machine that can receive input from an apparatus and direct the apparatus to perform certain functions.

Typically it has required months to years of experience on the part of an experimenter to master the techniques required to achieve and maintain high quality seals during their experiments. It is an object of the invention to produce a pressure protocol for achieving and maintaining seal quality parameters for automated patch clamp systems. The present invention provides a logic that can direct mechanical and automated patch clamp sealing of particles and membranes.

The program logic includes: a protocol for providing feedback control of pressure applied to an ion transport measuring means of an ion transport measuring apparatus, comprising: steps that direct the production of positive pressure; steps that direct the production of negative pressure; steps that direct the sensing of pressure; and steps that direct the application of negative pressure in response to sensed pressure in the form of multiple multi-layer if-then and loop logic, in which the positive and negative pressure produced is generated through tubing that is in fluid communication with an ion transport measuring means of an apparatus, and in which negative pressure is sensed through tubing that is in fluid communication with an ion transport measuring means of an apparatus. Preferably, these steps are performed in a defined order that depends on the feedback the apparatus receives. Thus, the order of steps of the protocol can vary according to a defined script depending on whether a seal between a particle and the ion transport measuring means is achieved during the operation of the program, and the properties of the seal achieved.

An apparatus for ion transport measurement that is controlled at least in part by the pressure program preferably comprises: at least one ion transport measurement device comprising two or more ion transport units (each comprising at least a portion of a biochip that has an ion transport measuring means, at least a portion of an upper chamber, and at least a portion of a lower chamber, and is in electrical contact with at least one recording electrode and at least one reference electrode), tubing that connects to the device and is in fluid communication with the two or more ion transport measuring means of an apparatus, and pumps or other means for producing pressure through the tubing. Preferably, the apparatus is fully automated, and comprises means for delivering cells to upper chambers (such means can comprise tubing, syringe-type injection pumps, fluid transfer devices such as one or more automated fluid dispensers) and means for delivering solutions to lower chambers (such means can comprise tubing, syringe-type injection pumps).

Preferably, in addition to promoting and maintaining a high resistance seal, the pressure protocol program can also direct the rupture of a cell or membrane delineated particle that is sealed to an ion transport measuring means. Such rupture can be by the application of pressure after sealing, and can be used to achieve whole cell access.

In operation, the program directs the apparatus to generate a positive pressure in the range of 50 Torr to 2000 Torr, preferably between 500 and 1000 Ton, to purge any blockage of the recording holes. Then the program directs the apparatus to generate a positive holding pressure between 0.1 to 50 Torr, preferably between 1 to 20 Torr to keep the recording aperture of an ion transport measuring chip clear of debris during the addition of cells to the upper chamber. After cell addition, the program directs the release of pressure and holds the pressure at null long enough to allow cells to approximate the aperture. The program then directs a negative pressure to be applied draw a cell onto (and partly into) the ion transport recording aperture for landing and the formation of a gigaohm seal. Additional pressure steps as described Example 7 may be required for achieving gigaohm seals if a seal does not occur upon cell landing.

To achieve whole-cell access, negative pressure is increased in progressive steps until the electrical parameters indicate the achievement of whole-cell access. Alternatively, the program can direct the application of a negative pressure to a "sealed" cell that is insufficient to gain whole-cell access, and then use a electric "zap" method to disrupt the membrane patch within the aperture and thereby achieve whole-cell access. Upon achieving whole-cell access the pressure is released either immediately, or held for a few seconds then released, depending on the cell quality. Finally, during whole-cell access procedures, the seal quality could be improved after access has been achieved, then held at optimal parameters by a more complex pressure protocol.

The pressure protocol involves many branch-points or "decisions" based upon feedback from the seal parameters. It is easiest to describe the protocol as a series of steps in programming logic. An example of such logic (underlined items are user-defined parameters) is provided as Example 7.

Novel Ion Transport Measuring Biochip Designs

The present invention also includes novel methods of making high density and/or multiplex ion transport measuring biochips and biochips made by these methods. These devices can be used to record ion transport activity of more than one particle or cell simultaneously or in rapid sequence. In preferred aspects, the ion transport measuring biochips and biochips made by these methods are designed to be high density the ion transport measuring biochips. By "high density" is meant that the chips comprise a large number of ion transport measuring means. Typically, the ion transport measuring means are holes through the surface of the biochip, and a high density transport measuring biochip has multiple ion transport recording sites via multiple holes. In this way, multiple assays can be conducted simultaneously, or in rapid sequence, allowing for high-throughput ion transport measuring assays that can facilitate, for example, compound assays.

As used herein, "high throughput" means high quantity of independent data collected in a defined period of time. For example, 48 or more assays that can be conducted within a short time span where multiple assays are initiated simultaneously or in rapid succession, then share experimental time as parallel or multiplexed recordings, and ten completed simultaneously or independently but in parallel (less than one hour from loading of cells to completing ion channel recording, preferably, less than one half hour from loading of cells to completing ion channel recording, and more preferably, less than fifteen minutes from loading of cells to completing ion channel recording). More preferably, more than 96 high throughput ion transport measurements can be completed in less than one half hour, and more preferably yet, the high density ion transport measuring devices of the present invention are capable of performing more than 100 ion transport assays within one half hour or less. In some preferred aspects of these embodiments, high density ion transport measuring devices can perform hundreds or over one thousand assays within one half hour or less. For example, in some preferred aspects of high density ion transport measuring devices described herein, the devices can be designed to perform 384 assays or, for example, 1536 assays, within one half hour or less. For another example, 48 or more assays that can be conducted within a time span during which continuous and repetitive data sampling are performed for kinetic studies with high temporal resolution. In another example, multiple lower density assays, such as 16-assay devices, may be utilized in parallel to result in a high density assay.

While the devices herein can be described as high-throughput, the designs are not limited to high throughput uses and can be used for any number of ion transport assays, in assays that can last from seconds to several hours.

MCP-Based Chip

One aspect of the present invention is an ion transport measuring device that comprises a microchannel plate (MCP). Microchannel glass plates that comprise an array of microchannels and their fabrication are known in the art of electronics and optics for their use as electron multipliers and photomultipliers. Some aspects of their fabrication and use are described in Wiza (1979) Microchannel Plate Detectors Nuclear Instruments and Methods 162: 587-601. In brief, they can be made by providing glass fibers that have a core glass and a cladding that comprises lead glass. The fibers are arranged together side-by-side in a desirable configuration, drawn, surrounded by a glass envelope, and fused to produce a boule. The boule can be sliced (cutting perpendicular to the fiber lengths) to produce slices that are cross-sections of the boules. These slices can be finished, for example, by polishing. The cores of the glass fibers are then chemically etched away, to form the microchannel plate.

An MCP made for use as part of an ion transport measuring device can be made by fusing from 2 to over 1,000 glass fibers. An MCP ion transport measuring chip can, for example, be a high-density ion transport measuring chip that comprises 48 or more microchannels that serve as ion transport measuring holes, and preferably, 96 or more microchannels that serve as ion transport measuring holes. The core of the fibers (the portion made of etchable glass) used to make an MCP chip can be as wide as 40 microns in diameter (for chips used for ion transport assays using large cells, such as oocytes) but preferably are from 0.2 to 8 microns in diameter, and are more preferably from 0.5 to 5 microns in diameter, even more preferably from 0.5 to 3 microns in diameter, and most preferably about 2 microns in diameter. The thickness of the lead glass cladding around the core can vary depending on the desired spacing of the resulting ion transport measuring holes. The length of the fibers used in making an MCP ion transport measuring chip are not limiting, and can be of any feasible length. Preferably, after fusing the glass fibers, the boule is sliced into sections that are from about 5 microns to 5000 microns thick, most preferably from about 10 to about 50 microns thick.

The core glass fibers can be randomly arranged or configured into a pattern to make the boule.

Figure 35A:
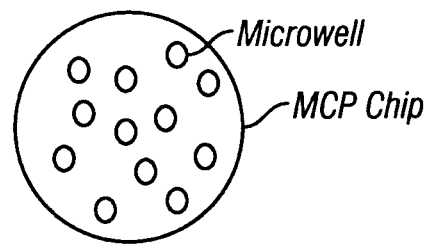
FIG. 35 depicts one embodiment of an ion transport measuring chip made from an MCP. A) Top view. B) cross-sectional view showing etched microwells and through-holes.
Figure 35B:
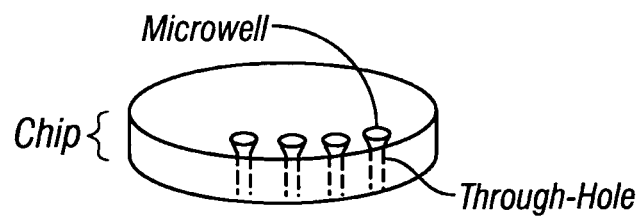

In one design, depicted in FIG. 35, the area surrounding the ion transport measuring holes on the upper side of the MCP chip can be chemically wet-etched to produce microwells that can be used as upper chambers. These upper chambers can be used for measuring solution, cells or particles, and test compounds. The MCP chip can be bonded to a bottom piece that comprises one or more lower chambers. The MCP plate can also be bonded to an upper piece that comprises the ES chambers.

The surface of the MCP chip can be chemically treated, such as using methods disclosed herein, to enhance the electrical seal of a particle or membrane with the ion transport measuring means. The entire MCP chip or a portion thereof can be treated to enhance its electrical sealing properties. Preferably, at least a portion of the surface of the MCP chip to which cells or particles are to be sealed is treated. One or both surfaces, or one or more portions of one or both surfaces, of the MCP chip can also be coated, or one or more portions of one or both surfaces, with one or more materials that can increase its sealing properties. In some embodiments, one or both surfaces, or one or more portions of one or both surfaces, of the MCP chip can be coated with one or more hydrophobic materials that can be used to promote fluidic isolation of individual microwells of the MCP chip. Designs in which hydrophobic surfaces are used to promote fluidic isolation of individual microwells of a chip are further described as Aspect 19 of this application (below).

In designs in which the bottom piece forms individual lower chambers, reference electrodes can be within or electrically connected with the upper wells and recording electrodes can be within or electrically connected with the lower wells for ion transport measurement, or recording electrodes can be within or electrically connected with the upper wells and reference electrodes can be within or electrically connected with the lower wells for ion transport measurement.

In one possible design involving etched microwells on the upper surface, a common reference electrode can connect all of the upper microwells. The electrode, which can be a conductive material such as metal, can follow paths along the top surface of the MCP chip and contact measuring solution only where it contacts the interior of the microwells. The electrode can optionally be coated with a nonconductive material where it traverses the chip surface, and be exposed where it contacts the interior of the wells.

Where a device comprising an MCP chip is configured to have a common electrode that contacts multiple lower wells of the device, the same design can be used.

In designs in which the bottom piece forms a bottom chamber that contacts more than one ion transport measuring hole, the bottom chamber preferably comprises or is in electrical contact with a reference electrode, and individual upper chambers comprise individual recording electrodes. Alternatively, the bottom piece can comprise multiple lower chambers with individual recording electrodes, and the device has a common upper chamber with a reference electrode. In this embodiment, compounds can be added using compound delivery mechanisms such as, for example, fluid block delivery, chamber separators, or other mechanisms described herein.

In an alternative design for an ion transport measuring device that comprises an MCP chip, upper chambers can be constructed by attaching a manufactured piece that comprises well openings such that each well of the upper chamber piece aligns with one of the ion transport measuring holes (the microchannels of the MCP). Individual upper chambers preferably have a volume of from about 0.5 microliters to about 5 milliliters, and more preferably from about 2 microliters and about 2 milliliters, and more preferably yet between about 10 microliters and about 0.5 milliliter. The upper chamber piece can be irreversibly or reversibly attached to the MCP ion transport measuring chip using gaskets, clamps, adhesives, welding, or other means. The upper chamber piece can comprise glass, ceramics, coated metals, or (preferably) plastics or polymers. In one preferred embodiment, the upper chamber piece comprises a separate MCP. In this design, the glass fibers used to make the upper chamber piece MCP are of a wider diameter than those used to make the ion transport measuring chip MCP. The glass fibers used to make the upper chamber piece MCP also comprise a cladding of sufficient thickness to provide chamber spacing over the ion transport measuring holes of the ion transport measuring chip MCP. Conduits can connect to the wells of the upper chamber piece for the addition of solutions, cells, or compounds. Alternatively, a fluid dispensing device can interface with the upper chamber wells to dispense solutions, cells, or compounds.

A lower chamber piece can also comprise multiple chambers that connect to individual ion transport holes of the MCP chip. The lower chamber piece can be constructed by attaching a manufactured piece that comprises wells spaced such that each well of the lower chamber piece aligns with one of the ion transport measuring holes (the microchannels of the MCP). The lower chamber piece can be irreversibly or reversibly attached to the MCP ion transport measuring chip using gaskets, clamps, adhesives, welding, or other means. The upper chamber piece can comprise glass, ceramics, coated metals, or (preferably) plastics or polymers. In one embodiment, the lower chamber piece comprises a separate MCP. In this design, the glass fibers used to make the upper chamber piece MCP are of a wider diameter than those used to make the ion transport measuring chip MCP. The glass fibers used to make the lower chamber piece MCP also comprise a cladding of sufficient thickness to provide chamber spacing over the ion transport measuring holes of the ion transport measuring chip MCP. Conduits can connect to the wells of the lower chamber piece for the addition of solutions, and allowing pneumatic control.

In using devices having individual upper chambers and individual lower chambers recording electrodes (or connections to recording electrodes) can be provided in or attached to upper chambers, and reference electrodes (or connections to reference electrodes) can be provided in or attached to lower chambers. In the alternative, recording electrodes (or connections to recording electrodes) can be provided in or attached to lower chambers, and reference electrodes (or connections to reference electrodes) can be provided in or attached to upper chambers.

In some preferred embodiments, however, a device that comprises an MCP ion transport measuring chip can have a single lower chamber that accesses all ion transport measuring holes of the MCP chip. In this case, the lower chamber can also comprise ceramics, coated metals, glass, plastics, or polymers, and preferably connects to conduits that connect to pressure sources and can deliver and remove fluids to and from the chamber. Pressure control may be performed from either bottom chambers or upper chambers, or both. In these embodiments, the lower chamber preferably comprises or is in electrical connection with a reference electrode during use of the device, and each upper chamber comprises or is in electrical connection with a recording electrode during use of the device.

In some other preferred embodiments, a device that comprises an MCP ion transport measuring chip can have a single upper chamber that accesses all ion transport measuring holes of the MCP chip. In this case, the upper chamber can also comprise ceramics, coated metals, glass, plastics, or polymers and it preferably comprises or is in electrical connection with a reference electrode during use of the devices. In this case each lower chamber comprises or is in electrical connection with a recording electrode during use of the device. Pressure control may be performed from either bottom chambers or upper chambers or both.

The present invention comprises ion transport measuring devices comprising an MCP chip having greater than two through holes, and at least one upper chamber. Preferably an ion transport measuring device comprising an MCP chip has multiple upper chambers that are reversibly or irreversibly attached to the MCP chip. Preferably an ion transport measuring device that comprises an MCP chip can be reversibly or irreversibly attached to at least one lower chamber. The present invention also comprises ion transport measuring devices comprising an MCP chip having multiple microchannel through holes, and an MCP chip having multiple microchannel upper chambers.

The present invention also comprises methods of using MCP chips for measuring ion transport activity and properties, as well as for other assays.

Chip with Hydrophobic Surface Coating

Another aspect of the present invention is a hydrophobic ion transport measuring biochip that comprises ion transport measuring means in the form of holes having counterbores, where the counterbores are microwell upper chambers, and where the surface of the biochip has a hydrophobic surface.

A hydrophobic ion transport measuring biochip of the present invention can have any number of holes, from 1 to more than one thousand. In preferred embodiments, a hydrophobic ion transport measuring biochip is high-density, and can be used for high throughput screening (such as, but not limited to, compound screening), and has 384 or more ion transport measuring holes. In some embodiments, a hydrophobic ion transport measuring biochip can have 1536 or more ion transport measuring holes.

A hydrophobic chip having microwell upper chambers can be made by providing a suitable substrate, such but not limited to a glass, quartz, silicon, silicon dioxide, or one or more polymers, and coating the substrate with a hydrophobic material. Suitable materials for providing a hydrophobic coating include plastics and polymers, such as, for example, polyethylene, polyacrylate, polypropylene, polystyrene, or polysiloxane. After coating the chip, two or more holes are made, such as by laser drilling into the chip. The laser drilling has the effect of melting and burning the polymer in the area surrounding the drilled hole, provided an uncoated (hydrophilic) surface in the area where a cell (or other particle) can seal. Preferably, a counterbore is also drilled into the chip, where the counterbore can serve as a microwell on the upper surface of the chip.

Figure 36:
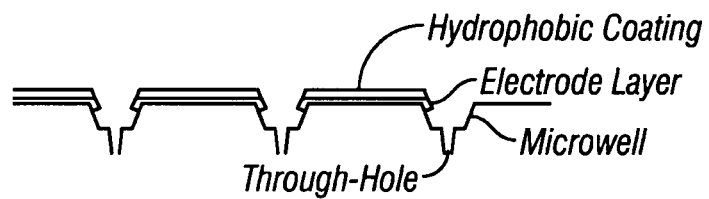
FIG. 36 depicts a cross-sectional view of a portion of a chip having a hydrophobic coating and microwells.

This design provides upper microwells (made by laser drilling) that are in liquid fluid isolation from one another, as the hydrophobic surface between wells repels aqueous liquids such as buffers and measuring solutions. The ion transport holes and areas immediately surrounding them (such as counterbore microwells) have hydrophilic surfaces that have been exposed by the laser drilling and therefore will retain buffers and solutions. The upper microwells can be connected to a common reference electrode that is coated with a non-conducting (and hydrophobic) material, such as a plastic or polymer used to coat the chip surface and traverses the surfaces of the chip. The electrode can be uncoated where it contacts the microwells, so that the microwells are in electric communication without the possibility of solution exchange or mixing between wells (see FIG. 36).

One preferred embodiment of the electrode on the hydrophobic chip is a metallized layer on the substrate coated by deposition, growing, condensing, or other means. The metallized layer can be removed at and near the recording sites by laser shots or masking. The hydrophobic layer is then coated on top of the metallized layer to allow for fluidic liquid separation between two adjacent recoding sites, leaving a ring of metallized layer uncovered near the recording sites to allow for electrical connection of each recording sites (in form of a hole, or a hole and a microwell) with the metallized layer which services as a reference electrode. The metallized layer can be made of any conductive material or materials including metals, non-metals, metal derivatives, or combinations thereof.

As alternatives, individual recording electrodes can also be physically or electrically connected (such as through electrolyte bridges) to each of the upper chamber microwells. In these designs, there can be individual or common lower chambers that engage the chip, and the one or more lower chambers comprise or are electrically connected to one or more reference electrodes.

Where the coating material is resistant to treatment chemicals, such as base and/or acid, the surface of the hole on the hydrophobic chip can be chemically treated, such as by using methods described herein, to enhance the electrical sealing properties of the chip.

The present invention also includes methods of making the hydrophobic chip described herein, devices comprising the hydrophobic chip described herein, where the devices can employ any feasible lower chamber, electrode, fluidic and pneumatic designs. The present invention also includes methods of using a hydrophobic ion channel measuring chip to measure ion channel activity or properties of one or more cells or particles.

Flexible Ion Transport Measurement (ITM) Chip

Another aspect of the present invention is a method of making a flexible ion transport measuring biochip that comprises a flexible sheet of material, preferably coated with glass, comprising multiple ion transport measuring holes. The flexible sheet of material can be wound around a spool and unwound to form either a curved or an essentially flat surface for ion transport measurement. Alternatively, the flexible sheet of material can be curved to form a tube, on the surface of which ion transport measurement assays can be performed.

The method comprises: providing a substrate that comprises a sheet of flexible material; creating (for example, by laser drilling, chemical etching, micromachining, molding, etc) at least two holes in the substrate that extend through the substrate; and optionally coating the substrate with $SiO_2$ or glass to provide an ITM chip.

The substrate can comprise any material that can be provided as a thin sheet (for example, of within the range of between 5 and 5000 microns in thickness) and has a flexibility that allows the sheet to be curved completely around (such as to make a tube) yet is hard and rigid enough to allow manufacture of ion transport measuring holes through the substrate (that is, holes of a diameter within the range of from about 0.2 to about 8 microns in diameter, although larger diameters can be used depending on the cell type to be assayed). For example, rubber, plastics, polymers or other flexible sheet materials can be used. One such material is polyimide or Kapton. Kapton sheets of from about 5 to 5000 microns in thickness, preferably from about 10 to about 200 microns in thickness, can be laser drilled to produce through holes of within the range of from about about 0.2 to about 8 microns in diameter, preferably from about 0.5 to 5 microns in diameter, and more preferably from about 0.5 to about 3 microns in diameter. Counterbores that can be used as microwells can also optionally be drilled into the polyimide sheet, as described herein. From 2 to over 50,000,000 holes can be drilled into a single polyimide sheet, depending on the application, which can be further rolled around a spool. For example, where a flexible biochip is to be used as a "chip roll" in which section of the flexible biochip are used to be used sequentially, the sheet can comprise a very large number of holes, a subset of which are to be used in any given assay.

Before or after laser drilling of holes in the flexible substrate, the substrate is preferably treated or coated with a material that allows for efficient and high-resistance sealing of particles such as cells to the ion transport measuring holes. The treatment or coating can comprise any material that promotes high-resistance sealing of particles such as cells to the ion transport measuring holes of the chip, and can comprise organic or inorganic molecules, synthetic molecules (for example, polymers) or naturally occurring ones, in liquid or non-liquid form. The coated surface can be hydrophobic or hydrophilic, charged or uncharged, and can be linked to the substrate covalently or non-covalently. In one preferred embodiment, the substrate is coated with glass.

If the coating is a naturally rigid material, such as glass, the coating should be thin enough, or physio-chemically altered to permit curving of the coated flexible sheet. The coating thickness can range from a single molecule layer to several micrometer. The optimal thickness for the degree of curvature that is desirable (depending on the application) can be determined empirically. The degree of curvature required in the use of the device that comprises the flexible biochip can also be adjusted (for example, by adjusting spool diameter, if the substrate is to be wound around a spool, or by adjusting tube diameter, if the substrate is to form a tube structure) to accommodate the coating if necessary.

The coating can be applied in any appropriate way: vapor deposition, dipping, soaking, direct application, spraying, "painting", chemical grafting etc. If the coating is a polymer, in some cases polymerization can be promoted on the substrate surface. The coating can be adhered to the substrate by absorption or chemical bonding. A glass coating can be applied, for example, by vapor deposition (if the substrate material is resistant to the heat required, or by allowing solgel (hydrolyzed siloxane) to polymerize to glass as it dehydrates on the substrate surface.

The surface of the flexible chip or portions thereof can optionally be chemically treated, such as by using the methods described herein, to improve the electrical sealing properties of the chip.

Figure 37A:
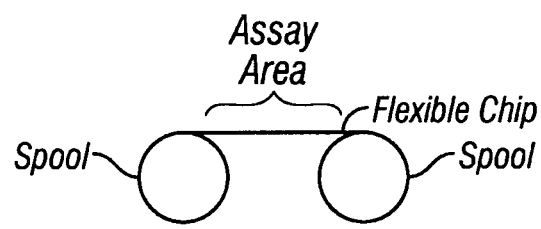
FIG. 37 depicts two embodiments of a flexible chip of the present invention. A) the chip extends between two spools, with the assay area localized to the extended portion of the chip between them. B) the assay area of the chip corresponds to a portion chip that curves over a spool, which can comprise or engage lower chambers for ion transport assays.
Figure 37B:
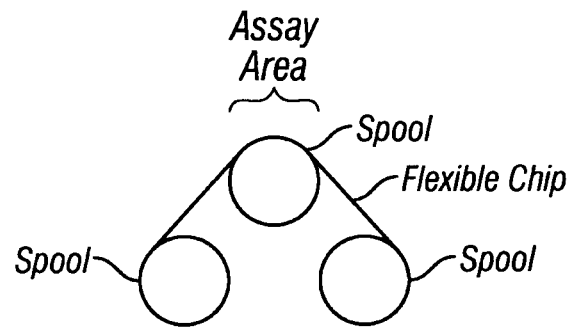

In one aspect of this embodiment of the present invention, an ion transport measuring device can be made using a flexible ion transport measuring biochip of the present invention that is wound around a spool (see FIG. 37). In this embodiment, the leading edge of the flexible biochip extends from the spool to either a second spool, or to a guide into which is inserted. The second spool or guide is positioned at a particular distance from the first spool such that an expanse of the flexible biochip is extended to be used for ion transport assays. The extended portion of the flexible biochip can be essentially flat or somewhat curved. Preferably, the extended portion of the flexible biochip comprises multiple ion transport measuring holes that matches the number of wells in multi-well plate for compound testing. Preferably, the extended portion of the flexible biochip comprises at least 12 ion transport measuring holes, more preferably, at least 24 ion transport measuring holes, even more preferably, at least 48 ion transport measuring holes, and yet more preferably, at least 96 ion transport measuring holes. For example, the extended portion of the flexible biochip can comprise 384 or 1536 ion transport measuring holes.

The present invention includes flexible ion transport measuring biochips made using these methods, and devices that include flexible ion transport measuring biochips.

An upper chamber piece can engage the upper side of the flexible biochip and a lower chamber piece can engage the lower side of the flexible biochip. In preferred aspects of these embodiments, the upper and lower chamber pieces are reusable, and the flexible biochip is single-use. In these aspects, the upper and lower chamber pieces reversibly engage the flexible biochip for ion transport assays. Upon completion of a set of assays, the upper and lower chamber pieces disengage and move away from the flexible biochip, a new section of the flexible biochip is unwound from the spool as the leading edge is pulled through guides and the old portion is optionally wound on a second spool, similar to camera film winding (in an alternative the used section can be pulled through guides and clipped off, similar to use of a tape dispenser). The new section of the flexible biochip that is unwound from the spool is to be used in the subsequent assay. The upper chamber piece and lower chamber piece (preferably one or both is reusable, but this is not a requirement of the present invention) now move to engage the new extended portion of the flexible biochip.

In aspects in which the extended portion of the flexible biochip is somewhat curved, such as by curving against the surface of another, "chamber spool" (FIG. 37B), in which the contact surface of the spool also comprises the upper or lower chamber pieces, the upper and lower chamber pieces can be adapted to fit a curved biochip.

The upper chamber piece, the lower chamber piece, or both can be part of a chamber "wheel" in which multiple chamber pieces, each of which is used in performing a set of assays, can sequentially engage the flexible biochip. For example, a first set of assays can be performed using the first extended portion of the flexible biochip and a first lower chamber piece that is part of a chamber wheel that can rotate below the surface of the flexible biochip. Upon completion of the first set of assays, the used portion of the flexible biochip is pulled away from the wheel as a new portion of flexible biochip comes into proximity with the chamber wheel. During this period of time, the chamber wheel rotates so that the used chamber piece moves away from the assay site, and a new chamber piece also attached to the wheel engages the new extended portion of flexible biochip at the assay site.

Various upper and lower chamber configurations can be combined with the flexible biochip. For example, an upper chamber piece that engages the flexible biochip can have multiple upper chambers, such that each ion transport measuring hole is associated with a single upper chamber, and a lower chamber piece can also have multiple lower chambers, such that each ion transport measuring hole is associated with a single lower chamber. It is also possible to have a single lower chamber that accesses all of the ion transport holes used in an assay and multiple individual upper chambers. In other cases a single upper chamber that accesses all of the ion transport holes used in an assay and multiple individual lower chambers. Different chamber arrangements can have different electrode connections and connections to fluidic and pneumatic channels.

In one preferred design, both the upper chamber piece and the lower chamber piece comprise multiple chambers that align with the extended portion of the flexible biochip such that each ion transport measuring hole is associated with a single upper chamber and a single lower chamber. In this design, cells, extracellular solutions, and compounds can be added to the top chambers either by individual conduits or by fluid dispensing systems. Pneumatic conduits connect with the lower chambers to produce high resistance seals. Electrodes can be provided in the reusable chamber pieces, or can be provided in fluid conduits or as part of the ion transport recording machinery that can be brought into electrical contact with the chambers through electrolyte bridges.

In yet another aspect of a flexible ion transport measurement biochip, the flexible biochip can form an at least partially tubular structure. The flexible biochip can form at least a portion of a tube. Where the flexible biochip does not form the complete circumference of a tube, the same flexible substrate material or a different material can form the remainder of the circumference of the tube. Where the flexible biochip does not form the complete circumference of a tube, the same flexible substrate material or a different material can form a basin or bottom surface of a trough-like structure that is continuous with the curved chip but can be at least in part flat or have a lesser degree of curvature. In this embodiment, the interior of the "tube" can form a single intracellular chamber, and an "upper" chamber piece can fit around the tube to provide upper chambers. In this aspect, cells, measuring solution (such as extracellular solution) and compounds can be added to individual upper chambers that can also contain, or be in electrical connection with, recording electrodes. The inner tube chamber can be a common chamber that has fluidic and pneumatic connections for providing measuring solutions and applying pressure for sealing of cells or particles to ion transport measuring holes. Preferably in this embodiment the lower chamber comprises or is in electrical connection with a reference electrode.

The present invention also includes a method of using a flexible biochip for measuring ion transport activity or properties. The flexible biochip can be part of a device in which sections of the flexible biochip are sequentially unwound for sequential sets of assays, or can be used as an at least partly curved surface.

The flexible biochip concept can be applied to not only ion transport assays, but also other high-throughput tests, in which a expanse of the biochip is used for testing at a time, where the top and optional the bottom surface of the biochip can be engaged in activities such as reagent delivery, detection, separation, etc.

Theta Tubing-Based Chip

Another aspect of the present invention is a method of making a multiplex ion transport measuring device using theta tubing: Either semicircular or rectangular theta tubing can be used, however, in some cases rectangular theta tubing can be preferred because the septum between the theta openings (referred to herein as "compartments") is typically of a more uniform thickness in rectangular theta tubing. In this method, multiple segments of theta tubing can be stacked on top of one another or arranged side-by-side, where each segment comprises an ion transport measuring means (recording site).

The method comprises: providing at least two segments of theta tubing, each of which comprises an upper compartment and a lower compartment, where the upper compartment and lower compartment is separated by a glass septum; cutting an opening in the top of the theta tubing segments to provide access to the upper compartment; using the access at the top of the upper compartment to make at least one hole through the glass septum that separates the upper and lower compartments of each piece of theta tubing; and attaching the at least two segments of theta tubing one on top of another, such that the bottom compartment of a second theta tubing segment is on top of the upper compartment of a first theta tubing segment.

Figure 38A:
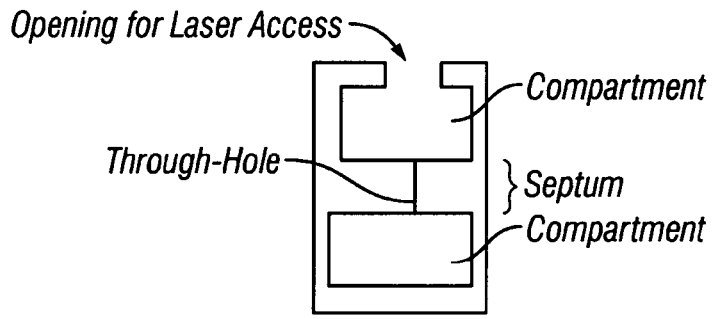
FIG. 38 depicts preferred embodiments of the present invention: ion channel measuring devices that comprise theta tubing. A) a segment of theta tubing shown "face on" in which the opening for laser access (used in making the hole) is shown. B) an ion transport measuring device comprising multiple theta units arranged vertically. The upper and lower chambers of each unit have separate conduit attachments for ES and IS, respectively. "U" labels conduits leading to and away from upper chambers. "L" labels conduits leading to and away from lower chambers. Pressure can be applied from either the inflow or outflow lower chamber conduits. C) an ion transport measuring device comprising multiple theta units arranged side-by-side. Although conduits connecting with only one of the units are shown, each of the upper and lower chambers of each unit have separate conduit attachments for ES and IS, respectively.

Preferably, openings cut in the top that are made to provide access for laser drilling or etching or the hole are sealed prior to stacking the theta tubing segments on top of one another. FIG. 38A depicts a theta segment in which a hole has been cut in the top for laser access. For example, plastic, rubber, or even glass can be used to close the opening using adhesives or heat for sealing. For example, the opening in the top of the top compartment can be sealed when the theta segments are stacked on top of one another, preferably by placing a gasket (such as a piece of flexible rubber, plastic, or silicone) over the opening and stacking the next theta segment on top of it. The gasket can be held in place by adhesives clamps, or f heat can also be used to attach the stacked units to one another. Sealing of the hole can be done such that a port is left in the top of the top chamber. In embodiments where the units are attached side-by-side, the port can be used for adding compounds or cells.

In the assembled device, each theta tubing segment comprises at least one (preferably one) ion transport recording site, and each theta tubing segment comprises an ion transport recording unit, having an upper chamber (upper compartment of the theta tubing segment) and a lower chamber (lower compartment or opening of the theta tubing segment). The multiple ion transport measuring units can be arranged vertically (FIG. 38B), with the upper and lower chambers of each unit open on either side. In an alternative design, multiple ion transport measuring units can be arranged side-by-side (FIG. 38C), with the upper and lower chambers of each unit open each open on either side.

The open sides of each chamber are used to attach conduits for fluid flow, cell and compound delivery, and pneumatic control. In some preferred embodiments of the present invention, depicted in FIGS. 38B and 38C, individual conduits for providing extracellular solution, compounds, and cells, are attached to one side of each upper compartment of the theta structure, and individual conduits lead out of each upper chamber at the opposite side of the theta structure. In these designs, individual conduits providing intracellular solution can be attached to one side of each lower compartment of the theta structure, and individual conduits for outflow of intracellular solution lead out of each lower chamber at the opposite side of the theta structure. Pressure can be applied either from the intracellular inflow conduit or the intracellular outflow conduit.

Many different arrangements are possible for providing solutions, compounds, cells or particles, and pressure to a theta multiplex ion transport measuring device. For example, cells can be introduced to the lower chamber, and pressure for sealing of cells can be applied to the upper chamber. Conduits can be arranged in any way that can provide pressure for particle sealing and fluid flow for the addition of solutions, compounds, and particles such as cells.

In making the device, commercially available theta tubing can be used. The glass tubing can be cut into segments of any size that will allow the segment to function as ion transport measuring unit. For example, in some preferred embodiments, the segments can be from about 0.1 mm to about 80 mm in width, more preferably from about 1 mm to about 10 mm in width. The volumes of the upper and lower chambers of the units can be the same or different. Preferably, the extracellular chamber has internal measurements of at least 20 microns by 20 microns, and the intracellular chamber has internal measurements of at least 10 microns by 10 microns.

Dimensions of the ion transport measuring through holes that are made (for example, by laser drilling or etching) into the theta separator segments are preferably from about 0.3 to about 8 microns in diameter. The ion transport measuring holes can also include etched or laser drilled counterbores, as described previously in this application.

As described herein, the surface of the theta segment can be treated or coated to promote sealability of the surface as described previously in this application.

Figure 38B:
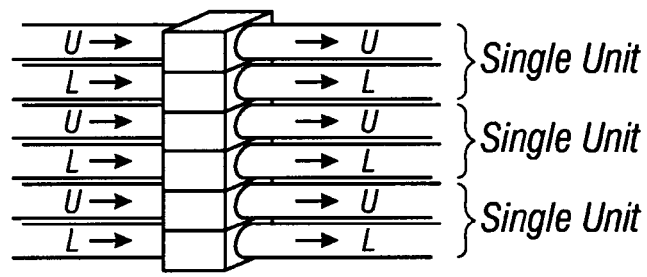
Figure 38C:
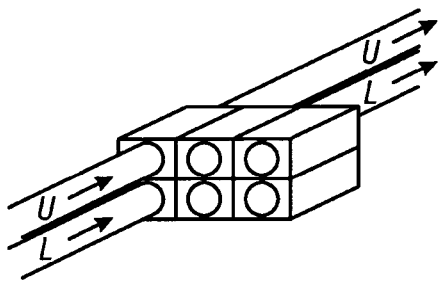

From two to 100 or more theta segments can be attached in vertical or parallel orientation (see FIGS. 38B and 38C). Attachment can be through the use of adhesives, gaskets, and the like. As mentioned above, the opening in the upper chamber can be sealed before or during attachment of the units. Conduits for the addition of solutions, cells, and compounds, and for the application of pressure can be attached both open ends of the chamber in any functional way, and can also use gaskets, adhesive, adaptors, etc. Electrodes, if provided within the chambers, can be inserted into chambers before or after assembling the multiplex structure.

Electrodes can be situated within upper and lower chambers of the segments. Alternatively, for a theta multiplex device, an electrode provided external to a chamber can be in electronic contact with one or more upper chambers through an electrolyte (solution) bridge. For example, one or more electrodes can be provided in one or more conduits leading to one or more upper chambers of the device, or provided as part of the ion transport recording machinery (signal source/amplifier) such that the electrode or electrodes are in electrical contact with an ion transport measuring solution. Similarly, one or more electrodes can be provided in one or more conduits leading to one or more lower chambers of the device, or provided as part of the ion transport recording machinery (signal source/amplifier) such that the electrode or electrodes are in electrical contact with an ion transport measuring solution. In some preferred embodiments of the present invention in which a device is used for whole cell ion transport measurement, the upper chamber of each theta ion transport measuring unit is the "extracellular chamber" that comprises or is in electrical contact with a reference electrode. In this case, multiple upper chambers can optionally be in electrical contact (for example, through conduits that provide solution bridges) with a single reference electrode.

Many other electrode arrangements are possible, however, including but not limited to a single reference electrode in electrical contact with multiple lower chambers (which can be "intracellular" or "extracellular" chambers of the units), individual reference electrodes for each lower chamber, individual reference electrodes for each upper chamber, etc. Recording electrodes can also be provided within chambers or in electrical contact (for example, through conduits that provide solution bridges) with chambers.

The present invention also includes ion transport measuring devices made using the methods of the present invention. These ion transport measuring devices comprise at least two attached theta tubing segments, wherein the theta separator segment of each of the theta tubing segments comprises an ion transport measuring hole. Preferably, the upper and lower chambers of each theta tubing segment comprises or is in electrical contact with at least one electrode. Preferably, the theta ion transport measuring device comprises conduits that attach to upper and lower chambers of each theta tubing segment. The theta ion transport measuring device can comprise any functional arrangement of electrodes or electrical connections to electrodes, and any functional arrangement of fluidic and pneumatic structures (such as conduits, valves, and can connect systems for controlling fluid flow and pressure (for example, pumps), and electronic equipment for ion transport measurement.

The present invention also includes methods of using ion transport measuring devices comprising at least two attached theta tubing segments to measure at least one ion transport activity or property of at least one particle (such as a cell). Methods of ion transport measurement are well known in the art and also described herein. The present device can be used for any type of ion transport measurement, including whole cell, single channel, outside-out patch and inside-out patch recording. The multiplex theta device can be used for testing the effect of known and unknown compounds on ion transport activity of cells and particles.

Fluidic Systems

The present invention provides novel fluidic systems for delivering solutions, compounds, and particles (such as cells) to compartments of ion transport measuring devices. These fluidic systems can in many cases be applied to a number of chip designs and device designs that may vary in their structures, electrode arrangements, and pressure systems.

Upper Chamber Conduit with Openings for on Transport Recording Sites

Figure 39:
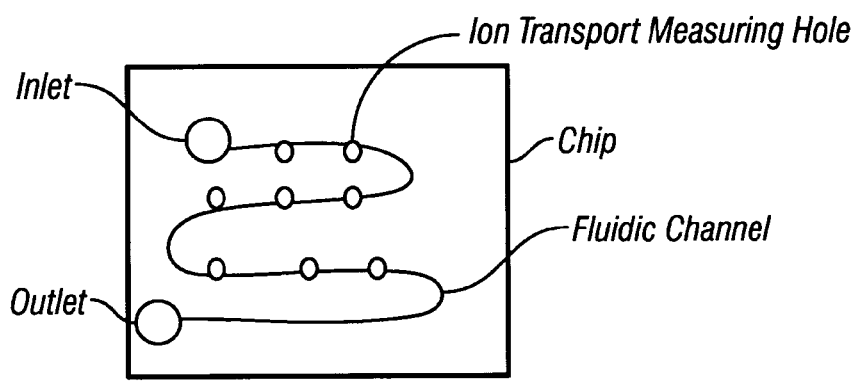
FIG. 39 is a top view of one embodiment of the present invention comprising a chip having a fluidic channel on its upper surface that has openings localized to ion transport measuring holes.

One aspect of novel fluidic systems of the present invention is an ion transport measuring device comprising an upper chamber conduit that comprises multiple openings each of which accesses a single ion transport measuring hole, schematically depicted in FIG. 39. The device comprises: a biochip comprising at least two ion transport measuring holes; at least one conduit on the upper side of said biochip, in which the conduit comprises at least one opening for each of said at least two ion transport measuring holes; at least one inlet; and at least one outlet. Each conduit can have more than one opening. Preferably, the chip of the device comprises 2 or more holes, more preferably 16 or more, more preferably yet 48 or more, and most preferably 96 or more. In a variation, the conduits comprise interfacing piezo actuators that can change the solutions dispensed over the ion transport measuring sites very quickly.

Different compounds and/or solutions can be delivered to the recording site through these channels. Measuring solutions (such as ES) and cells or compounds can be added at the channel inlet. A reference electrode is provided within or in electrical connection with the upper chamber. In one embodiment of this aspect of the present invention, there are additional openings at the top of the upper chamber channel over the ion transport recording sites. Particles such as cells can be added through these openings. Interfacing piezo actuators that can change the solutions dispensed over the ion transport measuring sites very quickly can also be localized to opening over the ion transport recording sites. Preferably, a lower chamber piece engages the ion transport measuring device, where the lower chamber piece preferably comprises individual chambers, such that each ion transport measuring hole of the biochip accesses its own lower chamber. The lower chambers preferably comprise or are in electrical connection with individual recording electrodes and have connections to a pump or other pressure-generating device, and conduits for the addition and removal of measuring solution.

In using this type of device, a single cell type can be added to this type of device for screening different compound solutions. Alternatively, different cell types or particles comprising different ion transports can be added at different ion transport recording sites. Immediately after cell addition, pressure applied from the bottom of the chip can allow the cells (or other particles) to seal at ion transport measuring holes. In this way, a particular ion transport recording site has particular type of cell or particle sealed to it. Compounds can be added through the channel inlet, and ion transport recordings can simultaneously measure the response of various cell types or ion channel types to a given compound. Optionally, the upper chamber channel can be flushed to remove the compound of interest, and a second compound can be added by pushing or pumping a second compound-containing solution into the channel. In this way, multiple compounds (or different concentrations of one or more compounds) can be assayed for their effects on one or more cell types or one or more ion transport types.

Alternatively, the solution—delivering channels can be tips such as pipette tips, in this case, solutions or compounds are filled into the tips by suction, and delivered out to the recording sites by positive pressure through the same tip.

In other related designs, the upper chamber channel may not have openings localized over ion transport recording sites, and after the addition of particles such as cells, a compound-containing solution can be added through the channel inlet. After ion transport measurement, the channel is flushed with solution lacking compound, and then a new compound-containing solution can be added through the channel inlet. In this case, replica assays can be conducted simultaneously using the same type of cell or ion transport.

The present invention includes ion transport measuring devices that include upper chamber channels with openings at multiple ion transport recording sites, including devices that comprise ion transport chips as they are known in the art and described herein, including, for example, planar chips, flexible chips, and MCP chips. Where feasible, chips used in the devices having upper chamber channels can be treated, such as using methods described herein, to improve their sealing properties.

The present invention also includes methods of using ion transport measuring devices that include upper chamber channels with openings at multiple ion transport recording sites to measure ion transport function and properties. In preferred embodiments, the methods are high throughput.

One use of such conduits is to deliver tiny amount of compounds in drops to cells already sealed to the recording sites in low volume of solutions. In this case, the surface of the chip can comprise a hydrophobic material, with the exception of the surface immediately surrounding ion transport measuring holes or microwells, to reduce fluid flow between ion transport recording sites in the absence of directed fluid flow through the chamber, for example, by coating chips with a hydrophobic material as described above in Aspect 21. Fusion of the compound drop and the small volume of solutions at the recording sites allows for fast and efficient compound delivery. The fused drops will not fuse together to cross-contaminate recording sites since the drops are bounded by the hydrophobic coating. Wash out can be achieved by flushing the entire upper chamber with wash solution and subsequent removal of wash solution. After washout, recording sites are ready to receive the next delivery of compounds.

Upper Chamber Channel Strips

Yet another aspect of the present invention is an ion transport measuring device comprising a biochip that comprises multiple ion transport measuring holes, in which the device has at least one upper chamber channel that has access to two or more of the multiple ion transport measuring holes. The device also has at least one lower chamber channel that that has access to two or more of the multiple ion transport measuring holes. The one or more upper chamber channel strips are arranged approximately perpendicularly to the at least one lower chamber channel. The device also comprises a compound delivery system for delivering compounds or solutions to individual ion transport measuring sites.

In preferred embodiments, the device has multiple upper chamber channels, each of which has access to two or more ion transport measuring holes, and multiple lower chamber channels, each of which has access to two or more ion transport measuring holes. The upper channels extend in the m direction, and the lower channels extend in the n direction, such that each ion transport measuring hole that contacts a particular upper channel strip (for example, $M_1$) contacts a different lower channel (for example, lower channel $N_1$, $N_2$, $N_3$, $N_4$, $N_5$, or $N_6$), and each ion transport measuring hole that contacts a particular lower channel (for example, $N_1$) contacts a different upper channel strip (for example, upper channel strip $M_1$, $M_2$, $M_3$, $M_4$, $M_5$, or $M_6$).

In some preferred embodiments, each upper channel strip comprises, or is in electrical contact with, an independent recording electrode, and each lower channel comprises, or is in electrical contact with, an independent reference electrode. Alternatively, each upper channel strip can comprise, or be in electrical contact with, an independent reference electrode, and each lower channel can comprise, or be in electrical contact with, an independent recording electrode.

In preferred embodiments, the upper channel strips are used as extracellular chambers that, during ion transport assays, comprise measuring solution, cells (or other particles), and, preferably, compounds to be tested. Various designs can be used that allow individual compounds (or compound concentrations) to be localized to individual recording sites within an upper chamber channel. For example, the "piped in" compound delivery system described above, in which individual conduits (pipes) deliver compounds directly over an ion transport measuring site can be applied to this channel matrix device. Preferably, however, peizo controlled tips deliver compounds directly over an ion transport measuring site. In this case, the upper microfluidics channels fill by hydrophilicity to wet all individual recording sites with measuring solution. Preferably, the biochip has depressions or microwells at the ion transport recording sites that promote retention of solution (such as recording solution and compound-containing solution) at the ion transport recording sites. The upper chamber channels have a low diameter to length ratio that retards mixing, and the compounds are delivered to individual recording sites simultaneously so as to prevent hydrostatic pressure from forcing them to flow into adjacent chambers.

Before or after compound delivery, ion transport recording takes place by sequentially recording using reference electrode 1 (in combination with all possible recording electrodes), then using reference electrode 2 (in combination with all possible recording electrodes), then using reference electrode 3 (in combination with all possible recording electrodes), etc., and optionally return to electrode 1 for a next cycle.

In a related aspect, upper chamber channel strips can contact ion transport recording sites along the upper side of an ion transport measuring chip, and each ion transport recording site can have an independent lower chamber that comprises or is in electrical contact with a recording electrode. Preferably, the biochip has depressions or microwells at the ion transport recording sites that promote retention of solution (such as recording solution and compound-containing solution) at the ion transport recording sites. A common reference electrode is present in the upper chamber channels, in which the electrode is a narrow strip of conductive material (for example, metal) built along the surface of the interconnected upper chamber channels. The electrode strip is coated along its upper surface with a nonconductive material (for example, a polymer), and is exposed to solution only at recording sites. In this way the upper chamber channels remain in electrical communication, but fluid communication between ion transport measuring sites is minimized.

The present invention includes ion transport measuring chips that comprise upper chamber channels, and devices comprising ion transport measuring chips that comprise upper chamber channels. The chamber strips concept can be applied together with the various chip designs, including for example, the flexible biochips described above that provide the ion transport measuring holes.

The present invention also includes methods of using includes ion transport measuring chips that comprise upper chamber channels to measure ion transport activity and properties of particles such as cells.

Compound Delivery into Upper Chamber by Fluidic Pipes

Figure 40:
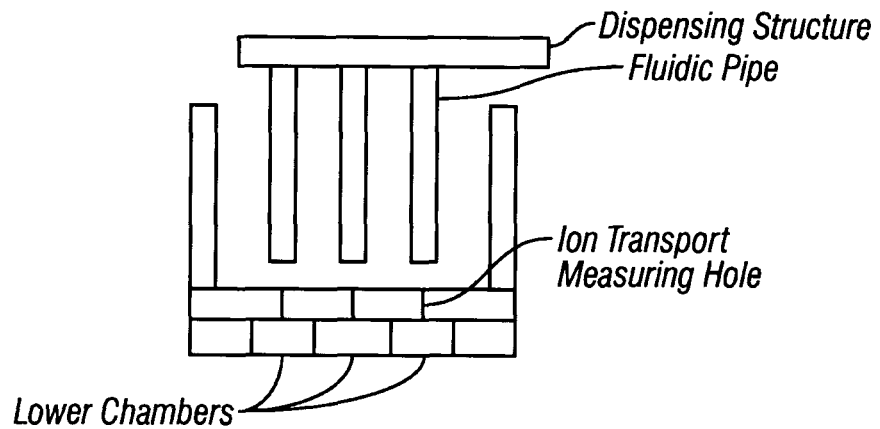
FIG. 40 is a cross-sectional depiction of one embodiment of an ion transport measuring device comprising a fluidic pipe compound delivery system.

The invention also includes devices that comprise a substrate that comprises at least two ion transport measuring holes (ion transport measuring chip); at least two lower chambers that engage the ion transport measuring chip, such that each or the at least two ion transport measuring holes is in register with an individual lower chamber; at least one upper chamber that has fluid access to the at least two ion transport measuring holes; and at least two conduits or "pipes" that can be positioned over the at least one upper chamber, where each of the at least two conduits aligns directly over and in close proximity to an ion transport measuring hole (see, for example, FIG. 40).

The device can have a single common upper chamber, or can have a series of upper chamber channels that may or may not connect with one another. Where they are non-interconnecting channels, more than one reference electrode and more than one inflow and outflow conduit is required.

In preferred embodiments, an upper chamber comprises a reference electrode, and is connected to inflow and outflow conduits such that fluid flow of measuring solution can be established through the upper chamber. Cells can be added through the inflow conduit, and after sealing of cells at ion transport measuring sites, compounds can be added at individual recording sites through the fluidic pipes. In preferred embodiments, the ion transport measuring chip comprises an array of ion transport measuring holes, and an array of fluidic pipes can be moved over the chip. The structure supporting the pipes engages a structure on the chip that precisely aligns and gauges the travel of the tubes so that they are positioned just over the recording apertures and can provide concentration clamping of delivered compounds in the immediate vicinity of the cell.

The pipes can deliver tiny amount of compounds in drops to cells already sealed to the recording sites in low volume of solutions, such as those in the microwells of hydrophobic chip. Fusion of the compound drop and the small volume of solutions at the recording sites allow for fast and efficient compound delivery. The fused drops will not fuse together to cross-contaminate since the drops are bounded by hydrophobic coatings. Wash out can be achieved by flushing the entire upper chamber with wash solution and subsequent removal of wash solution. The recording sites are now ready to receive the next delivery of compounds.

The present invention also includes methods of using ion transport measuring devices that comprise pipe arrays for delivering compounds at ion transport measuring sites of upper chambers. In broad outline, such methods include: providing measuring solution in the lower chambers of the device; providing particles in measuring solution in an upper chamber of the device; sealing particles at ion transport measuring holes; providing continuous flow of measuring solution through the upper chamber; halting the flow of measuring solution through the upper chamber; positioning an array of pipes over the upper chamber; delivering compounds continuously at recording sites through the pipes, and measuring ion transport function or properties. The upper chamber of the ion transport measuring device can optionally be flushed after ion transport measurement, and optionally new compounds can be added to upper chamber recording sites using the pipe array. The process can be repeated multiple times.

Nozzle Delivery of Compounds

Figure 41:
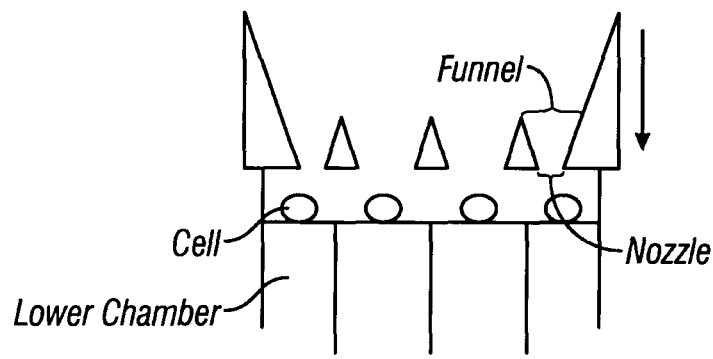
FIG. 41 depicts one embodiment of an ion transport measuring device having a nozzle compound delivery system.

The invention also includes devices that comprise a substrate comprising at least two ion transport measuring holes; an upper chamber that comprises or is in electrical contact with at least one reference electrode, in which the upper chamber accesses the two or more ion transport measuring holes; and a compound delivery system that can deliver compound or solution to each ion transport measurement site individually, in which the compound delivery system comprises a fluidics block that comprises funnel structures terminating in outflow nozzles that can be aligned over the chip such that a single nozzle is positioned over each ion transport recording site (see FIG. 41). Preferably, the device comprises or engages at least two lower chambers in register with the two or more holes of the chip. During ion transport measurement, each of the individual lower chambers preferably comprises or is in electrical contact with a recording electrode.

When the fluidics block is aligned over the chip, the outflow nozzles are positioned close to the surface of the measuring solution of the upper chamber, but not in contact with it. Preferably, the nozzle is at the end of a funnel structure, the nozzle diameter is greater than ten times the diameter of the cells, and the funnel size is large enough to allow the compound solution within it to flow out of the nozzle over sufficient time that more compound solution can be delivered to the funnels (such as by dispensing pipette tips) without creating bubbles within the funnel or nozzle area.

In using the device, lower chambers are filled with measuring solutions, and the the upper chamber is filled with measuring solution and cells (or other particles) are added. Cells (or other particles) are sealed to the ion transport measuring holes by applying suction to the lower chambers. By controlling fluid flow through the upper chamber, an even but shallow bath is produced that has continuous flow. Optionally the inflow into the upper chamber will be by microfluidics channels opening near each aperture. The fluidics block for compound addition is positioned over the holes on the chip such that the outflow nozzles are close to the surface of the measuring solution in the hole within the upper chamber, but not in contact with it. After control currents are recorded, compounds are added to the fluidics block from above. As long as the block is held above the measuring solution of the upper chamber, the compounds do not flow beyond into the upper chamber due to the surface tension of the small droplets that form at the bottoms of the nozzles. The voltage protocol sweeps are coordinated such that once the drugs are requested, the entire block may be lowered to contact the upper chamber measuring solution, and brought down to within half of a nozzle width of the cells such that the drug-containing solution is allowed to flow out of the nozzles by gravity to clamp the concentration of drug in the immediate vicinity of the cells.

The present invention includes ion transport measuring devices that include a biochip comprising ion transport measuring holes and a compound delivery system that can deliver compound or solution to each ion transport measurement site individually using a fluidics block that comprises outflow nozzles that can be aligned over one or more upper chambers of a chip such that a single nozzle is positioned over each ion transport recording site. In preferred embodiments, the devices are high-throughput devices that comprise at least 48, at least 96, or at least 384 ion transport measuring sites and a multiplicity of nozzles for dispensing compounds at the ion transport measuring sites. Preferably, the number of dispensing nozzles of the fluidics block is equal to the number of ion transport measuring sites of the ion transport measuring chip.

The devices of the present invention can comprise ion transport chips as they are known in the art and described herein, including, for example, planar chips, flexible chips, and MCP chips. Where feasible, chips used in the devices having upper chamber channels can be treated, such as using methods described herein, to improve their sealing properties.

Chamber Separator

In yet another aspect of the present invention, an ion transport measuring device comprises a substrate comprising at least two ion transport measuring holes; a common upper chamber, and a physical separator unit that can be lowered onto the chip to separate the common upper chamber into multiple individual chambers. Preferably, the device comprises or engages one or more lower chambers.

The physical separator unit can be lowered into the upper chamber (which can be in the form of a tank with ion transport measuring holes in the bottom) after measuring solution and cells (or other particles) have been introduced into upper chamber and preferably after particles have been sealed to the ion transport measuring holes. The physical separator can reversibly fasten on to the substrate. The physical separator can comprise any fluid-impermeable material, and preferably comprises a compressible material where it contacts the surface of the chip to form seals against the chip so that the attached separator forms fluid-impermeable separated channels. For example, the separator unit can comprise multiple electrodes, each of which can contact a separate chamber when the separator engages the chip. In this case, sealing can occur after the separator has been positioned to form the chambers.

The device can also engage a lower chamber that can comprise a reference electrode.

After cells have sealed to the chip and the separator unit has formed separate upper chambers, compounds can be added to the individual upper chamber, either by conduits or fluid dispensing systems. Ion transport recording can then be performed using upper chamber recording electrodes and a bottom chamber reference electrode.

It is also possible to have multiple lower chambers that engage the chip. In this case the lower chambers can optionally have recording electrodes. In this case the upper chambers can comprise or be in electrical contact with independent reference electrodes, or alternatively, a common electrode (for example, an electrode that traverses the upper surface of the chip) can contact or be brought into electrical contact with the multiple upper chambers and be used as a reference electrode.

The devices of the present invention that comprise physical separator units for forming chambers can comprise ion transport chips as they are known in the art and described herein, including, for example, planar chips, flexible chips, and MCP chips. Where feasible, chips used in the devices having upper chamber channels can be treated, such as using methods described herein to improve their sealing properties.

Pneumatic and Electronic Matrix

In a related aspect, the present invention includes an ion transport measuring device comprising: a biochip that comprises multiple ion transport measuring holes, in which the device has at least one upper chamber channel that has access to two or more of the multiple ion transport measuring holes. The device also has at least one lower chamber channel that that has access to two or more of the multiple ion transport measuring holes, where each lower chamber channel has separate pneumatic connections for generation pressure for sealing particles at ion transport measuring holes.

The one or more upper chamber channels are arranged approximately perpendicularly to the at least one lower chamber channel. The device also comprises a compound delivery system for delivering compounds or solutions to individual ion transport measuring sites.

In preferred embodiments, the device has multiple upper chamber channels, each of which has access to two or more ion transport measuring holes, and multiple lower chamber channels, each of which has access to two or more ion transport measuring holes. The upper channels extend in the m direction, and the lower channels extend in the n direction, such that each ion transport measuring hole that contacts a particular upper channel (for example, $M_1$) contacts a different lower chamber channel (for example, lower channel $N_1$, $N_2$, $N_3$, $N_4$, $N_5$, or $N_6$), and each ion transport measuring hole that contacts a particular lower channel (for example, $N_1$) contacts a different upper channel (for example, upper channel strip $M_1$, $M_2$, $M_3$, $M_4$, $M_5$, or $M_6$).

In preferred embodiments, the upper channels are used as extracellular chambers that, during ion transport assays, comprise measuring solution, cells (or other particles), and, preferably, compounds to be tested. Various designs can be used that allow individual compounds (or compound concentrations) to be localized to individual recording sites within an upper chamber channel. For example, the "piped in" compound delivery system described in Aspect 26, above, in which individual conduits (pipes) deliver compounds directly over an ion transport measuring site can be applied to this channel matrix device. Preferably, however, peizo controlled tips deliver compounds directly over an ion transport measuring site. Preferably, the biochip has depressions or microwells at the ion transport recording sites that promote retention of solution (such as recording solution and compound-containing solution) at the ion transport recording sites.

Immediately following compound delivery, ion transport recording takes place by sequentially recording using by applying pneumatic pressure to lower channel 1 to seal particles at ion transport holes that access lower channel 1, then by applying pneumatic pressure to lower channel 2 to seal particles at ion transport holes that access lower channel 2, then by applying pneumatic pressure to lower channel 3 to seal particles at ion transport holes that access lower channel 3, etc.

Device Having Compound Delivery Plate

Figure 42:
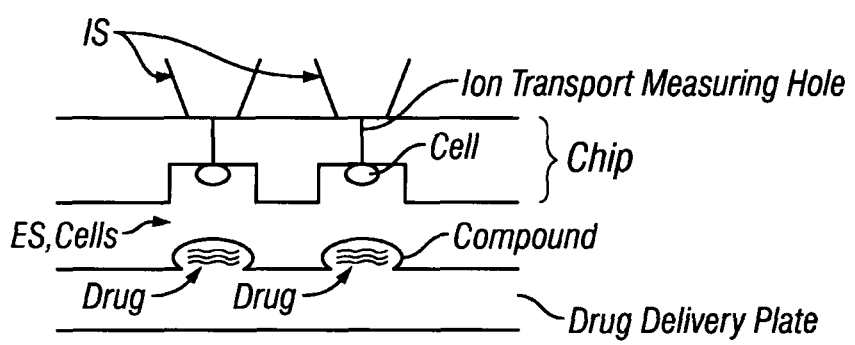
FIG. 42 depicts one embodiment of an ion transport measuring device having a compound delivery plate that delivers compounds to cells sealed at ion transport measuring hole on the lower side of a chip.
Figure 43A:
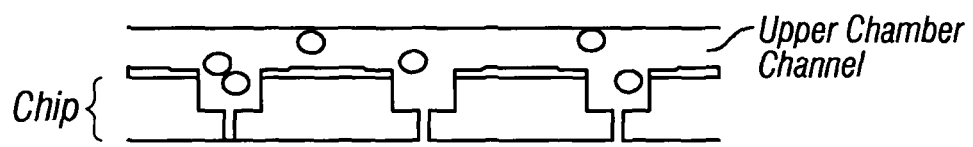
FIG. 43 depicts one embodiment of an ion transport measuring device in which compound is delivered by fluid dispensing tips at ion transport measuring sites. In this embodiment, an electrode traverses the surface of the chip. A hydrophobic layer coats the electrode, except in the immediate vicinity of microwells. A) cells have been added to an upper chamber channel comprising ES. B) cells seal to ion transport measuring holes within microwells that access the channel. C) compound drops are dispensed directly over the ion transport measuring sites. D) compound solution floods the microwell, but does not flow into neighboring microwells.
Figure 43B:
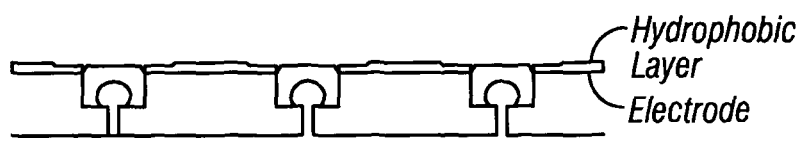
Figure 43C:
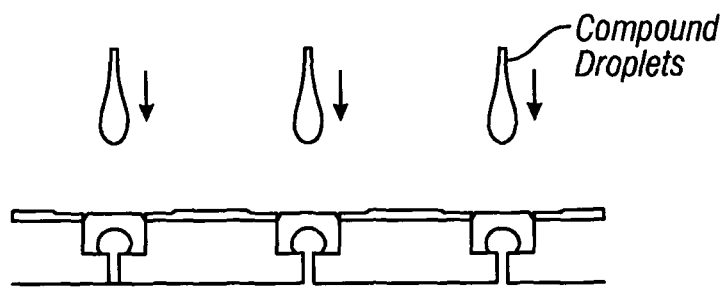
Figure 43D:
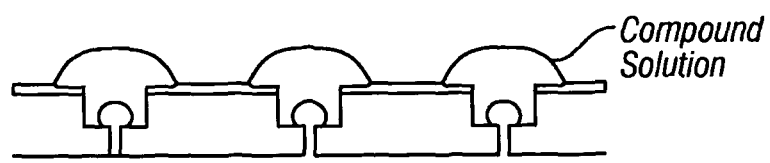

Yet another aspect of the present invention is an ion transport measuring device that comprises a substrate comprising at least two ion transport measuring holes, at least two upper chambers in register with the two or more ion transport measuring holes; at least two lower microwells, each of which is positioned around an ion transport measuring hole, and each of which is connected to a common lower chamber channel; and a compound delivery plate, in which the compound delivery plate has drug delivery sites in register with the lower microwells, where the compound delivery plate can reversibly come into contact with the lower microwells. In this design, depicted in FIG. 42, the two or more upper chambers are connected to a pneumatic system for sealing cells to the ion transport measuring holes on the lower side of the substrate and each of the upper chambers comprises or is in electrical contact with an individual (recording) electrode.

Electrical and pneumatic connection to the upper wells of the ion transport measuring chip can be provided by a separate adaptor plate. Preferably, each independent upper well connects to a separate recording electrode.

The lower channel (which accesses the lower microwells) is connected to conduits to provide fluid flow of measuring solution through the channel. The bottom surface of the chip, with the exception of the microwell surfaces, is preferably hydrophobic to aid in maintaining fluid separation between microwells when fluid is removed from the lower chamber. A reference electrode can preferably be provided on the lower surface of the chip, connected to the compound delivery plate, or in electrical contact with the lower channel.

In some preferred designs, at the time of operation of the device, the drug delivery sites have compounds spotted, or printed on them in drops or dried form. In some other preferred designs, the drug delivery sites of the compound delivery plate are apertures through which droplets of compound-containing solution can be pushed up from below.

In operation, measuring solution is added to the upper chambers, and measuring solution and cells are introduced into the lower chamber channel through conduits. Pressure is applied to the upper wells (either individually or commonly connected to pressure controls) to pull cells up from the lower channel into the lower microwells and seal them against the ion transport measuring holes of the chip. Sealing occurs in the presence of complete solution superfusion of the bottom chamber. After the seals have formed, solution is removed from the channel, with the exception of the microwells, which in the case of coated surface electrodes, are in electrical connection with the electrodes. At this time compounds are applied to the microwells as the delivery plate is brought into contact with the lower surfaces of the microwells. Ion transport measurement can then be performed.

The same device can be used in inverted orientation, with cells sealing to the top of the chip, and the compound delivery plate is positioned above the chip to apply compounds from the top side of the chip.

Devices Featuring Multichannel Pipeting Delivery of Compounds

Yet another aspect of the present invention is an ion transport measuring device that comprises a substrate comprising at least two ion transport measuring holes; at least two upper microwells each of which is positioned around an ion transport measuring hole, and each of which is connected to a common upper chamber channel; at least one lower chamber; and a compound dispensing system that can dispense compound solution into the upper microwells. In this design, the one or more lower chambers are connected to a pneumatic system for sealing cells to the ion transport measuring holes on the upper side of the substrate.

The upper channel (which accesses the upper microwells) is connected to conduits to provide fluid flow of measuring solution through the channel. The top surface of the chip, with the exception of the microwell surfaces, is preferably hydrophobic to aid in maintaining fluid separation between microwells when fluid is removed from the upper chamber.

The compound delivery system can comprise conduits or fluid dispensing tips, for example, of a multichannel pipeting system, that can be arranged in an array that can align with the array of microwells. The compound delivery system can deliver compound solution over the microwells in droplets that localize to the microwells and do not spread to other wells due in part to the hydrophobicity of the chip upper surface, as depicted in FIG. 43. Preferably, the compound drops are very large compared to the microwell volume, so that there is little compound dilution when it is delivered.

Various electrode arrangements can be used with this device. For example, the upper surface of the chip can comprise a common reference electrode that is coated with a hydrophobic material except where it contacts the individual microwells. In this case, the device has multiple independent lower wells, each of which is associated with a single ion transport measuring hole. Each lower well comprises or is in electrical contact with an independent electrode that can be used for ion transport recording. The lower well electrodes can optionally be provided by a separate, replaceable adaptor plate that can also optionally comprises connections to pneumatic devices for pressure control. In an alternative, the device can have a single bottom chamber that comprises a reference electrode. Individual recording electrodes can be provided in connection with the upper microwells. For example, the recording electrodes can be attached to the compound delivery system, such that positioning of the compound delivery system over the microwells can also serve to position and dip an electrode into the microwell.

In operation, measuring solution is added to the lower chambers, and measuring solution and cells are introduced into the upper chamber channel through conduits. Pressure is applied from the bottom of the chip to seal cells against the ion transport measuring holes of the chip. Sealing occurs in the presence of complete solution superfusion of the upper chamber. After the seals have formed, solution is removed from the upper channel, with the exception of the microwells, which in the case of a coated surface electrode, are in electrical connection with the reference electrode. At this time compounds are applied to the microwells by position the compound delivery system over the biochip and dispensing compound drops over the microwells. Ion transport measurement can then be performed on the cells sealed at the microwells.

The lower well electrodes can optionally be provided by a separate, replaceable adaptor plate that can also optionally comprises connections to pneumatic devices for pressure control. This adaptor plate design can be applied to all designed for biochips, fluid delivery mechanisms, as well as electrical and/or pneumatic control systems known in the art or described in this entire application.

Further Embodiments

The present invention includes chips, devices, and methods for ion transport measurement that can be used to efficiently assay test particles such as cells. The devices allow ion transport assays that can be used in a variety of ion transport measurement applications, including but not limited to determining the effects of compounds (such as compounds of interest or test compounds) on ion transport activity. The assays can also be used to assess cell condition, "sealability", responsiveness to compounds or treatments before performing a battery of tests using the cells, or to rapidly determine the effects of growth conditions, developmental stages, hormone responsiveness on the ion transport activity of cells. In some embodiments, the ion transport measuring devices can be used for other assays in addition to ion transport measurement assays. In some embodiments, the ion transport measuring devices can designed such that cells in a chamber of the device can be microscopically viewed before, during, and/or immediately after an ion transport measurement assay.

Figure 44:
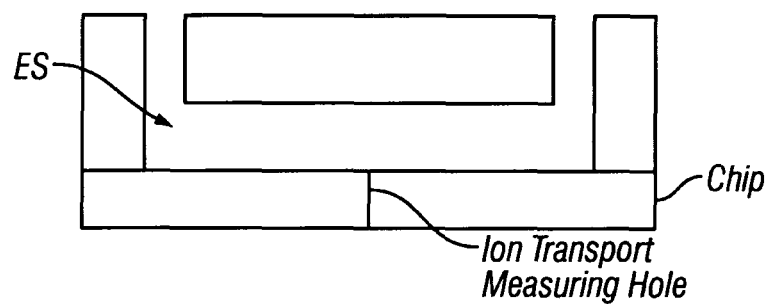
FIG. 44 depicts one embodiment of an ion transport measuring device having a single flow-through upper chamber.

Another aspect of the present invention is a device for ion transport measurement that comprises a chip having at least one ion transport measuring hole and an upper chamber piece comprising at least one chamber, where the one or more upper chambers comprise at least two openings, and where one of the two or more openings is on one side of the one or more ion transport measuring holes and the other of the two or more openings is on the other side of the one or more ion transport measuring holes. In this device, the upper chamber is a "flow-through" perfusion chamber that accesses at least one ion transport measuring hole (depicted in FIG. 44).

In some embodiments of this device, one of the two or more openings comprises a reservoir at its end where cells and, potentially, compounds can be added to the upper chamber such as by a fluidic system or pipette.

The upper chamber can comprise an electrode, or, during use of the device, can be in electrical contact with an electrode that can be part of the signal amplifier machinery, or can be provided in tubing leading to the chamber.

In preferred embodiments, the device has a single upper chamber with two upper chamber openings, one on either side of the one or more ion transport measuring holes, such that measuring solution buffers, or compound containing solutions (such as Extracellular Solution, ES) can flow through the upper chamber. For example, measuring solution can be pumped through the upper chamber to fill or wash the chamber. In preferred embodiments in which one opening comprises a reservoir at its end, particles such as cells and compounds can optionally be added via the reservoir. In the alternative, either particles, compounds, or both can be added to the upper chamber at an opening that is not connected to a reservoir. Preferably, the upper chamber of the flow-through upper chamber device is transparent, so that cells in the upper chambers can be viewed microscopically.

Figure 45:
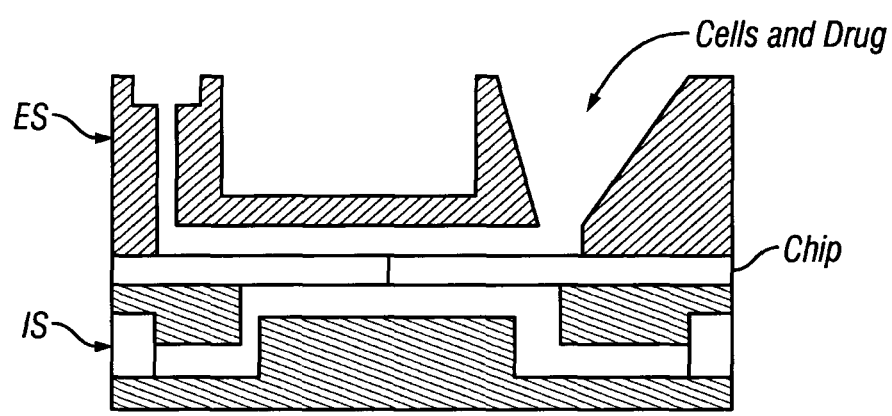
FIG. 45 depicts one embodiment of an ion transport measuring device having a single flow-through upper chamber and a single flow-through lower chamber.

In using the device, the upper chamber of the flow-through upper chamber device can engage a lower chamber piece. The lower chamber piece can be in the form of a tray or tank, and preferably has at least one inlet and at least one outlet for allowing measuring solution (such as IS, intracellular solution) to flow into the chamber and for the application of pressure for sealing particles to the one or more ion transport measuring holes. In some preferred embodiments, such as that depicted in FIG. 45, the lower chamber is also a single flow-through channel, with an opening at one end for the introduction of solutions such as measuring solution, and an opening at the other end for outflow of solutions, and preferably, connection to pneumatic devices for applying pressure to seal particles to the one or more ion transport measuring holes.

The present invention also includes ion transport measuring devices with flow-through upper chambers that are reversibly or irreversibly attached to lower chamber pieces, such as, for example, the single flow-through channel lower chamber piece described above and depicted in FIG. 45. In the preferred embodiment of FIG. 45, the device comprises a biochip having a single ion transport measuring hole, a flow-through upper chamber and a flow-through bottom chamber, where the cells can be viewed through the top of the upper chamber using a microscope.

Another aspect of the present invention is an ion transport measuring device comprising a chip having at least two ion transport measuring holes, an upper chamber piece comprising a single upper chamber; and a lower chamber piece comprising two or more isolated bottom chambers (depicted in FIG. 46). Preferably, each lower chamber is connected in at least two conduits for inflow and outflow of measuring solution (such as IS) and the application of pressure for sealing cells. Preferably, the upper chamber is connected in at least two conduits for inflow and outflow of measuring solution and for the addition of cells and, optionally, compounds. In the alternative, the upper chamber can have openings (for example, at the top) where solutions, cells, and optionally compounds can be added. The common upper chamber can be open, or can have a transparent top so that cells in the chamber can be viewed microscopically or fluorescence measurement can be performed from the top.

Preferably, during operation of the device each of the lower chambers comprises or is in electrical contact with an individual electrode. Preferably, during operation of the device the upper chamber comprises or is in electrical contact with a common electrode.

Simple Chip

A further aspect of the present invention is a glass chip comprising at least one ion transport measuring hole (see, for example, FIG. 47). The chip can be single use, and can insert into or assemble with structures that comprise upper chamber pieces and lower chamber pieces.

The chip can comprises any solid material such as metals, ceramics, polymers, inorganic and organic hybrid materials, plastics, silicon dioxide, or glass, and the ion transport measuring holes can be etched, laser drilled, cut, punched out, or bored into the material. In preferred embodiments, the chip is a glass chip and the ion transport measuring holes are laser drilled. Preferably, the chip is surface-treated, such as by using methods described herein.

Preferably, during use, the chip is inserted into or assembled with an upper chamber piece having isolated upper chamber wells and a lower chamber piece having isolated lower chamber wells, but other designs are possible. For example, the chip can be inserted into or assembled with an upper chamber piece having isolated upper chamber wells and a lower chamber piece having a common lower chamber well, or can be assembled with an upper chamber piece having a common upper chamber well and a lower chamber piece having isolated lower chamber wells.

In preferred embodiments, the chip is single-use and disposable, and the upper and lower chamber pieces, as well as associated electrodes (which can be part of the signal amplifier machinery or electrodes that can be attached or connected to the wells), are reusable.

Devices Comprising Chips Having Wells Made of Compressible Material

In a related aspect, the present invention comprises a chip comprising at least one ion transport measuring hole, in which the chip comprises at least one upper well on its top surface that comprises a layer of wax.

The chip can comprises any hard material such as metals, ceramics, polymers, inorganic and organic hybrid materials, plastics, silicon dioxide, or glass, and the ion transport measuring holes can be etched, laser drilled, cut, punched out, or bored into the material. In preferred embodiments, the chip is a glass chip and the ion transport measuring holes are laser drilled. Preferably, the chip is surface-treated, such as by using methods described herein.

Preferably, the wax on the upper surface of the chip forms individual wells, after a single ion transport measuring hole is created on the top surface of the chip (see, for example, FIG. 48). As in the previous embodiment, during use, the chip is assembled with one or more structures to form an ion transport measuring device. In this case, however, the chip comprises upper chamber wells on its surface, and the chip engages a structure that preferably comprises as upper piece top surface that forms the top of the upper wells, as well as a lower chamber piece. The wax-formed upper chamber structures on the upper surface of the chip are at least somewhat compressible, allowing sealing of the upper chamber structures to the upper piece surface when the device is assembled.

The upper piece top surface that engages the chip can also include conduits and, optionally, electrodes that can connect with the one or more upper chambers of the device when the device is assembled.

Preferably, the chip comprises multiple wax-formed upper chambers and the lower chamber piece it assembles with has multiple isolated lower chamber wells, but other designs are possible. For example, the chip can have a single wax-formed upper chamber, and can be assembled with a structure that comprises multiple isolated lower chambers. In an alternative, the chip comprises multiple wax-formed upper chambers and the lower chamber piece has a single common lower chamber.

In preferred embodiments, the chip having wax-formed upper chambers is single-use and disposable, and the lower chamber piece and the structure that comprises the upper piece top surface, as well as associated electrodes (which can be part of the signal amplifier machinery or electrodes that can be attached or connected to the wells), are reusable.

Another material that can be used for forming wells on the surface of a biochip is any photoresist, such as SU-8. SU-8 is a photo-curable epoxy oligomer, commonly used for computer chip manufacture. To make one or more wells on the surface of a chip using SU-8, the liquid form of the oligomer is distributed on the surface of the chip. A mask is used to pattern one or more wells. Light induces polymerization of SU-8 in areas not covered by the mask. After polymerization, the unpolymerized SU-8 is washed away to leave chamber walls that comprise SU-8 polymer.

Chip with O-Ring Upper Chambers

In a related aspect of the present invention, a chip comprising at least one ion transport measuring hole is provided with at least one O-ring that forms an upper chamber around the at least one ion transport measuring hole (see, for example, FIG. 49). The chip having O-ring upper chambers can be assembled with at least one structure to form an ion transport measuring device.

The chip can comprises any hard material such as metals, ceramics, polymers, plastics, silicon dioxide, or glass, and the ion transport measuring holes can be etched, laser drilled, cut, punched out, or bored into the material. In preferred embodiments, the chip is a glass chip and the ion transport measuring holes are laser drilled. Preferably, the chip is surface-treated to increase its sealing properties, such as by using methods described herein.

To assemble an ion transport measuring device, the chip preferably engages a structure that preferably comprises as upper piece top surface that forms the top of the upper wells that can be reversibly attached to the top of the chip, as well as a lower chamber piece that can be reversibly attached to the bottom of the chip. The upper chamber O-ring structures on the upper surface of the chip are at least somewhat compressible, allowing sealing of the upper chamber structures to the upper piece surface when the device is assembled. The O-ring can also be sealed to the top of chip surface using an adhesive.

The upper piece surface can also include conduits and, optionally, electrodes that can connect with the one or more upper chambers of the device when the device is assembled.

Preferably, the chip comprises multiple O-ring upper chambers and the lower chamber piece has multiple isolated lower chamber wells, but other designs are possible. For example, the chip can have a single O-ring upper chamber, and can be assembled with a structure that comprises multiple isolated lower chambers. In an alternative, the chip comprises multiple O-ring upper chambers and the lower chamber piece has a single common lower chamber well.

In preferred embodiments, the chip having O-ring upper chambers is single-use and disposable, and the upper piece surface and lower chamber piece, as well as associated electrodes (which can be part of the signal amplifier machinery or electrodes that can be attached or connected to the wells), are reusable.

Method for Performing Excised Patch Voltage Clamp Recordings

Excised voltage clamp recordings such as inside-out or outside in configurations as known in the art of voltage clamp studies can be performed by any planar or non-planar electrode configurations known in the art, or described in this application or previous applications. This is done by adding magnetic beads labeled with antibody(s) against common cell surface markers after the cell is sealed to the ITM sites; incubation to allow for bead binding to the cell surface; and applying magnets to the beaded sealed cells from the open access. Magnetic forces will remove the beads, together with associated cell membrane, which allows the formation of "excised patch" configuration at the ion transport measuring sites for single channel or macropatch recordings.

Method of Shipping Ion Transport Measuring Chips

The present also provides methods for shipping ion transport measuring chip and devices in which the upper and lower chambers of the devices or chips are pre-filled with an ion transport measuring solution. For example, where the devices are intended for use in performing ion transport measurement assays on whole cells, the devices can be packed with upper and lower chambers filled with intracellular solution (IS). This can reduce the time required to perform an assay, and also can reduce the complexity of the machinery that interfaces with the device and provides fluidic controls and conduits, since the machinery does not need to add measuring solution to, for example the lower chambers of a device, but instead can simply flush the upper chamber with an appropriate measuring solution such as extracellular solution (ES) prior to adding cells. This increases the efficiency and reduces the time needed for assays, such as high throughput screens. (In cases such as that described in Aspect 28, where cells are distributed in lower chambers, the machine flushes the lower chamber with, for example, ES, prior to adding cells.)

The devices or chips can be shipped in blister packs that lock in the measuring solution, and the entire assembly can optionally be kept refrigerated until use. The measuring solution used can be specialized for different types of ion transport assays, different cell types, and the like. The measuring solution can also be simplified for more general use with more than one cell or assay type.

To use devices shipped in measuring solution, after flushing extracellular solution through and adding cells to the one or more upper chambers, a vacuum can be applied to the one or more intracellular chambers that already contain IS to seal cells to ion transport measuring holes.

Ion Channel Chip Having Chemical Surface Modification on Plastics and Methods of Use Another aspect of the present invention is an ion channel chip having chemical surface modification on plastics, such as a plastic surface or substrate, and methods of use. Preferably, the plastic surface is modified to improve the chip's ability for form tight seals for ion transport measurement. Preferably, plastic surfaces can be plasma etched, which makes the surface clean and creates chemical functional groups that can be used for further chemical reactions and/or polymerizations to provide functionalities on the surface. These modifications are preferably made after holes are provided on the chip, such as through laser drilling. A variety of formats of holes can be provided, preferably in a standard format or footprint, such as between 1 and 1536 holes or more on a chip. These chips can be used in methods of determining ion channel activities, including high throughput methods.

In one embodiment the ion channel chip includes a substantially planar polymer plastic substrate treated with an ionized gas, at least one hole, also referred to as an aperture, positioned substantially perpendicular to the plastic substrate and a gasket positioned about the aperture defining the perimeter of a chamber. The ionized gas treatment may include exposure to a gas such as plasma gas. Preferably the ionized gas treatment forms at least one functional group or moiety positioned sufficiently close to the aperture such that a cell can simulataneously contact the functional group or moiety and the aperture. This permits and enhance seal between the chip and a cell.

Chips of the present invention are preferably planar or substantially planar in configuration and made of thin plastic, also referred to as polymer plastic, material. The plastic material can be any that can be laser drilled to form a hole, also referred to as an aperture or throughbore, useful for ion transport measurement.

The plastic material chosen for the chip can be any appropriate plastic material, including but not limited to polyimide (such as but not limited to Kapton™), polyolefin or copolymers thereof (such as but not limited to Zeonor™), polyacrylate, silicon containing polymer, wax, paraffin wax, Parafilm™, fatty acid based polymers, acrylics or the like and combinations thereof or copolymers thereof. The plastic materials are generally characterized as being thin films between 5 and 300 in thickness, preferably a thin film that is rigid or flexible.

The laser and its wavelength can be chosen based on the characteristics of the plastic, such as the material, thickness, transparency, opaqueness, color and energy or electromagnetic absorptive or reflective characteristics. A variety of lasers are commercially available, such as Excimer Excitation, MO:YAG excitation and Argon and/or Krypton excitation lasers. Preferably lasers are in the visible, UV or infrared spectrum. The choice of laser, and the power of the laser to be used, that matches a candidate chip material can readily be determined by test drilling a material with one or more lasers and determining the effectiveness and desirability of the resulting hole. For opaque materials, such as but not limited to plastics, lasers preferably in the visible spectrum are used. Solid state lasers or copper vapor lasers described herein or known in the art preferable. Preferred laser wavelengths are between about 157 nanometer and about 590 nanometers, although others can be use. Such determination can be made using visual inspection, such as through microscopy, including optical and electron microscopy. The resulting hole and surrounding surface is preferably the size, shape and texture that are appropriate for use in ion transport measurement methods. The resulting surface surrounding or generally about the hole is preferably smooth where a seal is to be made during ion transport measurement methods.

Once a plastic chip has been provided with one or more appropriately configured laser drilled holes, it is then treated with a plasma to modify the surface. Plasma refers to ionized gases, such as oxygen, air, a combination thereof or other appropriate ionizeable gases. The characteristics, determination and duration of the plasma used can be determined using routine experimentation and screened using ion transport measurement methods described herein or in the applications incorporated by reference herein.

Generally, the plasma treatment cleans the surface of the material and surface of the hole. Such cleaning includes removing or reducing conduction substrates and unwanted contaminants. The plasma treatment preferably results in a change in charge of the surface and/or surface surrounding the hole to charged or more charged, where the preferred charge is negative, and/or the hydrophilicity to hydrophilic or more hydrophilic. The plasma treatment can also result in the removal or reduction or carbonation and/or conductive surfaces and/or materials. Not wishing to be limited to a particular mechanism, the plasma would also create chemical reactive functional groups on the surface, such as the surface of the hole. These functional groups can be used in further modification of the characteristics of the surface by, for example, further chemical reactions and/or polymerizations to create new or additional functionalities on the surface, such as the surface of a hole and/or environs thereof. Such modifications preferably would result in a more hydrophilic and/or electronegative characteristic of the surface, more preferably the surface of the hole and surrounding environs on the chip. The resulting functional groups exposed on the surface of the substrate would be believed to include, but not be limited to, hydroxyl groups, carboxyl groups, free radicals and the like. The resulting modified surface would result in a surface that would provide a high quality seal for use in ion transport measurement.

Surfaces can be modified to contain negatively charged groups, including but not limited to, sulfate, phosphate, borate, silicate, carboxyl, thiosulfates, thiophosphates, thiocarbonates, borates and the like. The negatively charged groups can be provided alone or in combination. The choice of chemistry of the modification is within the routine skill of an artisan and can be made using chemical reactions known in the art. The amount of charge can be varied by altering the negatively charged groups, a combination of negatively charged groups, the chemical reaction used, the duration of the chemical reaction and the like. Other functional groups that can be added, alone or in combination with the negatively charged groups, include, but are not limited to positive charge, neutral charge or hydrophobic.

Once a surface has been modified, the resulting chip can be tested for the ability to form a tight seal in an ion transport measurement. The devices and methodologies described herein and in the applications incorporated by reference can be used the screen chips to determine preferable modification methodologies. Generally, it is desired to create negatively charged and hydrophilic characteristics of the surface of the hole and/or surrounding surfaces is desirable.

The size and shape of the chip can be varied depending on the instrumentation to be used for ion transport measurement using the chip. Preferably, the chip has a footprint that is appropriate for existing ion transport measurement, such as those described herein and in the applications incorporated by reference. For example, 16 holes arranged in a linear chip in a linear configuration can be used in these devices and methodologies. The density of the holes and number of holes can also be varies. Preferably, the footprint of the chip would be that of a standard microtiter plate that has, for example, between 9648 and 1536 wells, or greater, preferably in multiples of 96. The holes would preferably form a matrix where the holes would generally align where wells would be in such standard microtiter plates. In that way, existing robotics and instrumentation could be used to provide reagents and materials to locations on a chip.

Another example of the chip and method of making includes a Kapton chip drilled by laser at about 248 nm, which results in an exit hole the size of about 2 micrometers in diameter. The entrance hole would be about 100 micrometers in diameter with a thickness of about 150 micrometers. The drilled chips are plasma treated for about three minutes.

The plasma treated chips are exposed to a 5% solution of $SO_3$-triethylamine complex in DMF and shaken for about 30 minutes. The resulting chips are washed with water and stored in water. The resulting chips are used in ion transport measurement as described herein or in the applications incorporated by reference.

Higher throughput ion transport measurement is made possible using chips with higher hole density and hole numbers. For example, a chip having 384 wells can perform 384 simultaneous ion transport measurement assays as opposed to the relatively small number of holes in existing ion transport measurement chips having between about one and sixteen holes.

Bilayer-Bilayer Junction For Forming Tight Seals And Method Of Use

Surface modification has come to play an important role in a large number of technologies from different disciplines, including adhesion, corrosion inhibition, and chemical separation sciences. The last decade has witnessed an increasing expansion and interest in supported lipid bilayers as models of biological membranes and as a physiological matrix for studying a number of phenomena, including membrane-receptor, cell-cell interactions. Another aspect of the present invention is the introduction of a lipid bilayer, or portion thereof, to produce an interaction, via a spanning divalent cation, with the lipid bilayer of a cell or portion of a cell that is to be the subject of the measurement. Such bilayer-bilayer junction for forming tight seals and method of use are claimed. In this method, a lipid bilayer may be provided to cover the surface or a portion of the surface of a chip used for ion transport measurement. The lipid is preferably attached to a surface of a chip, such as through covalent or non-covalent attachment. Preferably, head groups of a lipid bilayer are attached to the surface, and a second, inverted layer of lipid is attached via van der Waals forces (a hydrophilic exclusion phenomenon) on top of the first layer such that the polar head groups of the second layer are oriented outwards from the substrate. The surface thus has a charge that would promote the formation of a tight seal for use in ion transport measurement. Any appropriate bilayer can be used, preferably having a negatively charged surface. In a specific example, one preferable lipid bilayer is one comprising phosphatidyl-ethanolamine lipid. The lipid head group is attached to the surface of a hole. The surface of the hole can be of any appropriate material, such as plastic, glass or a combination thereof, such as those described herein, in the applications incorporated by reference, or described in the art. The attachment can be covalent or non-covalent. Preferably, covalent attachment of lipid head group to the glass surface will be achieved through PE liposome fusions using methodologies known in the art. In this configuration the negatively charged lipid head group moiety, from the lipid outer layer, and the negatively charged species, of a target membrane, such as a cell membranes, can be bridged using divalent cations that can coordinate between the two polar head units without the necessity for forming a covalent or ionic bond. The resulting interaction between the membranes is expected to form a tight seal for ion transport measurement. The area of membrane bilayer that is then left bound within the hole on the chip can be ruptured using methods described herein, in the applications incorporated by reference or as known in the art. Examples include positive pressure, negative pressure and treatment with chemical or biological agents that can form pores in biological or synthetic bilayers. The resulting structures can be evaluated for the formation of tight seals and efficacy in ion channel activity determinations using the methods and devices described herein or in the applications incorporated by reference or as known or described in the art.

In another aspect of the present invention, one half of a lipid bilayer is attached to the surface of a chip, preferably in areas in close proximity to a hole, or aperture, on a chip for use in ion transport measurement. The hydrophobic tails of the one half of the lipid bilayer are attached to the chip such that the polar heads are facing outwards on the chips surface such that the polar heads can interact with cells when the chip is used for ion transport measurement.

In another aspect of the present invention, only polar heads are attached to the chip. In yet another aspect of the present invention, only charged heads are attached to the chip, and in yet another aspect only the functional units (which includes only the chemical units that participate in the coordination chemistry that is used to form a seal, via a divalent cation, with the membrane on a cell or particle that is the subject of the measurement) of the polar heads are attached to the chip. These modified chips can interact with cells to assist in the formation of tight seals for use in ion transport measurement. These structures can be evaluated for the formation of tight seals and efficacy in ion transport measurement using the methods and devices described herein or in the applications incorporated by reference or as known or described in the art.

A Method of Making a Pre-Assembled Ion Transport Measurement Cartridge and Method of Use Another aspect of the present invention is a method of making a pre-assembled ion transport measurement cartridge and method of use. In this aspect of the present invention, a chip without a hole is provided in a cartridge, such as described herein or in the applications incorporated by reference. The assembled cartridge is then oriented for laser drilling of the chip to form holes for use in ion transport measurement. The resulting cartridge with a chip with holes can then be treated for surface modification to promote the formation of tight seals for ion transport measurement. The treatment can be any appropriate treatment; preferably those described herein, the applications incorporated by reference herein, or as known or described in the art. These cartridges can be used to perform ion transport measurement as described herein, the applications incorporated by reference herein, or as known or described in the art.

In another aspect of the present invention, a chip without a hole is provided. The chip can be made of any appropriate material, such as glass, plastic or a combination thereof. The chip can be of any appropriate thickness, preferably between about 20 microns and about 180 microns. The chip is assembled to a cartridge using methods described herein, the applications incorporated by reference or as known or described in the art. For example, the chip can be attached to the cartridge using adhesives, sonic welding, melting or the like. The choice of materials for the chip and cartridge can be readily evaluated, determined and selected depending on the proposed modifications of the structure, if any. For example, if the structure is to be treated with acid, base, solvents, reactants or a combination thereof, then the materials should be resistant to degradation or contamination by these chemicals. Preferable materials for the cartridge include, but are not limited to plastics of any sort, preferably cyclo-olefins, acrylics, imides, styrenes, and/or copolymers thereof. Likewise, if the structure is to be treated by heat, cold or irradiation, then the structure should be resistant to degradation by these conditions. The chip-cartridge combination would form one or more wells. Preferably, the chip forms the bottom of a well and the cartridge forms the remainder of the well itself. Such structures are described herein and in the applications incorporated by reference herein.

The resulting chip-cartridge combination is provided on a laser drilling platform. The chip-cartridge can be provided in any configuration, preferably chip side up or chip side down, more preferably chip side facing the laser drill. The laser drilling apparatus would have the coordinates of the location of the hole to be drilling stored in a memory device that is operated by a central processing unit. The chip-cartridge combination would be oriented on the drilling apparatus using appropriate structures, such as pins, jigs, flanges, depressions and the like as is known in the art. The hole to be drilled would preferably be in the center of a well formed by the chip-cartridge combination, but that need not be the case. The laser drilling apparatus can be any known or described in the art or commercially available. Such laser drilling apparatus can be readily configured and/or programmed for these operations by the skilled artisan. The laser drilling apparatus drills holes in the chip in a configuration appropriate for ion transport measurement as described herein, the applications incorporated by reference or as known or described in the art. Preferably, a counter-bore is made in the chip. Then the hole used to perform ion transport measurement is made. The type, wavelength and energy of the laser used for drilling is a choice of the artisan based on the type of material, the thickness of the chip, and the desired characteristics of the hole.

The drilled chip-cartridge combination can then be treated to enhance the formation of tight seals for use in ion transport measurement. Such modifications can be any known in the art, but are preferably those which make the chip, the hole and/or the surrounding environs more electronegative, electronegative, more hydrophilic, hydrophilic or a combination thereof. Preferable methods of modification are described herein or in the applications incorporated by reference herein.

The untreated or treated drilled chip-cartridge combination can be used in ion transport measurement using the methods and devices described herein, in the applications incorporated by reference herein or as known or described in the art. The effectiveness of the chip-cartridge combination, with or without treatment, and the assembly and drilling process can be evaluated based on the results obtained and by inspection. For example, the characteristics of the hole can be evaluated using optical and/or electron microscopy. The appropriateness of the materials for the chip and/or cartridge can be evaluated by visual inspection, physical testing such as physical stress testing and the like. Effectiveness of treatment procedures and overall performance of the unit can be evaluated using ion channel detection methods described herein or in the applications incorporated by reference herein.

In another aspect of the present invention, the cartridge is made of polysulfone attached to a glass plate having counter-bore holes having a diameter between about 50 micrometers and about 100 micrometers in diameter. The counter-bores would be drilled by a laser of about 193 nm wavelength until about 15 to about 30 micrometers of glass remains. A secondary hole is drilled to penetrate through to the other side of the substrate, with an exit hole the size of about 2 micrometers in diameter with an entry hole of about 7 micrometers in diameter. The chips are then treated to increase tight seal during ion transport measurement, such as by treatment with base. The structure is then used in ion transport measurement using the methods and/or devices described herein, in the applications incorporated by reference or as known or described in the art. The manner by which the cartridge is employed on the measurement device is either with cartridge side up wherein the cartridge itself forms the upper chamber to which particles are added to become the subject of the measurements, or with cartridge side down wherein the cartridge forms the bottom chamber that may form a seal with the measurement device to provide isolated bottom chambers during the measurements.

A Method Of Layering A Plastic Chip With Glass And Method Of Use Another aspect of the present invention is method of layering a plastic chip with a thin sheet of glass and method of use. Generally, a plastic chip is layered with glass wherein the plastic portion forms a support structure to maintain the integrity of the thin glass sheet. The glass layered chip is laser drilled to form holes useful for determination of ion channel activity.

In this aspect of the present invention, a plastic material used to form a chip for ion transport measurement is provided. The plastic material can be any appropriate, to including but not limited to polyimide (such as but not limited to Kapton), polyolefin, cyclo-olefin, or copolymers thereof (such as but not limited to Zeonor), polyacrylate, silicon containing polymer, wax (eg, paraffin wax), Parafilm, fatty acid based polymers or the like and combinations thereof or copolymers thereof. The plastic materials are generally characterized as being capable of providing a rigid support structure to prevent the fracturing of the layered glass substrate. The glass substrate is characterized as being 10 and 100 gm in thickness.

The plastic material is layered with glass by gluing, by proximity adhesion, or by using methods known in the art. For example, the glass may be bound to the plastic substrate by UV-curable adhesives, by pressure sensitive adhesives, or by thermal adhesives. Further, a sheet of thin glass may comprise one sheet that covers multiple recording holes, or may be cut or diced to provide only sufficient glass to cover a single recording hole. Holes can be drilled through the glass-layered plastic using a variety of methods. Preferably laser drilling using methods described herein, in the applications incorporated by reference herein or as known or described in the art can be used. The choice of laser type, strength, wavelength and duration are the choice of the skilled artisan based on the materials and the nature of the resulting hole desired. Preferably, the surface surrounding or partially surrounding the hole is smooth where cells are to interact and ion transport measurements are to be made. Characteristics and dimensions of such holes, and optional counter-bores are described herein, in the applications incorporated by reference and as known or described in the art.

The holes can be drilled into or thorough the glass layered plastic before or after the glass layered plastic chip is attached to a cartridge. When attached to a cartridge, the glass layered chip preferably forms at least a portion of the bottom of a well while the cartridge forms the remainder of the well, but that need not be the case.

The chips can be treated to increase tight seals when used in ion transport measurement procedures. For example, the chips can be treated with acid, base, oxygen plasma or other plasma, reactive groups, alone or in combination. Generally, such modifications result in a chip, hole and/or hole surface that is electronegative, more electronegative, hydrophilic, more hydrophilic, or a combination thereof. Methods of modification are described herein, in the applications incorporated by reference and as known or described in the art. Chips can be treated before or after assembly with a cartridge, if such assembly takes place.

The physical nature of the holes and chips, with and without cartridge structures, can be determined by a variety of procedures. Visual observation of the holes using light or electron microscopy can be used to evaluate the dimensions, quality and physical characteristics of the hole and surrounding environs. Stress testing can be used to determine fragility of the structure, such as by dropping a structure from a predefined or variety of heights or subjecting to a predetermined or variety of pressure measured, for example, in pounds per square inch.

The ability of the chip to perform ion transport measurements, preferably by forming tights seals can be evaluated. The chip, either alone or in combination with a cartridge, is used to perform ion transport measurement as set forth herein, in the applications incorporated by reference or as known or described in the art. Preferable procedures are readily determined by this method.

A Method of Protecting Fragile Devices and Parts by Packing and Shipping in a Fluid Such as Water Another aspect of the present invention is a method of protecting fragile devices and parts by packing and shipping in a fluid such as water. Many of the chips, either alone or in combination with cartridge structures, can be fragile and difficult to transport without breakage. By packaging, storing and shipping fragile structures in a fluid such as water, breakage can be reduced.

Small, fragile devices and parts are routinely used in a variety of industries, including the biological, semiconductor, aerospace, defense and the like. In the biological industry, a variety of fragile devices and parts are made of glass. Such fragile devices and parts tend to be difficult to make and the outsourcing of their manufacture is desirable. For example pipette tips using in ion transport measurement are quite fragile. Also, the chips of the present invention, with or without cartridge structures, can be fragile. In order to allow outsourcing of manufacture of these fragile structures, it is desirable to have methods of storage and/or packaging that would reduce breakage during storage at the manufacture site, shipping, and/or storage at the site of receipt from shipping or some other location. The reduction in breakage or damage to such fragile structures would result in cost savings to the manufactures, recipients and users of such structures.

In order to reduce damage of such fragile structures, the present invention provides such fragile structures in a fluid environment within a container. The fluid environment and container are chosen such that the fluid does not appreciably degrade the container or the fragile structure. Preferably, the fluid environment does not cause elements from the container and/or fragile structure to leach out. The fluid environment can completely or incompletely fill the container. The fluid environment can be a single or multiple fluids. The fluid environment can be a single or multiple phases. Multiple phases would include an aqueous and hydrophilic fluid. The fluid environment can be of any viscosity. The fluid environment is preferably liquid at temperatures used for storage and shipping. Preferable fluid environments include water, alcohol, oils and the like.

A Method of Laser Beam Splitting and Method of Use to Laser Drill Holes in Ion Channel Chips Another aspect of the present invention is a method laser beam splitting and method of use to laser drill holes in ion channel chips. The method may or may not require a homogenizer to obtain a "top hat" power profile from a laser beam source. The laser beam is then optionally masked at this point in order to provide one or more profiles for laser drilling a substrate for use as an ion channel detection structure. The laser beam is then passed through a beam splitter to make two or more laser beamlets. The laser beamlets are then optionally masked to provide one or more profiles for laser drilling a substrate for use as an ion channel detection structure. Either the first, second or both of the masking steps can be used. The laser beamlets are then focused through a single or multiple lenses onto a work-piece. The work-piece is in one or more parts and is laser drilled to form structures for use in ion channel detection methods.

The material to be laser drilled can be any appropriate material. Preferred materials include, but are not limited to, glass, ceramics, plastic, silicon, or a combination thereof. Preferred materials are discussed herein, in the applications incorporated by reference and as known and described in the art. The selection of a laser—material pair has been discussed herein, in the applications incorporated by reference and as known and disclosed in the art.

The laser used in these methods can be any appropriate for the material to be laser drilled. The selection of a laser and material combination is within the skill of the artisan and can be determined using methods described herein, in the applications incorporated by reference and what is known and described in the art. Preferably, excimer laser processing is used. Excimer laser processing can be useful for projection mask technologies to machine small features on a parallel scale. Three components of excimer laser processing are the laser, optics and mask.

The laser can be any appropriate laser. A variety of excimer lasers are commercially available, including but not limited to 351 nm, 308 nm, 248 nm, 193 nm and 157 nm wavelength lasers. The choice of wavelength depends on the factors of the material to be ablated and the material's etching behavior at that wavelength. Most organic materials ablate at almost all of the excimer wavelengths, materials such as glass, ceramics and silicon can provide better results at lower wavelengths. The choice of laser wavelength can also depend on the damage threshold of optical components, such as lenses, grids, mirrors and masks, at a given wavelength.

A preferable optical design for excimer laser ablation is a 5× or 4× reduction ratio optical train. However, other optical designs can be used in the present methods, such as one which incorporates a 20× to 35× reduction ratio. The optical system includes one or more of the following: beam shaping module, beam homogenizer, grids, mirrors, projection lens, and mask. Factors to consider for designing an appropriate optical train design include the damage threshold of components at a given wavelength of laser, fluence required for ablation, area to be ablated, feature size to be ablated and the repetition rate.

The mask can be made of any appropriate material. Preferred materials include, but are not limited to, chrome on quartz, aluminum on quartz, dielectric on quarts and metals. Preferred metals include, but are not limited to, stainless steel and molybdenum. The choice of materials for masks includes a consideration of the process fluence and repetition rate of laser. Masks should be chosen to withstand the thermal load generated by laser irradiation during processing cycles. The optics train design should be chosen such that laser irradiation at the mask plane is lower than the mask damage threshold.

Laser ablation of holes in a substrate to form structures for ion transport measurement can take a variety of shapes. Preferred shapes are conical, characterized by a plurality of counter-bores and a final hole through the substrate. The following dimensions are provided by way of example and are not intended to be limiting. The first, and largest, counter-bore is preferably about 100 micrometers in diameter at its opening and about 100 micrometers deep. A second counter-bore is preferably about 60 micrometers in diameter at its opening and about 40 micrometers deep. The last hole, which passes through the structure, is preferably about 7 micrometers in diameter at its widest opening, about 20 micrometers in depth, and emerges from the piece at about 1.8 micrometers to about 2.0 micrometers in diameter at is smallest opening. The total depth of the hole is about 150 to about 160 micrometers deep and made of glass assuming that all holes are drilled from the same side, which need not be the case. For the three holes, two counter-bores and one through hole, operating parameters follow: Fluence (mJ/cm2) range from about 3,000 to about 4,000. Repetition Rate (Hz) range from about 200 to about 400. Number of pulses range from about 150 to about 800. Etch depth (micrometers) range from about 10 to about 140. Etch rate (micromters/pulse, range from about 0.05 to about 0.15.

Figure 51:
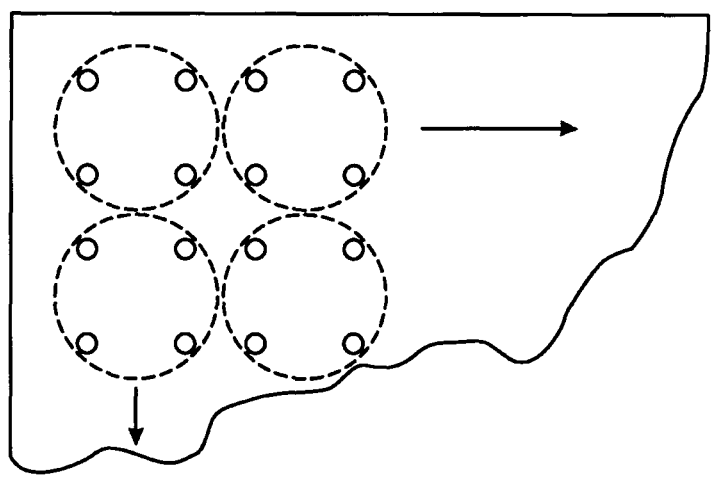
FIG. 51 depicts the production of 4 laser drilled holes at one time to make a plurality of holes for ion channel chip designs, such as in FIG. 50(A).
Figure 52:
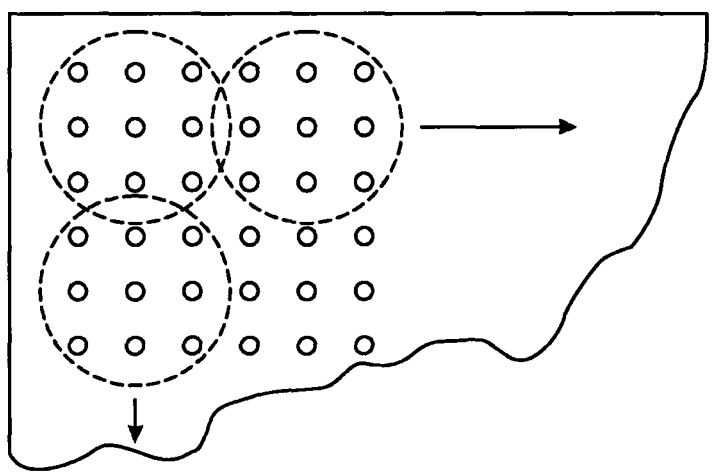
FIG. 52 depicts the production of 9 laser drilled holes at one time to make a plurality of holes for ion channel chip designs, such as in FIG. 50(A).

For example, as shown in FIG. 50, FIG. 51, and FIG. 52, a variety of chip configurations can be made using this technology. As shown in FIG. 50, a 16×24 array of holes or a 16×1 array can be made using a single drill time. Alternatively, as shown in FIG. 51, four holes can be drilled at a time to form any number of holes, including the 16×24 array of FIG. 50. As shown in FIG. 52, nine holes can be drilled at a time to form any number of holes, including the 16×24 array of FIG. 50. Alternately, two, three, or six holes may be drilled at one time by the same approach. A large objective lens can be used to make a large number of holes in a chip. Alternatively, multiple laser beamlets may be directed to multiple parts to fabricate multiple parts at a time, using regular objective lenses for each beamlet.

The chips made using this method can be tested for ion channel detection using methods described herein, in the applications incorporated by reference and as known and disclosed in the art. The quality and character of the holes can be evaluated visually, such as by light and/or electron microscopy, to evaluate the structures provided by these methods.

A Method Of Making Glass More Readily Wet Etched, Ion Channel Chips Made Using This Method, And Methods Of Use Thereof Another aspect of the present invention is a method of making glass more readily wet etched, ion channel chips made using this method, and methods of use thereof. Generally, the invention converts glass to a form that is more readily wet etched by interaction with a laser in the UV range. The glass that is exposed to such laser light becomes modified and is more readily wet etched. The methods are preferably used for making counter-bores, glass thinning and through-holes. Glass appropriate for such procedures is an amorphous glass or glass ceramic that it thermal sensitive. The methods can also make the glass more biologically compatible. An example of such glass is commercially available from Invenions or Schott, and has a product name of Foturan.

In one example, a piece of Foturan ceramic glass about 160 micrometers thick is exposed to UV laser light with a diameter of about 100 micrometers. The glass is then wet etched and the resulting hole or counter-bore evaluated via light or electron microscopy. Depending on the energy of the laser and the duration of exposure, the laser does not need to appreciably ablate the glass and therefore the lower energy requirements for the laser allow a single exposure to cover a larger area that may be the size of the entire substrate at once, which through a projection mask may be used to expose all of the counter bore areas at once on a chip. Upon wet etching, however, a hole or counter-bore is provided. By altering the characteristics of the laser and exposure times, and by altering the characteristics of the wet etching, counter-bores and/or through holes can be made through glass. The size and shape of the counter-bores and through-holes preferably have characteristics of size and shape as described herein, but that need not be the case. The resulting holes can be treated as described herein or in applications incorporated by reference herein. The treated and untreated chips can be tested for effectiveness in ion channel detection methods using methods described herein an applications incorporated by reference.

A Method for Bonding Glass to Glass and a Products Produced by this Method

Another aspect of the present invention is a method for bonding glass to glass and the products produced by this method. The method makes use of flat surfaces of glass that an operator desires to bond together. The surfaces of the two pieces of glass that are to be bonded can be untreated or treated independently with acid and/or base, then brought in close apposition to one another to produce a laminate of the two pieces. The resulting laminate is heated to bond the two pieces of glass together. Alternatively, the two pieces of glass can be untreated or treated independently with acid and/or base. A thin layer of $Na_2SiO_3$ powder or solution is placed between the two pieces of glass that are brought in close apposition to one another. The laminate is heated to melt the $NaSiO_3$, which requires a lower temperature to melt, and thus bond the two pieces of glass together. The invention includes products produced by this method.

In one preferred aspect of the invention, a first surface of glass is treated with acid. A second surface on another piece of glass is treated with base. The acid treated surface is placed in close apposition or contact with the base treated surface. The laminate is heated such that the first piece of glass and second piece of glass are bonded together.

In another preferred aspect of the invention, a first piece of glass may be treated with base. A second piece of glass may be treated with base. The first surface is placed in close apposition or contact with the second surface after $Na_2SiO_3$ powder or solution has been layered between them. The laminate is heated such that the first piece of glass and second piece of glass are bonded together.

The resulting bonded glass can be used for a variety of purposes, including bonding glass with multiple large holes (for example, 384 holes through a 2 or more mm thick glass) to a thinner piece of glass intended to be laser drilled to form structures for use in ion channel detection methods. Such laser drilled structures can be used in the methods and devices of the present invention to detect ion channel activities. Such methods are described herein and in the applications incorporated by reference.

An In Situ Method of Making a Cartridge for Use in Ion Transport Measurement and Methods of Use.

Another aspect of the present invention is an in situ method of making a cartridge for use in ion transport measurement and methods of use. A chip with at least one hole for use in ion transport measurement is provided to an instrument used to make ion transport measurement. The chip is placed such that gaskets are provided on the top surface of the chip and the bottom surface of the chip to form top and bottom chambers. The chambers leave the hole or holes exposed for use in ion transport measurement. A cross section of such a configuration wherein the gaskets engage a chip with holes is provided in FIG. 53.

In this aspect of the present invention, a bare chip of the present invention for use in ion transport measurement is provided without a cartridge or with a cartridge that comprises only a frame intended to provide edge support for the fragile substrate. The cartridge is formed in situ within an instrument for use in ion transport measurement. The cartridge is formed by gaskets within the instrument that result in upper chambers and lower chambers for use in methods of ion transport measurement. In this way, a completed cartridge need not be provided. The gaskets can be cleaned and reused with a series of chips.

The chip can be any chip with one or more holes for use in ion transport measurement described herein, in the applications incorporated by reference or known or described in the art. The holes can be provided in any appropriate configuration, but are preferably in a linear or matrix arrangement that corresponds with standard multiwell plate configurations that are commonly available on the market, and for which standard robotics interfaces are available to interface with the chip.

The gaskets can be of any appropriate material that can form a water-tight or water resistant seal with the chip. Preferable materials include, but are not limited to, rubbers, plastics, silicone, gels and the like.

In operation, a chip is provided and inserted into an instrument used for ion transport measurement. The chip is oriented such that when the gaskets engage the chip, the holes remain exposed and upper and lower chambers are formed. The gaskets engage the chip to form such chambers. The upper and lower chambers have electrodes for use in ion transport measurement. Appropriate reagents are provided to the upper and lower chambers for ion transport measurement. Cells are provided to one chamber, preferably the upper chamber, and a cell engages the hole to form a tight seal. Methods described herein and the applications incorporated by reference to assist in forming a tight seal. For example, negative and/or positive pressure in either chamber, and preferably in the bottom chamber, can be used to encourage a cell to form a tight seal with the hole. Ion transport measurement is then performed.

After ion transport measurements are performed, the reagents and chip are removed and the gaskets cleaned and dried. Another chip is then inserted into the instrument and the process is repeated. The process can be automated such that an operator of the instrument need not handle the chips during engagement and/or disengagement with the gaskets.

A Vacuum Gasket For Use In Ion Transport Measurement And Methods Of Use Thereof

Another aspect of the present invention is a vacuum gasket for use in ion transport measurement and methods of use thereof. One aspect of the present invention is depicted in FIG. 54. A gasket is provided to engage a chip for use in ion transport measurement. The gasket can be made of any appropriate material that can form a water tight or water resistant seal with a chip. Preferred materials include, but are not limited to, plastics, rubbers, silicones, gels and the like. The gasket includes a variety of structures to engage a chip and form chambers for use in ion transport measurement. These structures include O-rings, vacuum holes and vents.

O-rings are provided at locations to correspond to holes on chips for use in ion transport measurement. The O-rings can be provided in any appropriate configurations, but are preferably in a linear or matrix configuration. The O-rings are used to engage a chip and form bottom chambers for use in ion transport measurement. The shape of the O-rings may be round and contain a conduit connection to a pressure controller apparatus, or the may be elongated to allow connection to two conduits that may be used for both pressure control and for introduction and exchange of ion transport measurement fluid into the bottom chambers.

Vacuum holes are provided such that negative pressure can be applied to the chip to assist in maintaining a firm seal between the chip and the gasket. The vacuum holes are located within the interstitial spaces not bound byoutside the O-rings to produce a vacuum chamber, in the space between the gasket and the chip, designed to attract and retain the chip on the gasket, and at the same time to produce the appropriate amount of compression of the O-rings to ensure airtight seals are formed between the O-rings and the chip surface such as to seal off the inside of the O-rings as independent and electrically isolated chambers that are able to provide pressure control for the engagement of cells or other particles having ion transport. The vacuum can also reduce or prevent crosstalk between wells during ion transport measurement by preventing accumulation of fluids or reducing exchange of fluids or electrical signals between wells. The amount of negative pressure to be used can be readily determined using routine experimentation based on a variety of factors, such as the strength of the materials used to make the chip and the quality of the firm seal between the gasket and chip.

Vents are optionally provided to allow inflow of air into the interstitial spaces formed when a chip engages the gasket. The inflow of air when negative pressure is applied can be used to regulate the quality and character of the firm seal between the chip and gasket. The inflow of air also allows the interstitial spaces to be cleared of excess or leaked fluids from the chambers and/or wells. Ridges are optionally provided along the outside edge or perimeter of gasket. The ridge or ridges are used to assist in having the gasket engage the chip.

Upper chambers for use in ion transport measurement may be provided on the chip itself, or can be provided by the instrumentation as disclosed herein, in the applications incorporated by reference or as known or disclosed in the art.

In operation, a gasket is provided, optionally within an instrument for use in ion transport measurement. A chip for use in ion transport measurement is provided and engaged with the gasket. The chip engages with the gasket such that holes in the chip align with the o-rings provided on the gasket. In that way, chambers, and preferably lower chambers, are formed for use in ion transport measurement. The lower chamber includes electrodes for use in ion transport measurement. Upper gaskets are provided on the chip or the instrumentation. Upper chambers include electrodes for use in ion transport measurement.

When the assembly is completed, negative pressure is provided through the vacuum hole to form a firm seal between the chip and the gasket. The o-ring structure results in the formation of interstitial spaces due to the elevation of the o-ring structure as set forth in FIG. 54(B) as "d".

Reagents are provided in the upper and lower chambers for ion transport measurement. Cells are added to the upper or lower chamber, preferably the upper chamber. Cells are encouraged to engage the hole on the chip to form a tight seal as described herein, the applications incorporated by reference and as known or described in the art. For example, positive and/or negative pressure, applied to either chamber independently of the vacuum applied to the interstitial space, can be used to encourage a cell to engage a hole. Ion transport measurements are then performed. Upon completion of such determinations, the chip is removed from the gasket, a new chip is provided, and the process is repeated.

A System for Automated Processing of Chips for Use in Ion Transport Measurement

Another aspect of the invention is provided in FIG. 55. Briefly, a chip is provided in a treatment solution. A treated chip is picked up by a structure having negative pressure to engage a chip. The chip is passed over structures providing negative and positive pressure to dry the chip. The chip is then further dried in a structure having negative pressure and optionally moving the chip from side to side. The chip is then removed using the structure having negative pressure and assembled into a cartridge, a storage structure or an instrument for use in ion transport measurement.

Figure 55A:
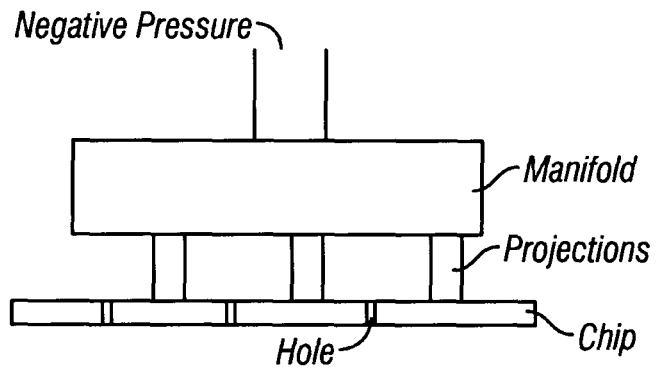
FIG. 55 depicts one aspect of the present invention wherein a system, device and method of processing, handling and assembling chips for use in ion transport measurement are provided.

A structure having negative pressure in order to engage and move a chip is provided in FIG. 55(A). Negative pressure is provided to a manifold having a plurality of projections all in operable communication with a source for negative pressure. The negative pressure is provided at a level that is sufficient to engage a chip but not damage a chip and can be determined using routine experimentation. The chip engages the projections preferably in a configuration such that the holes in the chip are not engaged by the projections. A chip can be released by reducing or stopping the negative pressure.

Figure 55B:
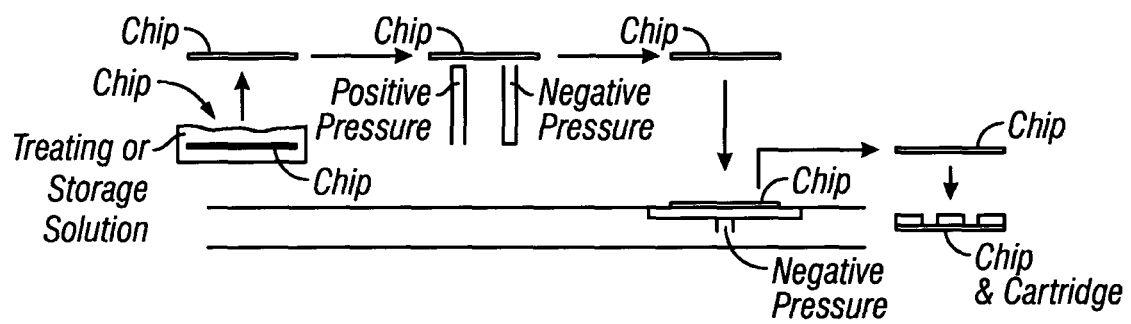

The structure of FIG. 55(A) can be used to transport chips for any purpose. One use of such a structure is depicted in FIG. 55(B). The structure of FIG. 55(A) can be used in one or more of the chip transport steps depicted in FIG. 55(B). A chip is provided and is placed in a treating solution. Once treatment is completed, the chip is passed near a negative pressure source and a positive pressure source to dry the chip. The chip is then placed in a drying structure having negative pressure to further dry the chip of any solution that may be present on top of the chip and seep around to the bottom side. The chip can be placed in a holding structure such as described herein, in applications incorporated by reference or known or described in the art. The chip can be moved in any direction in order to promote drying of the chip. The chip is then transported to another location for packaging, storage, use or further processing. Further processing includes incorporation into a cartridge as described herein, in applications incorporated by reference or as known or described in the art. In one aspect of the present invention, the chip is provided to an instrument for use in ion transport measurement as described herein, in the applications incorporated by reference or as known or described in the art.

A Method For Making A Silicon-Based Chip With Laser-Drilled Holes, And Surface Modifications In another preferred embodiment, holes can be drilled into a silicon wafer using a green laser. A copper vapor laser (CPL) that produces wavelengths of 510.6 nm (green) and 578.2 nm (yellow) at an intensity ratio of about 2:1 can be double-staged to produce 255 nm and 289 nm UV power. The CVL produces high power (about 10W) at 10-20 kHz. After laser drilling of the holes, the surface of the wafer can be oxidized to produce a $SiO_2$ surface.

Figure 56A:
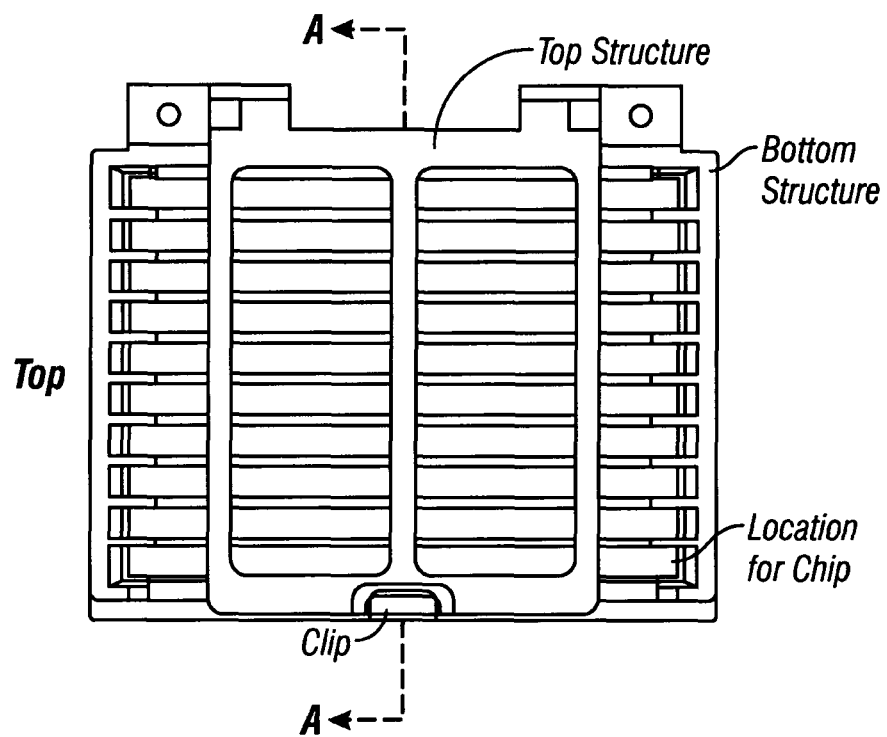
FIG. 56 depicts on aspect of the present invention wherein a device for holding chips for storage and/or treatment are provided.
Figure 56B:
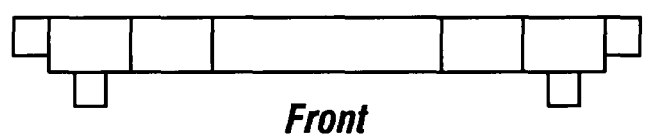

A Device that can Hold Chips for Methods of Treating Chips and/or for Storage of Chips Another aspect of the present invention is provided in FIG. 56. The structure has a hinged top structure that engages a bottom structure, wherein the top structure and bottom structure are reversibly engaged using a clip. The bottom structure includes separate structures to hold or otherwise engage chips of the present invention at a location for chips. In the structure set forth in FIG. 56, the location for chip is configured for long thin chips. Other configurations for other chip sizes can be readily designed and made within the scope and spirit of the present invention. In operation, the top structure is lifted away from the bottom structure via the hinge. One or more chips are placed individually in the location for chips. Preferably, only one chip is placed in one location for chip. The top structure engages the bottom structure and is reversibly held in place by the clip. When loaded with chips and clipped in the closed position, a small gap space is allowed for free movement and wetting of the chips within a fluid environment. Further, the design of the structure allows complete wetting of all areas of all chips while held within a fluid environment. The structure with the chips can be used to store chips or be used to hold chips during treatment or various steps of fabrication. Alternatively, the structure with chips can be provided to instrumentation and/or robotics for movement of chips, such as during assembly. The structure can be made of any appropriate material, such as but not limited to plastic, glass, rubber and the like. The structure is preferably made of plastic and is preferably made using injection molding.

The aspects of the invention disclosed herein can be combined to make new embodiments that are also within the scope of the invention. The aspects of the invention disclosed herein, such as, but not limited to chip designs, chamber designs, electrode arrangements and connections, through-hole designs and manufacture, fluidics arrangements, etc. can be combined with other features described herein, known in the art, or features that are developed in the future.

The following applications are incorporated herein by reference in their entireties: U.S. patent application Ser. No. 10/428,565, filed May 2, 2003; U.S. patent application Ser. No. 10/351,019, filed Jan. 23, 2003; U.S. patent application No. 60/380,007, filed May 4, 2002; PCT application PCT/US03/14000, filed May 2, 2002; U.S. patent application Ser. No. 10/104,300, filed Mar. 22, 2002 entitled "Biochips Including Ion Transport Detecting Structures and Methods of Use" naming Wang et al. as inventors; U.S. patent application No. 60/351,849 filed Jan. 24, 2002 entitled "Biochips Including Ion Transport Detecting Structures and Methods of Use" naming Wang et al. as inventors; U.S. patent application No. 60/311,327 filed Aug. 10, 2001, entitled "Biochips Including Ion Transport Detecting Structures and Methods of Use" naming Wang et al. as inventors; U.S. patent application No. 60/278,308 filed Mar. 24, 2001, entitled "Biochips Including Ion Transport Detecting Structures and Methods of Use" naming Wang et al. as inventors; PCT application PCT/US02/11161, entitled " ", filed Mar. 22, 2001, naming as inventors; U.S. application Ser. No. 10/642,014 filed Aug. 16, 2003; and U.S. provisional patent application No. 60/474,508 entitled "Biochip Devices for Ion Transport Measurement, Methods of Manufacture, and Methods of Use" filed May 31, 2003, naming Xu et al. as inventors.

All headings are for the convenience of the reader and should not be used to limit the meaning of the text that follows the heading, unless so specified.

EXAMPLES

Example 1

Device for Ion Transport Measurement Comprising Upper Chamber Piece and Biochip

Upper chamber pieces with 16 wells having dimensions of 84.8 mm(long) ×14 mm(wide)×7 mm(high) were injection molded with polycarbonate or NORYL® material. The distance between centers of two adjacent wells was 4.5 mm. The well wall was slanted by 16 degrees on one side and 23 degrees and contoured on the other side to allow guidance for cell delivery. The well holes had a diameter of 2 mm.

A biochip with 16 laser-drilled recording apertures had dimensions of 82 mm (long)×4.3 mm (wide)×155 microns (thick). The distance between the first hole and a narrow edge is 7.25 mm. The holes were laser drilled to have two counter-bores of 100 microns (diameter)×100 microns (deep) and 25 microns (diameter)×35 microns (deep), respectively. A final through hole was drilled from the side of the counterbores and had a 7 to 9 micron entrance hole and a 2.0 micron exit hole with a total through hole depth of 20 microns. Chemical treatment with acid and base was done as described in Example 3.

The treated chip was attached to the upper chamber using UV epoxy glue.

Devices produced using this methods had na Re of ~2MOhm with standard ES and IS solutions, and an average Ra of ~6.0MOhm using RBL cells with a standard pressure protocol described herein.

Example 2

A 52-Chip Bench Mark Study

We have conducted a bench mark study using 52 single-hole biochips tested using a CHO cell line expressing the Kv1.1 potassium channel. The result demonstrated a 75% success rate as determined by the following criteria: 1) achievement of sealing of at least one gigaOhm (a "gigaseal") within five minutes of cell landing on a hole, and 2) maintenance of Ra of less than 15MOhm, and Rm of greater than 200MOhm throughout 15 minutes of whole cell access time.

Chip Fabrication

Patch clamp chips were designed at Aviva Biosciences and fabricated using a laser-based technology (without an on-line laser measurement device). The K-type chips were made from ~150 micron thick cover glass. The ion transport measuring hole structures had ~140 micron double counterbores and final through-holes of ~16.5±2 micron depth. The apertures on the recording surface had a diameter of 1.8±0.5 microns. The recording surface was further smoothed (polished) by laser.

Surface Treatment

Chips were received from FedEx overnight service and were inspected for integrity and cleanness. About 5% of the chips were excluded from further treatment in this process. Selected chips were then treated according to Example 3. Treated chips were stored in ddH$_2$O for 12 to 84 hours before the tests.

Batch QC for Chips

Chips were acid and base treated in batches of 20-25. Four to six pieces of each batch were randomly picked for testing their patch clamp performance with CHO-Kv1.1 cells in terms of speed to seal and stability of the whole cell access. Batches with <75% success rate were excluded for the 50-chip tests.

Cell Passage

CHO-Kv1.1 cells (CHO cells expressing the Kv1.1 ion channel) between passage 47 and 54 were split daily at 1:10 or 1:15 for next-day experiments. Complete Iscove media (Gibco 21056-023) with 10% FCS, 1×P/S, 1×NEAA, 1×Gln, 1×HT with 0.5 mg/ml Geneticin was present in media used to passage cells and not present in media used to grow cells for next-day experiments.

Cell Preparation

Cells were isolated using the protocol for CHO cell preparation described in Example 6. After isolation, cells were resuspended in PBS complete media and passed through a 20 micron polyester filter into an ultra-low cluster plate (Costar 3473). The cells were used for the study between 30 minutes and 3 hour 30 minutes after the filtration.

Cell QC

Isolated cells were QC'ed with conventional pipette patch clamp recordings for their speed to seal, break-in pressure, and Rm and Ra stability. Freshly pulled pipettes were typically used within 3 hrs. Only cell preparations that passed the pipette QC were used for the 50-cell tests. About 50% of the preparations out of approximately 30 cell isolations passed and were used for this study.

Solutions

Intracellular solution was made according to the following formula: 8 mM NaCl; 20 mM KCl; 1 mM MgCl2; 10 mM HEPES-Na; 110 mM K-Glt; 10 mM EGTA; 4 mM ATP-Mg; pH 7.25 (1M KOH3); 285 mOsm.

Aliquoted at 10 ml per 15 ml corning centrifuge tube, and stored at 4° C.

Extracellular solution (PBS complete) was DPBS (1×), with glucose, calcium and magnesium (Gibco cat#14287-080). This solution contained:

0.9 mM CaCl2, 2.67 mM KCl, 1.47 mM KH2PO4, 0.5 mM MgCl2, 138 mM NaCl, 8.1 mM Na2HPO4, 5.6 mM Glucose, 0.33 mM Na-pyruvate, pH 7.2-7.3, 295 mOsm.

Chip QC (Quality Control)

For each recording, the chip was assembled into a two-piece cartridge, and the lower and upper chambers were filled with intracellular and extracellular solutions, respectively. The chip was further QC'ed by inspection under the microscope and seal-test resistance measurement. Chips that showed a dirty surface, visible cracks and/or had a sealtest resistance greater than 2.1 MOhm were excluded.

Experiment Settings

Chips that passed QC underwent electrode offset and the overall recordings were done with 4 KHz bass filter. Cell landing was monitored on computer screen.

Criteria

A simple description of a positive result is: chips that achieved gigaseals and gave Ra<15MOhm and Rm>200MOhm throughout 15 min recording period.

Results

A total of 58 chips were tested, 6 of which were excluded from final analysis. Out of the 52 cells included, 39 (75%) passed the test criteria. 43 (83%) achieved at least 12 minutes of continuous high quality recordings (Ra<15MOhm; Rm>200MOhm); 47 (90%) achieved gigaseals.

Success Rate

Figure 24A:
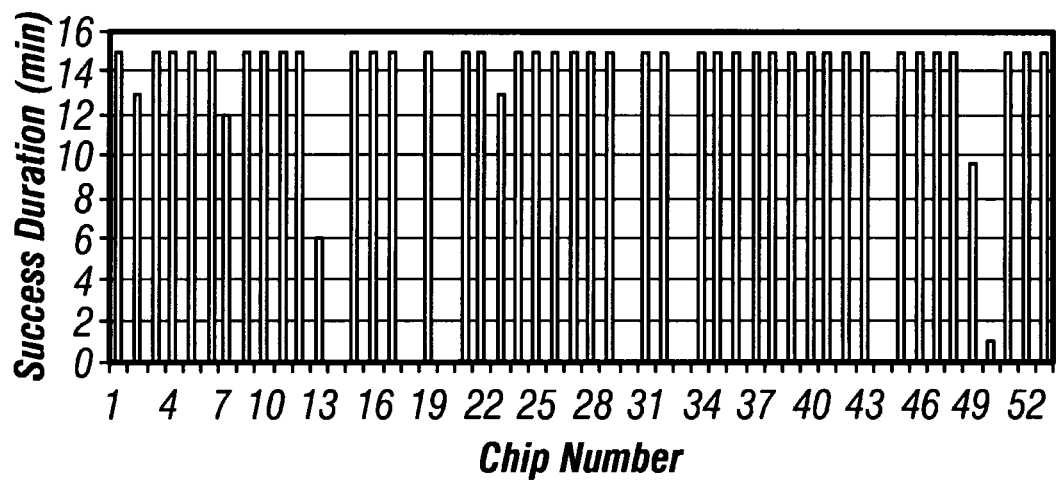
FIG. 24(A) shows the duration of successful high quality recordings from 52 chips tested successively.
Figure 24B:
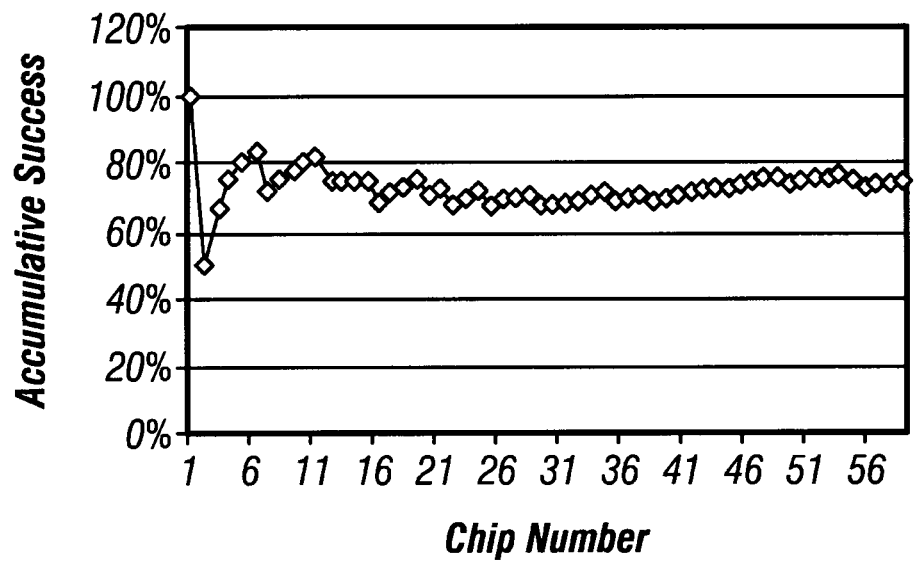
FIG. 24(B) shows an embarrassing spelling mistake intended to represent cumulative success rate determination from the experiments depicted in FIG. 24(A).

Success duration is plotted in FIG. 24a. Accumulative success rate is plotted in FIG. 24B. Success rate was consistent throughout the tests, which suggests that most of the critical experimental parameters were under control. 75% is a representative success rate under the current controlled conditions.

Figure 25A:
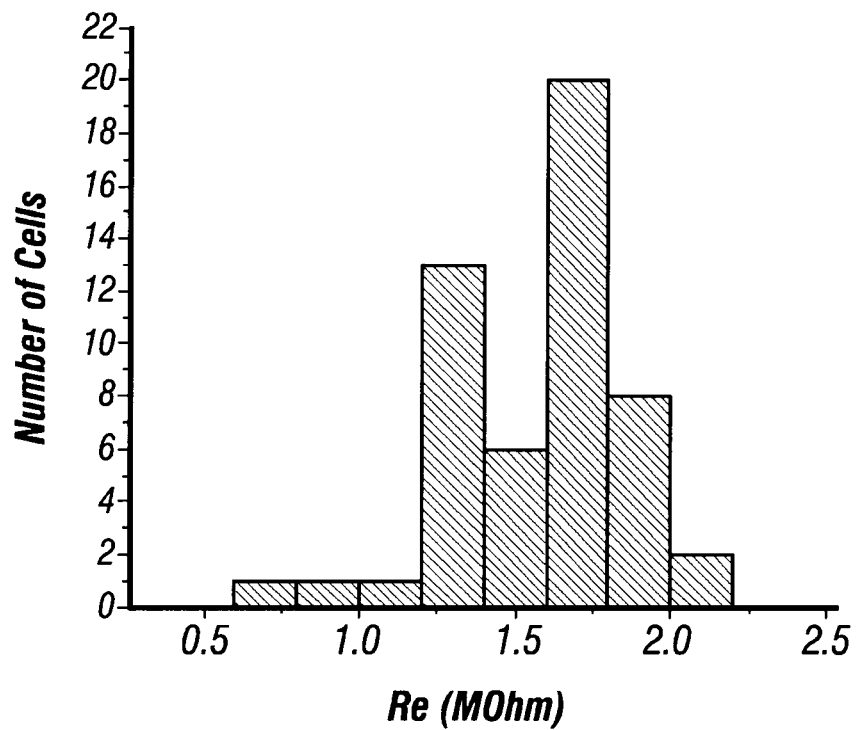
FIG. 25(A) is a histogram of the measured resistance across the holes of the chips used for the 52-chip test depicted in FIG. 24.
Figure 25B:
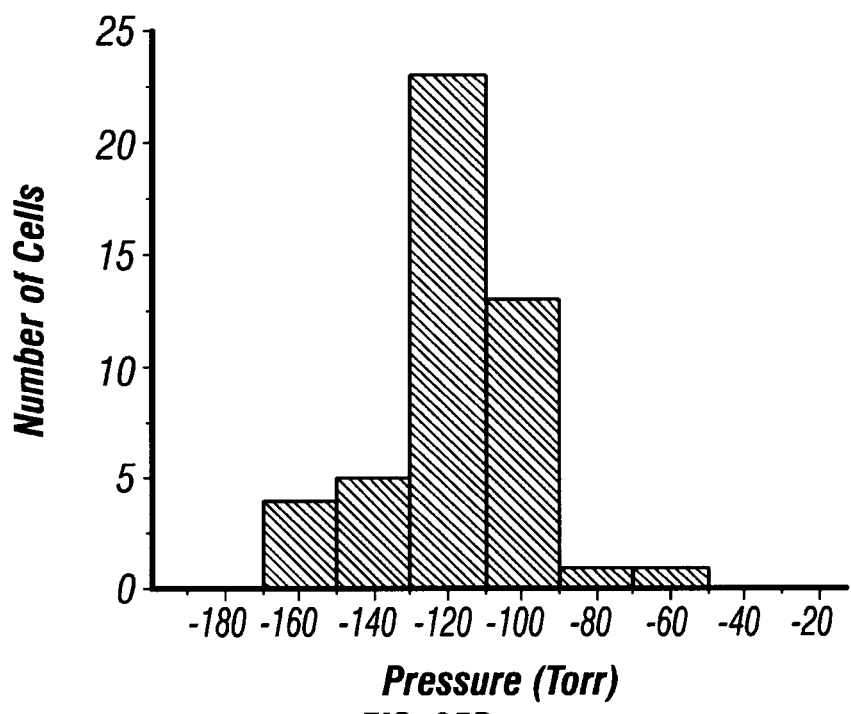
FIG. 25(B) is a histogram of the pressure required to gain access to the cell interior once sealed, for the 52-chip test depicted in FIG. 24.

Electrode Resistance (Re) 90% of the electrodes selected for the tests had Re between 1.3 to 2.0 MOhms (FIG. 25). A total of 81 chips were mounted and tested. 23(28%) failed the QC test, among which 15(18.5%) were due to Re>2.1 MOhms. 5(6%) chips were screened out because of their dirtiness of surface; 3(4%) had blocked or cracked holes. Chips were not screened at low Re values. The reason behind the 2.1 MOhm cut off is that historically chips with the current geometry (double counterbore) showed lower than 75% success rate in achieving the test criteria. Re is more or less normally distributed except for a slightly higher peak at ~1.3MOhm.

Break-in Pressure

Break-in Pressure is an important parameter for cell condition. During the tests, break-in pressures were tightly distributed between −100 to −130 Torr (FIG. 25). Our previous findings suggest that seals with more negative break-in pressure are likely to have higher and unstable Ra, while seals with lower break-in pressure are likely to have lower and unstable Rm.

Membrane Resistance (Rm)

Figure 26A:
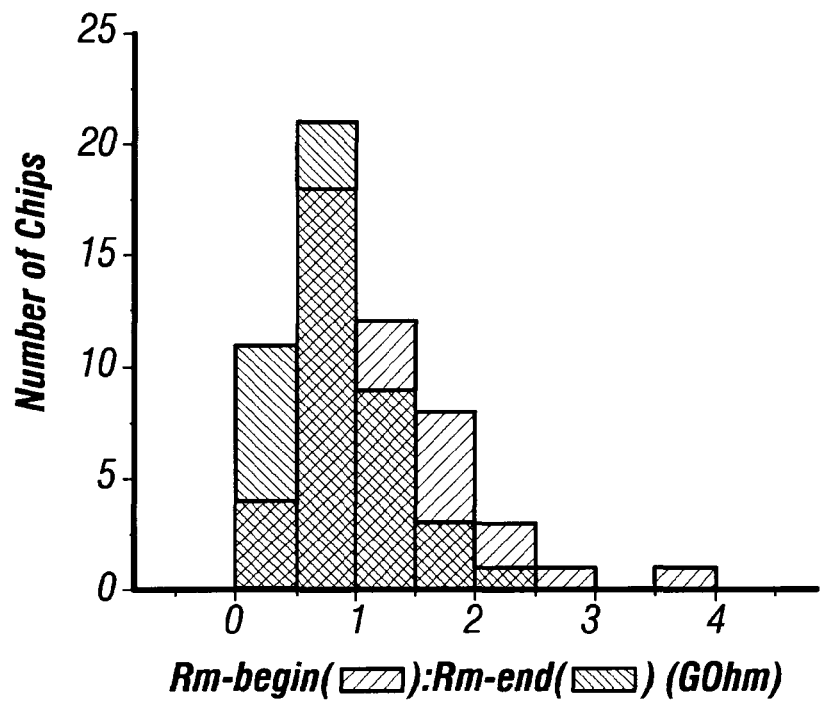
FIGS. 26 (A) and (B) are histograms of the relevant parameters relating to the gigaseals and whole-cell access, as measured at the beginning and again at the end of each experiment during the 52-chip test depicted in FIG. 24, where Rm is the total resistance measured during whole-cell access and Ra is the access resistance value as determined from a capacitive spike during a step change in the command voltage.
Figure 26B:
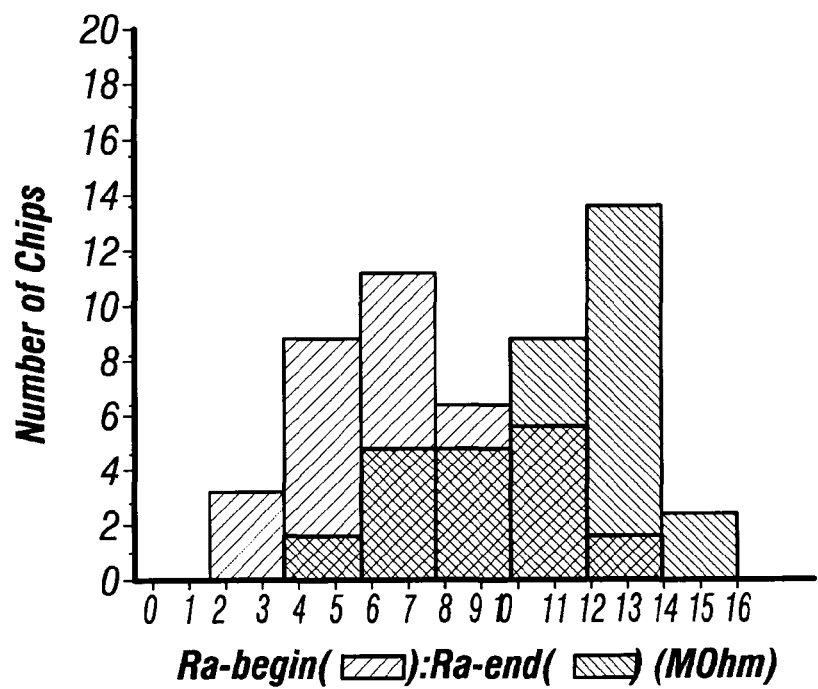

After break-in, Rm was mostly between 0.5 to 2MOhm (FIG. 26). Ending Rm had a similar distribution, but more skewed to lower values. This is consistent with the deterioration of Rm over time. However, the amount of Rm deterioration was surprisingly small, which suggests that the seals were very stable during the 15 minutes test periods.

Access Resistance (Ra)

Initial Ra had a normal distribution centered at 7MOhm. 80% of the seals had Ra starting from below 10 MOhm. In most cases, Ra increased during the 15 minutes with an ending value near 11~13MOhm. In order to minimize disruption of the seals, great effort was not made trying to maintain minimal possible Ra. It is not known what the ending Ra would be and what percentage of seals would lose Rm if such efforts were made.

Typical Recordings

Figure 28:
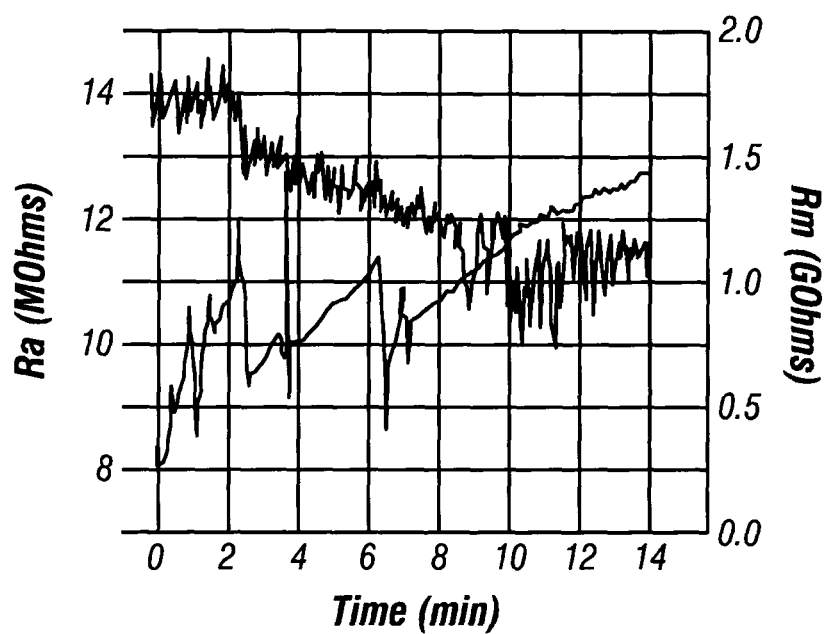
Figure 29:
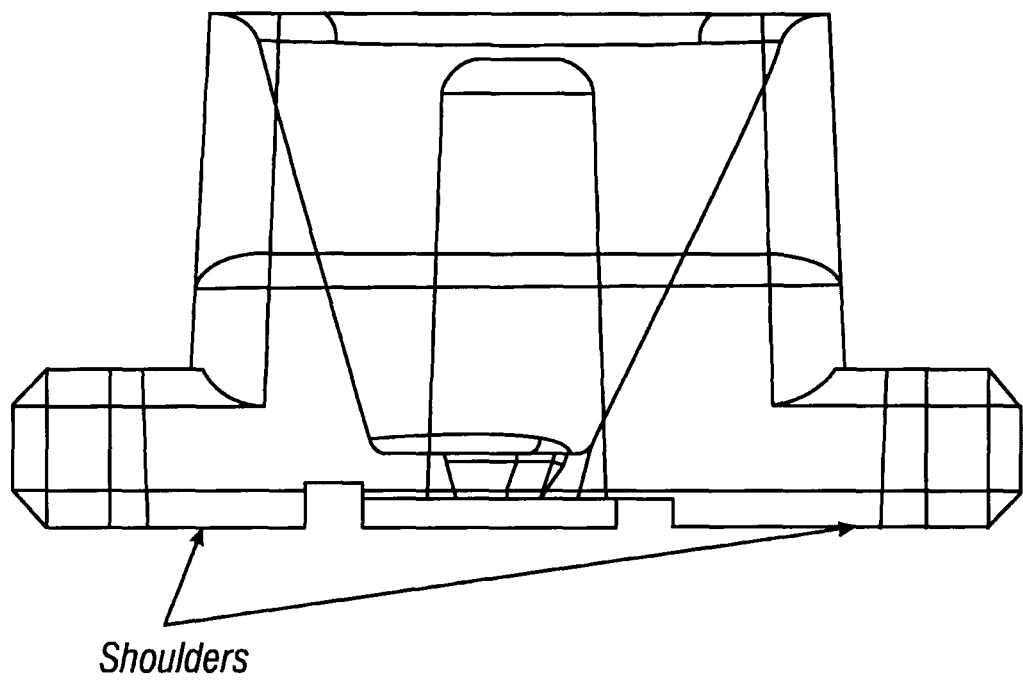
FIG. 29 depicts a cross section of one embodiment of a plastic injection molded carrier or cartridge for the purpose of holding the chip, specifically indicating the shoulder regions of the plastic part which are meant to interact with the automation devices.
Figure 30:
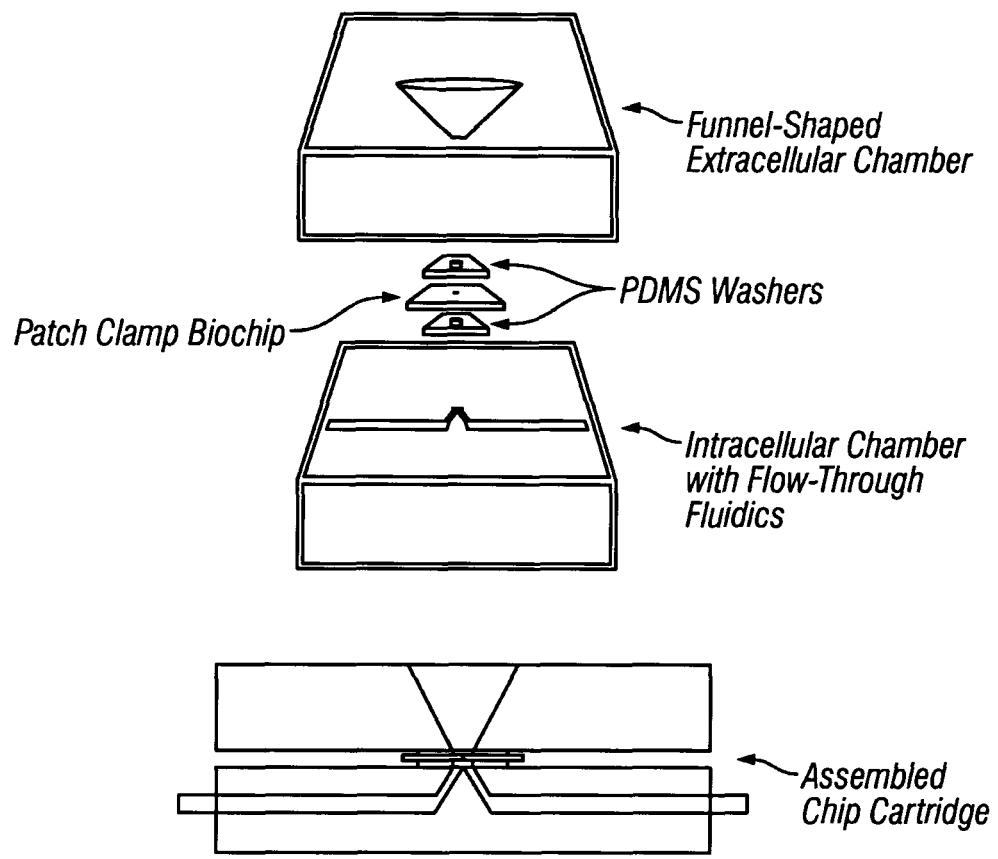
FIG. 30 depicts another embodiment of a plastic carrier or cartridge for the purpose of holding the chip. In this embodiment, the chip is suspended between two PDMS gaskets shaped to allow access from below to the intracellular chamber using flow-through fluidics, as well as access from above to a funnel-shaped extracellular chamber. Below is a further depiction of same in cross-section as it may appear once assembled into a functional device.
Figure 32A:
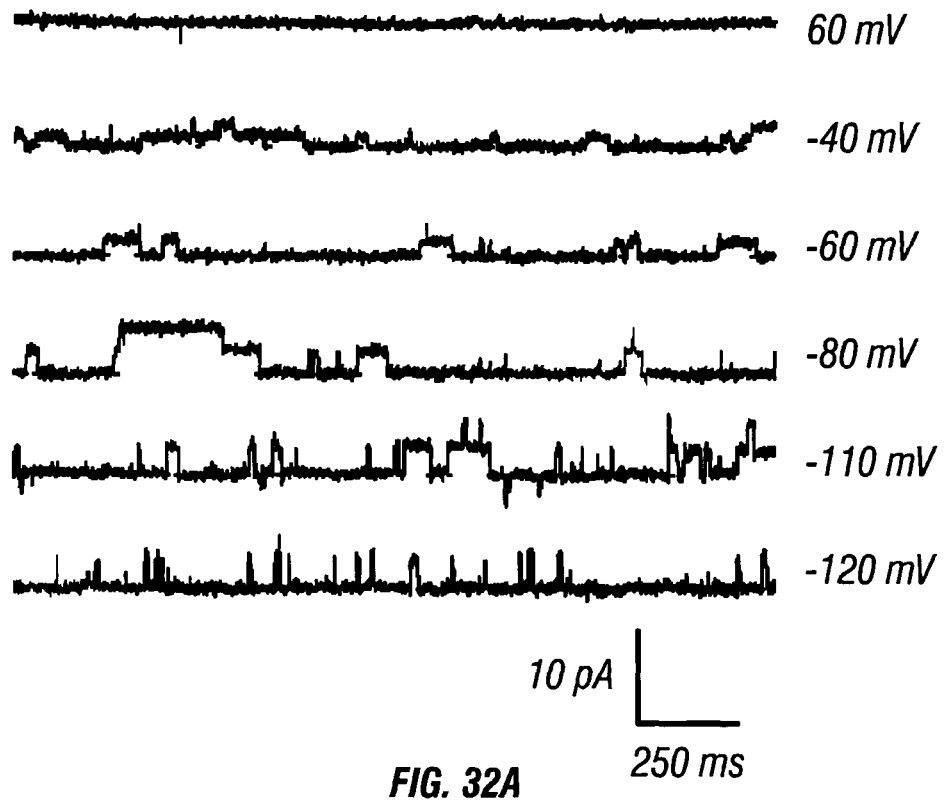
FIGS. 32 (A)-(D) depict an exemplary single channel recording.
Figure 32B:
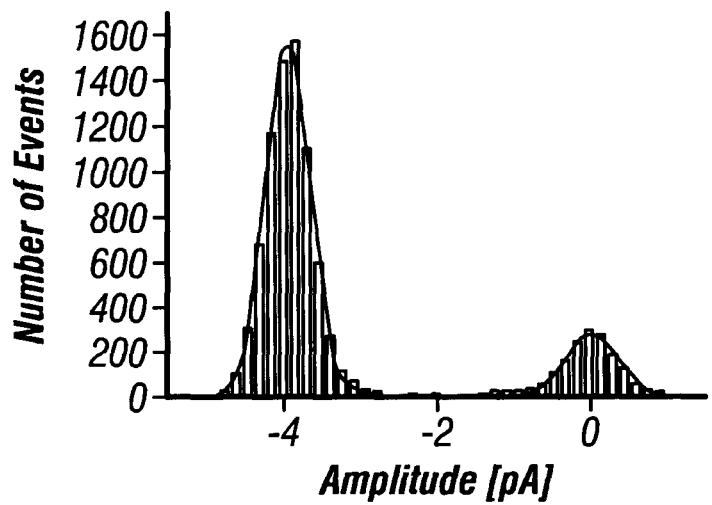
Figure 32C:
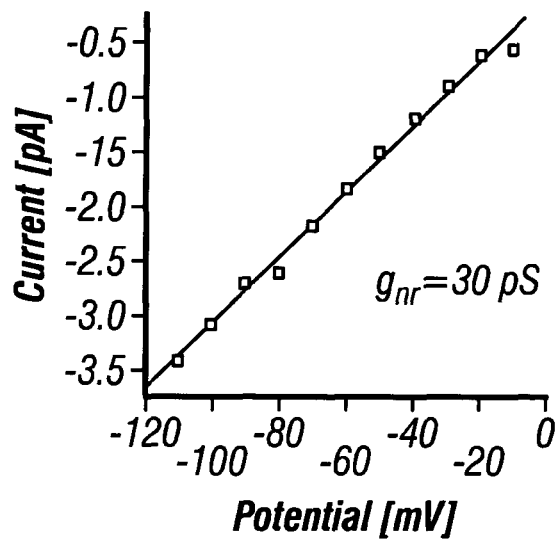
Figure 32D:
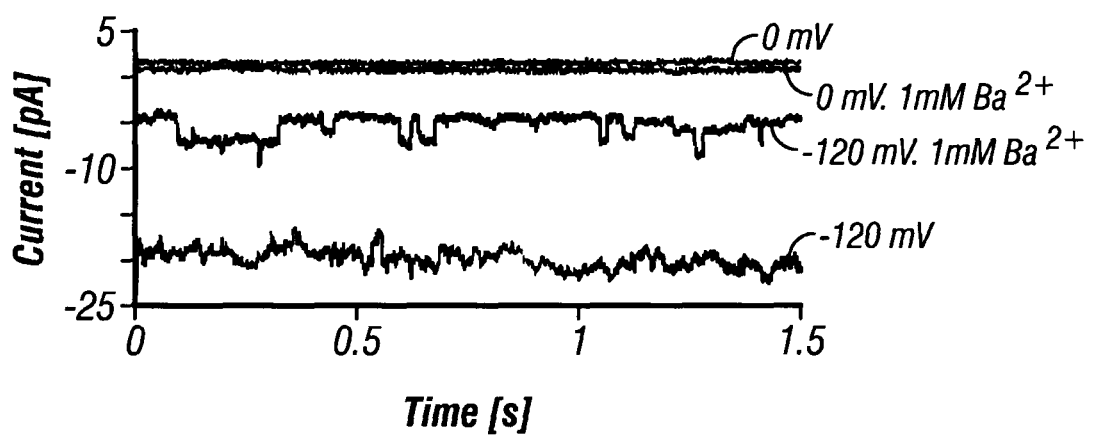
Figure 33A:
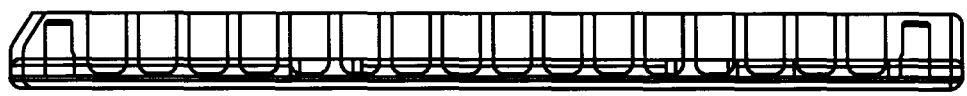
FIG. 33(A) shows a side-view.
Figure 33B:
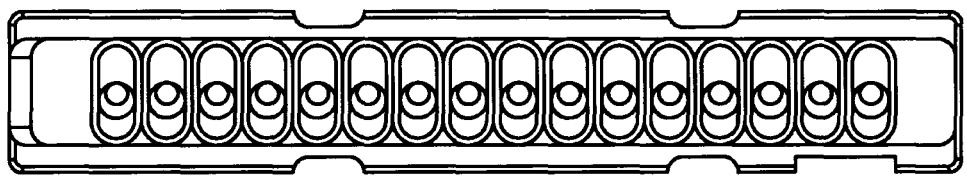
FIG. 33(B) shows a top-view.
Figure 34:
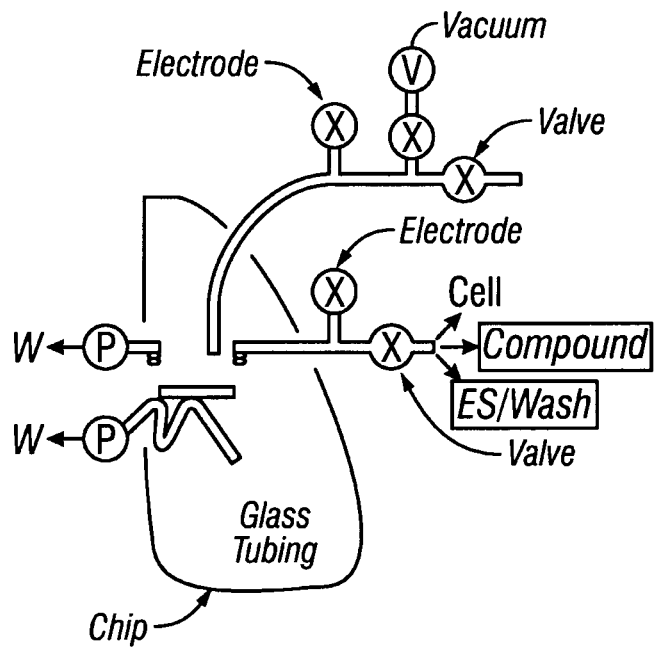
FIG. 34 depicts an exemplary chip having channel upper and lower chambers.

FIGS. 27 (A)-(B) and FIG. 28 show the recordings from a typical experiment. The top panel shows recordings right after break-in, while the bottom panel shows recordings at the end of 15 minutes. The middle graph plots the Rm and Ra values over the 15-minute period. There is no observable decrease in current in most of the cells recorded. The decrease in Rm and increase in Ra are typical. In addition, Rm and Ra typically plateau out after .about.10 minutes to steady levels. We recorded the last cell (#58) for an extended period of time. The cell lasted for about 30 minutes within the constraint of our test parameters.

Example 3

Treatment of Ion Transport Measurement Chips to Enhance their Electrical Sealing Properties Detailed Procedure:

(referenced to step numbers below). All incubation processes were carried out in self-made Teflon or Noryl fixtures assembled in a glass tank while shaking (80 rpm, with C24 Incubator Shaker, Edison, N.J., USA). Water was always as fresh as practical from a water purification system (NANOpure Infinity UV/UF with Organic free cartridge). Nitric acid was ACS grade (EM Sciences NX0407-2, 69-70%). Sodium hydroxide was 10 N, meeting APHA requirements (VWR VWR3247-7). When necessary, chips were inspected for QC before and after treatment.

The protocol used was:
1. 3 hour shaking incubation in 6M nitric acid at 50 degrees C.
2. 6×2 minute rinses in DI water at room temperature.
3. 60 minute incubation in DI water (shaking)
4. 2 hour shaking incubation in 5M NaOH at 33 degrees C.
5. 6×2 minute rinses in DI water at room temperature.
6. 30 minute incubation in DI water (shaking) at 33 degrees C.
7. Chips were stored in DI water at room temperature. A vial used for storage was filled to the neck to minimize air space.

Chips treated according to this protocol demonstrated enhanced electrical sealing when tested in ion transport detection devices.

Example 4

Achieving Seals with Inverted Chips

A biochip was fabricated from Bellco D263 or Corning 211 glass of thickness of .about.155 micron. The 16 laser-drilled recording apertures on the chip had dimensions of 82 mm (long).times.4.3 mm (wide).times.155 microns (thick). The distance between the first hole and a narrow edge is 7.25 mm. The apertures were laser drilled to have one counterbore of 100 microns (diameter).times.125 microns (deep). A final through hole was drilled from the side of the counterbores and had a .about.10 micron entrance hole and 4.5 micron exit hole with a total through hole depth of 30 microns. After standard chemical treatment as described in Example 3, the biochip was mounted to an upper chamber piece described in Example 1 in inverted configuration such that the counterbore side faced the upper chamber piece (where RBL cells were added). Recordings were done with a device adapted to Nikon microscope as described in Example 5. Typical recording parameters such as Rm and Ra over time are shown in FIGS. 27 (A)-(B) and FIG. 28. The table in the figure shows the average and standard error of parameter values measured.

Example 5

A Biochip Device Adapted to a Microscope and Having Flow-Through Lower Chambers

This device is shaped to take advantage of an existing mounting point on the Nikon microscopes by positioning the device into an aperture within the microscope stage. It is round, with an edge intended to prevent it from falling through the hole on the stage. The depth of the device is intended to hold the functional portion of the biochips as well as the cells that are added to the biochip at testing time at a convenient focal point within the focal range of the microscopes, ie: at essentially the same level as the upper platform of the microscope stage.

In this design, a biochip cartridge that has a base-treated glass chip sealed to an upper chamber piece may be assembled onto a microscope stage-mounted lower chamber piece that allows simultaneous or sequential testing of all recording apertures while simultaneously observing the experiment's progression microscopically. The tester consists of a metallic base plate, in this case made of aluminum, shaped to insert onto a microscope stage, and sculpted to support and align a multi-well perfusion lower chamber piece. A gasket is inserted over the lower chamber piece, then the cartridge, which is clamped onto the gasket by compression via a clamp assembly that bolts onto the base plate using four thumb-screws. The lower chamber piece is made of plastic and contains an array of 16 holes for inflow of intracellular solution, and another 16 holes for outflow of same. The 32 holes emerge on the top surface of the part in alignment with the recording apertures of the biochip. The gasket is made of PDMS and situates between the lower chamber piece and the chip, and contains slits, or holes, that also align between the emerging holes of the perfusion conduits of the lower chamber piece, and the recording apertures of the chip, such than an intracellular "lower" chamber is formed within the array of slits or holes in the gasket. An electrode of silver-silver chloride is introduced into each of the 16 holes along one side of the bottom chamber to function as the voltage-clamp electrode.

The device is made up of 1) a metallic base, specifically, but not exclusively, stainless steel, 2) a transparent lower chamber piece, made from polycarbonate (but could be any other convenient transparent substance) 3) electrodes inserted into the tubes of the inner chamber array, made from wires of silver or any other conductor capable of being used as a voltage sensing and current-delivering electrode, and attached to a connector on the outer side of the inner chamber array, 4) inert tubing glued to the tubes of the inner chamber or any other means that may provide a connection for a fluid conveyance system, in this case made from glass, 5) a gasket that provides a seal between the inner chamber tubing and the biochip cartridge, where the gasket simultaneously comprises the inner chamber, in this case made of PDMS, 6) a biochip mounted onto the test apparatus over the gasket, and held in place by a guidance system, in this case pins inserted into the plastic bottom chamber array body in such a way as to restrict movement of the biochip while simultaneously guaranteeing alignment of the biochip's recording surface with the inner chambers, 7) a clamp assembly intended to apply sufficient pressure onto the biochip cartridge so as to generate a seal between the bottom the chip and the gasket, and 8) an array of electrodes shaped and oriented so as to enter into the top wells of the biochip cartridge, all 16 at a time, and where all electrodes are connected together so as to provide a reference electrode in the top-chamber of the cartridge.

1) Metallic Base Plate:

This base plate serves multiple functions. First, the metallic body serves as an electrical noise shield for the bottom side of the test chamber. It completes a type of faraday cage that is contiguous with the grounded stage of the microscope, and with a small cage that must be installed around the stage of the microscope if no faraday cage is to be present in a wider area around the microscope. Secondly, the metal base is carved on the top side so as to catch any fluids that may leak or spill and prevent the contamination of the microscope with said fluids. To this end, the base plate is sealed, with silicone glue or with silicone grease (vacuum grease) or with any other such viscous immiscible substance (eg: Vaseline) to the transparent inner chamber array described in (2). Third, the base plate may be shaped to optimize its use with a particular microscope. Specifically, in our case it was desirable for the base plate to be cut to fit onto the 107 mm circular cutout hole of a Nikon microscope. Fourth, the base plate is drilled and tapped so as to provide a mounting point for the inner chamber array and for the clamp of the tester. Its design is such that it will ultimately hold the recording aperture of the cartridge within a few millimeters of the level of the top of the microscope stage so as to ensure that the chip function may be monitored within the focal range of the microscope. FIG. 2 illustrates the design of the base plate as adapted for the Nikon Microscope.

2) Transparent Inner Chamber Array:

The lower chamber piece may also be referred to as an inner chamber array, or an intracellular chamber array. For the convenience of being able to view under a microscope the progression of an experiment, it should be made of a transparent material. Polycarbonate was chosen for its ease of machining. It is shaped to support a cartridge over it, and provide tubing connections along the long edges of either side the cartridge, as well as to provide connections to electrodes placed inside one of each pair of tubes (holes in the material that function as such) supplying each recording aperture of the chip. The tubes drilled into each side provide a connection between the edge of the part and somewhere near the center, then another tube drilled perpendicularly from the top surface to connect to each tube coming from the edge. The emerging tubes at the top surface are located so as to provide an inflow and an outflow of solution in the bottom wells. No well is contained within this part but the bottom wells are instead created by an opening within the gasket material. The inflow and outflow holes are separated from one another so as to leave an untouched area of surface that will be easy to see through with a microscope so as to visualize the recording aperture during experimentation. To this end, the top surface that is in opposition to the chip should remain untouched with the exception of the emerging inflow and outflow holes and as well the bottom surface should remain untouched so as to not disrupt transparency of the part. Each tube (or hole) leading to the edges of the part should consist of a means for interfacing it to external tubing (see description of part 4) that provides delivery of solutions, as well as pneumatic pressure control. One of the tubes going to the edge of the part is left longer so as to house an electrode (wire) that is introduced into the lumen of the tube. The added length also allows for a second segment to be glued onto the top surface so as to house the connectors for the electrodes. The top surface of this part is trimmed down around the periphery of area covered by the cartridge so as to provide an edge that functions to hold the gasket in place during mounting and unmounting of the cartridge. Further, between each pair of inflow and outflow holes for each bottom well is a cut intended to prevent wetting of the gasket material to span from one bottom chamber to adjacent bottom chambers. This part as a whole contains 6 holes 2 mm in diameter to hold 6 pins that function to keep the cartridge aligned during mounting. It also contains a further 4 holes to hold 4 spring-pin compression contacts that function to provide an electrical connection for an early version of the cartridge. The present version of the cartridge does not require these contacts, however they were kept in place so as to prevent contact with the gasket before the clamp part is pressed down during the mounting. Finally, two more holes are present so as to use two screws to hold the part onto the base plate. FIGS. 4-10 illustrates the arrangement of the lower chamber piece.

3) Inner Chamber Electrodes:

Each bottom well segment contains an electrode, which in this case is a silver wire that will be periodically chlorided. The wire is inserted into the lumen of the longer hole and bent upward into the connector array. The segment of wire is sufficiently long that it will remain exposed within the lumen of the longer tube after the inert tubing interface parts are glued into place, and the other end is soldered to a connector, in this case an array of 1 mm female pin-connector sockets inserted into holes in the part.

Figure 7:
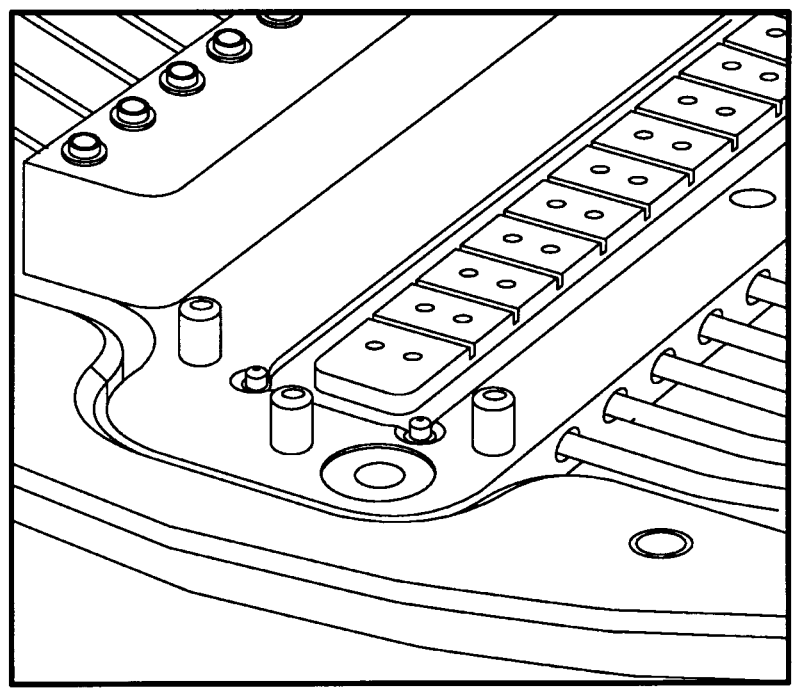
FIG. 7 shows glass tubing inserted into the plastic lower chamber piece shown in FIG. 6. The tubing has been cemented into place with 20 minute epoxy glue. Silicone tubing is ten pressed over the glass tubing to complete the conduit to deliver fluids into the lower chambers.

4) Inert Tubing interface:

Into each hole is inserted an inert tube segment (in this case made from glass) that is fixed in place with epoxy glue. Epoxy is chosen only in-so-much-as it is preferred for bonding glass to polycarbonate. The tubing segments are sufficiently long to butt against a countersunken segment of the tube drilled into the inner chamber array and stick out of the part enough to hold a segment of silicone tubing that is press-fit onto the glass segment. This junction should withstand a pressure greater than two atmospheres positive pressure, and greater than 700 mmHg vacuum pressure. It was determined that 3 to 5 mm insertion into the silicone tubing was sufficient to accomplish this requirement. FIG. 7 illustrates the glass tubing mounted into the polycarbonate inner chamber array.

Figure 8A:
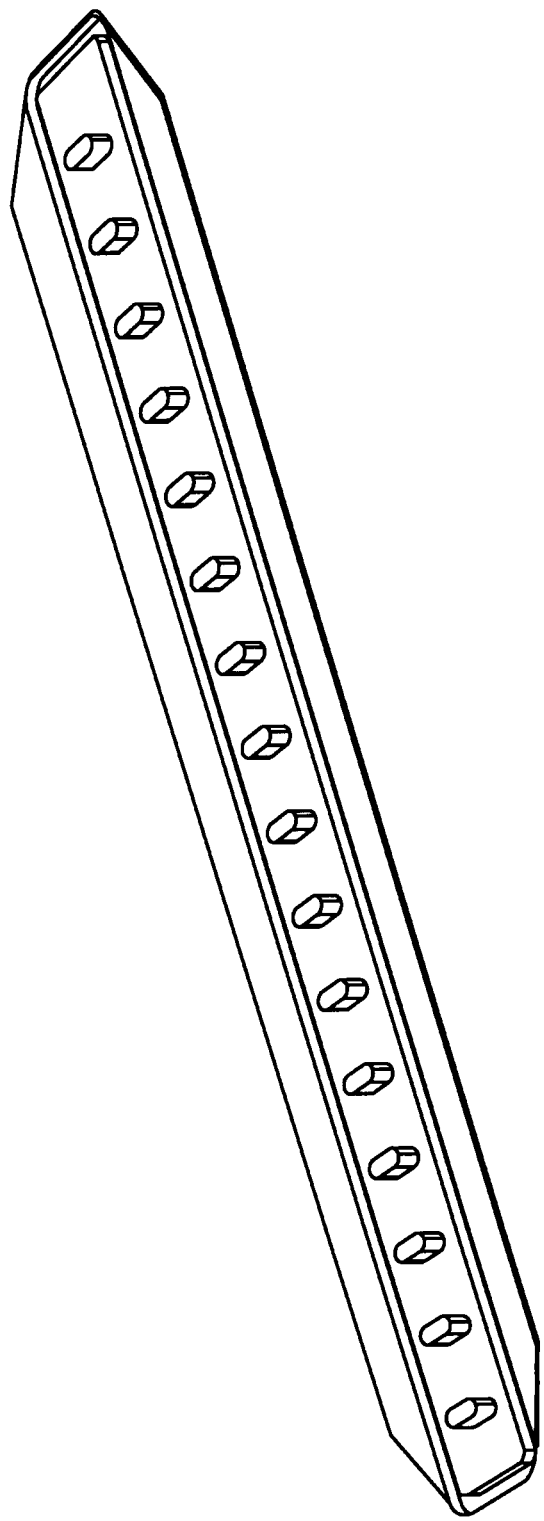
FIG. 8 depicts a PDMS gasket viewed from the top (A), from the side (B) and (C) a schematic demonstrating the formation of the inner wells by the holes within the gasket.
Figure 8B:
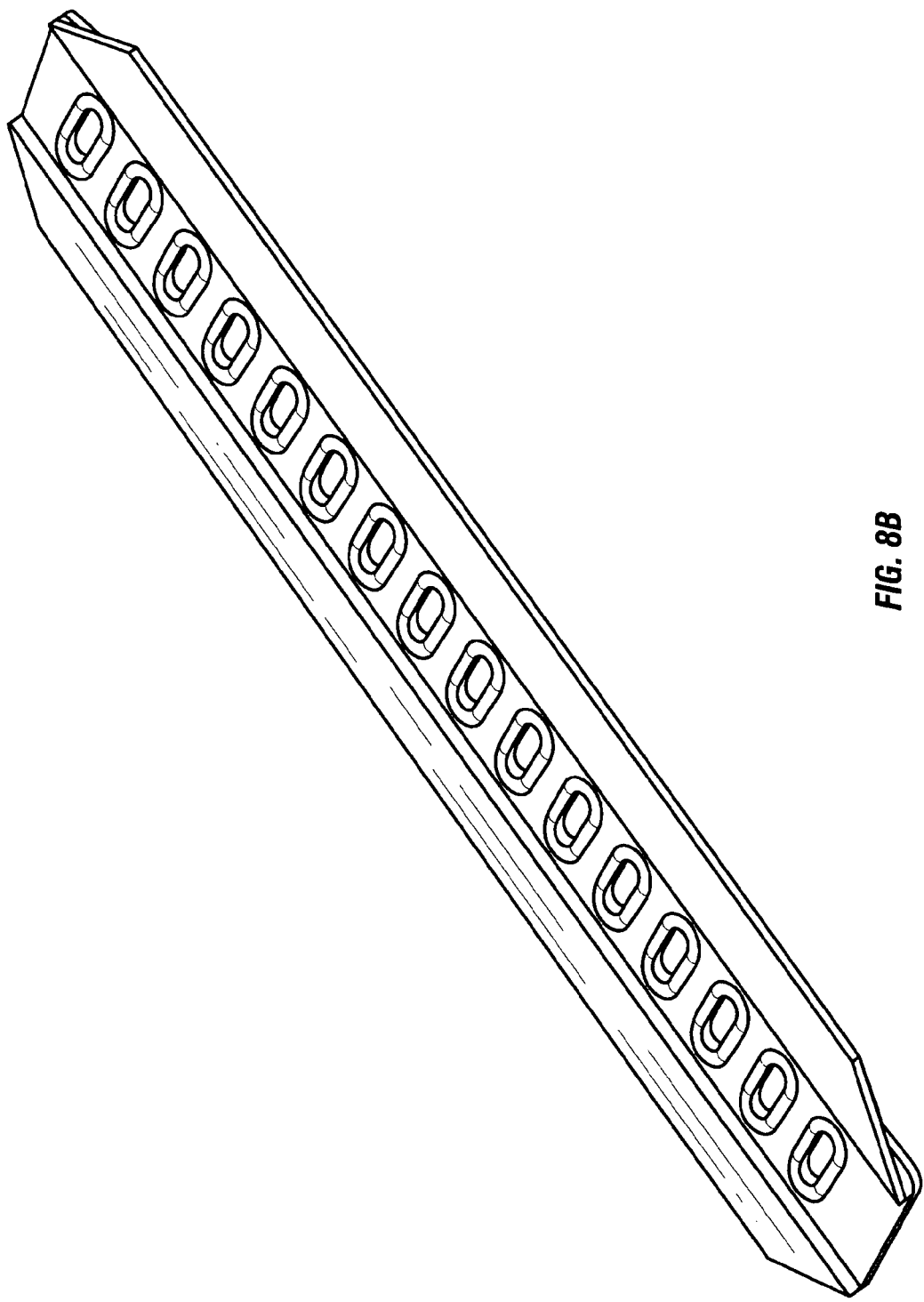
Figure 8C:
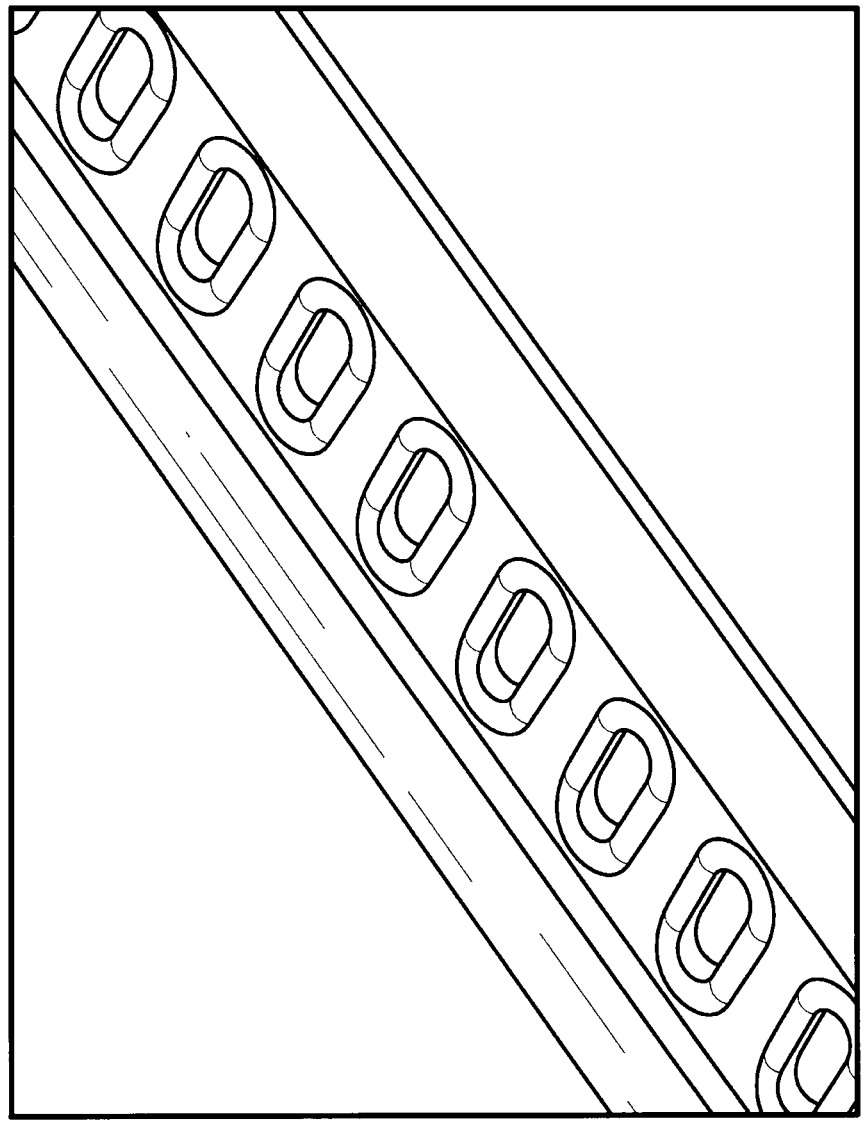
Figure 9A:
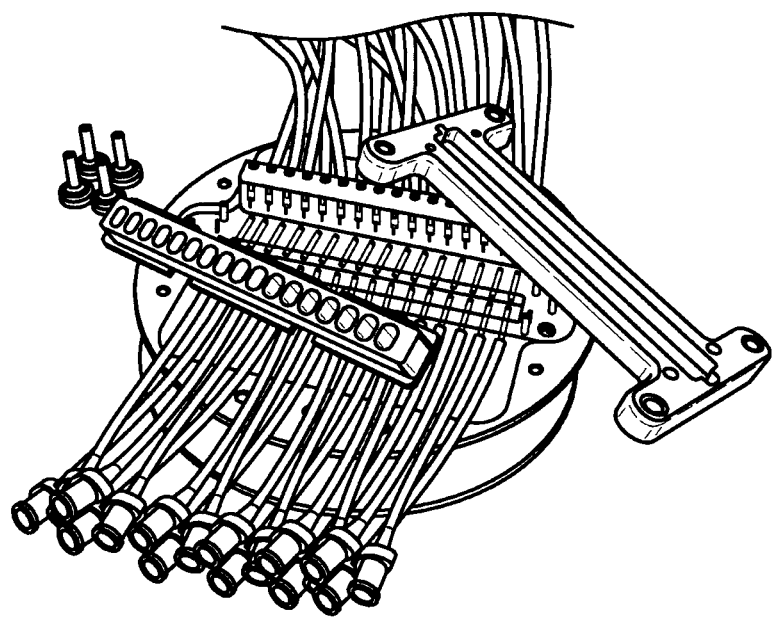
FIG. 9 shows a cartridge of the present invention (black item) is shown in relation to the rest of the parts of a device adapted for a microscope (A) and after installation into the device B).
Figure 9B:
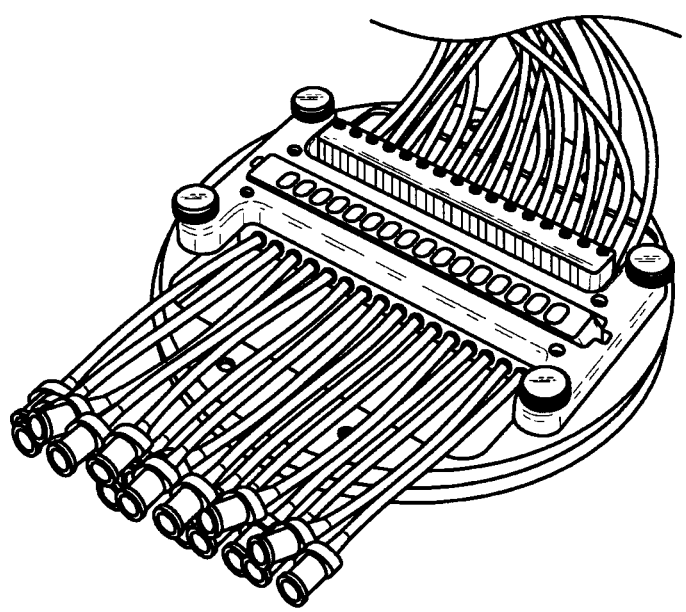

5) Gasket:

For convenience the flexible gasket may be molded from curing PDMS. The gasket contains a raised edge on the bottom side that surrounds the chambers as a whole and is intended to hug an edge present in the same periphery on the inner chamber array so as to hold the gasket in place. The gasket has oblong holes in it that align over the exit and entrance holes of the inner chamber array for each chamber of the array. On the top surface of the gasket is a set of squared O-rings that are part of the gasket but raised sufficiently to form a seal onto the cartridge when pressed against it with the clamp part. The gasket is illustrated in FIG. 8.

5) Biochip

The fabrication of chips having holes for ion transport measurement is described elsewhere. In this device, the chip is made of glass and has 16 laser drilled holes. The chip is laser polished on the top surface, and treated in acid and base prior to attaching the chip to an upper chamber piece with a UV adhesive.

Figure 10A:
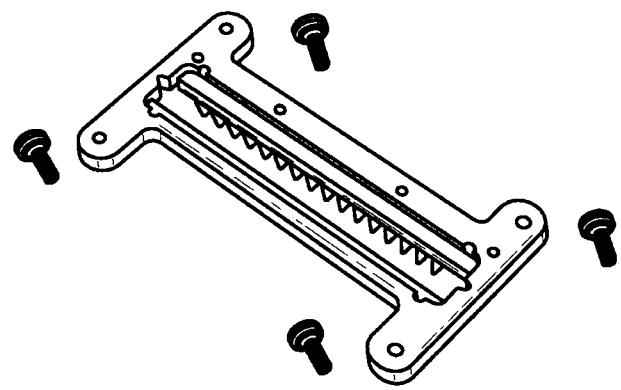
FIG. 10 (A) shows a clamp part upside down to illustrate the cutout that fits the cartridge. The top view of the clamp on the cartridge (B) reveals the presence of an array of top chamber electrodes that reach into the cartridge wells (C).
Figure 10B:
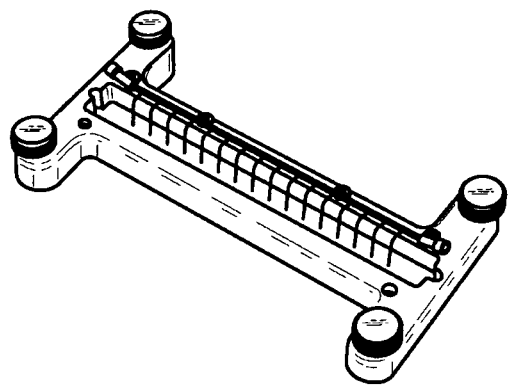
Figure 10C:
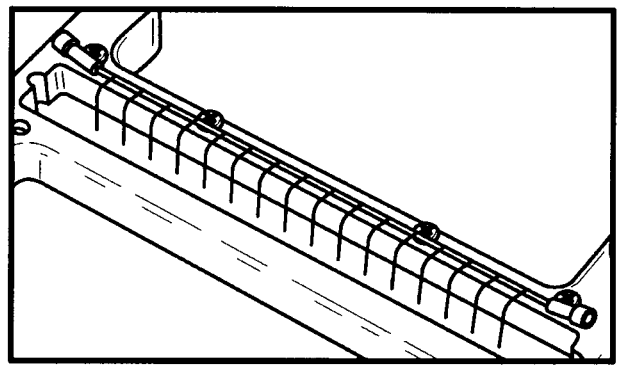

6) Clamp Assembly:

A clamp is made from an inflexible material so as to not allow bowing of the cartridge during compression onto the gasket while mounted on the tester. In this case it is made of stainless steel for its inertness when wetted with physiological buffers. The clamp is shaped so as to fit snugly over the cartridge and is drilled so as to accommodate and be positioned by the guide-pins sticking out of the inner chamber array. Four screws are finger-tightened to the base plate at each corner of the clamp assembly so as to press down the cartridge to seal it against the gasket. This part is shown in FIG. 10.

7) Upper Chamber Electrodes:

In early development it was expected that compression pins would contact the bottom of the cartridge during testing to provide a connection to the reference electrodes built in to the cartridge. The present embodiment of the cartridge does not contain reference electrodes, therefore these electrodes must be introduced into the top wells of the cartridge. To this end, periodically chlorided silver wires are used as electrodes. The electrodes are shaped to dip deep inside each well, and on the outside of the wells are soldered to a wire running along the top of the clamp part. At each end of this wire is a 1 mm female pin connector that is used to interface with the voltage clamp amplifier. The electrode array is pictured in FIG. 5.

Method:

Before use the device should be clean and dry.

A SealChip cartridge is removed from its carrier, and rinsed with a jet of deionized water of approximately 18 MOhms resistance. The product is them dried under a stream of pressurized dry air filtered through a 0.2 μm air filter to remove water from the recording apertures and their vicinity.

The clean cartridge is then placed with top-wells upward onto the pressure contact pins of the tester such that movement of the cartridge is limited by the six alignment pins of the bottom-chamber. The cartridge should be supported above the PDMS gasket but without yet touching the gasket. The clamp is them placed over the cartridge such that the 4 mounting holes align with their threaded counterparts on the base plate. The 4 mounting screws are them used to press down the clamp uniformly thereby pressing the cartridge down onto the PDMS gasket with sufficient pressure to form a tight seal between the chip and the gasket and between the gasket and the bottom chamber array. The recording aperture within each chamber of the cartridge should already be aligned with openings in the gasket that form the bottom chambers.

The bottom chambers are then filled from one side with sufficient solution (analogous to intracellular solution) to fill the bottom chamber and fill enough of the tubing on the other side such that capacitative distension of the tubing on the filling side will not introduce air into the recording chamber, and will not introduce air into the area of the tubing that contains the bottom-chamber electrode. For this purpose, it is best to fill the chamber starting from the side that does not contain the electrode since higher pressures will be used for vacuum pressure than for positive pressure, thereby ensuring that the electrode will remain in full contact with the solution at all times. Once the bottom chamber is filled and is free from visible bubbles, the tubing should be sealed off by a clamp or valve or any means that ensures electrical isolation between the bottom chambers of the array. Sufficient positive pressure should be applied to the free end of the inner chamber tubing so as to cause solution to be forced into the counterbore and through the hole of the recording aperture of the chip.

Once solution is seen emerging into the top chamber, the pressure should be released, and immediately the top chamber should be filled with sufficient solution (analogous to extracellular solution) so as to completely immerse the top side of the chip without bubbles remaining on the chip surface, and fill the top well sufficiently to provide good contact with the electrode in the top well. It is also of benefit to fill the top well sufficiently to avoid a strong meniscus effect (60 to 70 μL with the present version of the SealChip product) whenever it is intended to view under an inverted microscope the progression of the experiment (for upright microscopes it is necessary to fill with more solution, ~90 μL, to allow good contact with a coverslip that must be placed over the well to enable a good view of the bottom of the well).

The assembled tester is now ready for testing and should be placed on the microscope (or appropriate shielded location if observation of the experiment is not necessary) and connected to the voltage clamp amplifier(s) as well as to the pressure control device(s) for testing.

After the termination of the experiment, the tester is disconnected and removed from its testing location. The extracellular medium is suctioned from each well, and each well is rinsed once with deionized water to removed any leftover particulate (debris or cellular) material that may be left over from the experiment. Both ends of the tubing of the bottom chambers are then opened and the solution is suctioned out of the bottom wells. Each well should be well rinsed with clean deionized water, then dried completely with pressurized air. Finally the screws holding down the clamp are removed and the cartridge is disassembled from the tester. Any wetting at the gaskets should be wicked away with a lint-free tissue. If any liquid is pooled around the gasket, then the gasket should be removed, rinsed then dried, and the bottom chamber array should be likewise rinsed and dried, ensuring that the tubing is also rinsed and completely dried.

Quality Control/Quality Assurance of SealChip product:

Internally to the company, the tester has been used for QC/QA of the SealChip product before it is sent to customer, and before it is used internally for further research. The success rate with product that passes the QC has been as good as that with older testers that tested a single chamber at a time.

Quality Control/Quality Assurance of Cells:

Internally to the company, the tester has been used to verify the quality of the cells used for QC/QA using known good SealChip product.

Research and Development:

The tester has been used by our company for testing variations to the SOP for the SealChip product. In the future it may be used for discovery and screening of compounds that require exchanging of solutions on the bottom well or where compounds or particles must be delivered to the cytosolic chamber after a seal is formed with the cell membrane.

A great number of results have been achieved on the microscope adapted device ("Tester Unit") since its discovery. The tester was verified as comparable to the original tester based on a single-aperture test in December, 2002. Since January $14^{th}$ it has been the tool of choice for performing quality control experiments on the SealChip product. The following is examples of the quality of data obtained from it.

| Chip Lot# | Hole ID | Cell Type | Re (G) | Rm (G) | Ra (M) | Seal Qty | Note |
|---|---|---|---|---|---|---|---|
| S2N22-40 | C | RBL | 3.4 | 0.5 | 5.7 | +++ | |
| | G | | 3.3 | 5 | 6.7 | +++ | |
| | I | | 3.3 | 2 | 2 | +++ | |

-continued

| Chip Lot# | Hole ID | Cell Type | Re (G) | Rm (G) | Ra (M) | Seal Qty | Note |
|---|---|---|---|---|---|---|---|
| | M | | 3.2 | 0.25 | 8.8 | +++ | |
| | O | | 3.2 | 0.5 | 6.5 | +++ | |
| S2D18-114 | A | | 3.9 | 2.4 | 7.2 | ++ | |
| | C | | 3.9 | 2.2 | 18 | + | |
| | G | | 3.7 | 4 | 10.8 | ++ | |
| S2D20-28 | B | | 4.5 | 2.6 | 9.1 | ++ | |
| | C | | 4.2 | 1 | 13.3 | −S | |
| | D | | 4.4 | 0.6 | 10.5 | + | |
| | E | | 4.3 | 2.7 | 10 | ++ | |
| | F | | 4.3 | 1.6 | 10 | ++ | |
| | G | | 4.2 | 3.5 | 9.4 | ++ | |
| | H | | 4.3 | 3.3 | 8.8 | ++ | |
| S2D20-8 | A | | 4.1 | 1.7 | 12.2 | ++ | |
| | C | | 4.1 | 2.7 | 9.3 | ++ | |
| | G | | 4.2 | 1.7 | 8.4 | ++ | |
| | I | | 4.1 | 2 | 11 | + | |
| | M | | 4.1 | 1.6 | 11.7 | S | Debris landed before cell |
| | O | | 4.1 | 2.6 | 7.6 | ++ | |
| S2D20-50 | A | | 4.3 | 2.9 | 12.4 | + | |
| | B | | 4.3 | 7 | 10.7 | +++ | |
| | C | | 4.1 | 1.1 | 10 | +++ | |
| | D | | 4.3 | 2.1 | 8.8 | +++ | |
| | E | | 4.2 | 4.5 | 8 | ++ | |
| | F | | 4.4 | 4.9 | 7.1 | ++ | |
| | G | | 4.3 | 1.5 | 10 | ++ | |
| | H | | 4.3 | 6.9 | 8.3 | ++ | |
| | I | | 4.2 | 6.2 | 8.3 | +++ | |
| | J | | 4.2 | 0.6 | 8.1 | +++ | |
| | K | | 4.3 | 0.9 | 9.8 | ++ | |
| | L | | 4.4 | 6.5 | 7.4 | +++ | |
| | N | | 4 | 6 | 7.7 | +++ | |
| | O | | 4 | 5.6 | 7.8 | ++ | |
| | P | | 4.1 | 6.5 | 12.8 | +++ | |
| S2D219-21 | D | | 3.1 | 4.5 | 4.6 | +++ | |
| | E | | 3 | 1.5 | 11.6 | + | |
| | F | | 3 | 1.5 | 5.6 | ++ | |
| | G | | 3 | 2.8 | 5.8 | +++ | |
| | H | | 3 | 3.1 | 4.8 | +++ | |
| | I | | 3 | 3.2 | 8 | ++ | |
| | J | | 3.1 | 3 | 5.7 | ++ | |
| S2D18-191 | A | | 3.5 | 3.3 | 8.5 | ++ | |
| | C | | 3.5 | 2 | 13.9 | ++ | |
| | D | | 3.3 | 1.6 | 8.9 | ++ | |
| | E | | 3.6 | 2.5 | 9.2 | +++ | |
| | F | | 3.6 | 2 | 8 | +++ | |
| | G | | 3.5 | 0.4 | 7.7 | +++ | |
| | H | | 3.7 | 1.4 | 6 | ++ | |
| S2D18-206 | A | | 3.3 | 4.1 | 7 | +++ | |
| | C | | 3.2 | 2.1 | 6.2 | ++ | |
| | D | | 3.3 | 4.6 | 6.7 | ++ | |
| | E | | 3.4 | 3.4 | 5.2 | ++ | |
| | F | | 3.1 | 0.7 | 5.8 | +++ | |
| | H | | 3.4 | 0.6 | 11 | S | |
| S2D20-6 | B | | 4.1 | 1.5 | 8.8 | ++ | |
| | C | | 4.3 | 0.5 | 8.9 | ++ | |
| | D | | 4.1 | 3.2 | 8.9 | +++ | |
| | E | | 4.1 | 3.3 | 6.8 | +++ | |
| | G | | 4.3 | 3.8 | 7.8 | +++ | |
| | H | | 4.3 | 3.2 | 10.4 | +++ | |
| S2D20-133 | A | | 4.3 | 3.5 | 9.6 | S | |
| | B | | 4.5 | 4.4 | 7.5 | ++ | |
| | C | | 4.4 | 5 | 11.4 | ++ | |
| | D | | 4.5 | 3.1 | 10.8 | + | |
| | E | | 4.5 | 5.3 | 10 | +++ | |
| | F | | 4.4 | 5.1 | 8.8 | ++ | |
| | G | | 4.4 | 5.1 | 8.5 | ++ | |
| | H | | 4.3 | 1.1 | 10.5 | + | |
| S2D21-70 | A | | 4.2 | 2.1 | 22 | + | Spec near the hole |
| | B | | 4.2 | 2.7 | 8 | +++ | |
| | C | | 4.3 | 2.8 | 7.6 | +++ | |
| | D | | 4.3 | 1.3 | 12.3 | ++ | |
| | E | | 4 | 2.3 | 10.2 | ++ | |
| | F | | 4.2 | 0.5 | 7.2 | +++ | |
| S2D20-130 | A | | 3.2 | 0.8 | 7.6 | + | |
| | B | | 3 | 0.5 | 8.9 | ++ | |
| | E | | 3 | 1.3 | 11.1 | ++ | |
| | F | | 3.3 | 2 | 7.9 | +++ | |
| | G | | 3.3 | 0.5 | 11.9 | S | |
| | H | | 3.1 | 2.1 | 7.8 | ++ | |
| S2D20-194 | A | | 3.7 | 2.3 | 9.8 | +++ | |
| | C | | 3.6 | 3 | 7.9 | ++ | |
| | D | | 3.8 | 2.4 | 14 | S | |
| | E | | 3.6 | 2.4 | 5.9 | ++ | |
| | F | | 3.9 | 2.1 | 12.1 | ++ | |
| | G | | 3.7 | 2.1 | 6.7 | +++ | |
| | H | | 3.8 | 0.9 | 8.3 | ++ | |
| S2D18-81 | A | | 3 | 1.6 | 5.5 | ++ | |
| | C | | 3.1 | 2.1 | 6 | ++ | |
| | D | | 3.3 | 3.4 | 7.8 | ++ | |
| | E | | 3.3 | 2 | 6.6 | ++ | |
| | F | | 3.3 | 2.4 | 8.6 | ++ | |
| | G | | 3.4 | 2.9 | 8.6 | + | |
| | H | | 3.3 | 2.8 | 5.7 | +++ | |
| S2D20-171 | C | | 3.8 | 2.3 | 9.5 | ++ | |
| | E | | 3.8 | 2.7 | 8.3 | ++ | |
| | F | | 3.9 | 3.4 | 8.1 | ++ | |
| | G | | 3.7 | 3.3 | 6.2 | +++ | |
| | H | | 3.7 | 2.8 | 7.8 | +++ | |
| | I | | 3.7 | 2.8 | 12.7 | + | |
| | J | | 3.8 | 3.3 | 5.9 | +++ | |
| S2D16-26 | A | | 3.3 | 1.5 | 5.5 | ++ | |
| | C | | 3.5 | 1.9 | 7.5 | +++ | |
| | D | | 3.7 | 1.2 | 6.8 | ++ | |
| | E | | 3.5 | 1.7 | 7.5 | +++ | |
| | F | | 3.7 | 1.7 | 6.4 | +++ | |
| | H | | 3.7 | 1.7 | 8.8 | ++ | |
| S2D19-20 | A | | 2.5 | 1.4 | 5.7 | ++ | |
| | C | | 2.5 | 1.8 | 4.5 | +++ | |
| | D | | 2.5 | 1.5 | 5.8 | ++ | |
| | E | | 2.5 | 1.1 | 5 | ++ | |
| | F | | 2.4 | 1.8 | 1.6 | +++ | |
| | G | | 2.7 | 1.4 | 4.8 | ++ | |
| | H | | 2.8 | 1.6 | 5 | ++ | |
| S2D16-1 | B | | 3.2 | 1.2 | 10.3 | S | |
| | C | | 3.1 | 1.6 | 6.5 | + | |
| | D | | 3.1 | 0.6 | 17 | S | |
| | E | | 2.9 | 2.3 | 6.1 | ++ | |
| | F | | 3.1 | 2.7 | 6.1 | ++ | |
| | G | | 3.1 | 2.7 | 7.8 | +++ | |
| S3210-181 | A | Cho-Herg | 4.6 | 0.3 | 14 | +++ | |
| | B | | 4 | 0.5 | 11 | +++ | |
| | D | | 4 | 0.2 | 14 | ++ | |
| | E | | 4 | 1.3 | 17 | ++ | |
| | G | | 4 | 2.1 | 10 | +++ | |
| | H | | 4.1 | 0.6 | 12 | S | |
| S3214-60 | A | | 3.6 | 1.2 | 7 | ++ | |
| | B | | 2.9 | 1 | 7 | +++ | |
| | C | | 2.9 | 0.4 | 17 | −S | |
| | D | | 2.9 | 1.3 | 11 | + | |
| | G | | 3.1 | 1.7 | 10 | +++ | |
| | H | | 3 | 0.2 | 10 | ++ | |
| 031103-A1 | B | RBL | 3 | 1 | 4 | ++ | |
| | D | | 3.4 | 0.5 | 5.2 | ++ | |
| | F | | 3.1 | 1.1 | 4.1 | +++ | |
| | H | | 3 | 1.2 | 7 | ++ | |
| | N | | 3.2 | 0.4 | 4.4 | ++ | |
| | P | | 3.1 | 0.3 | 5.5 | + | |
| 031103-A2 | A | | 3.8 | 0.6 | 4.1 | ++ | |
| | C | | 4.3 | 2.1 | 4.1 | ++ | |
| | I | | 4 | 2.3 | 8.1 | ++ | |
| | K | | 4.4 | 2.1 | 5.3 | +++ | |
| | M | | 4.8 | 2.3 | 7.8 | ++ | |
| | O | | 4.4 | 2.7 | 9.9 | ++ | |
| 030703-A1 | A | | 3.6 | 1.9 | 4.9 | ++ | |
| | C | | 3.7 | 2.3 | 3.6 | +++ | |
| | E | | 3.8 | 2.2 | 5.8 | ++ | |
| | G | | 3.7 | 1.8 | 5.2 | ++ | |
| | I | | 3.4 | 1.7 | 4.1 | ++ | |

-continued

| Chip Lot# | Hole ID | Cell Type | Re (G) | Rm (G) | Ra (M) | Seal Qty | Note |
|---|---|---|---|---|---|---|---|
|  | M |  | 3.5 | 2.1 | 5.4 | ++ |  |
|  | O |  | 3.7 | 1.7 | 4.6 | ++ |  |
| 031103-A3 | A |  | 4.8 | 2.5 | 5.2 | ++ |  |
|  | C |  | 4.6 | 1.4 | 5.4 | ++ |  |
|  | E |  | 4.8 | 1 | 4.6 | ++ |  |
|  | I |  | 4.9 | 0.3 | 6.1 | ++ |  |
|  | D |  | 4.9 | 1.6 | 6.1 | ++ |  |
|  | F |  | 4.9 | 0.7 | 8.1 | ++ |  |
| 030603-A2 | B |  | 4.3 | 1.2 | 4.2 | +++ |  |
|  | C |  | 4.3 | 4 | 9.2 | ++ |  |
|  | F |  | 4.3 | 2 | 8.2 | ++ |  |
|  | H |  | 4.4 | 2.2 | 7 | ++ |  |
|  | G |  | 4.6 | 2 | 7.7 | +++ |  |
|  | I |  | 4.2 | 2.2 | 7.2 | +++ |  |
|  | J |  | 4.3 | 1.2 | 5.8 | ++ |  |
| 030603-A1 | A |  | 4.4 | 1.8 | 6.4 | + |  |
|  | B |  | 4.4 | 1.2 | 8 | ++ |  |
|  | C |  | 4.6 | 1.2 | 8 | + |  |
|  | F |  | 4.8 | 1.5 | 8.5 | + |  |
|  | G |  | 4.4 | 0.7 | 4.4 | ++ |  |
|  | H |  | 4.3 | 1.4 | 5.9 | + |  |
|  | I |  | 4.2 | 1.1 | 8.6 | ++ |  |
| 030603-A3 | B |  | 4 | 1.7 | 6.9 | +++ |  |
|  | D |  | 4 | 0.28 | 6.9 | ++ |  |
|  | F |  | 4.2 | 0.35 | 4.4 | ++ |  |
|  | H |  | 4.3 | 0.27 | 6.9 | ++ |  |
|  | L |  | 4.4 | 0.25 | 7.2 | ++ |  |
|  | N |  | 4.5 | 0.85 | 7.2 | ++ |  |

*SealChip Data Since Jan. 14th, 2003

Example 6

Cell Preparation for Ion Transport Measurement

PART I. CHO wt. and CHO.Kv cells
1. Use cells @ 50%~70% confluency. (18 hrs after cells seeded 1:10~1:15)
2. Remove medium and wash ×2 with $X^{++}$-free PBS (extra wash might be necessary if the final cell suspension has too much small debris)
3. Treat for 2'15" with 1:10 trypsin-EDTA, at this time the supernatant might be a little turbid due to release of cells into the buffer.
4. Rock gently, aspirate to discard supernatant. Wait for 1'25".
5. Add 1 volume of $X^{++}$-free DMEM complete with 10% FCS, NEAA, etc, rock gently to loosen and detach cells, and spin down (do not try to blow to remove the remaining cells sticking to the bottom)
6. Wash ×1 with PBS complete
7. Resuspend in PBS, triturate, and pass through 15~20 μm filter into non-stick plate.

Cells can be used after 10 minutes of recovery and should last for up to 4 hr

PART II. Transiently Transfected CHO Cells.
1. Remove medium and wash x2 with $X^{++}$-free PBS
2. Treat for 1' with 5 ml 1:10 trypsin-EDTA (0.5 ml 0.05% trysin 0.53 mM EDTA from GIBCO cat. No. 25300-54 in 4.5 ml PBS)
3. Rock gently, aspirate to discard supernatant.
4. Add 0.5 ml fresh 1:1 trypsin-EDTA, Wait for 6 mins.
5. Add 5 ml of $X^{++}$-free DMEM complete with 10% FCS, NEAA, etc, rock gently to loosen and detach cells, leave cell at RT for 1 hour, and spin down (do not try to blow to remove the remaining cells sticking to the bottom)
6. Wash ×2 with 1 ml PBS complete
7. Resuspend in PBS, triturate, and pass through 15 to 20 micron filter into non-stick plate.

Part III. CHO-Herg Cells.
1. Use cells at 50%~70% confluency in T-25 flasks (VWR, Cat. No. 29185-302).
2. Remove medium and wash ×2 with $X^{++}$-free PBS (extra wash might be necessary if the final cell suspension has too much small debris)
3. Treat for 1' with 2 ml trypsin-EDTA(0.5 ml 0.05% trysin 0.53 mM EDTA from GIBCO cat. No. 25300-54 in 1.5 ml PBS)
4. Rock gently, aspirate to discard supernatant. Wait for 2 mins.
5. Add 5 ml volume of $X^{++}$-free DMEM complete with 10% FCS, NEAA, etc, rock gently to loosen and detach cells, leave cell at RT for 30 min, and spin down (do not try to blow to remove the remaining cells sticking to the bottom)
6. Wash ×2 with 1 ml PBS complete
7. Resuspend in PBS, triturate, and pass through 15~20 μm polyester filter into non-stick plate if cells still cluster together.

Part IV. Protocol for isolation of CHO
1. Use cells at 70~80% confluences in T-25 flasks (24 hrs after seeding).
2. Remove medium and wash x2 with $X^{++}$-free PBS ((cell should not be leave in $X^{++}$-free PBS more than 10 mins, otherwise, the minimal digestion time will be decreased)
3. Wash once with 1:4 AccuMax (wait about 20 second, rocking to removed the loose attached cell)
4. Treat at 37° C. w 4 ml volume of 1: 4 Accumax (diluted with $X^{++}$-free PBS) for minimal time (cell dissociate from the flask and floated in the Accumax) or 1.5 times minimal time.

CHO-KV
  a. 1: 4 AccuMax 5' (1 ml AccuMax+3 ml $X^{++}$-free PBS) w/o rocking
  b. 1: 4 AccuMax 8' (1 ml AccuMax+3 ml $X^{++}$-free PBS) w/o rocking CHO-HERG
  c. 1: 4 AccuMax 8' (1 ml AccuMax+3 ml $X^{++}$-free PBS) w/o rocking
  d. 1: 4 AccuMax 12' (1 ml AccuMax+3 ml $X^{++}$-free PBS) w/o rocking 5. Add 5 ml volume of $Ca^{++}$-free DMEM with 10% FBS, into the flasks, and removed all cell suspension to a 15 ml centrifuge tube, spin down ~300 g×3 min (do not try to blow to remove the remaining cells sticking to the bottom).
6. Discard supernatant, add 1 ml 1:4 (PBSC: PBS), gently triturate to resuspend cell, centrifuge 2000 rpm×1 min in an micro centrifuge tube.
7. Discard the supernatant, add 800 μl to 1 ml 1:4 (PBSC*: PBS), triturate, and pass through 15~20 μm filter into non-stick plate.

| | | | | | |
|---|---|---|---|---|---|
| DMEM w/o Ca++ | Gibco | 500 ml | 21068-028 |  | 4° C. |
| AccuMax | Innovative cell Tech | 100 ml | AM105 | $ 36.00 | −20° C. |
| Dubbecco's PBS (PBSC*) | Gibco | 500 ml | 14287-080 |  | RT 1X |
| Dubbecco's PBS $X^{++}$- free | VWR | 500 ml | 16777-149 | $ 9.50 | RT 1X |
| FBS | Gibco | 500 ml | 10082-147 | inquire | −20° C. |
| 24 well non-stick plate | VWR |  | 29443-032 | 176.55 |  |

Part V. Protocol for Isolation of HEK
1. Use HEK-Na cells at 70~80% confluences in T-75 flasks (16 hrs after seeding).
2. Remove medium and wash×2 with $X^{++}$-free PBS
3. Add 6 ml $X^{++}$-free PBS, incubate at 37° C. for 5 mins, aspirate supernatant
4. Add 6 ml $X^{++}$-free PBS, incubate at 37° C. for 10 mins or until all cells dissociate from flask.
5. Add 2 ml Accumax directly into flask to finalize the Accumax concentration to 1:4, incubate cell at 37° C. for 4 mins
6. Add 6 ml volume of $Ca^{++}$-free DMEM with 10% FCS into the flasks to stop the digestion
7. Put cell mixture into a 15 ml tube, and spin down 300 g×3 min
8. Discard supernatant, gently suspend cell in 4 ml $Ca^{++}$ free DMEM with 10% FCS, incubate cell at 37° C. incubator at least 30 mins or until use it.
9. Carefully remove the supernatant, wash ×1 with PBS with 100 nM $Cacl_2$, 1 mM $Mgcl_2$
10. Triturate, resuspend cell in PBS with 100 nM $Cacl_2$, 1 mM $Mgcl_2$, filter cell mixture through 21 gm filter into non-stick plate.

Example 7

Program Logic and Pressure Profile

The following is a typical program logic for software pneumatic control. It includes procedures for cell landing, form seal, break-in, and Ra control.

```
#start of program
Count=0
Turn off compensations
Procedure Landing:
    Reset button_pressed
    Label window "Attempting Landing"
    Run washer # deliver clean ES to top chamber
    Wait 5 seconds
    Stop washer
    Repeat twice:
        Apply −300torr pressure # clear holes of any remaining debris after filling
        Wait 0.5 seconds
        Apply 0torr pressure
        Wait 2 seconds
    End repeat
    Zero junction potential
    Wait for stable reading
    Record average Re value
    Save Re to logs
    Initiate cell addition
    Wait until 0.5 seconds before cell delivery # before pipette touches ES
    Apply +10torr # before and during delivery
    Wait for pipette removal # from ES chamber
    Apply 0 torr
    Wait 3 seconds
    Apply −50torr
    Wait until Seal > 2Re for 0.5sec or elapsed=15 seconds
    If elapsed then
        Count=count+1
        If count >= 3 then abort test and write to log
        Apply +50torr
        Run proc Landing
    Endif
    Run FormSeal
End procedure
Reset elapsed
Procedure FormSeal
    Reset button_pressed
    Label window "Attempting Seal"
    Apply −80mV HP #negative holding immediately after landing
    Apply −50torr #this may not necessarily be the same as that used for landing
    While Seal increasing >20MOhms/second
        Wait until Seal >= 1Gohm or elapsed=10 seconds
    Endwhile
    Apply 0torr
    Wait 2 seconds
    While seal increasing >20MOhms/second and seal<1GOhm,
        Wait 1 second
    Endwhile
    #start ramping to attempt seal
    Unless seal>1GOhm, Apply ramp from 0torr to −50torr over 20 seconds
    Unless seal>1GOhm, Wait 5 seconds
    Unless seal>1GOhm, Apply 0torr
    Unless seal>1GOhm, wait 5 seconds
    Unless seal>1GOhm, Apply ramp from −30torr to −80torr over 30 seconds
    Unless seal>1GOhm, Wait 5 seconds
    Unless seal>1GOhm, Apply 0torr
    Unless seal>1GOhm, wait 5 seconds
    Unless seal>1GOhm, Apply ramp from −50torr to −100torr over 40 seconds
    Unless seal>1GOhm, Wait 5 seconds
```

```
        Unless seal>1GOhm, Apply 0torr
        Unless seal>1GOhm, wait 5 seconds
        Unless seal>1GOhm, Apply ramp from 0torr to -200torr over 120 seconds
        Unless seal>1GOhm, Wait 5 seconds
        Unless seal>1GOhm, Apply 0torr
        Unless seal>1GOhm, wait 5 seconds
        If not seal>1GOhm
                Check button_pressed
                If button_pressed = "continue" then abort test and write to log
                Run FormSeal
        Endif
        #Seal detected, now check stability
        Stop ramping and hold last pressure
        Wait 1 second # let seal stabilize
        If seal>1GOhm,
            Apply 0torr
            Record Seal value into Rseal, save to logs
            Unless Seal<(Rseal-200MOhms) or Seal decreasing >200MOhms/second
                Wait 5 seconds
            End unless
            If Seal<(Rseal-200MOhms) or Seal decreasing >200MOhms/second
                Check button_pressed
                If button_pressed = "continue", goto Procedure BreakIn
                Run FormSeal
            Endif
            #cell sealed
        Endif
End Procedure
Procedure BreakIn:
    Reset button_pressed
    Label window "Attempting break-in"
    Null chamber capacitance
    Until capacitance > 3.5pF or Pressure>300torr or Seal<(Rseal-200MOhms) or Seal
decreasing >200MOhms/second
        Wait 1 second
        Apply -20 delta torr
    End until
    If capacitance > 3.5pF
        Record break-in pressure value
        Wait 0.5 seconds
        Apply 0torr
        Run procedure RaControl
    Endif
    If Pressure>300torr
        Apply 0torr
        Until capacitance > 3.5pF or Pressure>300torr or Seal<(Rseal-200MOhms) or
Seal decreasing >200MOhms/second
            Wait 1 second
            Apply -20 delta torr
            Apply Zap
        End until
        If pressure>300torr then abort test and write to log
    Endif
    If capacitance > 3.5pF
        Record break-in pressure value
        Wait 0.5 seconds
        Apply 0torr
        Run procedure RaControl
    Endif
    If Seal<(Rseal-200MOhms) or Seal decreasing >200MOhms/second
        Check button_pressed
        If button_pressed = "continue", goto Procedure BreakIn
        Run FormSeal
    Endif
End Procedure
Elapsed = 0
Procedure RaControl:
    Reset button_pressed
    Label window "Adjusting seal quality"
    Record Cm, Rm, Ra to logs
    Assign RmInitial = Rm, RaInitial = Ra
    If Ra < RaIdeal then end #RaIdeal does not need adjustment
    If Ra < RaMax and Ra decreasing then end #no need for adjustment
    If Ra < RaMax then countdown = 20 seconds else countdown = "true"
    While countdown
        Check button_pressed
        If button_pressed = "continue" then end
```

```
            If Ra increasing and Rm > 300MOhms
                Apply −50torr
                Wait 0.5seconds # max 2 seconds
                Apply 0torr
                Wait 1.5 seconds
            Endif
            If Ra increasing and Rm > 500MOhms
                Apply −80torr
                Wait 0.5seconds # max 2 seconds
                Apply 0torr
                Wait 1.5 seconds
            Endif
            If Rm>0.8GOhm then apply −50torr else apply −10torr
            While Ra>RaIdeal and Rm>(RmInitial−25%) and countdown
                Unless Ra<RaIdeal or Rm<(RmInitial−25%), wait 5 seconds
                If Ra<RaMax then countdown=20 seconds
                If Ra<RaIdeal then Endwhile
                If Ra not decreasing
                    If Rm not decreasing and Rm>1GOhm then Apply −10 delta torr
                    If Rm not decreasing and Rm<1GOhm then Apply −5 delta torr
                    If Rm decreasing and Pressure>10torr then Apply +5 delta torr
                    If Rm<(RmInitial−25%) then apply 0torr
                Endif
                If pressure>BreakInPressure then apply 0torr
                If elapsed > 120 seconds then apply 0torr and end
                If Rm<300MOhms then apply (reakInPressure−10torr)
            Endwhile
            If −10torr>pressure>−50torr
                Apply 0torr
                If Ra increasing then apply −60torr
                If Ra increasing then run RaControl Procedure
            Endif
        Endwhile
End Procedure
```

The pressure profile of Example 6 was employed in a 52-cell test as described in Example 2. The criteria for the test was the achievement of at least 75% success rate, defined as achieving a gigaohm seal to initiate a patch clamp, then during the patch clamp membrane maintaining resistance above 200 MOhms and maintaining access resistance (or series resistance) below 15 MOhms for at least 15 minutes. Table 1 demonstrates the conclusion from this experiment, showing that the goals of the 52-cell test were met. FIGS. 27 (A)-(B) and FIG. 28 give a sample of the time-course of an experiment where membrane resistance and access resistance values are kept within the required parameters. At many locations in the recording there are deflections in the access resistance trace. These deflections represent locations where the pressure protocol was applied to maintain the seal quality parameters. The success rate at achieving gigaohm seals is demonstrated in FIG. 24. This data is a graphical representation of the data identified in Table 1, where 90% of the chips produced a gigaohm seal with CHO cells. FIG. 25 shows a histogram of the parameters achievable with this pressure control protocol. Data shown in blue represents initial values for Ra and Rm, and values in red represent values for Ra and Rm after 15 minutes of continuous whole-cell access under voltage clamp conditions. These data demonstrated that overall, 75% of the cells achieved gigaohm seals, and then whole-cell access was attained with acceptable parameters that were well-controlled for at least 15 minutes.

Example 9

Single Channel Recording Using a Biochip Comprising a Hole for Ion Transport Measurement RBL cells were prepared for patch clamp recording by simple centrifugation. The cells were then delivered onto an ion transport measurement device with a single recording aperture. The biochip device was assembled according to Example 2. The biochip had been treated with acid and base to improve sealability. The upper chamber solution was PBS lacking calcium and magnesium. The lower chamber solution was: 150 mM KCl, 10 mM HEPES-K, 1 mM EGTA-Na, 1 mM ATP-Mg pH (KOH) 7.4 for A through C in FIG. [22], the lower chamber solution was: 8 mM NaCl, 20 mM KCl, 1 mM $MgCl_2$, 10 mM HEPES-Na, 125 mM K-Glu, 10 mM EGTA-K, 1 mM ATP-Mg pH (KOH) 7.2 for D in FIG. [22].

Seal formation was achieved as provided in the previous examples, but after gigaseal formation, no break-in step was performed. Single-channel recordings were obtained from a cell-attached membrane patch on an RBL cell. An inward rectifier IRK1 single channel was recorded in RBL cells. A low concentration of extracellular $K^+$ which does not depolarize the cell and does not inactivate the channel was used. ATP was present in the internal solution, which prevents the rundown of the channel activity. The noise level of the recordings was reduced from 10 pA to 1 pA in order to observe single channel events, which have an amplitude of a few picoamps.

What is claimed is:
1. An ion channel chip comprising:
   (a) a planar polymer plastic substrate treated with an ionized gas;
   (b) at least one aperture positioned substantially perpendicular to said planar polymer plastic substrate; and
   (c) a gasket positioned about said aperture defining the perimeter of a chamber, wherein said treatment forms at least one functional group or moiety positioned sufficiently close to said aperture such that a cell simultaneously contacts said at least one functional group or moiety and said aperture, and wherein said ion channel chip is stored in an environment having decreased car- bon dioxide relative to the ambient environment, such that an enhanced electrical sealing property of the ion channel chip is preserved.

2. The ion channel chip of claim 1, wherein the environment is selected from the group consisting of water, an aqueous solution, a salt solution, a buffered salt solution, acetone, a vacuum, a drying agent, a desiccant, nitrogen and an inert gas.

3. The ion channel chip of claim 2, wherein the environment comprises a desiccant selected from the group consisting of a silica gel, $CaCl_2$ and NaOH.

4. The ion channel chip of claim 2, wherein the environment is water or an aqueous solution.

5. The ion channel chip of claim 2, wherein the environment is an aqueous solution.

6. The ion channel chip of claim 5, wherein the pH of the aqueous solution is greater than 4.

7. The ion channel chip of claim 5, wherein the pH of the aqueous solution is greater than 6.

8. The ion channel chip of claim 5, wherein the pH of the aqueous solution is greater than 7.

9. The ion channel chip of claim 5, wherein the pH of the aqueous solution is about 8.

10. The ion channel chip of claim 1, wherein said ionized gas is a plasma gas.

11. The ion channel chip of claim 1, wherein said ionized gas is a silicon-based vapor.

12. A storage system for an ion channel chip comprising:
(a) a fluid tight container capable of accepting an ion channel chip;
(b) an ion channel chip according to claim 1; and
(c) a fluid.

13. The storage system of claim 12, wherein the fluid is selected from the group consisting of water, an aqueous solution, a salt solution, a buffered salt solution and acetone.

14. The storage system of claim 13, wherein the fluid is water or an aqueous solution.

15. The storage system of claim 12, wherein the fluid tight container comprises a top structure and a bottom structure comprising a series of chip engaging structures, wherein each engaging structure is capable of engaging the ion channel chip, and wherein said bottom structure reversibly engages said top structure.

16. A method for storing a treated ion channel chip according to claim 1, which method comprises storing said treated ion channel chip in an environment having decreased carbon dioxide relative to the ambient environment.

17. The method of claim 16, wherein the ion channel chip is stored in a fluid tight container capable of accepting an ion channel chip.

18. The method of claim 17, wherein the fluid tight container comprises a fluid selected from the group consisting of water, an aqueous solution, a salt solution, a buffered salt solution and acetone.

19. The method of claim 18, wherein the fluid is water or an aqueous solution.

20. A method of transporting a treated ion channel chip according to claim 1, which method comprises transporting said treated ion channel chip in an environment having decreased carbon dioxide relative to the ambient environment.

21. The method of claim 20, wherein the ion channel chip is stored in a fluid tight container capable of accepting an ion channel chip.

22. The ion channel chip of claim 1, wherein said functional group or moiety provides a negative charge.

23. The ion channel chip of claim 22, wherein the surface density of said functional group or moiety is more than about 1%, more than about 10%, or more than about 30%.

24. The ion channel chip of claim 1, wherein said functional group or moiety comprises a $SiO^-$ group.

25. The ion channel chip of claim 24, wherein the surface density of the $SiO^-$ group is more than about 1%, more than about 10%, or more than about 30%.

* * * * *